(12) United States Patent
Lee et al.

(10) Patent No.: US 12,137,964 B2
(45) Date of Patent: Nov. 12, 2024

(54) END TOOL OF SURGICAL INSTRUMENT AND ELECTRIC CAUTERIZATION SURGICAL INSTRUMENT COMPRISING SAME

(71) Applicant: LIVSMED INC., Seongnam-si (KR)

(72) Inventors: Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/207,640

(22) Filed: Jun. 8, 2023

(65) Prior Publication Data

US 2023/0389979 A1 Dec. 7, 2023

Related U.S. Application Data

(63) Continuation of application No. PCT/KR2022/004705, filed on Apr. 1, 2022.

(30) Foreign Application Priority Data

Feb. 20, 2021 (KR) .................. 10-2021-0022973
Feb. 20, 2021 (KR) .................. 10-2021-0022984
May 29, 2021 (KR) .................. 10-2021-0069611

(51) Int. Cl.
*A61B 18/14* (2006.01)
*A61B 34/00* (2016.01)
*A61B 17/29* (2006.01)
*A61B 18/00* (2006.01)

(52) U.S. Cl.
CPC .......... *A61B 18/1445* (2013.01); *A61B 34/71* (2016.02); *A61B 2017/2933* (2013.01); *A61B 2017/2938* (2013.01); *A61B 2018/00595* (2013.01); *A61B 2018/1455* (2013.01)

(58) Field of Classification Search
CPC ............ A61B 2018/1455; A61B 34/71; A61B 18/1445
See application file for complete search history.

(56) References Cited

U.S. PATENT DOCUMENTS

| | | |
|---|---|---|
| 2012/0215220 A1 | 8/2012 | Manzo et al. |
| 2015/0305797 A1 | 10/2015 | Hassoun |
| 2020/0038127 A1* | 2/2020 | Chaplin ............. A61B 17/0218 |

(Continued)

FOREIGN PATENT DOCUMENTS

| | | |
|---|---|---|
| EP | 3266392 A2 | 1/2018 |
| JP | 2014-513570 A | 6/2014 |
| KR | 10-2010-0001823 A | 1/2010 |

(Continued)

*Primary Examiner* — Linda C Dvorak
*Assistant Examiner* — Ryan T Clark
(74) *Attorney, Agent, or Firm* — Bridgeway IP Law Group, PLLC; Sang Ho Lee; Hyun Woo Shin

(57) ABSTRACT

Provided are an end tool of a surgical instrument and a surgical instrument for electrocautery including the same, and in particular, an end tool of a surgical instrument and a surgical instrument for electrocautery including the end tool that is capable of rotating in two or more directions and intuitively matching a movement of a manipulation portion, wherein the surgical instrument may be installed on a robot arm or manually operable in order to be used in laparoscopic surgery or other various surgeries.

20 Claims, 132 Drawing Sheets

(56) References Cited

U.S. PATENT DOCUMENTS

2020/0107894 A1\* 4/2020 Wallace ............ A61B 17/3423
2021/0045825 A1 2/2021 Lee et al.

FOREIGN PATENT DOCUMENTS

| KR | 10-2012-0003091 A | 1/2012 |
| KR | 10-2013-0027688 A | 3/2013 |
| KR | 10-2019-0109449 A | 9/2019 |
| KR | 10-2122508 B1 | 6/2020 |
| KR | 10-2308205 B1 | 10/2021 |
| KR | 10-2308214 B1 | 10/2021 |
| KR | 10-2362194 B1 | 2/2022 |
| WO | 2020-055705 A1 | 3/2020 |
| WO | 2020-076447 A1 | 4/2020 |
| WO | 2020/089790 A1 | 5/2020 |
| WO | 2022-177366 A1 | 8/2022 |

\* cited by examiner

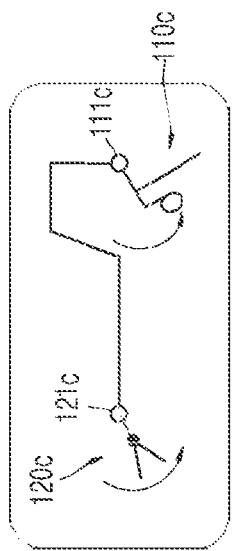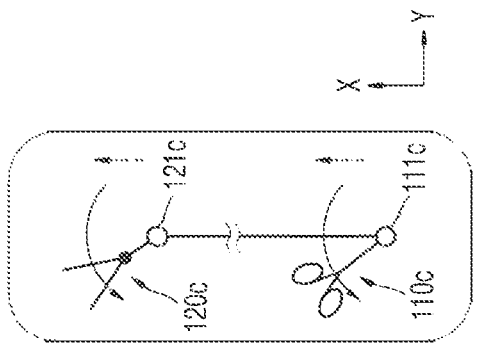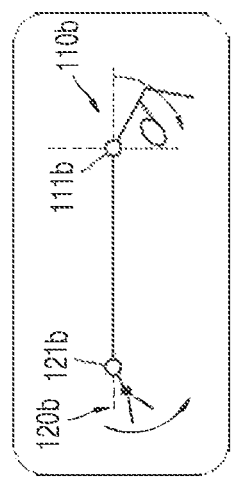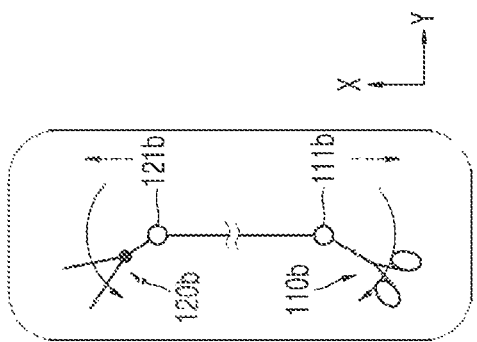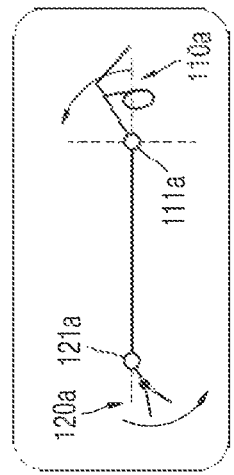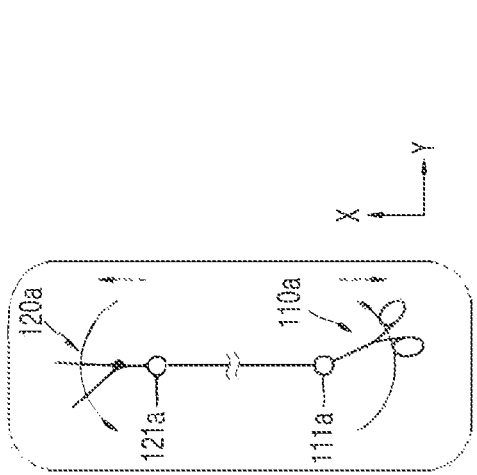

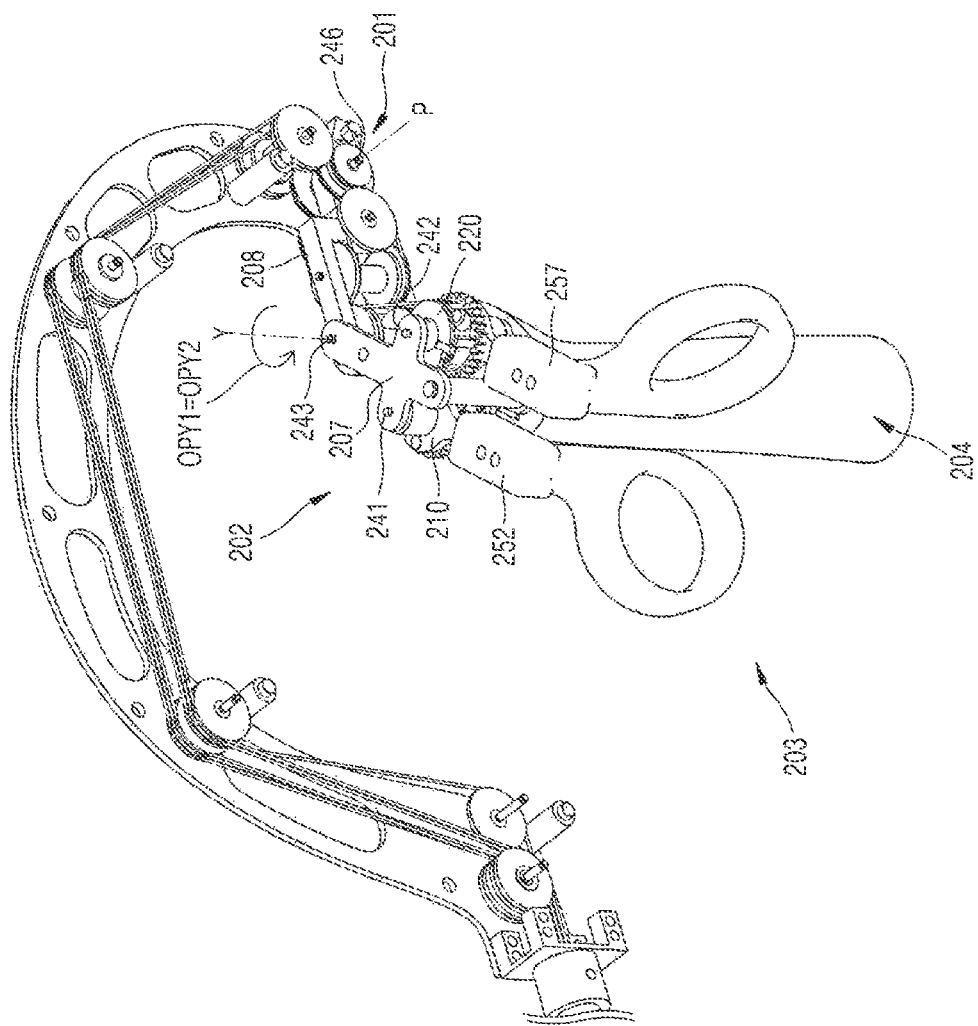
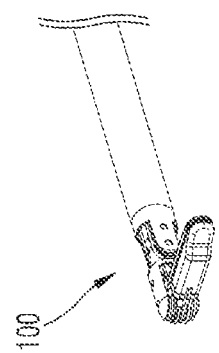
FIG. 26

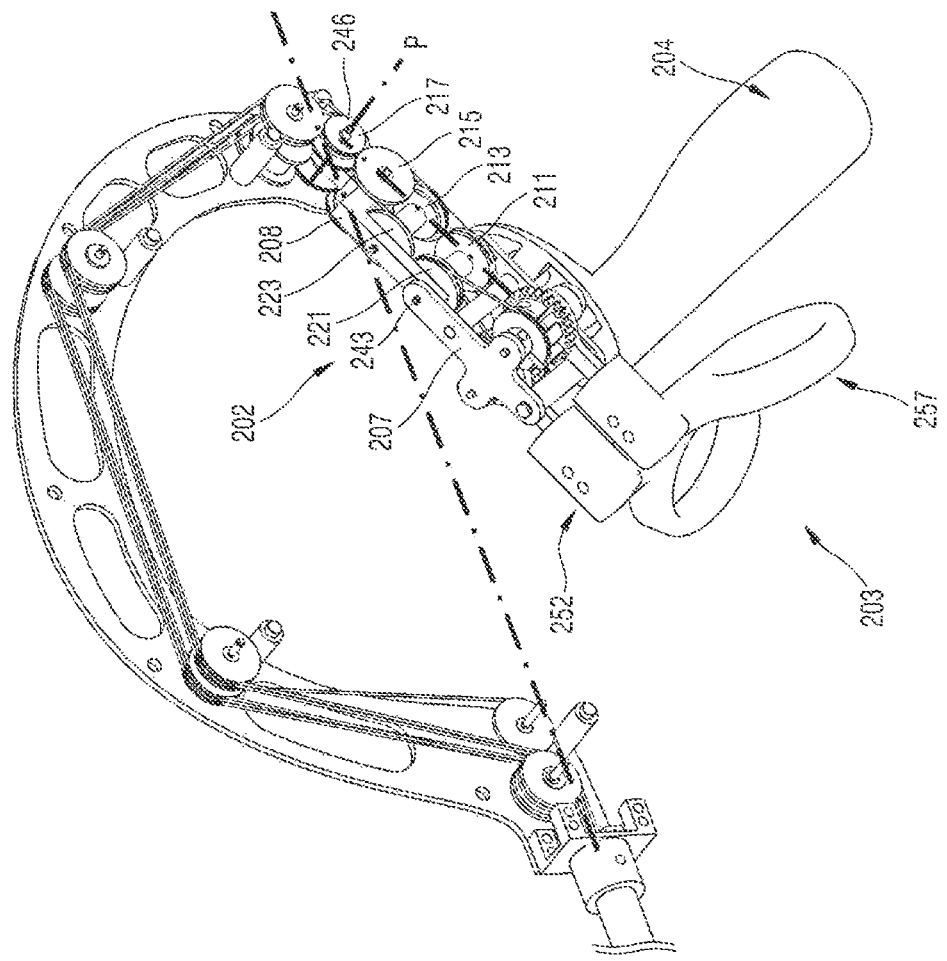
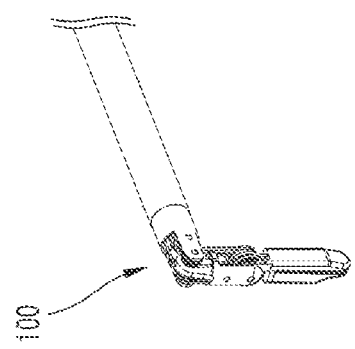
FIG. 32

FIG. 84
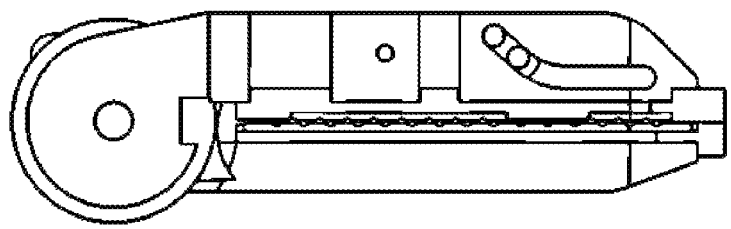
(a)
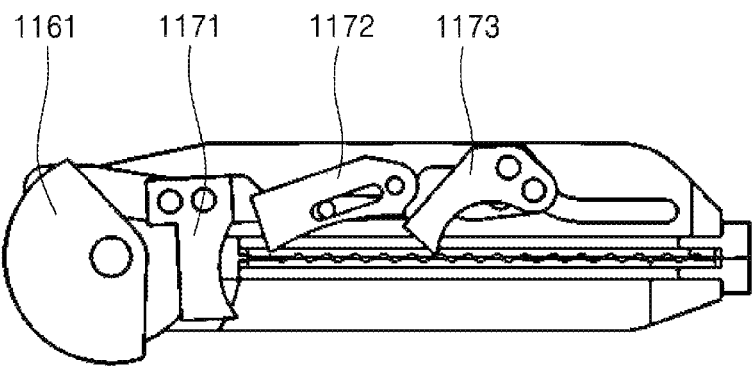
(b)

FIG. 85
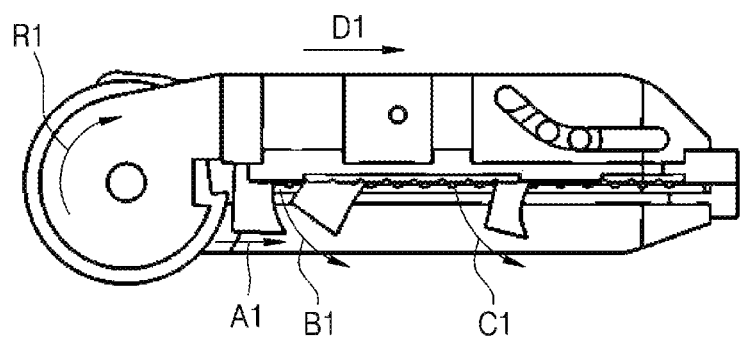
(a)
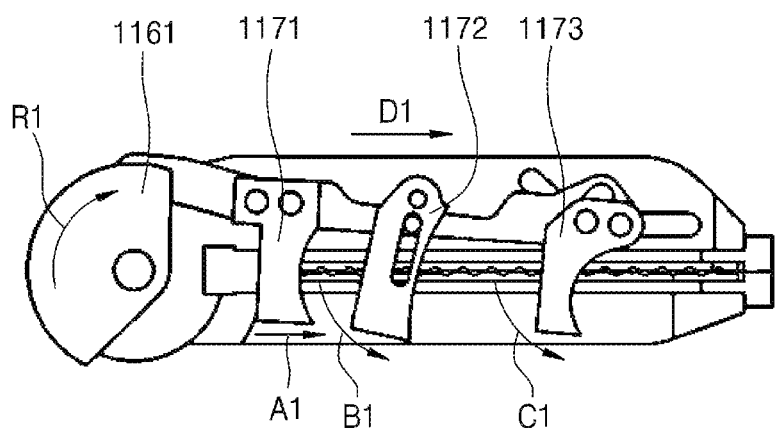
(b)

FIG. 86
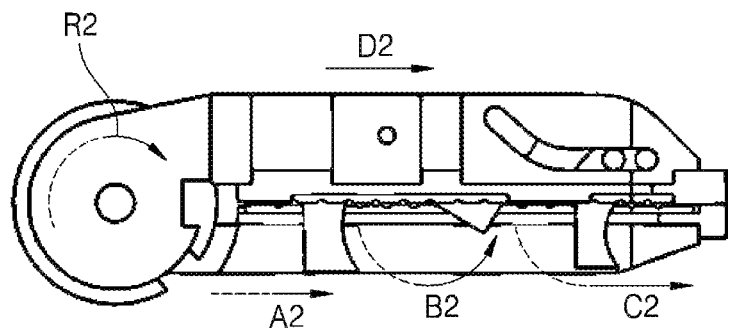
(a)
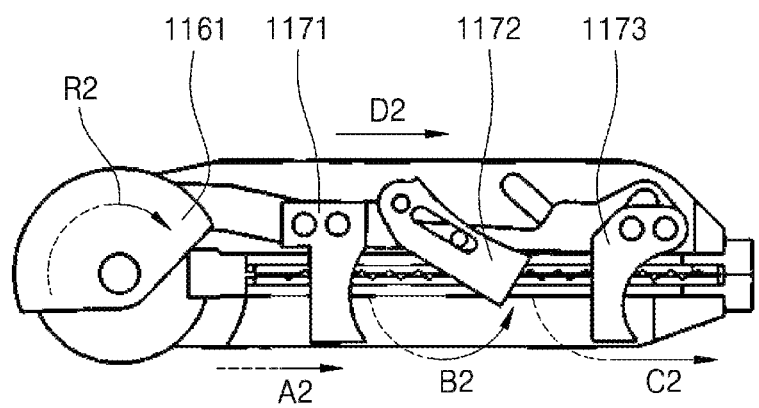
(b)

FIG. 128
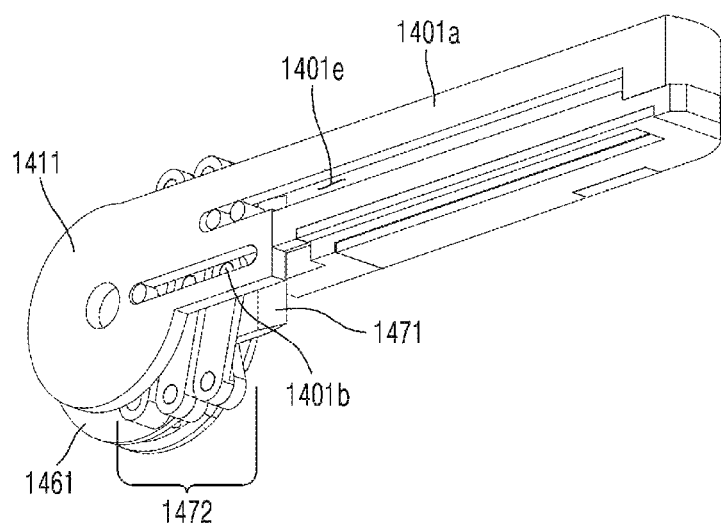
(a)
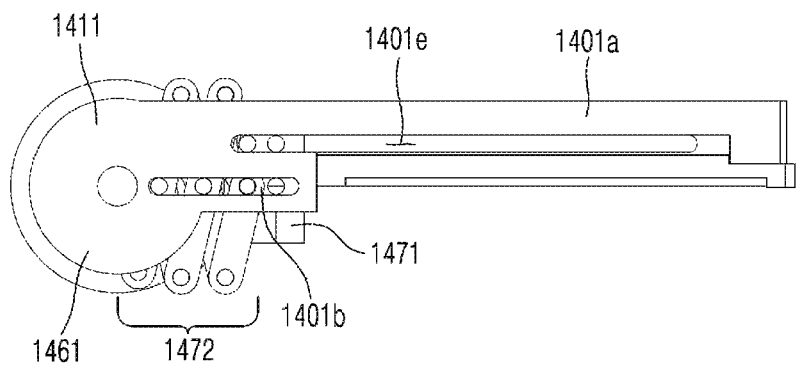
(b)

FIG. 129
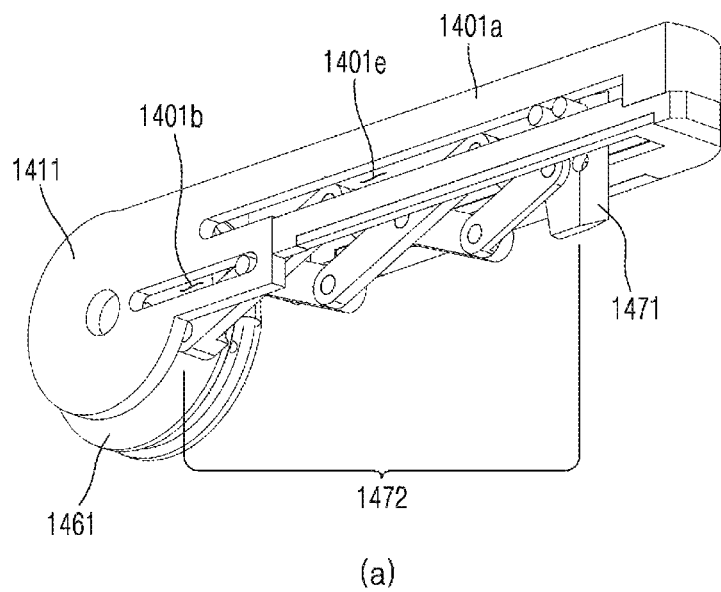
(a)
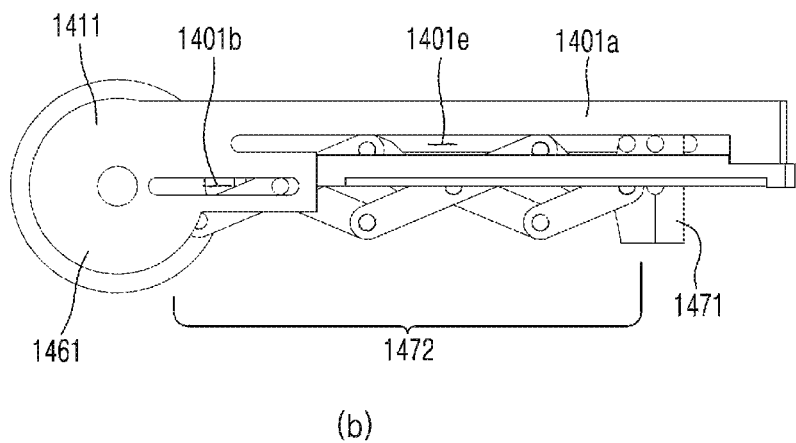
(b)

END TOOL OF SURGICAL INSTRUMENT AND ELECTRIC CAUTERIZATION SURGICAL INSTRUMENT COMPRISING SAME

CROSS-REFERENCE TO RELATED APPLICATION

This application is a continuation of international application No. PCT/KR2022/004705, filed on Apr. 1, 2022, which claims priority to Korean Patent Application No. 10-2021-0022973, filed on Feb. 20, 2021, Korean Patent Application No. 10-2021-0022984, filed on Feb. 20, 2021, and Korean Patent Application No. 10-2021-0069611, filed on May 29, 2021, with the Korean Intellectual Property Office, the disclosures of which are incorporated herein in their entirety by reference.

TECHNICAL FIELD

One or more embodiments of the present disclosure relate to an end tool of a surgical instrument and a surgical instrument for electrocautery including the same, and in particular, to an end tool of a surgical instrument and a surgical instrument for electrocautery including the end tool that is capable of rotating in two or more directions and intuitively matching a movement of a manipulation portion, wherein the surgical instrument may be installed on a robot arm or manually operable in order to be used in laparoscopic surgery or other various surgeries.

BACKGROUND ART

Surgical operations in many cases require cutting and joining of body tissues including organs, muscular tissues, connective tissues and blood vessels. Over the centuries, sharp blades and sutures have been used for cutting and joining. However, bleeding occurs when cutting body tissues, in particular, relatively highly vascularized tissue during surgical operation. Therefore, doctors have been in need of surgical instruments and methods to slow or reduce bleeding during surgical operations.

Recently, it has become possible to use an electric surgical instrument that uses electrical energy to perform certain surgical tasks. For example, in surgical instruments such as graspers, scissors, tweezers, blades, needles, and hooks, electric surgical instruments including one or more electrodes formed to receive electric energy have been developed. Electrical energy supplied through the electrodes may be used to coagulate, bond, or cut the patient's body tissues. In particular, when electrical energy is used, amputation and hemostasis may be performed at the same time.

Electric surgical instruments are typically divided into two types: monopolar and bipolar. In a monopolar electric surgical instrument, electrical energy of a specific polarity is supplied to one or more electrodes of the instrument. And electricity of different polarity is electrically connected to the patient. In a bipolar electric surgical instrument, one or more electrodes are electrically connected to a first polarity electrical energy source, and one or more electrodes are electrically connected to a second polarity electrical energy source opposite to the first polarity.

The above-mentioned background art is technical information that the inventor has possessed for the derivation of the present disclosure or acquired in the process of derivation of the present disclosure, and cannot necessarily be said to be a known technique disclosed to the general public prior to the filing of the present disclosure.

DESCRIPTION OF EMBODIMENTS

Technical Problem

One or more embodiments of the present disclosure provides a surgical instrument for electrocautery including an end tool that is capable of rotating in two or more directions and intuitively matching a movement of a manipulation portion, wherein the surgical instrument may be installed on a robot arm or manually operable in order to be used in laparoscopic surgery or other various surgeries.

Solution to Problem

According to an embodiment, an end tool of a surgical instrument includes: a first jaw and a second jaw that are rotatable independently from each other; a first jaw pulley coupled to the first jaw and formed to be rotatable about a first axis; a second jaw pulley coupled to the second jaw, formed to be rotatable about an axis that is substantially same or parallel to the first axis, and formed to be spaced apart a certain distance from the first jaw pulley; a blade assembly which includes a blade moving between a proximal end and a distal end of the first jaw, and of which at least a part is formed between the first jaw pulley and the second jaw pulley; and a blade wire that is at least partially in contact with the blade assembly and transfers a driving force required to move the blade to the blade.

The end tool may further include an end tool hub including a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion, wherein the first jaw pulley is arranged adjacent to the first jaw pulley coupling portion of the end tool hub, the second jaw pulley is arranged adjacent to the second jaw pulley coupling portion of the end tool hub, and at least a part of the blade assembly is formed between the first jaw pulley and the second jaw pulley.

The blade assembly may include a blade pulley, and the blade pulley may be arranged between the first jaw pulley and the second jaw pulley.

The first axis may be sequentially inserted through the first jaw pulley coupling portion, the first jaw pulley, the blade pulley, the second jaw pulley, and the second jaw pulley coupling portion.

The first jaw pulley, the blade pulley, and the second jaw pulley may be sequentially stacked in the end tool hub.

The first jaw pulley, the blade pulley, and the second jaw pulley may be formed to be rotatable independently from one another.

The end tool may further include a blade auxiliary pulley arranged between the blade pulley and the guide portion.

The blade wire may be located on a common internal tangent of the blade pulley and the blade auxiliary pulley, and a rotation angle of the blade pulley may be increased due to the blade auxiliary pulley.

Regions of the guide portion, which are adjacent to the first jaw pulley, the blade pulley, and the second jaw pulley, may be curved so as to have cross-sections having a certain curvature.

The blade wire may be located on a common internal tangent of the blade pulley and the guide portion, and a rotation angle of the blade pulley may be increased due to the guide portion.

The blade assembly may include a blade pulley, and the blade pulley may be arranged between the first jaw pulley and the second jaw pulley.

The blade wire may be connected to the blade pulley, the blade pulley may be connected to the blade, and when the blade pulley is rotated by the blade wire, the blade connected to the blade pulley may be moved between the proximal end and the distal end of the first jaw.

The blade assembly may further include a blade link which is connected to the blade pulley and the blade and transfers the rotation of the blade pulley to the blade.

A first electrode may be formed on a surface of the first jaw, the surface facing the second jaw, and a second electrode may be formed on a surface of the second jaw, the surface facing the first jaw.

Electrocautery on a tissue may be performed while an electric current flows in the first electrode and the second electrode.

When the electrocautery is finished, the blade wire may be moved and accordingly, the blade may move from a side of the proximal end toward a side of the distal end of the first jaw, thereby cutting the tissue.

When the blade is located at the proximal end of the first jaw, at least a part of the blade may be accommodated in the first jaw, and the blade may be moved toward the second jaw by the blade wire.

The blade may be drawn to the outside of the first jaw while moving toward the distal end of the first jaw.

The end tool may further include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially the same as or parallel to the second axis.

The end tool may be formed to be yaw-rotatable about the first axis, and simultaneously pitch-rotatable about the second axis.

The end tool may further include: a first jaw wire, of which at least a part is wound on the first jaw pulley and the pair of end tool first jaw pitch main pulleys; and a second jaw wire, of which at least a part is wound on the second jaw pulley and the pair of end tool second jaw pitch main pulleys.

According to another embodiment, an end tool of a surgical instrument includes: a first jaw and a second jaw that are rotatable independently from each other; a first jaw pulley coupled to the first jaw and formed to be rotatable about a first axis; a second jaw pulley coupled to the second jaw and formed to be rotatable about an axis that is substantially same or parallel to the first axis; a blade pulley formed to be rotatable about an axis that is substantially same as or parallel to the first axis, and arranged adjacent to the first jaw pulley or the second jaw pulley; and at least one blade connected to the blade pulley and moving between a proximal end and a distal end of the first jaw according to rotation of the blade pulley.

The end tool may further include a blade link which is connected to the blade pulley and the blade and transfers the rotation of the blade pulley to the blade.

The rotational motion of the blade pulley may be converted into a position movement of the blade by the blade link.

One end of the blade link may be coupled to the blade pulley and the other end of the blade link may be coupled to the blade, and when the blade pulley rotates in one direction, the blade link coupled to the blade pulley may move the blade while moving toward the proximal end or the distal end of the first jaw.

A blade accommodation portion in which the blade and at least a part of the blade link are accommodated may be formed in the first jaw.

The blade may be moved along the blade accommodation portion of the first jaw.

A slit in which at least a part of the blade drawn out from the first jaw is accommodated may be formed in the second jaw.

When the blade pulley rotates in one direction, the blade may be moved toward the proximal end of the first jaw, and when the blade pulley rotates in another direction, the blade may be moved toward the distal end of the first jaw.

The end tool may include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially same as or parallel to the second axis.

When the first jaw pulley and the second jaw pulley rotate about the second axis in a same direction, the blade pulley may be rotated along with the first jaw pulley and the second jaw pulley.

The end tool may further include a blade second auxiliary pulley arranged on one side of the blade pulley.

When the first jaw pulley and the second jaw pulley rotate about the first axis in a same direction, the blade pulley may be rotated along with the first jaw pulley and the second jaw pulley.

When the first jaw pulley and the second jaw pulley rotate about the first axis in different directions, the blade pulley may be rotated along with one of the first jaw pulley and the second jaw pulley.

While the blade pulley is rotated about the first axis by the blade wire, the first jaw pulley and the second jaw pulley may not rotate.

A first electrode may be formed on a surface of the first jaw, the surface facing the second jaw, and a second electrode may be formed on a surface of the second jaw, the surface facing the first jaw.

Electrocautery on a tissue may be performed while an electric current flows in the first electrode and the second electrode.

When the electrocautery is finished, the blade pulley may rotate and accordingly, the blade may move from a first position to a second position, thereby cutting the tissue.

The first jaw pulley, the blade pulley, and the second jaw pulley may be sequentially stacked.

The blade pulley may be formed between the first jaw pulley and the second jaw pulley.

The first jaw pulley, the blade pulley, and the second jaw pulley may be formed to be rotatable independently from one another.

A plurality of sawtooth portions may be formed on an edge portion of the blade.

The end tool may further include: a first jaw wire, of which at least a part is wound on the first jaw pulley; and a second jaw wire, of which at least a part is wound on the second jaw pulley.

According to another embodiment, an end tool of a surgical instrument includes: a first jaw and a second jaw that are rotatable independently from each other; a first jaw pulley coupled to the first jaw and formed to be rotatable about the first axis; a first jaw wire, of which at least a part is wound on the first jaw pulley; a second jaw pulley coupled to the second jaw and formed to be rotatable about the first axis; a second jaw wire, of which at least a part is wound on the second jaw pulley; a pair of end tool first jaw pitch main pulleys which are formed on one side of the first jaw pulley and formed to be rotatable about a second axis forming a certain angle with the first axis; a pair of end tool second jaw pitch main pulleys which are formed on one side of the second jaw pulley and formed to be rotatable about an axis that is substantially same as or parallel to the second axis; a blade pulley formed to be rotatable about the first axis and arranged between the first jaw pulley and the second jaw pulley; a blade wire, of which at least a part is wound on the blade pulley; and a blade which is connected to the blade pulley, of which at least a part is accommodated in the first jaw, and which moves toward the second jaw according to a rotation of the blade pulley.

The end tool may further include a blade link which is connected to each of the blade pulley and the blade and transfers the rotation of the blade pulley to the blade.

A rotational motion of the blade pulley may be converted into a position movement of the blade by the blade link.

When the blade pulley rotates, the blade link connected to the blade pulley may be moved, and when the blade link is moved, the blade coupled to the blade link may be moved.

A blade accommodation portion in which the blade and at least a part of the blade link are accommodated may be formed in the first jaw.

The blade may be moved along the blade accommodation portion of the first jaw.

A slit in which at least a part of the blade drawn out from the first jaw is accommodated may be formed in the second jaw.

The end tool may further include a first guide portion formed in the first jaw and a second guide portion formed on the blade, wherein a movement path of the blade may be guided by the first guide portion and the second guide portion.

The first guide portion having a groove shape may be formed in the first jaw, the second guide portion having a protrusion shape may be formed on the blade, and when the second guide portion is moved along the first guide portion while being inserted in the first guide portion, the blade may be moved between the distal end and the proximal end of the first jaw.

The first guide portion having the groove shape may be formed to be curved once or more.

The first guide portion may be formed to be inclined by a certain degree within a certain section, and when the blade passes through the inclined region of the first guide portion, the blade may be moved toward the distal end of the first jaw, and simultaneously may be moved to a direction protruding from an inside to an outside of the first jaw.

After the blade passes through the inclined region of the first guide portion, the blade may perform a linear motion in a direction toward the distal end of the first jaw.

The blade may be moved between a first position and a second position according to a rotation of the blade pulley.

The first position may be a position where the blade is accommodated in the first jaw, and the second position may be a position where at least a part of the blade protrudes outward from the first jaw.

When the blade is located at the first position, the blade may not protrude outward from the first jaw.

The blade may be drawn to the outside of the first jaw while moving toward the distal end of the first jaw.

The blade may be formed in a four-bar linkage type in which four links are connected to one another.

The blade may include an edge portion and a first link formed to face the edge portion, and when the blade pulley rotates, the edge portion and the first link may be moved in opposite directions.

The blade may be directly connected to the blade pulley.

When the blade pulley rotates, the blade may be moved in a direction toward a jaw other than the jaw in which the blade is accommodated, while rotating along with the blade pulley.

According to another embodiment, an end tool of a surgical instrument includes: a first jaw and a second jaw that are rotatable independently from each other; a first jaw pulley coupled to the first jaw and formed to be rotatable about a first axis; a second jaw pulley coupled to the second jaw and formed to be rotatable about an axis that is substantially same or parallel to the first axis; a blade pulley formed to be rotatable about the first axis and arranged adjacent to the first jaw pulley and the second jaw pulley; a plurality of blades moving between a proximal end and a distal end of the first jaw according to a rotation of the blade pulley; and a blade link which is respectively connected to the blade pulley and the plurality of blades and transfers the rotation of the blade pulley to the plurality of blades.

Moving trajectories of the plurality of blades may be substantially same as one another.

The plurality of blades may include a first blade and a second blade which are at least partially accommodated in the first jaw and arranged next to each other.

When the blade pulley rotates, the first blade and the second blade may be rotatably moved with respect to the first jaw.

When the blade link is located at the proximal end or the distal end of the first jaw, the first blade and the second blade may be inserted in the first jaw.

When the blade link is located between the proximal end and the distal end of the first jaw, at least a part of each of the first blade and the second blade may be drawn outward from the first jaw.

Moving trajectories of the plurality of blades may be different from one another.

The movement trajectories of the blades that are adjacent to each other may at least partially overlap each other.

The plurality of blades may include a first blade, a second blade, and a third blade, which are at least partially accommodated in the first jaw and are arranged adjacent to one another, and the first blade, the second blade, and the third blade may be sequentially arranged from the proximal end to the distal end of the first jaw.

The first blade may be fixedly coupled to the blade link and integrally moved with the blade link.

When the blade pulley rotates, the first blade may be substantially moved linearly.

When the blade pulley rotates, the second blade may be rotatably moved with respect to the first jaw.

The second blade may be axially coupled to the first jaw, and when the blade link is moved, the second blade may be rotatably moved with respect to the first jaw.

The end tool may further include a first guide portion formed in the first jaw and a second guide portion formed on the third blade, wherein a movement path of the third blade may be guided by the first guide portion and the second guide portion.

The first guide portion having a groove shape may be formed in the first jaw, the second guide portion having a protrusion shape may be formed on the third blade, and when the second guide portion is moved along the first guide portion while being inserted in the first guide portion, the third blade may be moved between the distal end and the proximal end of the first jaw.

When the blade link is located at the proximal end of the first jaw, at least a part of the first blade may be drawn outward from the first jaw, and the second blade and the third blade may be inserted in the first jaw.

When the blade link is located at the distal end of the first jaw, at least a part of each of the first blade and the third blade may be drawn outward from the first jaw, and the second blade may be inserted in the first jaw.

The rotational motion of the blade pulley may be converted into a position movement of the plurality of blades by the blade link.

The end tool may further include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially the same as or parallel to the second axis.

The end tool may be formed to be yaw-rotatable about the first axis, and simultaneously pitch-rotatable about the second axis.

The end tool may further include: a first jaw wire, of which at least a part is wound on the first jaw pulley; a second jaw wire, of which at least a part is wound on the second jaw pulley; and a blade wire, of which at least a part is wound on the blade pulley.

According to another embodiment, an end tool of a surgical instrument includes: a first jaw and a second jaw that are rotatable independently from each other; a first jaw pulley coupled to the first jaw and formed to be rotatable about a first axis; a first jaw wire, of which at least a part is wound on the first jaw pulley; a second jaw pulley coupled to the second jaw and formed to be rotatable about an axis that is substantially same as or parallel to the first axis; a second jaw wire, of which at least a part is wound on the second jaw pulley; a blade pulley formed to be rotatable about the first axis and arranged adjacent to the first jaw pulley and the second jaw pulley; a blade wire, of which at least a part is wound on the blade pulley; a blade moving between a proximal end and a distal end of the first jaw according to a rotation of the blade pulley; and a blade link assembly including a plurality of blade links, and connected to the blade pulley and the blade to transfer a rotation of the blade pulley to the blade.

When the blade pulley rotates, a length of the blade link assembly may be changed and the blade may be moved.

A rotational motion of the blade pulley may be converted into a linear motion of the blade by the blade link assembly.

At least a part of the blade may be located in the first jaw, and at least a part of the blade may be located in the second jaw.

At least some of the plurality of blade links may be rotated about a certain rotary shaft when the blade pulley rotates, and simultaneously, may be linearly moved between the proximal end and the distal end of the first jaw.

The plurality of blade links may be arranged to repeatedly cross one another in an X-shape.

When the blade pulley rotates, the blade link assembly may be compressed or stretched.

The end tool may further include a first guide portion formed in the first jaw and a second guide portion formed on the blade, wherein a movement path of the blade is guided by the first guide portion and the second guide portion.

The end tool may further include a first link guide portion formed in the first jaw and a second link guide portion formed on the blade link assembly, wherein a moving path of the blade link assembly is guided by the first link guide portion and the second link guide portion.

While the blade link assembly is moved along the first link guide portion, the blade connected to the blade link assembly may be linearly moved.

The blade link assembly may include: a first blade link connected to the blade pulley; a second blade link that is axially coupled to the first jaw and is connected to the first blade link; and a third blade link connected to the second blade link and the blade.

The first blade may be coupled to a region between both end portions of the second blade link.

The end tool may further include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially the same as or parallel to the second axis.

The end tool may be formed to be yaw-rotatable about the first axis, and simultaneously pitch-rotatable about the second axis.

According to another embodiment, a surgical instrument for electrocautery includes: an end tool having a first jaw and a second jaw, each formed to be rotatable, wherein the rotation is made in two or more directions; a manipulation portion configured to control rotation of the end tool in the two or more directions; a power transmission portion having a first jaw wire connected to the manipulation portion to transfer the rotation of the manipulation portion to the first jaw and a second jaw wire connected to the manipulation portion to transfer the rotation of the manipulation portion to the second jaw; and a connecting portion extending in a first direction (X-axis) and having one end coupled to the end tool and the other end coupled to the manipulation portion to connect the manipulation portion and the end tool, wherein the end tool includes: a first electrode coupled to the first jaw; a second electrode coupled to the second jaw and formed to face the first jaw; a first jaw pulley coupled to the first jaw and formed to be rotatable about a first axis; a second jaw pulley coupled to the second jaw and formed to be rotatable about an axis that is substantially same as or parallel to the first axis; a blade pulley formed to be rotatable about an axis that is substantially same as or parallel to the first axis, and arranged adjacent to the first jaw pulley or the second jaw pulley; and a blade connected to the blade pulley and moving between a proximal end and a distal end of the first jaw according to a rotation of the blade pulley.

At least a part of the manipulation portion may be extended toward the end tool.

When the manipulation portion is rotated in the two or more directions, the end tool may be rotated in directions substantially identical with manipulation directions of the manipulation portion.

A direction in which the end tool is formed at the end portion of the connecting portion and a direction in which the manipulation portion is formed at the other end portion of the connecting portion may be identical directions based on an extending axis (X-axis) of the connecting portion.

The manipulation portion may extend in a direction away from a user who grips the surgical instrument for electrocautery.

An end portion of the manipulation portion may be formed toward the end tool so that an end of a finger of a user gripping the manipulation portion faces the end tool.

The connecting portion may include a bent portion which is formed to be bent once or more while connecting the end tool to the manipulation portion.

The bent portion may have a cross-section formed as an approximately semi-circular shape, and a direction in which the manipulation portion is formed at an end portion of the bent portion and a direction in which the end tool is formed at a point where the connecting portion and the end tool are connected may be formed to be substantially identical.

At least a part of the manipulation portion may be formed to be accommodated in the bent portion during at least one movement of the manipulation portion.

The surgical instrument for electrocautery may further include an end tool jaw auxiliary pulley that is formed on one side of the first jaw pulley and the second jaw pulley, and is formed to be rotatable about a second axis.

Two strands of the first jaw wire wound on the first jaw pulley may be arranged, by the end tool jaw auxiliary pulley, on one side based on a plane that is perpendicular to the second axis and passes through the first axis, and two strands of the second jaw wire wound on the second jaw pulley may be arranged, by the end tool jaw auxiliary pulley, on the other side based on a plane that is perpendicular to the second axis and passes through the first axis.

Any one side of the first jaw wire wound on the first jaw pulley may be formed to pass between the first jaw pulley and the end tool jaw auxiliary pulley, and any one side of the second jaw wire wound on the second jaw pulley may be formed to pass between the second jaw pulley and the end tool jaw auxiliary pulley.

The first jaw wire may be located on an internal tangent of the first jaw pulley and the end tool jaw auxiliary pulley, and the second jaw wire may be located on an internal tangent of the first jaw pulley and the end tool jaw auxiliary pulley.

The surgical instrument for electrocautery may further include a blade link which is connected to the blade pulley and the blade and transfers the rotation of the blade pulley to the blade.

A rotational motion of the blade pulley may be converted into a position movement of the blade by the blade link.

The first jaw pulley and the second jaw pulley may be formed to be spaced a certain distance from each other, and the blade pulley may be formed between the first jaw pulley and the second jaw pulley.

The first jaw pulley, the blade pulley, and the second jaw pulley may be sequentially stacked.

Electrocautery of a tissue may be performed while an electric current flows in the first electrode and the second electrode.

When the electrocautery is finished, the blade pulley may rotate, and accordingly, the blade may move between the proximal end and the distal end of the first jaw, thereby cutting the tissue.

The surgical instrument for electrocautery may further include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially same as or parallel to the second axis.

The end tool may be formed to be yaw-rotatable about the first axis, and simultaneously pitch-rotatable about the second axis.

When the first jaw pulley and the second jaw pulley rotate about the second axis in a same direction, the blade pulley may be rotated along with the first jaw pulley and the second jaw pulley.

When the first jaw pulley and the second jaw pulley rotate about the first axis in a same direction, the blade pulley may be rotated along with the first jaw pulley and the second jaw pulley.

When the first jaw pulley and the second jaw pulley rotate about the first axis in different directions from each other, the blade pulley may be rotated along with one of the first jaw pulley and the second jaw pulley.

While the blade pulley is rotated about the first axis by the blade wire, the first jaw pulley and the second jaw pulley may not rotate.

According to another embodiment, a method for surgery by using a surgical instrument for electrocautery includes: arranging a tissue between a first jaw and a second jaw of an end tool of a surgical instrument for electrocautery; closing the first jaw and the second jaw by rotating a first jaw pulley, to which the first jaw is coupled, and a second jaw pulley, to which the second jaw is coupled, in opposite directions about a first axis; performing electrocautery of the tissue between the first jaw and the second jaw when an electric current flows in a first electrode connected to the first jaw and a second electrode connected to the second jaw; and cutting the tissue by moving a blade of a blade assembly from a proximal end to a distal end of the first jaw, the blade assembly being at least partially arranged between the first jaw pulley and the second jaw pulley.

The blade assembly may further include a blade pulley at least partially arranged between the first jaw pulley and the second jaw pulley, and a blade link connecting the blade pulley to the blade, and the cutting of the tissue may include: rotating the blade pulley; moving the blade link coupled to the blade pulley from the proximal end toward the distal end of the first jaw, according to the rotation of the blade pulley; and moving the blade coupled to the blade link from the proximal end toward the distal end of the first jaw, according to the movement of the blade link.

A rotational motion of the blade pulley may be converted into a position movement of the blade by the blade link.

The method may further include a blade wire coupled to the blade pulley and rotating the blade pulley, and the cutting of the tissue may be performed by the rotation of the blade pulley by the blade wire.

The first jaw pulley and the second jaw pulley may be formed to be spaced a certain distance from each other, and the blade pulley may be formed between the first jaw pulley and the second jaw pulley.

The first jaw pulley, the blade pulley, and the second jaw pulley may be sequentially stacked.

The end tool may include: a pair of end tool first jaw pitch main pulleys which are formed on one side of the first jaw pulley and formed to be rotatable about a second axis forming a certain angle with the first axis; and a pair of end tool second jaw pitch main pulleys which are formed on one side of the second jaw pulley and formed to be rotatable about an axis that is substantially same as or parallel to the second axis.

The end tool may be formed to be yaw-rotatable about the first axis, and simultaneously pitch-rotatable about the second axis.

When the first jaw pulley or the second jaw pulley is rotated about the first axis or the second axis by the first jaw wire or the second jaw wire, the blade pulley may be rotated along with the first jaw pulley or the second jaw pulley, and while the blade pulley is rotated by the blade wire, the first jaw pulley and the second jaw pulley may not rotate.

When the blade pulley rotates in one direction, the blade may be moved from the proximal end to the distal end of the first jaw, and when the blade pulley rotates in another direction, the blade may be moved from the distal end toward the proximal end of the first jaw.

The cutting of the tissue may be performed while the blade is moved from the first jaw toward the second jaw.

The method may further include a blade wire that is at least partially in contact with the blade assembly and transfers a driving force required to move the blade to the blade, and the cutting of the tissue may be performed by the movement of the blade by the blade wire.

Other aspects, features and advantages other than those described above will become apparent from the following detailed description of the drawings, claims and disclosure.

Advantageous Effects of Disclosure

According to the disclosure, a manipulation direction of a manipulation portion by an operator and an operating direction of an end tool are intuitively identical, so that the operator's convenience is improved, and the accuracy, reliability and speed of surgery may be improved.

BRIEF DESCRIPTION OF THE DRAWINGS

FIG. 1A is a conceptual diagram of a pitch movement of a conventional surgical instrument, and FIG. 1B is a conceptual diagram of a yaw movement.

FIG. 1C is a conceptual diagram of a pitch movement of another conventional surgical instrument, and FIG. 1D is a conceptual diagram of a yaw movement.

FIG. 1E is a conceptual diagram of a pitch movement of surgical instrument according to the present disclosure, and FIG. 1F is a conceptual diagram of a yaw movement.

FIG. 26 is a perspective view illustrating a yaw movement of the surgical instrument for electrocautery of FIG. 2.

FIG. 32 is a perspective view illustrating a pitch movement of the surgical instrument for electrocautery of FIG. 2.

FIGS. 84, 85, and 86 are side views illustrating a cutting movement of the end tool of the surgical instrument for electrocautery of FIG. 75, when jaws are closed.

FIGS. 128 to 132 are perspective views illustrating a cutting movement of an end tool of the surgical instrument for electrocautery of FIG. 125.

MODE OF DISCLOSURE

Figure 2:
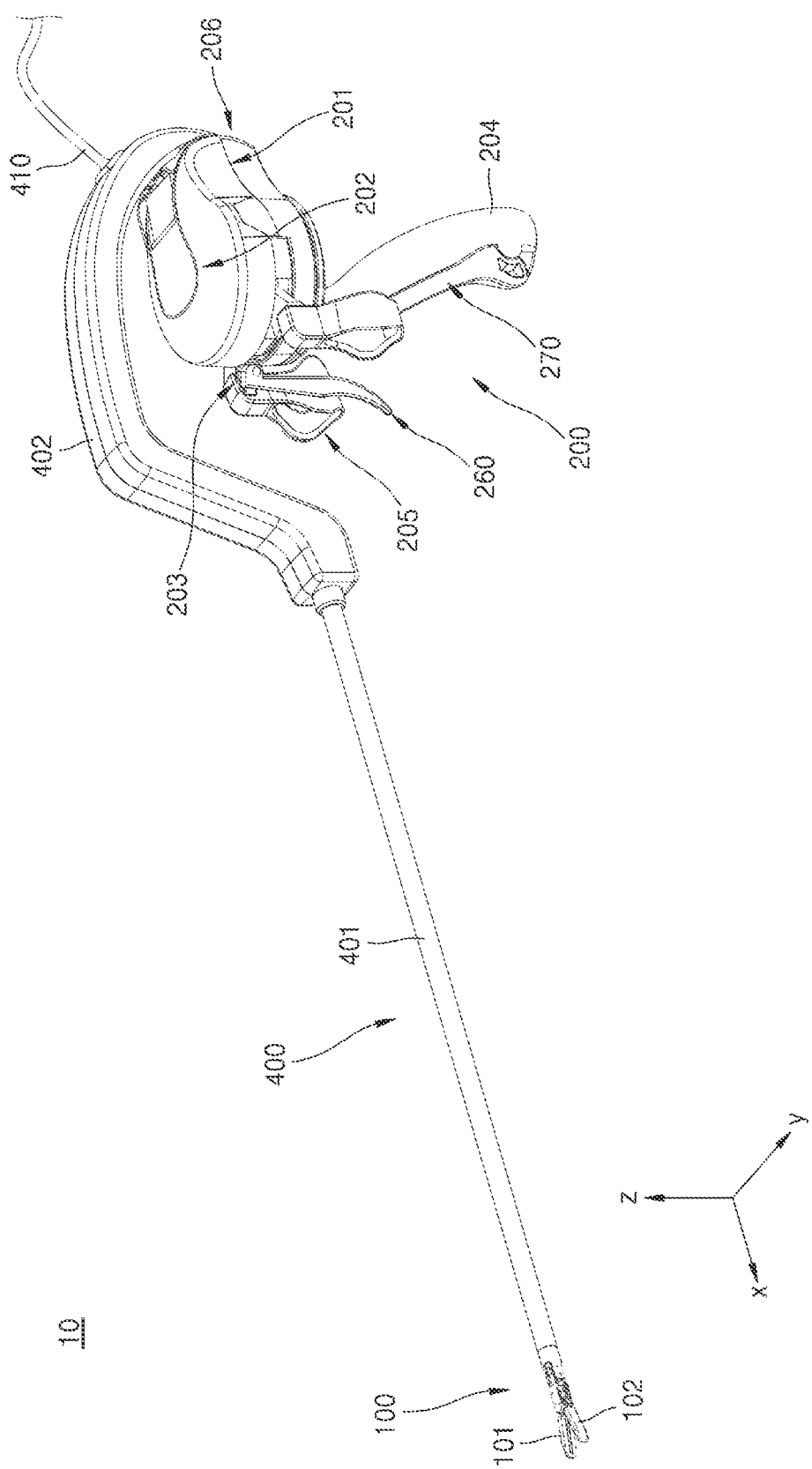
FIG. 2 is a perspective view illustrating a surgical instrument for electrocautery according to a first embodiment of the present disclosure.

As the present disclosure allows for various changes and numerous embodiments, exemplary embodiments will be illustrated in the drawings and described in detail. However, this is not intended to limit embodiments to particular modes of practice, and it is to be appreciated that all changes, equivalents, and substitutes that do not depart from the spirit and technical scope of the present disclosure are encompassed in embodiments. In the description of embodiments, certain detailed explanations of the related art are omitted when they are deemed as unnecessarily obscuring the essence of the present disclosure.

While such terms as "first," "second," etc., may be used to describe various components, such components must not be limited by the above terms. The above terms are used only to distinguish one component from another.

The terms used in the present application are merely used to describe exemplary embodiments, and are not intended to limit the present disclosure. As used herein, the singular forms "a," "an" and "the" are intended to include the plural forms as well, unless the context clearly indicates otherwise. In the present application, it is to be understood that the terms such as "including," "having," and "comprising" are intended to indicate the existence of the features, numbers, operations, actions, components, parts, or combinations thereof disclosed in the specification, and are not intended to preclude the possibility that one or more other features, numbers, operations, actions, components, parts, or combinations thereof may exist or may be added.

Hereinafter, embodiments of the present disclosure are described in detail with reference to the attached drawings. Like or corresponding reference numerals in the drawings denote like elements, and any redundant descriptions thereon will be omitted.

In addition, in describing various embodiments of the present disclosure, each embodiment does not have to be interpreted or practiced independently, and It should be understood that the technical concepts described in each embodiment may be interpreted or implemented in combination with other embodiments described individually.

In the surgical instrument for electrocautery according to the present disclosure, with respect to one or more motions from a pitch motion, a yaw motion, and an actuation motion, when a manipulation portion is rotated in one direction, an end tool may rotate in a direction intuitively the same as the manipulation direction of the manipulation portion.

FIG. 1A is a conceptual diagram of a pitch motion of a conventional surgical instrument, and FIG. 1B is a conceptual diagram of a yaw motion.

With reference to FIG. 1A, in performing a pitch motion of a conventional surgical instrument, with an end tool 120*a* formed in front of a rotation center 121*a* of the end tool 120*a* and a manipulation portion 110*a* formed behind a rotation center 111*a* of the manipulation portion 110*a*, when the manipulation portion 110*a* is rotated in the clockwise direction, the end tool 120*a* may also be rotated in the clockwise direction, and when the manipulation portion 110*a* is rotated in the counterclockwise direction, the end tool 120*a* may also be rotated in the counterclockwise direction. With reference to FIG. 1B, in performing a yaw motion of a conventional surgical instrument, with the end tool 120*a* formed in front of the rotation center 121*a* of the end tool 120*a* and the manipulation portion 110*a* formed behind the rotation center 111*a* of the manipulation portion 110*a*, when the manipulation portion 110*a* is rotated in the clockwise direction, the end tool 120*a* may also be rotated in the clockwise direction, and when the manipulation portion 110*a* is rotated in the counterclockwise direction, the end tool 120*a* may also be rotated in the counterclockwise direction. In this case, from the viewpoint of left and right sides of a user, when the user moves the manipulation portion 110*a* to the left, the end tool 120*a* may move to the right, and when the user moves the manipulation portion 110*a* to the right, the end tool 120*a* may move to the left. As a result, as the user manipulation direction is opposite to the end tool operation direction, the user may make a mistake, and have difficulty in manipulating the instrument.

FIG. 1C is a conceptual diagram of a pitch motion of another conventional surgical instrument, and FIG. 1D is a conceptual diagram of a yaw motion.

With reference to FIG. 1C, some of the conventional surgical instruments may be formed in a mirror-symmetrical manner, and in performing a pitch motion, in a state where an end tool 120*b* is formed in front of a rotation center 121*b* of the end tool 120*b*, and a manipulation portion 110*b* is formed behind a rotation center 111*b* of the manipulation portion 110*b*, when the manipulation portion 110*b* is rotated in the clockwise direction, the end tool 120*b* may rotate in the counterclockwise direction, and when the manipulation portion 110*b* is rotated in the counterclockwise direction, the end tool 120*b* may rotate in the clockwise direction. In this case, from the viewpoint of rotation direction of the manipulation portion 110*b* and the end tool 120*b*, a rotation direction in which a user rotates the manipulation portion 110*b* may be opposite to a resulting rotation direction of the end tool 120*b*. Not only this may result in causing confusion about the manipulation direction to a user, but also movements of joints are not intuitive, which may lead to a mistake. In addition, with reference to FIG. 1D, in performing a yaw motion, in a state where the end tool 120*b* is formed in front of the rotation center 121*b* of the end tool 120*b*, and the manipulation portion 110*b* is formed behind the rotation center 111*b* of the manipulation portion 110*b*, when the manipulation portion 110*b* is rotated in the clockwise direction, the end tool 120*b* may rotate in the counterclockwise direction, and when the manipulation portion 110*b* is rotated in the counterclockwise direction, the end tool 120*b* may rotate in the clockwise direction. In this case, from the viewpoint of rotation direction of the manipulation portion 110*b* and the end tool 120*b*, a rotation direction in which a user rotates the manipulation portion 110*b* may be opposite to a resulting rotation direction of the end tool 120*b*. Not only this may result in causing confusion about the manipulation direction to a user, but also movements of joints are not intuitive, which may lead to a mistake. As such, in the pitch or yaw manipulation by a user of the conventional surgical instruments, there may be a discrepancy between the user manipulation direction and the operation direction of the end tool in terms of rotation direction or left and right direction. This is due to a configuration difference between the end tool and the manipulation portion in the joint configuration of the conventional surgical instruments. That is, the end tool may be formed in front of the rotation center of the end tool, whereas the manipulation portion may be formed behind the rotation center of the manipulation portion. To overcome such issue, in the surgical instrument according to an embodiment of the present disclosure shown in FIGS. 1E-1F, an end tool 120*c* may be formed in front of a rotation center 121*c* of the end tool 120*c*, and a manipulation portion 110*c* may also be formed in front of a rotation center 111*c* of the manipulation portion 110*c* so that motions of the manipulation portion 110*c* and the end tool 120*c* are intuitively matched. In other words, unlike the existing examples of a configuration in which a manipulation portion approaches a user with respect to its joint (i.e., away from an end tool) as shown in FIGS. 1A-1D, in the surgical instrument according to an embodiment shown in FIG. 1E and FIG. 1F, at least a part of the manipulation portion may become closer to the end tool than the joint of the manipulation portion in more than one moments during a manipulation process.

In other words, in the case of the conventional surgical instruments shown in FIGS. 1A-1D, as the end tool may be formed in front of its rotation center whereas the manipulation portion may be formed behind its rotation center, the end tool of which front portion moves when its rear portion is fixed may move through a motion of the manipulation portion of which rear portion moves when its front portion is fixed, which is an intuitively unmatching structure. For this reason, a discrepancy in an aspect of left and right direction or an aspect of rotation direction in manipulation of a manipulation portion and motion of an end tool may occur, causing confusion to a user, and the manipulation of the manipulation portion may not be intuitively and quickly performed, which may lead to a mistake. On the contrary, in a surgical instrument according to an embodiment, as both of an end tool and a manipulation portion move based on rotation centers formed behind the end tool and the manipulation portion, respectively, structurally speaking, the motions thereof may intuitively match. In other words, as a moving portion of the end tool moves based on its rotation center formed therebehind, and similarly, a moving portion of the manipulation portion also moves based on its rotation center formed therebehind, structurally, the motions thereof may match intuitively. According to the foregoing, the user may intuitively and quickly control the direction of the end tool, and the possibility of causing a mistake may be significantly reduced. Hereinafter, a detailed mechanism enabling such function will be described.

First Embodiment of a Surgical Instrument for Electrocautery

Figure 3:
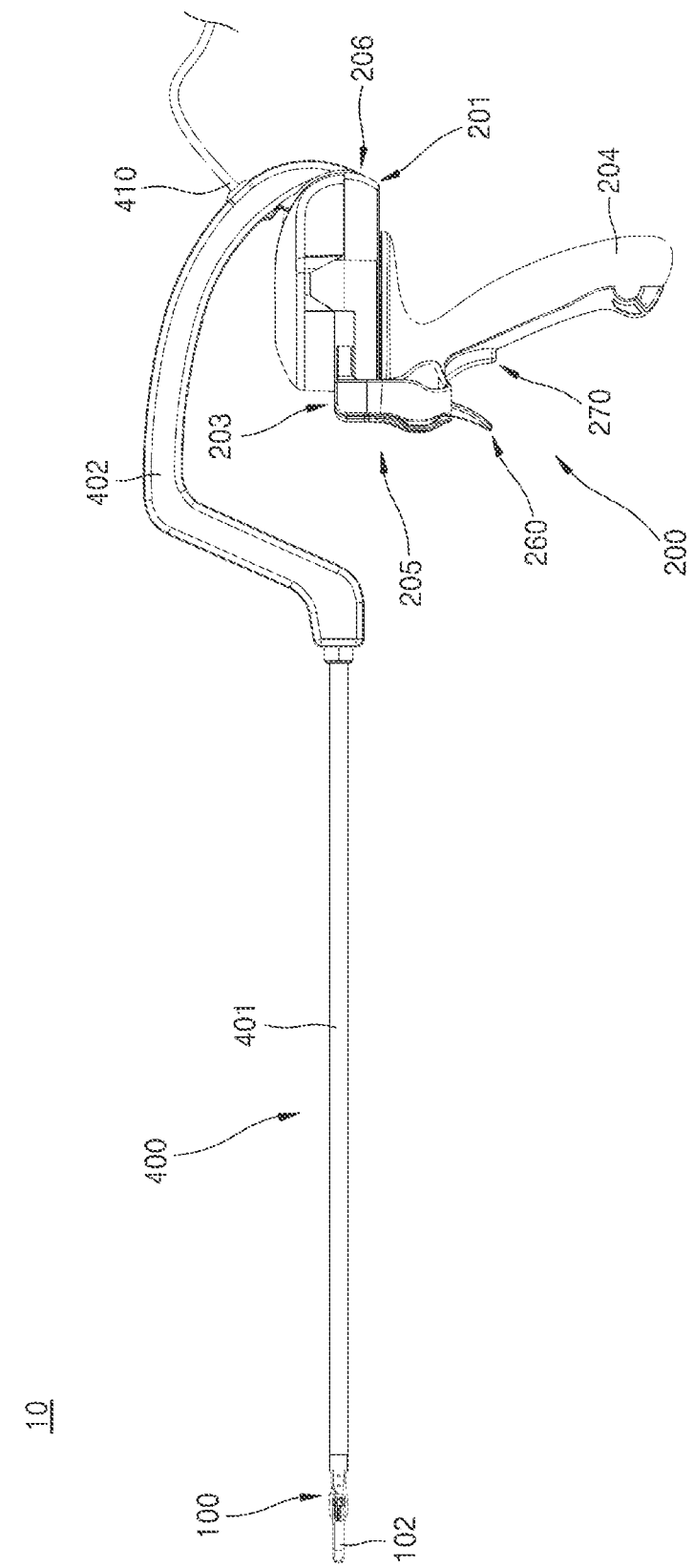
FIG. 3 is a side view of the surgical instrument for electrocautery of FIG. 2.
Figure 4:
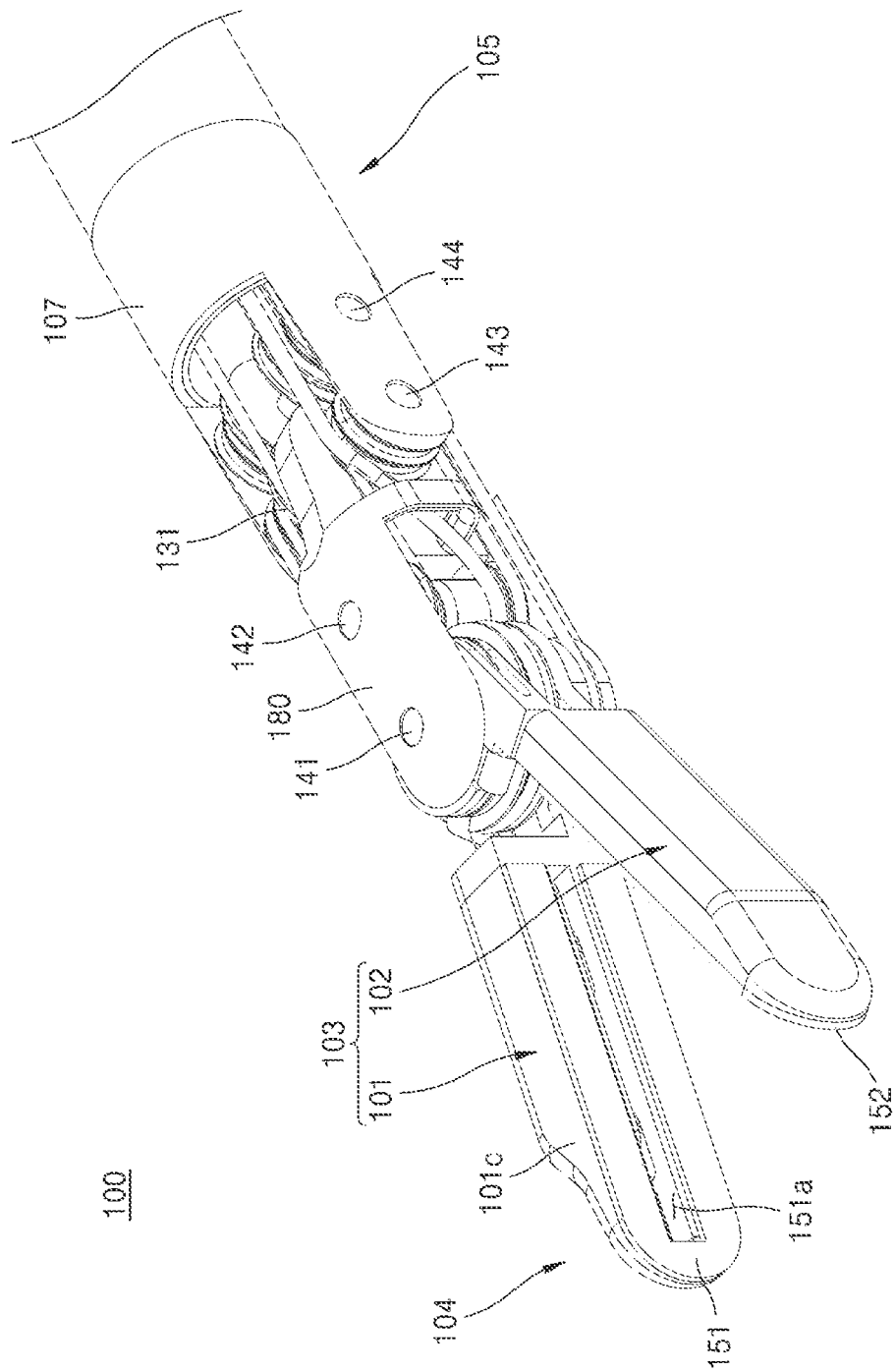
FIGS. 4 and 5 are perspective views illustrating an end tool of the surgical instrument for electrocautery of FIG. 2.
Figure 5:
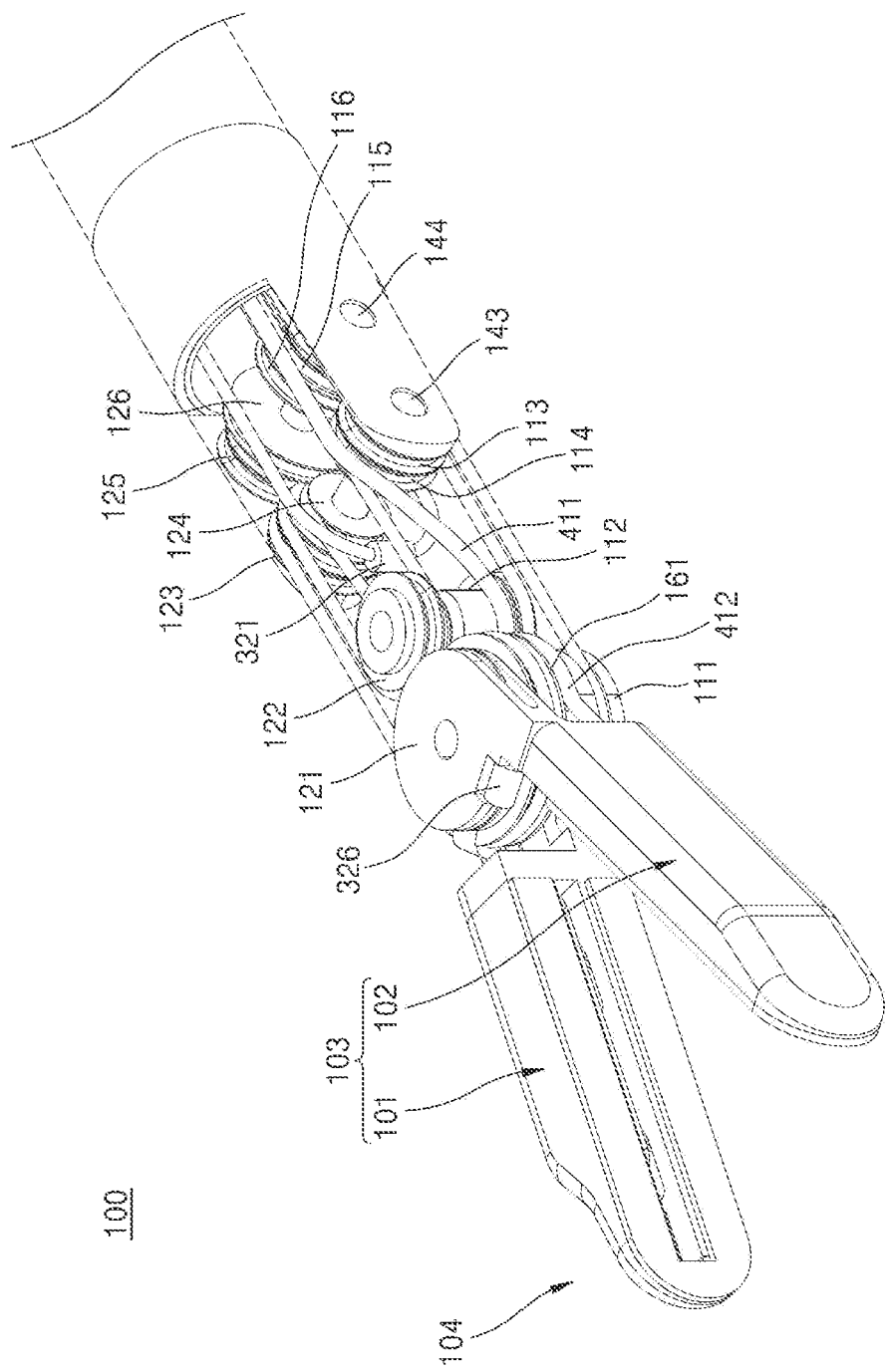
Figure 6:
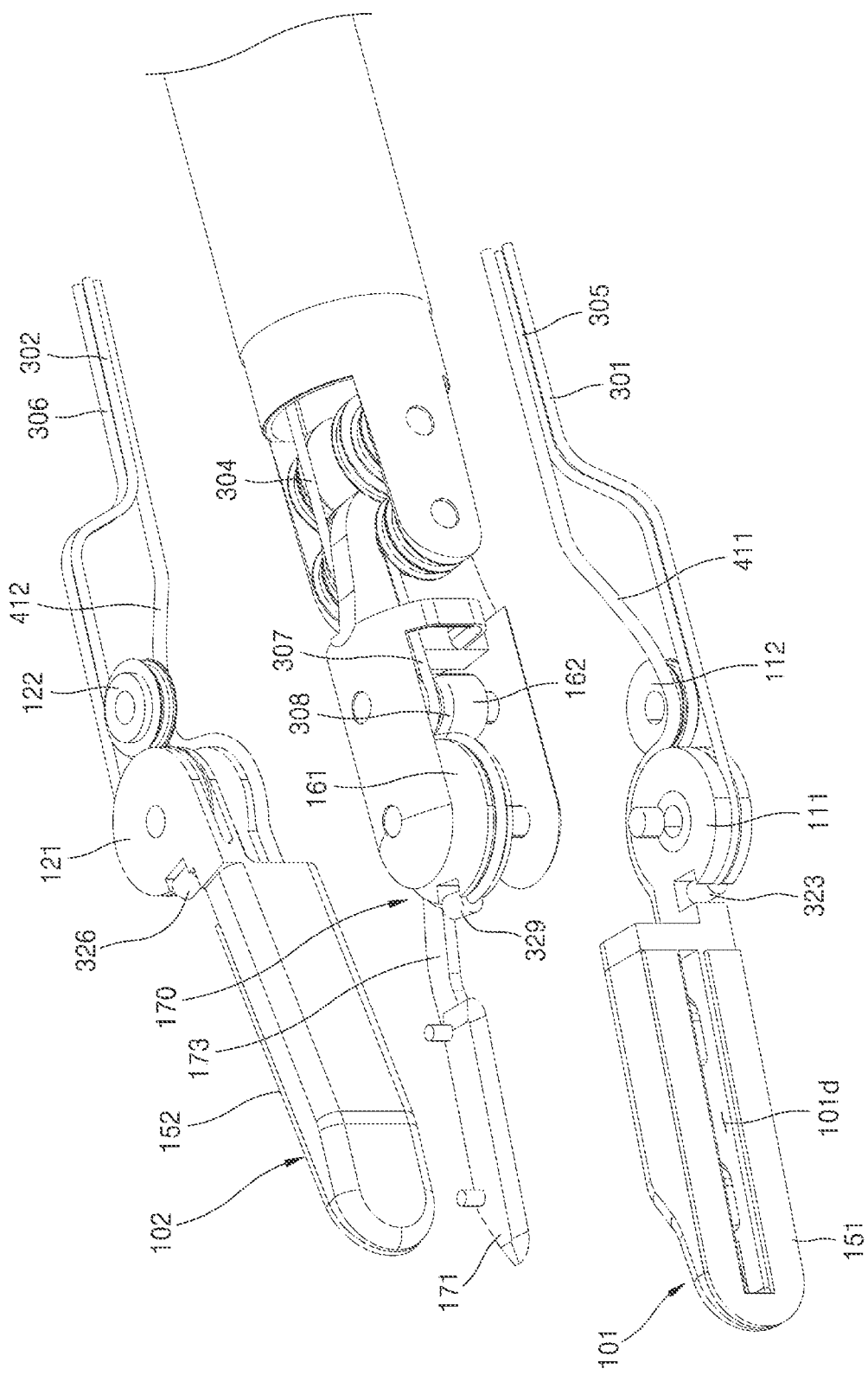
FIG. 6 is an exploded perspective view illustrating the end tool of the surgical instrument for electrocautery of FIG. 2.
Figure 7:
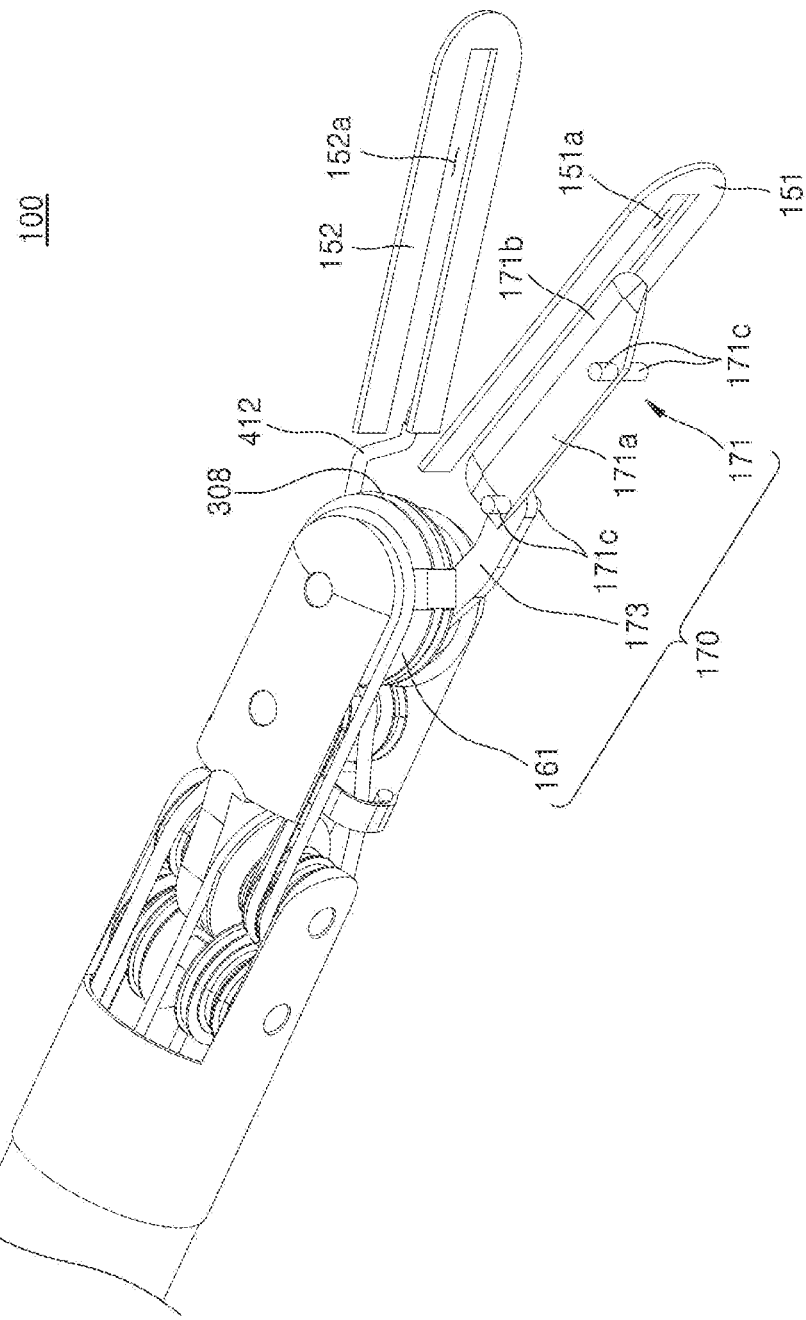
FIGS. 7 and 8 are bottom perspective views illustrating the end tool of the surgical instrument for electrocautery of FIG. 2.
Figure 8:
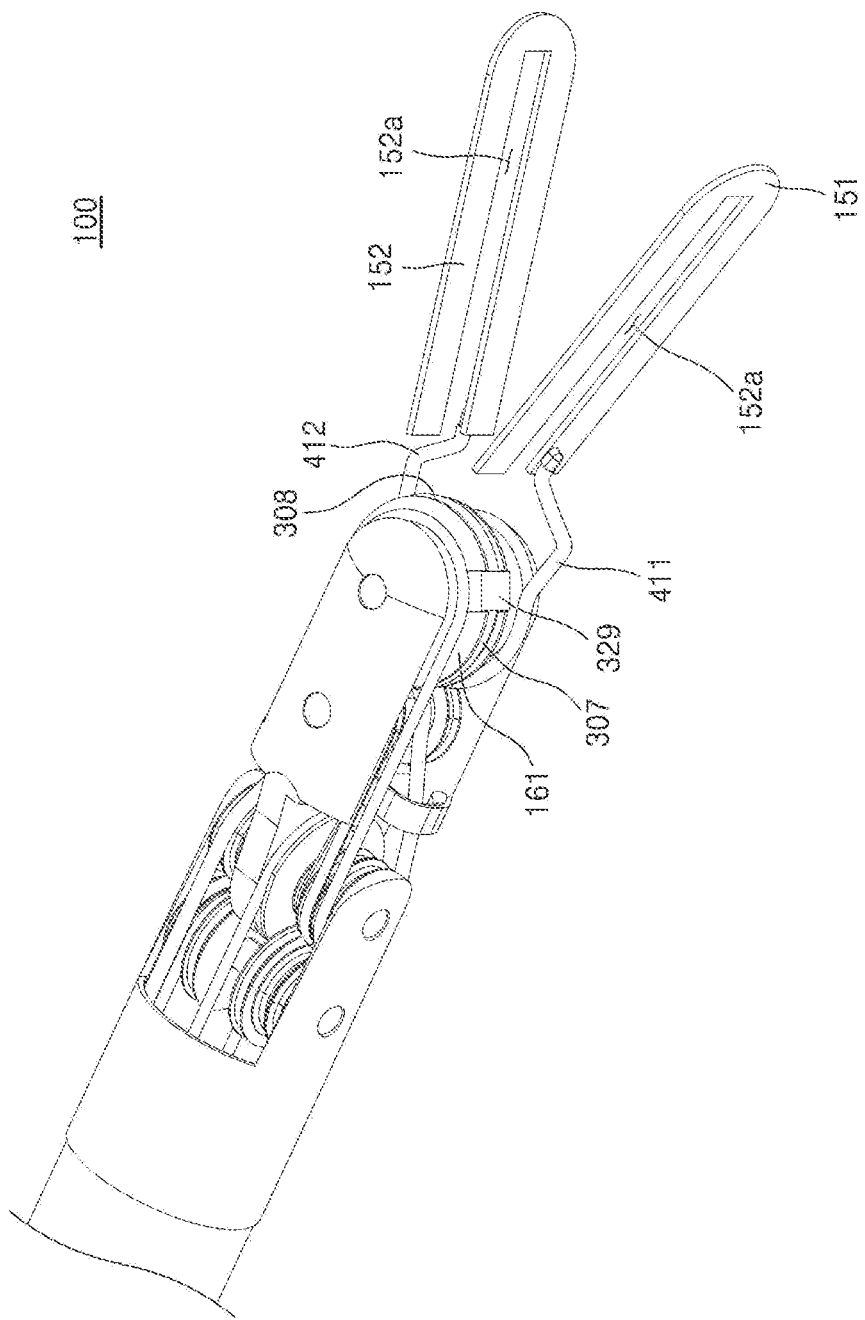
Figure 9:
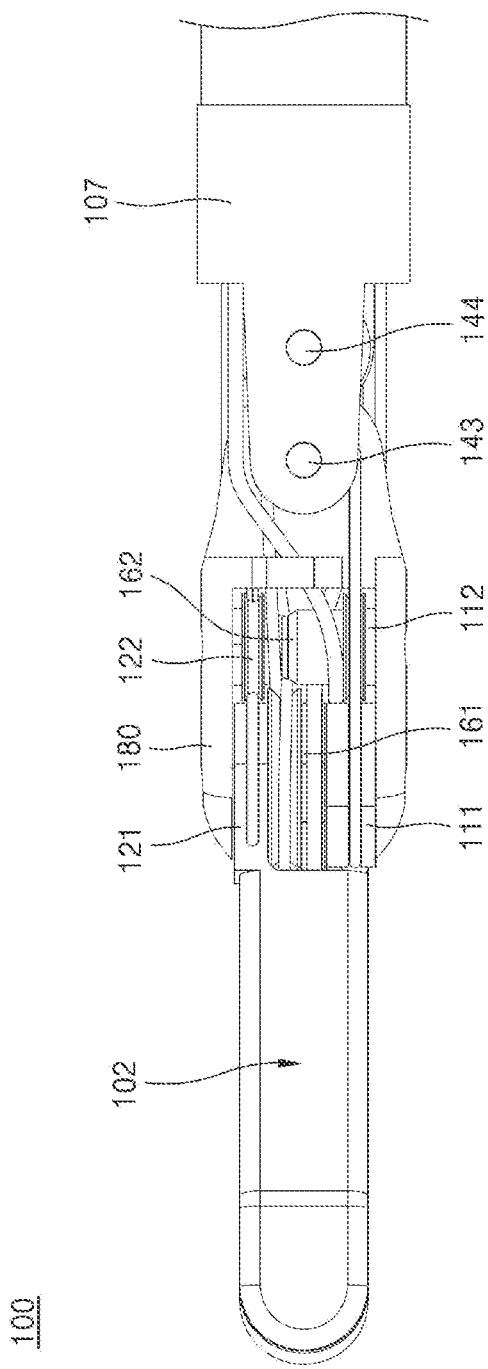
FIGS. 9 and 10 are side views illustrating the end tool of the surgical instrument for electrocautery of FIG. 2.
Figure 10:
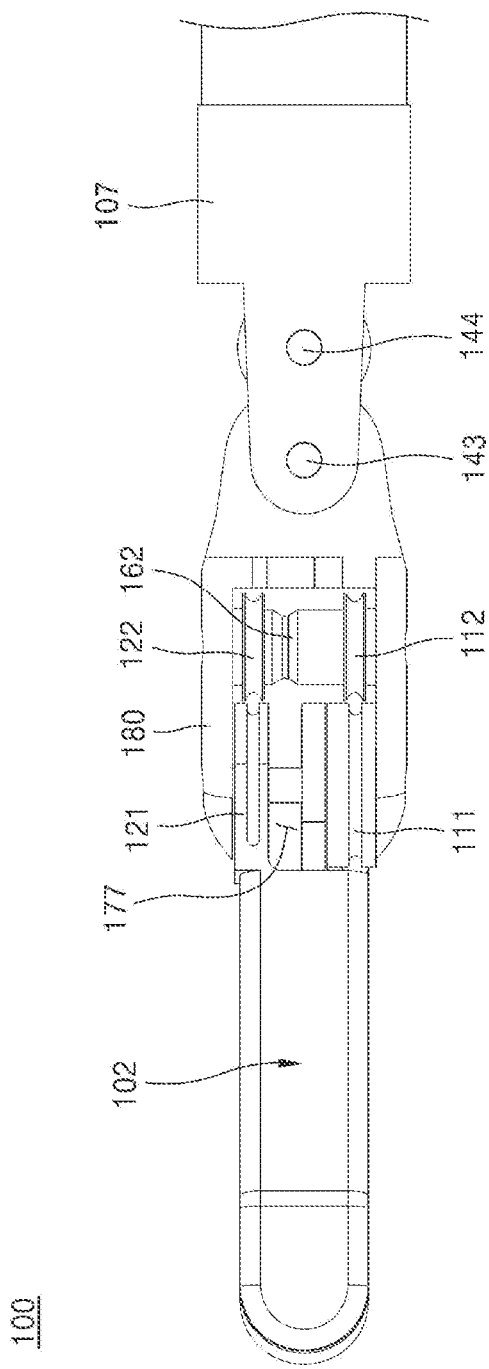
Figure 11:
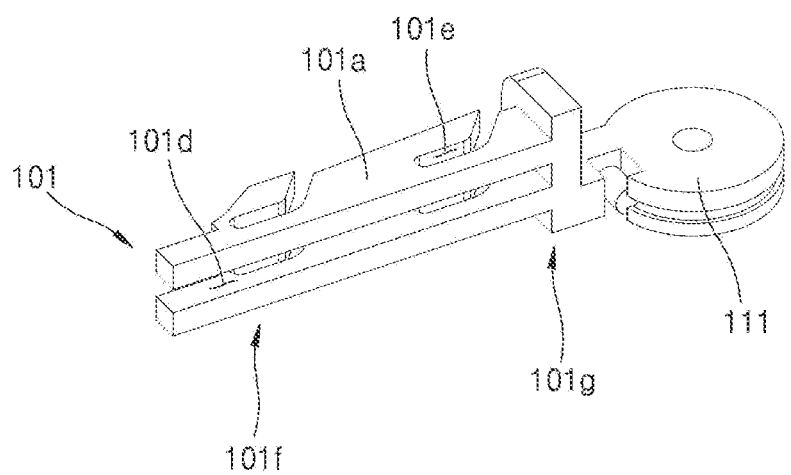
FIG. 11 is a perspective view illustrating a guide member of the end tool of the surgical instrument for electrocautery of FIG. 2.
Figure 12:
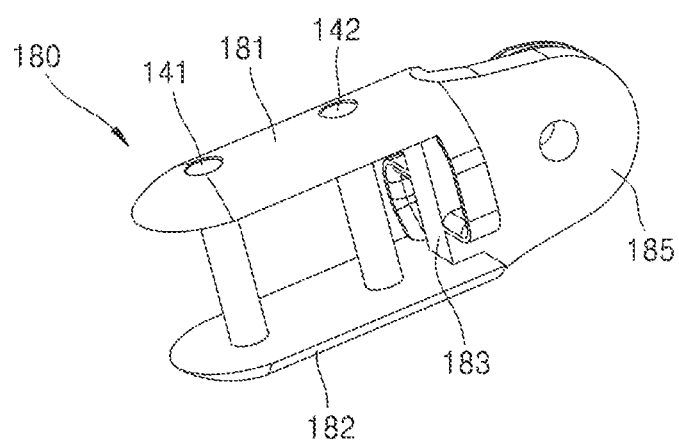
FIG. 12 is a perspective view illustrating an end tool hub in the end tool of the surgical instrument for electrocautery of FIG. 2.
Figure 13:
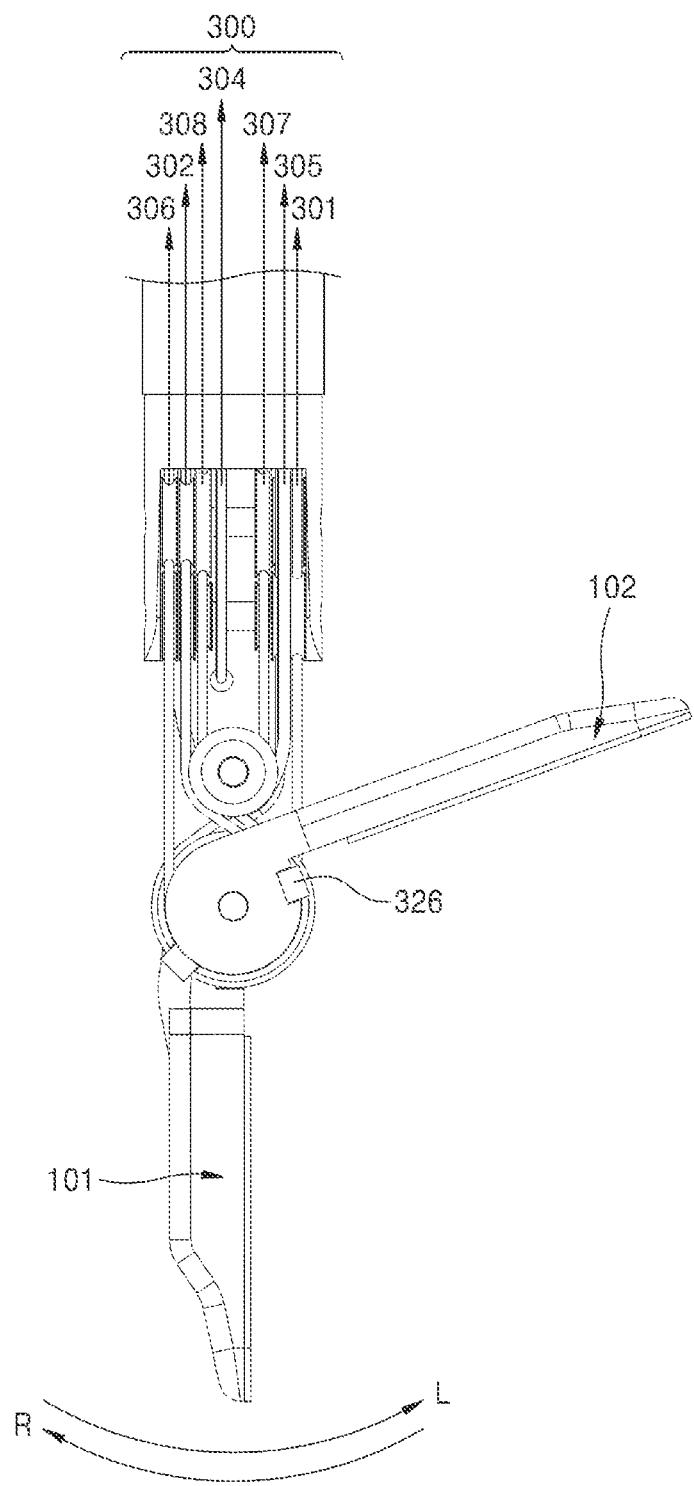
FIGS. 13 and 14 are plan views illustrating the end tool of the surgical instrument for electrocautery of FIG. 2.
Figure 14:
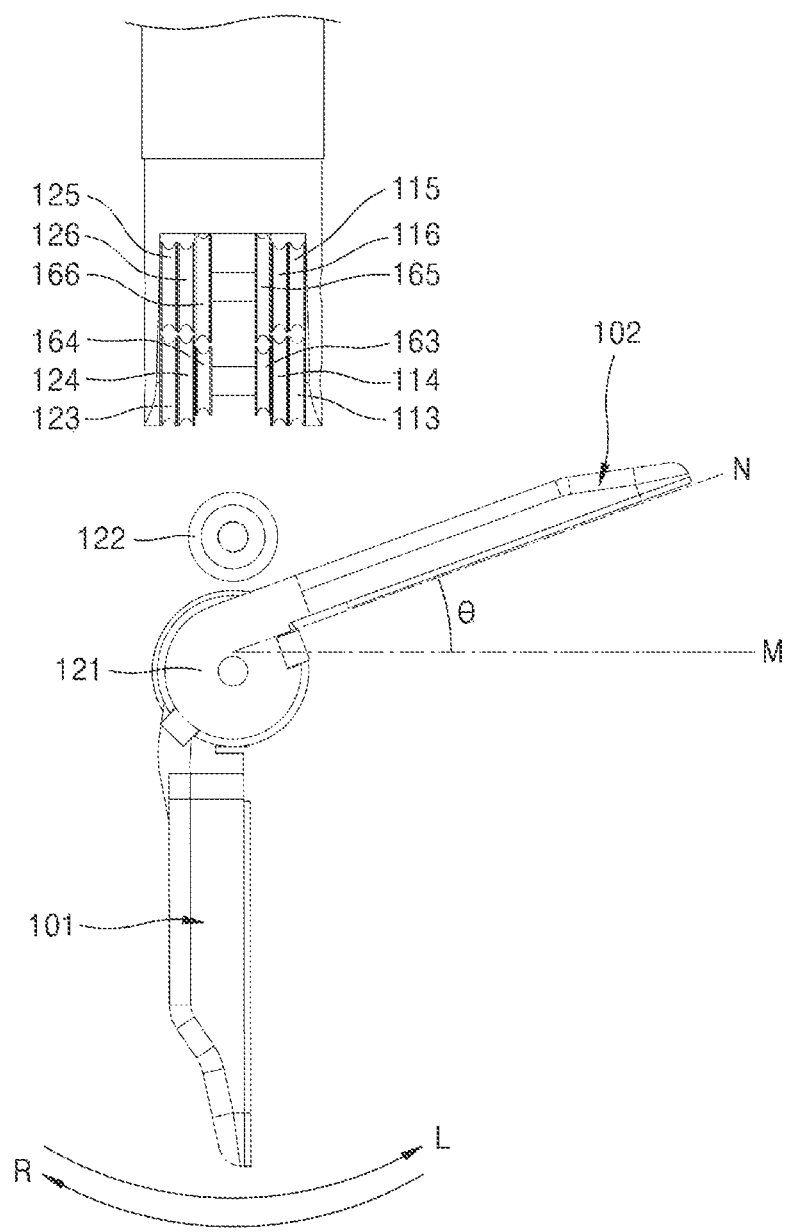

FIG. 2 is a perspective view of a surgical instrument for electrocautery 10 according to the first embodiment, and FIG. 3 is a side view of the surgical instrument for electrocautery of FIG. 2. FIGS. 4 and 5 are perspective views of an end tool 100 of the surgical instrument for electrocautery of FIG. 2, FIG. 6 is an exploded perspective view of the end tool 100 of the surgical instrument for electrocautery 10 of FIG. 2, and FIGS. 7 and 8 are bottom views of the end tool 100 of the surgical instrument for electrocautery 10 of FIG. 2. FIGS. 9 and 10 are side views of the end tool 100 of the electric cauterization surgical instrument 10 of FIG. 2, FIG. 11 is a perspective view of a guide member 101a of the end tool 100 of the electric cauterization surgical instrument 10 of FIG. 2, FIG. 12 is a perspective view of an end tool hub 180 of the end tool 100 of the electric cauterization surgical instrument 10 of FIG. 2, and FIGS. 13 and 14 are plan views of the end tool 100 of the electric cauterization surgical instrument of FIG. 2.

First, with reference to FIGS. 2 and 3, the electric cauterization surgical instrument 10 according to the first embodiment may include an end tool 100, a manipulation portion 200, a power transmission portion 300, and a connection portion 400.

Here, the connection portion 400 may be formed in the shape of a hollow shaft, and one or more wires and electric wires may be accommodated therein. As the manipulation portion 200 is coupled to one end of the connection portion 400, and the end tool 100 is coupled to the other end, the connection portion 400 may connect the manipulation portion 200 to the end tool 100. The connection portion 400 of the electric cauterization surgical instrument 10 according to the first embodiment may include a straight portion 401 and a bent portion 402. The straight portion 401 may be formed at a part of the connection portion 400 to which the end tool 100 is coupled, and the bent portion 402 may be formed at another part of the connection portion 400 to which the manipulation portion 200 is coupled. As such, as the end of the connection portion 400 coupled to the manipulation portion 200 is bent, a pitch manipulation portion 201, a yaw manipulation portion 202, and an actuation manipulation portion 203 may be arranged on an extension line of the end tool 100 or adjacent to the extension line of the end tool 100. In other words, at least a part of the pitch manipulation portion 201 and the yaw manipulation portion 202 may be accommodated in a concave portion formed by the bent portion 402. According to the shape of the bent portion 402 described above, the shape and motion of the manipulation portion 200 and the end tool 100 may match each other more intuitively.

Meanwhile, a plane on which the bent portion 402 is formed may be a pitch plane which is substantially the same as the XZ plane of FIG. 2. As such, as the bent portion 402 is formed on the plane substantially identical to the XZ plane, interference between the manipulation portions may be reduced. For intuitive operation of the end tool 100 and the manipulation portion 200, the plane may be configured otherwise in addition to the foregoing (i.e., the XZ plane).

Meanwhile, a connector 410 may be formed at the bent portion 402. The connector 410 may be connected to an external power supply (not shown), and the connector 410 may be connected to a jaw 103 through electric wires 411 and 412 to transfer electrical energy supplied from the external power supply (not shown) to the jaw 103. The connector 410 may be of a bipolar type having two electrodes, or the connector 410 may be of a monopolar type having one electrode.

The manipulation portion 200 may be formed at one end of the connection portion 400 and may include an interface which can be directly manipulated by a doctor, e.g., an interface in the shape of a pincer, a stick, a lever, etc. When the doctor manipulates the interface, the end tool 100, which is connected to the interface and inserted into the body of a patient, may be operated and perform a surgery. Here, although FIG. 2 illustrates that the manipulation portion 200 is formed in the shape of a handle which may be rotated while fingers are inserted, the present disclosure is not limited thereto, and various types of manipulation portions connected to the end tool 100 and manipulating the end tool 100 may be applicable.

The end tool 100 may be formed at the other end of the connection portion 400 and may be inserted into a body of a patient to perform operations required for a surgery. As an example of the end tool 100, a pair of jaws 103 for performing a grip motion may be used as illustrated in FIG. 2. However, the technical concepts of the present disclosure are not limited thereto, and various other surgical instruments may be used as the end tool 100. For example, an one-armed cautery may be used as the end tool 100. As the end tool 100 is connected to the manipulation portion 200 by the power transmission portion 300, the end tool 100 may receive driving power of the manipulation portion 200 through the power transmission portion 300 and perform motions required for a surgery, such as a grip motion, a cutting motion, a suturing motion, etc.

Here, the end tool 100 of the electric cauterization surgical instrument 10 according to the first embodiment may be formed to be rotatable in at least one direction, and for example, the end tool 100 may be formed to perform a yaw movement and an actuation movement around the Z-axis of FIG. 2 simultaneously with performing a pitch movement around the Y-axis of FIG. 2.

Each of the pitch, yaw, and actuation motions used in the present disclosure are defined as follows.

First, the pitch motion may refer to a motion that the end tool 100 rotates up and down with respect to an extending direction of the connection portion 400 (i.e., the X-axis direction of FIG. 2), that is, a movement of rotating around the Y-axis of FIG. 2. In other words, the pitch motion may refer to a movement that the end tool 100 extending from the connection portion 400 in the extending direction of the connection portion 400 (i.e., the X-axis direction in FIG. 2) rotates up and down around the Y-axis with respect to the connection portion 400.

Next, the yaw motion may refer to a motion that the end tool 100 rotates left and right with respect to the extending direction of the connection portion 400 (i.e., the X-axis direction of FIG. 2), that is, a motion of rotating around the Z-axis of FIG. 2. In other words, the yaw motion may refer to a movement that the end tool 100 extending from the connection portion 400 in the extending direction of the connection portion 400 (i.e., the X-axis direction in FIG. 2) rotates left and right around the Z-axis with respect to the connection portion 400. That is, the yaw motion means a movement that the two jaws 103 formed at the end tool 100 rotate around the Z-axis in the same direction.

The actuation motion may refer to a motion that the end tool 100 rotates around the same axis as in the yaw motion, and two jaws 103 rotate in opposite directions by which the jaws 103 are closed together or opened up. That is, the actuation motion may refer to a movement that the two jaws 103 formed at the end tool 100 rotate in opposite directions around the Z-axis.

The power transmission portion 300 may transfer the driving power of the manipulation portion 200 to the end tool 100 by connecting the manipulation portion 200 to the end tool 100, and may include a plurality of wires, pulleys, links, joints, gears, etc.

The end tool 100, the manipulation portion 200, the power transmission portion 300, etc. of the electric cauterization surgical instrument 10 of FIG. 2 will be described in detail later.

(Intuitive Driving)

Hereinafter, the intuitive driving of the electric cauterization surgical instrument 10 of the present disclosure is described.

First, a user may hold with his or her palm and rotate a first handle 204 around the Y-axis (i.e., a rotation shaft 246 of FIG. 25) to perform the pitch motion, and may rotate the first handle 204 around the Z-axis (i.e., a rotation shaft 243 of FIG. 25) to perform the yaw motion. In addition, the user may insert his or her thumb and index finger into a first actuation extension portion 252 and/or a second actuation extension portion 257 formed in the shape of a hand ring at one end of the actuation manipulation portion 203 and manipulate the actuation manipulation portion 203 to perform the actuation motion.

In the electric cauterization surgical instrument 10 according to the first embodiment of the present disclosure, when the manipulation portion 200 rotates in one direction with respect to the connection portion 400, the end tool 100 may rotate in a direction intuitively the same as a manipulation direction of the manipulation portion 200. In other words, when the first handle 204 of the manipulation portion 200 rotates in one direction, the end tool 100 may also rotate in a direction intuitively the same as the aforementioned direction to perform a pitch motion or a yaw motion. Here, the intuitively the same direction may indicate that the moving direction of a finger of a user holding the manipulation portion 200 is substantially the same as the moving direction of an end portion of the end tool 100. The same direction may not be a perfectly matching direction on three-dimensional (3D) coordinates. For example, the sameness of the direction may be understood as a certain degree of sameness, with which, when the finger of the user moves to the left, the end portion of the end tool 100 may also move to the left, and when the finger of the user moves downwards, the end portion of the end tool 100 may also move downwards.

To this end, in the electric cauterization surgical instrument 10 according to the first embodiment, the manipulation portion 200 and the end tool 100 may be formed in the same direction with respect to a plane perpendicular to the extension axis (the X-axis) of the connection portion 400. That is, when seen based on the YZ plane of FIG. 2, the manipulation portion 200 may be formed to extend in the +X-axis direction, and at the same time, the end tool 100 may also be formed to extend in the +X-axis direction. In other words, the formation direction of the end tool 100 at one end of the connection portion 400 and the formation direction of the manipulation portion 200 at the other end of the connection portion 400 may be described as the same direction based on the YZ plane. Alternatively, the manipulation portion 200 may be formed in a direction proceeding away from a body of a user holding the manipulation portion 200, i.e., a direction towards the end tool 100. That is, in the first handle 204, the first actuation manipulation portion 251, and the second actuation manipulation portion 256, etc., which are held and moved by a user for the actuation motion, the yaw motion, and the pitch motion, the moving portions thereof for the respective motions may extend in the +X axis direction in comparison with the rotation centers of each joint for the respective motions. Based on the foregoing, the moving portion of the end tool 100 may extend in the +X axis direction in comparison with the rotation center of each joint for the respective motions, and the manipulation portion 200 may also be configured in the same manner. Then, as described above with reference to FIG. 1, the user manipulation direction may match the operation direction of the end tool in terms of rotation direction and left and right direction, which leads to intuitively matching manipulation.

More specifically, in the case of a conventional surgical instrument, as a direction in which the user manipulates the manipulation portion and an actual operation direction of the end tool are different and not intuitively the same, an operator may have difficulty in intuitive operation, and may need to invest much time to become familiar with directing the end tool in a desired direction. In one embodiment, in some cases, a malfunction may occur, which can cause a damage to a patient.

To overcome such issue, in the electric cauterization surgical instrument 10 according to the first embodiment, the manipulation direction of the manipulation portion 200 may be intuitively identical to the operation direction of the end tool 100, and to this end, a portion of the manipulation portion 200 which actually moves for the actuation motion, the yaw motion, and the pitch motion may extend in the +X-axis direction in comparison with a rotation center of a joint for the respective motions as in the end tool 100.

Hereinafter, the end tool 100, the manipulation portion 200, the power transmission portion 300, etc. of the electric cauterization surgical instrument 10 of FIG. 2 will be described in more detail.

(Power Transmission Portion)

Hereinafter, the power transmission portion 300 of the electric cauterization surgical instrument 10 of FIG. 2 will be described in more detail.

With reference to FIGS. 2 to 25, the power transmission portion 300 of the electric cauterization surgical instrument 10 according to an embodiment may include a wire 301, a wire 302, a wire 303, a wire 304, a wire 305, a wire 306, a wire 307, and a wire 308.

Here, the wire 301 and the wire 305 may form a pair and serve as a first jaw wire. The wire 302 and the wire 306 may form a pair to serve as a second jaw wire. Here, a component encompassing the wire 301 and the wire 305, which are the first jaw wire, and the wire 302 and the wire 306, which are the second jaw wire may be referred to as a jaw wire. The wire 303 and the wire 304 may form a pair to serve as a pitch wire. The wire 307 and the wire 308 may form a pair to serve as a blade wire.

In addition, the power transmission portion 300 of the electric cauterization surgical instrument 10 according to an embodiment may include a fastening member 321, a fastening member 323, a fastening member 324, a fastening member 326, a fastening member 327, and a fastening member 329 which are coupled to each end of the respective wires to combine the wires with the pulleys. Here, each fastening member may have various shapes as needed, such as a ball shape, a tube shape, etc.

Here, on the end tool 100's side, the fastening member 321 may serve as a pitch wire-end tool fastening member, the fastening member 323 may serve as a first jaw wire-end tool fastening member, the fastening member 326 may serve as a second jaw wire-end tool fastening member, and the fastening member 329 may serve as a blade wire-end tool fastening member.

In addition, on the manipulation portion 200's side, the fastening member 324 may serve as a first jaw wire-manipulation portion fastening member, and the fastening member 327 may serve as a second jaw wire-manipulation portion fastening member. Furthermore, although it is not shown in the drawings, a pitch wire-manipulation portion fastening member and a blade wire-manipulation portion fastening member may be further arranged on the manipulation portion 200's side.

The combination relation among the wires, the fastening members, and each pulley is described in detail below.

First, the wire 301 and the wire 305, which are the first jaw wire, may be a single wire. The fastening member 323 which is the first jaw wire-end tool fastening member, may be fit into a middle point of the first jaw wire and when the fastening member 323 is fixed through crimping, two strands of the first jaw wire on either side of the fastening member 323 may be referred to as the wire 301 and the wire 305, respectively.

Alternatively, the wire 301 and the wire 305, which are the first jaw wire, may be formed as separate wires, and the wire 301 and the wire 305 may be connected to each other by the fastening member 323.

In one embodiment, as the fastening member 323 is coupled to a pulley 111, the wire 301 and the wire 305 may be fixedly coupled to the pulley 111. In this manner, the pulley 111 may rotate as the wire 301 and the wire 305 are pulled and unwound.

In the wire 301 and the wire 305, the first jaw wire-manipulation portion fastening member 324 may be coupled to an end opposite to the end to which the fastening member 323 is coupled.

As the first jaw wire-manipulation portion fastening member 324 is coupled to a pulley 210, the wire 301 and the wire 305 may be fixedly coupled to the pulley 210. As a result, when the pulley 210 is rotated by a motor or human force, the pulley 111 of the end tool 100 may rotate as the wire 301 and the wire 305 are pulled and unwound.

Similar to the above, each of the wire 302 and the wire 306, which are the second jaw wire, may be coupled to the second jaw wire-end tool fastening member 326 and the second jaw wire-manipulation portion fastening member 327, respectively. The fastening member 326 may be coupled to a pulley 121, and the second jaw wire-manipulation portion fastening member 327 may be coupled to a pulley 220. As a result, when the pulley 220 is rotated by a motor or human force, the pulley 121 of the end tool 100 may rotate as the wire 302 and the wire 306 are pulled and unwound.

Similar to the above, each of the wire 303 and the wire 304, which are the pitch wire, may be coupled to the pitch wire-end tool fastening member 321 and the pitch wire-manipulation portion fastening member (not shown), respectively. The fastening member 321 may be coupled to a pulley 131, and the pitch wire-manipulation portion fastening member (not shown) may be coupled to a pulley 231. As a result, when the pulley 231 is rotated by a motor or human force, the pulley 131 of the end tool 100 may rotate as the wire 303 and the wire 304 are pulled and unwound.

Similar to the above, each of the wire 307 and the wire 308, which are the blade wire, may be coupled to the blade wire-end tool fastening member 329 and a blade wire-manipulation portion fastening member (not shown), respectively. And, the fastening member 329 may be coupled to a blade pulley 161, and the blade wire-manipulation portion fastening member (not shown) may be coupled to a pulley 269 (see FIG. 29). As a result, when the pulley 269 rotates by a motor or human force, the blade pulley 161 of the end tool 100 may rotate as the wire 307 and the wire 308 are pulled and unwound.

(End Tool)

Hereinafter, the end tool 100 of the electric cauterization surgical instrument 10 of FIG. 2 will be described in more detail.

FIGS. 4 and 5 are perspective views of the end tool 100 of the surgical instrument for electrocautery 10 of FIG. 2, FIG. 6 is an exploded perspective view of the end tool 100 of the surgical instrument for electrocautery 10 of FIG. 2, and FIGS. 7 and 8 are bottom views of the end tool 100 of the surgical instrument for electrocautery 10 of FIG. 2. FIGS. 9 and 10 are side views of the end tool 100 of the surgical instrument for electrocautery 10 of FIG. 2, and FIGS. 13 and 14 are plan views of the end tool 100 of the surgical instrument for electrocautery 10 of FIG. 2.

FIG. 4 illustrates a state in which an end tool hub 180 and a pitch hub 107 are coupled to the end tool 100, and FIG. 5 illustrates a state in which the end tool hub 180 is removed. FIG. 7 illustrates a state in which a first jaw 101 and a second jaw 102 are removed, and FIG. 8 illustrates a state in which the first jaw 101, the second jaw 102, and a blade 171 are removed. FIG. 13 mainly illustrates the wires, and FIG. 14 mainly illustrates the pulleys.

With reference to FIGS. 4 to 13, the end tool 100 of the first embodiment may include a pair of jaws for performing a grip motion, i.e., the first jaw 101 and the second jaw 102. A component encompassing each of the first jaw 101 and the second jaw 102 or both of the first jaw 101 and the second jaw 102 may be referred to as a jaw 103.

In addition, the end tool 100 may include a pulley 111, a pulley 112, a pulley 113, a pulley 114, a pulley 115, and a pulley 116 associated with the rotational motion of the first jaw 101. The end tool 100 may include a pulley 121, a pulley 122, a pulley 123, a pulley 124, a pulley 125, and a pulley 126 associated with the rotational motion of the second jaw 102.

Although the drawings illustrate that the first jaw 101 and the pulley 111 are integrated, the technical concepts of the present disclosure are not limited thereto, and the first jaw 101 and the pulley 111 may be formed as separate members which may be coupled together. Furthermore, although the drawings illustrate that the second jaw 102 and the pulley 121 are integrated, the technical concepts of the present disclosure are not limited thereto, and the second jaw 102 and the pulley 121 may be formed as separate members which may be coupled together.

Here, the drawings illustrate that the pulleys facing each other are arranged in parallel with each other; however, the technical concepts of the present disclosure are not limited thereto, and each pulley may be formed in various positions and sizes suitable for the configuration of the end tool 100.

In addition, the end tool 100 of the first embodiment may include the end tool hub 180 and the pitch hub 107.

A rotation shaft 141 and a rotation shaft 142 to be described later may penetrate and be inserted into the end tool hub 180, and the end tool hub 180 may accommodate at least a part of the pulley 111 and the pulley 121 axially coupled to the rotation shaft 141. In addition, the end tool hub 180 may accommodate at least a part of the pulley 112 and the pulley 122 axially coupled to the rotation shaft 142.

More specifically, with reference to FIG. 12, the end tool hub 180 may include a first jaw pulley coupling portion 181, a second jaw pulley coupling portion 182, a guide portion 183, and a pitch pulley coupling portion 185.

The first jaw pulley coupling portion 181 and the second jaw pulley coupling portion 182 may face each other and accommodate the pulley 111, the pulley 121, and the blade pulley 161. In addition, a penetrating hole may be formed at each of the first jaw pulley coupling portion 181 and the second jaw pulley coupling portion 182, and the rotation shaft 141 may penetrate and axially couple the first jaw pulley coupling portion 181, the pulley 111, the blade pulley 161, the pulley 121, and the second jaw pulley coupling portion 182.

The first jaw pulley coupling portion 181 and the second jaw pulley coupling portion 182 may be connected to each other by the guide portion 183. That is, the first jaw pulley coupling portion 181 and the second jaw pulley coupling portion 182 which are parallel with each other may be coupled to each other by the guide portion 183 formed approximately perpendicular thereto, and accordingly, the first jaw pulley coupling portion 181, the second jaw pulley coupling portion 182, the guide portion 183 may form the shape of " " in which the pulley 111, the pulley 121, and the blade pulley 161 are accommodated.

Here, the pulley 111 which is the first jaw pulley may be arranged adjacent to the first jaw pulley coupling portion 181 of the end tool hub 180, and the pulley 121 which is the second jaw pulley may be arranged adjacent to the second jaw pulley coupling portion 182 of the end tool hub 180 so that a blade assembly accommodation portion 177 may be formed between the first jaw pulley coupling portion 181 and the second jaw pulley coupling portion 182. In addition, at least a part of a blade assembly 170 to be described later may be formed in the blade assembly accommodation portion 177. In other words, at least a part of the blade pulley 161 and a blade link 173 of the blade assembly 170 may be arranged between the first jaw pulley coupling portion 181 and the second jaw pulley coupling portion 182. As such, by arranging the blade assembly 170 including the blade 171 between the pulley 111 which is the first jaw pulley and the pulley 121 which the second jaw pulley, not only the pitch motion and the yaw motion of the end tool 100 but also a cutting motion using the blade 171 may be performed. This will be described in more detail later.

Meanwhile, the pulley 131 serving as an end tool pitch pulley may be formed at one end of the end tool hub 180. As illustrated in FIG. 4, the pulley 131 and the end tool hub 180 may be formed in one-body. That is, one end of the end tool hub 180 may be formed in the shape of a disk as in a pulley, and a groove around which a wire may be wound may be formed on an outer peripheral surface thereof. Alternatively, the pulley 131 may be formed as a member separate from the end tool hub 180 and may be coupled to the end tool hub 180. When the wire 303 and the wire 304 are coupled to the pulley 131 functioning as the end tool pitch pulley, and the pulley 131 rotates around a rotation shaft 143, the pitch motion may be performed.

The rotation shaft 143 and a rotation shaft 144 may penetrate and be inserted into the pitch hub 107, and the pitch hub 107 may be axially coupled to the end tool hub 180 and the pulley 131 by the rotation shaft 143. Accordingly, the end tool hub 180 and the pulley 131 may be formed to be rotatable around the rotation shaft 143 with respect to the pitch hub 107.

In addition, the pitch hub 107 may accommodate at least a part of the pulley 113, the pulley 114, the pulley 123, and the pulley 124 axially coupled to the rotation shaft 143. Furthermore, the pitch hub 107 may accommodate at least a part of the pulley 115, the pulley 116, the pulley 125, and the pulley 126 axially coupled to the rotation shaft 144.

The end tool 100 of the first embodiment may include the rotation shaft 141, the rotation shaft 142, the rotation shaft 143, and the rotation shaft 144. As described above, the rotation shaft 141 and the rotation shaft 142 may penetrate and be inserted into the end tool hub 180, and the rotation shaft 143 and the rotation shaft 144 may penetrate and be inserted into the pitch hub 107.

The rotation shaft 141, the rotation shaft 142, the rotation shaft 143, and the rotation shaft 144 may be arranged sequentially from a distal end 104 towards a proximal end 105. Accordingly, in the direction towards the proximal end 105 from the distal end 104, the rotation shaft 141 may be referred to as a first pin, the rotation shaft 142 may be referred to as a second pin, the rotation shaft 143 may be referred to as a third pin, and the rotation shaft 144 may be referred to as a fourth pin.

Here, the rotation shaft 141 may function as an end tool jaw pulley rotation shaft, the rotation shaft 142 may function as an end tool jaw auxiliary pulley rotation shaft, the rotation shaft 143 may function as an end tool pitch rotation shaft, and the rotation shaft 144 may function as an end tool pitch auxiliary rotation shaft of the end tool 100.

One or more pulleys may be fit into each of the rotation shafts 141, 142, 143, and 144, which will be described in detail below.

The pulley 111 may function as an end tool first jaw pulley, and the pulley 121 may function as an end tool second jaw pulley. The pulley 111 may be referred to as a first jaw pulley, and the pulley 121 may be referred to as a second jaw pulley. The two components may be collectively referred to as an end tool jaw pulley or simply as a jaw pulley.

The pulley 111 and the pulley 121 which are the end tool jaw pulley may face each other and may be formed to be independently rotatable around the rotation shaft 141 which is the end tool jaw pulley rotation shaft. Moreover, the pulley 111 and the pulley 121 may be spaced apart from each other at a certain distance, and the blade assembly accommodation portion 177 may be arranged between the pulley 111 and the pulley 121. In one embodiment, at least a part of the blade assembly 170 to be described later may be arranged in the blade assembly accommodation portion 177.

Here, although the drawings illustrate that the pulley 111 and the pulley 121 are formed to rotate around one rotation shaft 141, each end tool jaw pulley may be formed to rotate around separate shafts. The first jaw 101 may be fixedly coupled to the pulley 111 and rotate together with the pulley 111, and the second jaw 102 may be fixedly coupled to the pulley 121 and rotate together with the pulley 121. A yaw motion and an actuation motion of the end tool 100 may be performed according to the rotation of the pulley 111 and the pulley 121. That is, when the pulley 111 and the pulley 121 rotate around the rotation shaft 141 in the same direction, the yaw motion may be performed, and when the pulley 111 and the pulley 121 rotate around the rotation shaft 141 in opposite directions, the actuation motion may be performed.

Here, the first jaw 101 and the pulley 111 may be formed as separate members and be coupled to each other, or the first jaw 101 and the pulley 111 may be formed in one-body. Likewise, the second jaw 102 and the pulley 121 may be formed as separate members and be coupled to each other, or the second jaw 102 and the pulley 121 may be formed in one-body.

The pulley 112 may function as an end tool first jaw auxiliary pulley, and the pulley 122 may function as an end tool second jaw auxiliary pulley. The two components may collectively referred to as an end tool jaw auxiliary pulley or simply as an auxiliary pulley.

More specifically, the pulley 112 and the pulley 122 which are the end tool jaw auxiliary pulley may be additionally provided on one side of the pulley 111 and the pulley 121. In other words, the pulley 112 which is an auxiliary pulley may be arranged between the pulley 111 and the pulley 113/the pulley 114. In addition, the pulley 122 which is an auxiliary pulley may be arranged between the pulley 121 and the pulley 123/the pulley 124. The pulley 112 and the pulley 122 may be formed to be rotatable independently of each other around the rotation shaft 142. Here, although the drawings illustrate that the pulley 112 and the pulley 122 are formed to rotate around one rotation shaft 142, each of the pulley 112 and the pulley 122 may be formed to rotate around separate shafts. Such auxiliary pulley will be described in more detail later.

The pulley 113 and the pulley 114 may function as an end tool first jaw pitch main pulley, and the pulley 123 and the pulley 124 may function as an end tool second jaw pitch main pulley. The two components may collectively be referred to as an end tool jaw pitch main pulley.

The pulley 115 and the pulley 116 may function as an end tool first jaw pitch subsidiary pulley, and the pulley 125 and the pulley 126 may function as an end tool second jaw pitch subsidiary pulley. The two components may collectively be referred to as an end tool jaw pitch subsidiary pulley.

Hereinafter, components associated with the rotation of the pulley 111 will be described.

The pulley 113 and the pulley 114 may function as the end tool first jaw pitch main pulley. That is, the pulley 113 and the pulley 114 may function as a main rotation pulley of the pitch motion of the first jaw 101. Here, the wire 301, which is the first jaw wire, may be wound around the pulley 113, and the wire 305, which is the first jaw wire, may be wound around the pulley 114.

The pulley 115 and the pulley 116 may function as the end tool first jaw pitch subsidiary pulley. That is, the pulley 115 and the pulley 116 may function as a subsidiary rotation pulley of the pitch motion of the first jaw 101. Here, the wire 301, which is the first jaw wire, may be wound around the pulley 115, and the wire 305, which is the first jaw wire, may be wound around the pulley 116.

On one side of the pulley 111 and the pulley 112, the pulley 113 and the pulley 114 may be arranged to face each other. The pulley 113 and the pulley 114 may be formed to be rotatable independently of each other around the rotation shaft 143 which is the end tool pitch rotation shaft. In addition, on one side of each of the pulley 113 and the pulley 114, the pulley 115 and the pulley 116 may be arranged to face each other. The pulley 115 and the pulley 116 may be formed to be rotatable independently of each other around the rotation shaft 144 which is the end tool pitch auxiliary rotation shaft. Although the drawings illustrate that the pulley 113, the pulley 115, the pulley 114, and the pulley 116 are formed to be rotatable around the Y-axis direction, the technical concepts of the present disclosure are not limited thereto, and the rotation shafts of each pulley may be formed in various directions suitable for their respective configurations.

The wire 301, which is the first jaw wire, may be wound sequentially so that at least a part thereof is in contact with the pulley 115, the pulley 113, and the pulley 111. In addition, the wire 305 connected to the wire 301 by the fastening member 323 may be sequentially wound so that at least a part thereof is in contact with the pulley 111, the pulley 112, the pulley 114, and the pulley 116.

In other words, the wire 301 and wire 305, which are the first jaw wire, may be sequentially wound so that at least a part thereof is in contact with the pulley 115, the pulley 113, the pulley 111, the pulley 112, the pulley 114, and the pulley 116, and the wire 301 and the wire 305 may be formed to move along the pulleys while rotating the pulleys.

Accordingly, when the wire 301 is pulled toward the arrow 301 of FIG. 13, the fastening member 323 coupled to the wire 301 and the pulley 111 coupled to the fastening member 323 may rotate in the direction of the arrow L of FIG. 13. On the contrary, when the wire 305 is pulled toward the arrow 305 of FIG. 6, the fastening member 323 coupled to the wire 305 and the pulley 111 coupled to the fastening member 323 may rotate in the direction of the arrow R of FIG. 6.

Hereinafter, the pulley 112 and the pulley 122 serving as an auxiliary pulley will be described in more detail.

As the pulley 112 and the pulley 122 are in contact with the wire 305 which is the first jaw wire and the wire 302 which is the second jaw wire to change an arrangement path of the wire 305 and the wire 302 to a certain extent, the pulley 112 and the pulley 122 may perform the function of expanding a rotation angle of each of the first jaw 101 and the second jaw 102.

That is, when no auxiliary pulley is arranged, each of first jaw and the second jaw may rotate up to the right angle; however, in an embodiment, by additionally arranging the pulley 112 and the pulley 122, which are auxiliary pulleys, the maximum rotation angle may be increased by θ as shown in FIG. 14. This enables the opening motion of the two jaws of the end tool 100 for the actuation motion when the two jaws are yaw-rotated by 90° in the L direction. This is because the second jaw 102 may rotate by the additional angle θ as shown in FIG. 14. Likewise, the actuation motion may be performed even when the two jaws are yaw-rotated in the R direction. In other words, through the pulley 112 and the pulley 122, a range of yaw rotation allowing the actuation motion may be expanded.

This will be described below in more detail.

When no auxiliary pulley is arranged, as the first jaw wire is fixedly coupled to the end tool first jaw pulley, and the second jaw wire is fixedly coupled to the end tool second jaw pulley, each of the end tool first jaw pulley and the end tool second jaw pulley may rotate only up to 90°. In this case, when the actuation motion is performed in a state where the first jaw and the second jaw are placed on the 90° line, the first jaw may be opened, but the second jaw may not be able to rotate over 90°. Accordingly, in the state where the first jaw and the second jaw perform the yaw motion over a certain angle, the actuation motion may not be performed smoothly.

To overcome the foregoing issue, in the electric cauterization surgical instrument 10 of the present disclosure, the pulley 112 and the pulley 122, which are auxiliary pulleys, may be further arranged on one side of the pulley 111 and the pulley 121. By arranging the pulley 112 and the pulley 122, the arrangement path of the wire 305 which is the first jaw wire and the wire 302 which is the second jaw wire may be changed to a certain extent, and a tangential direction of the wire 305 and the wire 302 may also be changed, which allows rotation of the fastening member 322 coupling the wire 302 to the pulley 121 up to the N line of FIG. 14. That is, the fastening member 326, which is a coupling portion between the wire 302 and the pulley 121, may be rotatable until it is positioned on a common internal tangent of the pulley 121 and the pulley 122. Likewise, the fastening member 323, which is a coupling portion of the wire 305 and the pulley 111, may be rotatable until it is positioned on a common internal tangent of the pulley 111 and the pulley 112, which allows expansion of the rotation range in the R direction.

In other words, by the pulley 112, the wire 301 and the wire 305, which are two strands of the first jaw wire wound around the pulley 111 may be arranged on one side with respect to a plane perpendicular to the Y-axis and passing through the X-axis. At the same time, by the pulley 122, the wire 302 and the wire 306, which are two strands of the second jaw wire wound around the pulley 121 may be arranged on another side with respect to the plane perpendicular to the Y-axis and passing through the X-axis.

In other words, the pulley 113 and the pulley 114 may be arranged on one side with respect to the plane perpendicular to the Y-axis and passing through the X-axis, and the pulley 123 and the pulley 124 may be arranged on another side with respect to the plane perpendicular to the Y-axis and passing through the X-axis.

In other words, the wire 305 may be arranged on an internal tangent of the pulley 111 and the pulley 112, and the rotation angle of the pulley 111 may be expanded by the pulley 112. In addition, the wire 302 may be arranged on an internal tangent of the pulley 121 and the pulley 122, and the rotation angle of the pulley 121 may be expanded by the pulley 122.

According to the present disclosure, as the rotational radius of the first jaw 101 and the second jaw 102 is widened, the range of yaw motion allowing a normal open-and-shut actuation motion may be expanded.

Next, components associated with the rotation of the pulley 121 will be described.

The pulley 123 and the pulley 124 may function as an end tool second jaw pitch main pulley. That is, the pulley 123 and the pulley 124 may function as a main rotation pulley of the pitch motion of the second jaw 102. Here, the wire 306, which is the second jaw wire, may be wound around the pulley 123, and the wire 302, which is the second jaw wire, may be wound around the pulley 124.

The pulley 125 and the pulley 126 may function as an end tool second jaw pitch subsidiary pulley. That is, the pulley 125 and the pulley 126 may function as a subsidiary rotation pulley of the pitch motion of the second jaw 102. Here, the wire 306, which is the second jaw wire, may be wound around the pulley 125, and the wire 302, which is the second jaw wire, may be wound around the pulley 126.

On one side of the pulley 121, the pulley 123 and the pulley 124 may be arranged to face each other. The pulley 123 and the pulley 124 may be formed to be rotatable independently of each other around the rotation shaft 143 which is the end tool pitch rotation shaft. In addition, on one side of each of the pulley 123 and the pulley 124, the pulley 125 and the pulley 126 may be arranged to face each other. The pulley 125 and the pulley 126 may be formed to be rotatable independently of each other around the rotation shaft 144 which is the end tool pitch auxiliary rotation shaft. Although the drawings illustrate that the pulley 123, the pulley 125, the pulley 124, and the pulley 126 are formed to be rotatable around the Y-axis direction, the technical concepts of the present disclosure are not limited thereto, and the rotation shafts of each pulley may be formed in various directions suitable for their respective configurations.

The wire 306, which is the second jaw wire, may be wound sequentially so that at least a part thereof is in contact with the pulley 125, the pulley 123, and the pulley 121. In addition, the wire 302 connected to the wire 306 by the fastening member 326 may be sequentially wound so that at least a part thereof is in contact with the pulley 121, the pulley 122, the pulley 124, and the pulley 126.

In other words, the wire 306 and wire 302, which are the second jaw wire, may be sequentially wound so that at least a part thereof is in contact with the pulley 125, the pulley 123, the pulley 121, the pulley 122, the pulley 124, and the pulley 126, and the wire 306 and the wire 302 may be formed to move along the pulleys while rotating the pulleys.

Accordingly, when the wire 306 is pulled toward the arrow 306 of FIG. 13, the fastening member 322 coupled to the wire 306 and the pulley 121 coupled to the fastening member 322 may rotate in the direction of the arrow R of FIG. 13. On the contrary, when the wire 302 is pulled toward the arrow 302 of FIG. 13, the fastening member 326 coupled to the wire 302 and the pulley 121 coupled to the fastening member 326 may rotate in the direction of the arrow L of FIG. 13.

Hereinafter, the pitch motion of the present disclosure will be described in more detail.

When the wire 301 is pulled toward the arrow 301 of FIG. 13, and simultaneously the wire 305 is pulled toward the arrow 305 of FIG. 13 (i.e., both strands of the first jaw wire are pulled), as the wire 301 and the wire 305 are wound downward around the pulley 113 and the pulley 114 which are rotatable around the rotation shaft 143 which is the end tool pitch rotation shaft, as illustrated in FIG. 5, the pulley 111 fixedly coupled to the wire 301 and the wire 305 and the end tool hub 180 coupled to the pulley 111 may rotate in the counterclockwise direction around the rotation shaft 143, and as a result, the end tool 100 may rotate downwards performing the pitch motion. In this case, as the second jaw 102 and the wire 302 and the wire 306 fixedly coupled to the second jaw 102 are wound upwards around the pulley 123 and the pulley 124 which are rotatable around the rotation shaft 143, the wire 302 and the wire 306 may be unwound in a direction opposite to the directions 302 and 306, respectively.

On the contrary, when the wire 302 is pulled towards the arrow 302 of FIG. 13, and simultaneously the wire 306 is pulled towards the arrow 306 of FIG. 13, as the wire 302 and the wire 306 are wound upwards around the pulley 123 and the pulley 124 which are rotatable around the rotation shaft 143 which is the end tool pitch rotation shaft, as illustrated in FIG. 5, the pulley 121 fixedly coupled to the wire 302 and the wire 306 and the end tool hub 180 coupled to the pulley 121 may rotate around the rotation shaft 143 in the clockwise direction, and as a result, the end tool 100 may rotate upwards, performing the pitch motion. In this case, as the first jaw 101 and the wire 301 and the wire 305 fixedly coupled to the first jaw 101 are wound downwards around the pulley 113 and the pulley 114 which are rotatable around the rotation shaft 143, the wire 302 and the wire 306 may be unwound in a direction opposite to the directions 301 and 305, respectively.

The end tool 100 of the electric cauterization surgical instrument 10 of the present disclosure may further include the pulley 131, which is the end tool pitch pulley, the manipulation portion 200 may further include the pulley 231 and the pulley 232, which are the manipulation portion pitch pulley, and the power transmission portion 300 may further include the wire 303 and the wire 304, which are the pitch wire. More specifically, the pulley 131 of the end tool 100 may be rotatable around the rotation shaft 143 which is the end tool pitch rotation shaft, and may be integrated with the end tool hub 180 (or fixedly coupled to the end tool hub 180). In addition, the wire 303 and the wire 304 may perform the function of connecting the pulley 131 of the end tool 100 to the pulley 231 and the pulley 232 of the manipulation portion 200.

Accordingly, when the pulley 231 and the pulley 232 of the manipulation portion 200 rotate, the rotation of the pulley 231 and the pulley 232 may be transferred to the pulley 131 of the end tool 100 through the wire 303 and the wire 304, and the pulley 131 may also rotate. As a result, when the end tool 100 rotates, the pitch motion may be performed.

That is, the electric cauterization surgical instrument 10 of the first embodiment may include the pulley 131 of the end tool 100, the pulley 231 and the pulley 232 of the manipulation portion 200, and the wire 303 and the wire 304 of the power transmission portion 300 to transfer power for the pitch motion, and by transferring more perfectly the driving power of the pitch motion of the manipulation portion 200 to the end tool 100, the motion reliability may be improved.

Here, diameters of the pulley 113, the pulley 114, the pulley 123, and the pulley 124 which are the end tool jaw pitch main pulley, and diameters of the pulley 131 which is the end tool pitch pulley may be identical of different. Moreover, a ratio between the diameter of the end tool jaw pitch main pulley and the diameter of the end tool pitch pulley may be identical to a ratio between the diameter of the manipulation portion pitch pulley of the manipulation portion 200 and the diameter of the manipulation portion pitch main pulley. This will be described in detail later.

(Blade Pulley Related Components)

Hereinafter, the blade pulley 161 of the end tool 100 of the electric cauterization surgical instrument 10 of FIG. 2 will be described in more detail.

Figure 15:
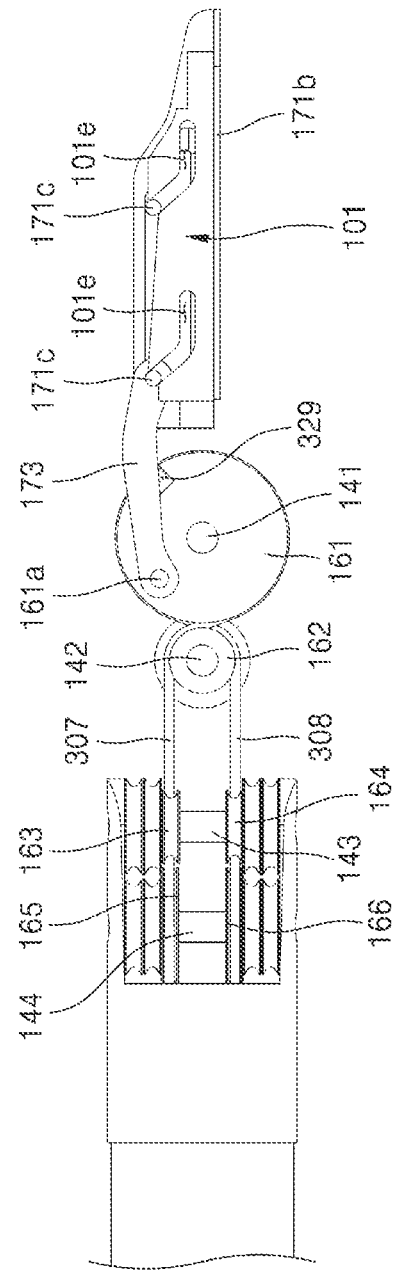
FIGS. 15, 16, and 17 are side views illustrating a cutting movement of the end tool of the surgical instrument for electrocautery of FIG. 2, wherein jaws are located at neutral positions.
Figure 16:
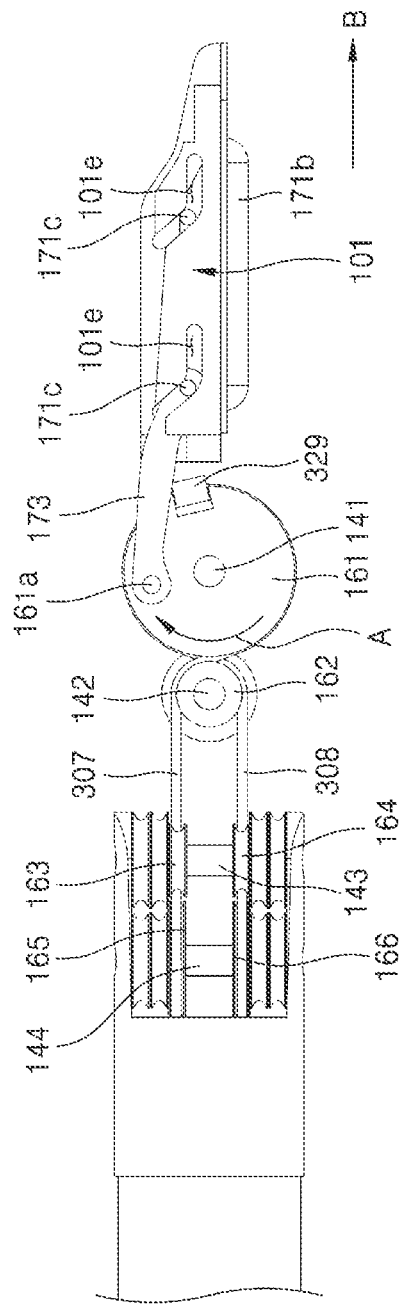
Figure 17:
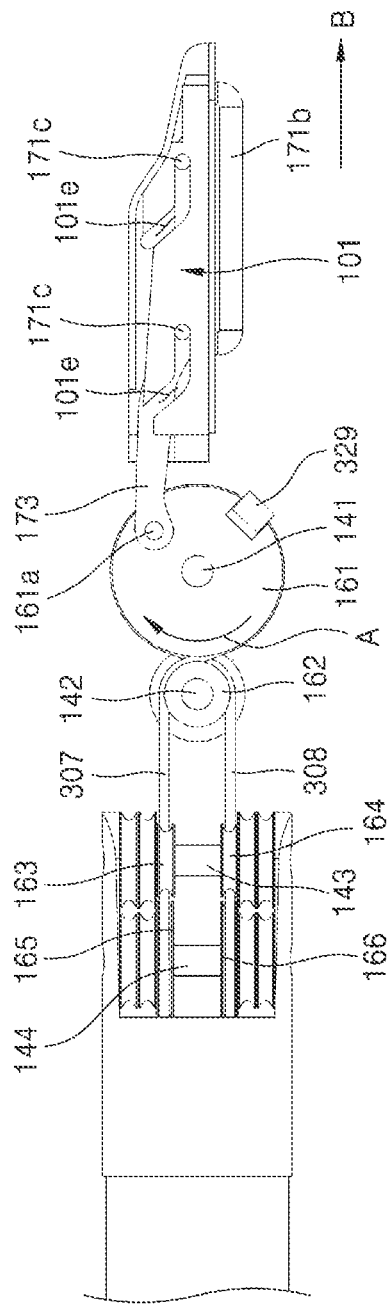

FIGS. 15, 16 and 17 are side views illustrating the cutting motion of the end tool 100 of the surgical instrument for electrocautery 10 of FIG. 2 when the jaws are located in a neutral position. FIGS. 15, 16 and 17 omit components which are not associated with the blade 171 and the blade pulley 161.

With reference to FIGS. 6 to 8, 15 to 17, etc., the end tool 100 of the first embodiment may include the blade pulley 161, a blade auxiliary pulley 162, a pulley 163, a pulley 164, a pulley 165, and a pulley 166 which are associated with a linear/rotational motion of the blade 171.

The blade pulley 161 may face the pulley 111 and the pulley 121, which are the end tool jaw pulley, and may be rotatable independently around the rotation shaft 141 which is the end tool jaw pulley rotation shaft. Here, although the drawings illustrate that the blade pulley 161 is arranged between the pulley 111 and the pulley 121, the technical concepts of the present disclosure are not limited thereto, and the blade pulley 161 may be arranged in various positions adjacent to the pulley 111 and the pulley 121.

The blade pulley 161, the pulley 111, and the pulley 121 may be formed to rotate around a substantially the same shaft. As such, as the blade pulley 161, the pulley 111, and the pulley 121 are formed to rotate around a substantially the same shaft, simultaneously with the pitch motion/yaw motion/actuation motion, a cutting motion using the blade 171 may also be performed. This will be described in more detail later. However, in the drawings, the blade pulley 161, the pulley 111, and the pulley 121 are formed to rotate around one rotation shaft 141, but each jaw pulley may be formed to be rotatable around separate shafts which are concentric.

In other words, the pulley 111, which is the first jaw pulley, the blade pulley 161, and the pulley 121, which is the second jaw pulley may be stacked sequentially along the rotation shaft 141. Alternatively, the blade pulley 161 may be described as being arranged between the pulley 111 and the pulley 121. Here, the pulley 111 which is the first jaw pulley, the blade pulley 161, and the pulley 121 which is the second jaw pulley may be formed to be rotatable independently of each other.

The blade auxiliary pulley 162 may be additionally provided on one side of the blade pulley 161, and in other words, the blade auxiliary pulley 162 may be arranged between the blade pulley 161 and the pulley 163/the pulley 164. The blade auxiliary pulley 162 may be formed to be rotatable independently of the pulley 112 and the pulley 122 around the rotation shaft 142. In the drawings, the blade auxiliary pulley 162, the pulley 112, and the pulley 122 are formed to rotate around one rotation shaft 142, but each of the blade auxiliary pulley 162, the pulley 112, and the pulley 122 may be formed to be rotatable around separate shafts. Such blade auxiliary pulley will be described in more detail later.

The pulley 163 and the pulley 164 may function as a blade pitch main pulley, and the pulley 165 and the pulley 166 may function as a blade pitch subsidiary pulley.

Hereinafter, components associated with the rotation of the blade pulley 161 will be described.

The pulley 163 and the pulley 164 may function as the blade pitch main pulley. Here, the wire 307, which is the blade wire, may be wound around the pulley 163, and the wire 308, which is the blade wire, may be wound around the pulley 164.

The pulley 165 and the pulley 166 may function as the blade pitch subsidiary pulley. Here, the wire 307, which is the blade wire, may be wound around the pulley 165, and the wire 308, which is the blade wire, may be wound around the pulley 166.

Here, on one side of the blade pulley 161 and the blade auxiliary pulley 162, the pulley 163 and the pulley 164 may be arranged to face each other. The pulley 163 and the pulley 164 may be formed to be rotatable independently of each other around the rotation shaft 143 which is the end tool pitch rotation shaft. In addition, on one side of each of the pulley 163 and the pulley 164, the pulley 165 and the pulley 166 may be arranged to face each other. The pulley 165 and the pulley 166 may be formed to be rotatable independently of each other around the rotation shaft 144 which is the end tool pitch auxiliary rotation shaft. Although the drawings illustrate that the pulley 163, the pulley 165, the pulley 164, and the pulley 166 are formed to be rotatable around the Y-axis direction, the technical concepts of the present disclosure are not limited thereto, and the rotation shafts of each pulley may be formed in various directions suitable for their respective configurations.

As described above, the rotation shaft 141, the rotation shaft 142, the rotation shaft 143, and the rotation shaft 144 may be arranged sequentially from the distal end 104 towards the proximal end 105. Accordingly, the blade pulley 161, the blade auxiliary pulley 162, the pulley 163/the pulley 164, the pulley 165/the pulley 166 may be sequentially arranged from the distal end 104 of the end tool 100 towards the proximal end 105.

The wire 307, which is the blade wire, may be sequentially wound so that at least a part thereof is in contact with the pulley 165, the pulley 163, the blade auxiliary pulley 162, and the blade pulley 161. In addition, the wire 308 connected to the wire 307 by the fastening member 329 may be sequentially wound so that at least a part thereof is in contact with the blade pulley 161, the blade auxiliary pulley 162, the pulley 164, and the pulley 166.

In other words, the wire 307 and the wire 308, which are the blade wire, may be sequentially wound so that at least a part there of is in contact with the pulley 165, the pulley 163, the blade auxiliary pulley 162, the blade pulley 161, the blade auxiliary pulley 162, the pulley 164, and the pulley 166, and the wire 307 and the wire 308 may be formed to move along the pulleys while rotating the pulleys.

Accordingly, when the wire 307 is pulled, the fastening member 329 coupled to the wire 307 and the blade pulley 161 coupled to the fastening member 329 may rotate in one direction. When the wire 308 is pulled, the fastening member 329 coupled to the wire 308 and the blade pulley 161 coupled to the fastening member 329 may rotate in the opposite direction.

Hereinafter, the blade auxiliary pulley 162 will be described in more detail.

The blade auxiliary pulley 162 may be in contact with the wire 307 and the wire 308, which are the blade wire, and change the arrangement path of the wire 307 and the wire 308 to a certain extent, which leads to expansion of a rotation angle of the blade pulley 161.

That is, when no blade auxiliary pulley is arranged, the blade pulley 161 may rotate up to the right angle; however, in an embodiment, by additionally arranging the blade auxiliary pulley 162, which is an auxiliary pulley, the maximum rotation angle may be increased by 0 in both directions. This enables the blade pulley 161 to rotate for the cutting motion, causing a linear motion of the blade 171 when the two jaws of the end tool 100 are yaw-rotated by 90°. In other words, through the blade auxiliary pulley 162, a range of yaw rotation allowing the cutting motion may be expanded.

This will be described below in more detail.

According to the electric cauterization surgical instrument 10 of the present disclosure, the blade auxiliary pulley 162 may be additionally arranged on one side of the blade pulley 161. As such, by arranging the blade auxiliary pulley 162 to change the arrangement path of the wire 307 and the wire 308, which are the blade wire, to a certain extent, a tangential direction of the wire 307 and the wire 308 may be changed, and a rotation angle of the fastening member 329 coupling the wire 307 and the wire 308 to the blade pulley 161 may be increased. That is, the fastening member 329, which is a coupling portion of the wire 307, the wire 308, and the blade pulley 161, may rotate until it is located on a common internal tangent of the blade pulley 161 and the blade auxiliary pulley 122.

In other words, the wire 307 and the wire 308 may be located on the internal tangent of the blade pulley 161 and the blade auxiliary pulley 162, and the rotation angle of the blade pulley 161 may be expanded by the blade auxiliary pulley 162.

According to the present disclosure, as the rotational radius of the blade pulley 161 is widened, the range of yaw motion allowing a normal cutting motion may be expanded.

(Components Associated with Cautery and Cutting)

With reference FIGS. 4 to 17, etc., the end tool 100 of the first embodiment may include the first jaw 101, the second jaw 102, a first electrode 151, a second electrode 152, the blade pulley 161, the blade 171, and the blade link 173 to perform the cautery motion and the cutting motion.

Here, components associated with the driving of the blade 171, such as the blade pulley 161, the blade 171, and the blade link 173, etc. may be collectively referred to as the blade assembly 170. In an embodiment, by arranging the blade assembly 170 including the blade 171 between the pulley 111 which is the first jaw pulley and the pulley 121 which the second jaw pulley, not only the pitch motion and the yaw motion of the end tool 100 but also the cutting motion using the blade 171 may be performed. This will be described in more detail.

The first jaw 101 may include a guide member 101a and a case 101c.

As illustrated in FIG. 11 and the like, a blade accommodation portion 101d and a first guide portion 101e may be formed at the guide member 101a. The guide member 101a may be coupled to the pulley 111 and may guide a movement path of the blade 171. For example, the guide member 101a may be formed in the form of two long bars facing each other, and the blade accommodation portion 101d in which at least a part of the blade 171 and the blade link 173 are accommodated may be formed inside the guide member 101a. The blade accommodation portion 101d may be formed in an elongated manner in a direction towards a distal end 101f from a proximal end 101g of the first jaw 101, and in the blade accommodation portion 101d, the blade 171 may be entirely accommodated or at least a part of the blade 171 may protrude from the blade accommodation portion 101d to the outside. In other words, as the blade 171 moves along the blade accommodation portion 101d, the cutting motion may be performed on the tissue. This will be described in more detail later.

In addition, the first guide portion 101e for guiding the movement of the blade 171 may be formed at the guide member 101a of the first jaw 101. Here, the first guide portion 101e may be formed on both sidewalls inside the guide member 101a forming the blade accommodation portion 101d. The first guide portion 101e may be formed in the shape of a groove formed along the movement path of the blade 171. In one embodiment, in a state where a second guide portion 171c of the blade 171 formed in the protrusion shape is fit into the first guide portion 101e in the groove shape, as the second guide portion 171c moves along the first guide portion 101e, the blade 171 may move with respect to the first jaw 101.

Here, the first guide portion 101e may be formed to be curved one or more times. For example, as shown in FIG. 15 and the like, the first guide portion 101e may be curved at a certain angle (approximately 120° in the drawing). In this case, a proximal end side of the first guide portion 101e may be formed in an inclined manner, and a distal end side of the first guide portion 101e may be formed in parallel with the X-axis direction.

Accordingly, when the blade 171 passes an inclined area of the first guide portion 101e, the blade 171 may move from the proximal end 101g towards the distal end 101f of the first jaw 101 and simultaneously in a direction protruding to the outside of the first jaw 101 from the inside. In one embodiment, when the blade 171 passes a parallel area of the first guide portion 101e, the blade 171 may move in a straight line from the proximal end 101g of the first jaw 101 towards the distal end 101f.

In other words, the movement path of the blade 171 may be determined according to the shape of the first guide portion 101e.

Although the drawings illustrate that the first guide portion 101e is integrated with the guide member 101a as one component of the first jaw 101, the technical concepts of the present disclosure are not limited thereto, and the first guide portion 101e may be formed as a separate member from the guide member 101a and be coupled to the guide member 101a.

In the drawings, the shape of the two grooves included in the first guide portion 101e are the same; however, the technical concepts of the present disclosure are not limited thereto, and a plurality of grooves included in the first guide portion 101e may have different shapes. As such, by adjusting the shape of the plurality of grooves included in the first guide portion 101e, the movement path of the blade 171 may be changed to a certain degree.

In addition, the first jaw 101 may further include the case 101c. This case 101c may cover an upper portion of the first jaw 101 so that the blade accommodation portion 101d, the first guide portion 101e, and the blade 171 accommodated therein are not exposed to the outside.

The first electrode 151 may be formed on a surface of the first jaw 101 facing the second jaw 102. The second electrode 152 may be formed on a surface of the second jaw 102 facing the first jaw 101.

Moreover, a slit 151a may be formed at the first electrode 151, and at least a part of the blade 171 may protrude to the outside of the first jaw 101 and the first electrode 151 through the slit 151a.

Furthermore, a slit 152a may be formed at the second electrode 152. In addition, at least a part of the blade 171 protruding to the outside of the first jaw 101 may pass through the slit 152a and be accommodated in the second jaw 102.

Although it is not shown in the drawings, a slit in which at least a part of the blade 171 drawn out from the first jaw 101 may be accommodated may be further formed at the second jaw 102. As such, by forming a slit (not shown) at the second jaw 102, the blade 171 may be drawn out from the first jaw 101 to perform the cutting when the first jaw 101 and the second jaw 102 are closed.

Although it is not shown in the drawings, a spacer (not shown) spacing the first electrode 151 apart from the second electrode 152 at a certain distance so that the first electrode 151 is not in direct contact with the second electrode 152 may be formed at at least one of the first jaw 101 and the second jaw 102. The spacer (not shown) may include an insulating material such as ceramic.

Although it is not shown in the drawings, one or more sensors (not shown) may be further formed at at least one of the first jaw 101 and the second jaw 102. The sensor (not shown) may measure at least some of a current, a voltage, a resistance, an impedance, a temperature, etc., when tissue is positioned between the first jaw 101 and the second jaw 102, a current flows into the first electrode 151 and the second electrode 152, and cautery is performed.

Alternatively, instead of providing a separate sensor, monitoring and control of at least some of a current, a voltage, a resistance, an impedance, and a temperature may be directly performed by a generator (not shown) which supplies power to the electrodes.

The blade pulley 161 may be axially coupled to the rotation shaft 141 to rotate around the rotation shaft 141. The blade pulley 161 may be arranged between the pulley 111 which is the end tool first jaw pulley and the pulley 121 which is the end tool second jaw pulley. Here, the pulley 111, the pulley 121, and the blade pulley 161 may be formed to be rotatable independently of each other.

The blade 171 may include a body portion 171a, an edge portion 171b, and one or more second guide portions 171c.

In an area of the body portion 171a, the edge portion 171b which is sharp and cuts tissue may be formed. At least a part of the edge portion 171b may be drawn to the outside of the first jaw 101 to cut the tissue positioned between the first jaw 101 and the second jaw 102.

In another area of the body portion 171a, the one or more second guide portions 171c may be formed. For example, the second guide portion 171c may be formed in the protrusion shape, and in a state where the second guide portion 171c is fit into the first guide portion 101e having the groove shape, when the second guide portion 171c moves along the first guide portion 101e, the blade 171 may move with respect to the first jaw 101. In addition, the blade link 173 to be described later may be axially coupled to the second guide portions 171c.

Although it is not shown in the drawings, the first guide portion 101e of the first jaw 101 may be formed in the protrusion shape, and the second guide portion 171c of the blade 171 may be formed in the groove shape.

The blade link 173 may connect the blade pulley 161 to the blade 171 and transmit the rotation of the blade pulley 161 to the blade 171 so that the blade 171 moves in a direction towards the distal end 101f from the proximal end 101g of the first jaw 101. The blade link 173 may be formed in the shape of an elongated bar, and one end of the blade link 173 may be connected to the blade pulley 161, and the other end may be connected to the blade 171.

For example, a penetrating hole may be formed at both ends of the blade link 173, and the penetrating holes may be fit into a protrusion portion 161a formed on one surface of the blade pulley 161 and the second guide portion 171c formed at the blade 171, respectively. In other words, the blade pulley 161 may be axially coupled to one end of the blade link 173 and simultaneously, the blade 171 may be axially coupled to the other end of the blade link 173.

In this state, when the blade pulley 161 rotates around the rotation shaft 141, the rotational motion of the blade pulley 161 may be transmitted to the blade 171 by the blade link 173 coupled to the blade pulley 161. Furthermore, as the position of the blade 171 is changed by the transmitted rotational motion of the blade pulley 161, the blade 171 may move in a direction towards the distal end 101f from the proximal end 101g of the first jaw 101, and may be drawn from the first jaw 101 or be pulled in into the first jaw 101.

That is, the blade link 173, the first guide portion 101e of the first jaw 101, and the second guide portion 171c of the blade 171 may be combined to form a kind of power transmission mechanism, and accordingly, when the blade pulley 161 rotates, the blade 171 connected thereto may move between a first position and a second position.

Here, the end tool 100 of the electric cauterization surgical instrument 10 according to an embodiment may include the blade pulley 161 arranged between the pulley 111 and the pulley 121 and the blade 171 which is connected to the blade pulley 161 and moves between the first position and the second position according to the rotation of the blade pulley 161. In other words, the blade 171 may move between the distal end 101f and the proximal end 101g of the first jaw 101 according to the rotation of the blade pulley 161. In addition, by providing the blade pulley 161 and the blade 171, a multi-joint/multi-degree-of-freedom surgical instrument capable of pitch/yaw/actuation motions may also perform cautery and cutting. This will be described below in more detail.

So far, various types of surgical instruments for electrocautery have been developed. Among the various types of surgical instruments for electrocautery, a blood vessel resection device called 'Advanced Energy Device' or 'Vessel Sealer' has a sensing function added to the existing bipolar cautery method, so that power of different polarities may be supplied to two electrodes, and after denaturing a vessel with the heat generated therefrom for hemostasis, the stanched part may be cut with a blade. The completion of cautery may be measured by measuring the impedance of the tissue (or blood vessels) during the current flow, and after the cautery is completed, the current supply may be automatically terminated and the tissue may be cut with the blade.

In the case of such a bipolar blood vessel resection device, as a blade for cutting the tissue after cautery is essential, and an instrument for facilitating a linear motion of the blade needs to be provided additionally in the end tool, joint movements, such as a pitch/yaw movement may not be performed.

There have been attempts to implement joint movements using a bent joint constituted by several nodes connected to each other in the bipolar type blood vessel resection device; however, in such a case, the rotation angle may be limited, and the motions of the end tool may not be accurately controlled.

When the hemostasis and cutting are performed by using vibration of ultrasonic waves, due to the physical features of the ultrasonic waves, having a joint may not be an option.

To overcome such issue, the end tool 100 of the electric cauterization surgical instrument 10 according to an embodiment may include the blade pulley 161 arranged between the pulley 111 and the pulley 121 and the blade 171 which is connected to the blade pulley 161 and moves between the first position and the second position according to the rotation of the blade pulley 161. By providing the blade pulley 161 and the blade 171, in a bipolar type surgical instrument for tissue cautery and cutting, the pitch/yaw/actuation motion may be performed using a pulley/wire method.

Figure 18:
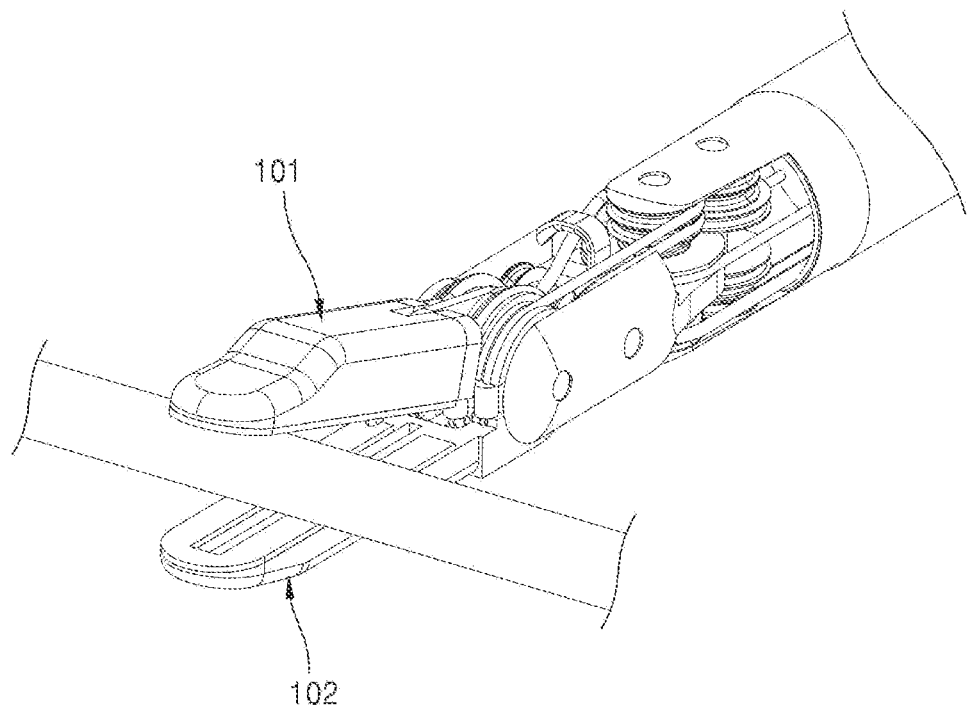
FIGS. 18 to 22 are diagrams illustrating processes of performing cautery and cutting by using the surgical instrument for electrocautery according to the present disclosure.
Figure 19:
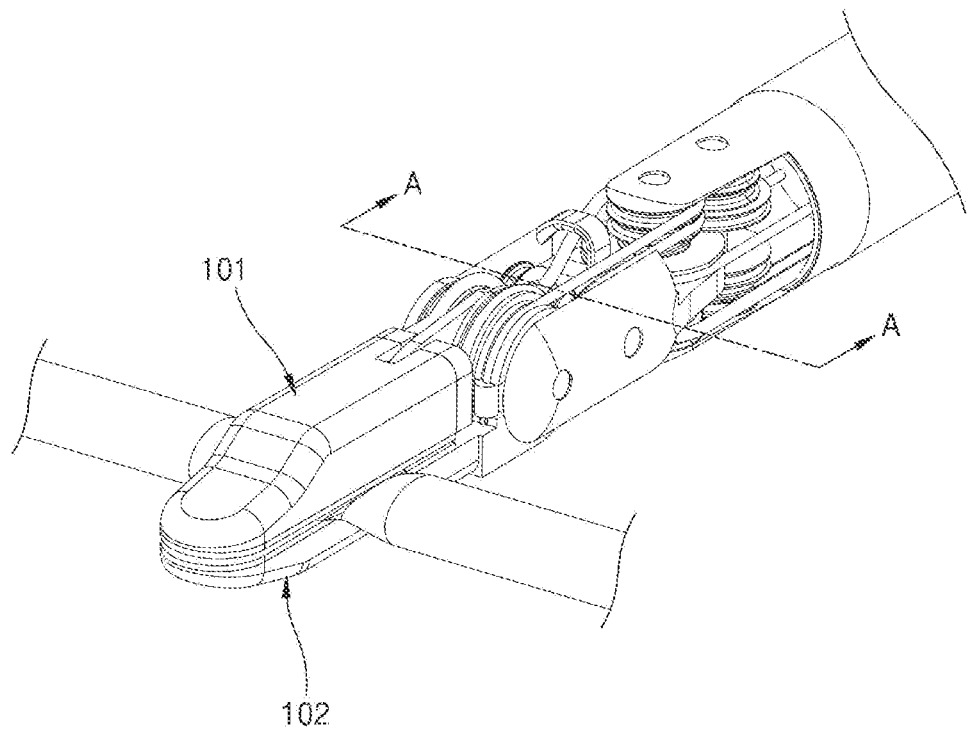
Figure 20:
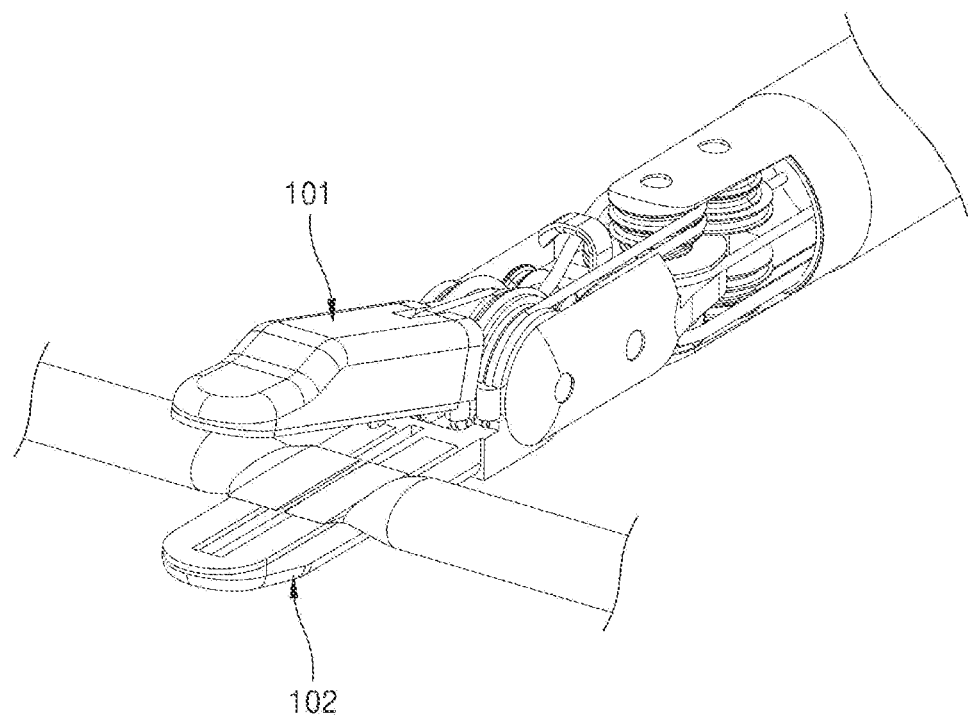
Figure 21:
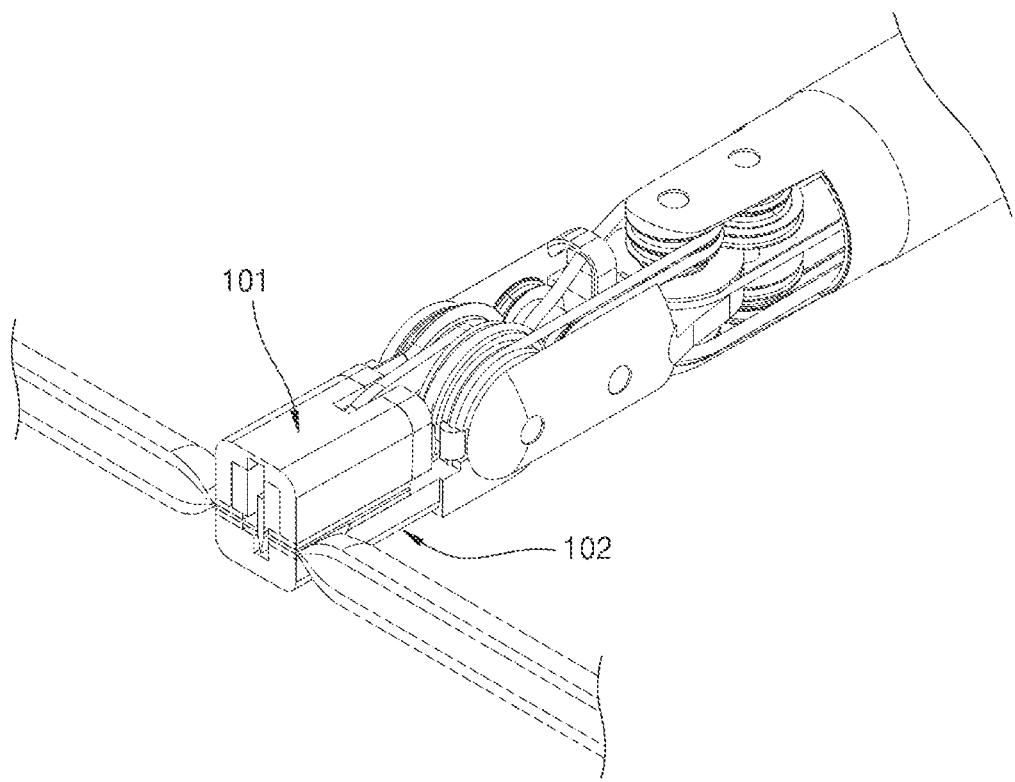
Figure 22:
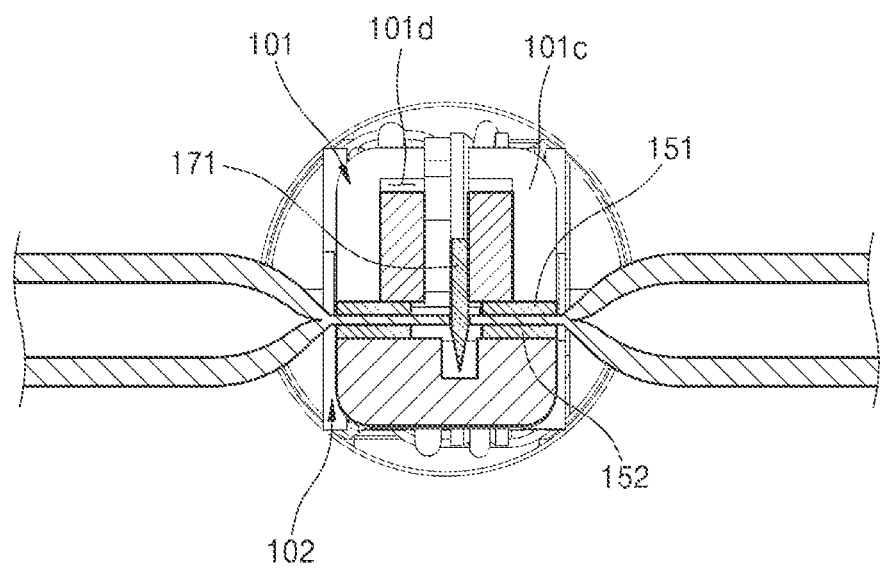

FIG. 15 is a view illustrating a state in which the blade pulley 161 and the blade 171 are located in the first position, FIG. 17 is a view illustrating a state in which the blade pulley 161 and the blade 171 are located in the second position, and FIG. 16 is a view illustrating a state in which the blade pulley 161 and the blade 171 are moving from the first position to the second position. FIG. 18 is a view illustrating a state before the first jaw 101 and the second jaw 102 are opened to cut the tissue, FIG. 19 is a view illustrating a state in which the first jaw 101 and the second jaw 102 are closed to cauterize and cut the tissue, and FIG. 20 is a view illustrating a state in which the first jaw 101 and the second jaw 102 are reopened after the cutting is completed. FIG. 21 is a perspective view of a cross-section taken along line AA of FIG. 19, and FIG. 22 is a front view of the cross-section taken along line AA of FIG. 19.

In other words, as in FIG. 19, in the state where the first jaw 101 and the second jaw 102 are closed, when the cutting motion of FIGS. 15 to 17 is performed, the tissue between the first jaw 101 and the second jaw 102 may be cut.

Here, the first position shown in FIG. 15 may be defined as a state in which the blade 171 is completely retracted in the first jaw 101. Alternatively, it may be defined as a state in which the second guide portion 171c of the blade 171 is located at any one end of the first guide portion 101e having the groove shape, more particularly, at the end of a side adjacent to the blade pulley 161.

The second position shown in FIG. 17 may be defined as a state in which the blade 171 is drawn out from the first jaw 101 to the maximum extent. Alternatively, it may be defined as a state in which the second guide portion 171c of the blade 171 is located at the other end of the first guide portion 101e having the groove shape, more particularly, at the end arranged on a side of the distal end 104.

First, as shown in FIG. 18, in the state where the first jaw 101 and the second jaw 102 are opened, after arranging tissue to be cut between the first jaw 101 and the second jaw 102, the actuation motion may be performed to close the first jaw 101 and the second jaw 102 as illustrated in FIG. 19.

Next, as shown in FIG. 15, in a state where the blade pulley 161 and the blade 171 are positioned at the first position, currents of different polarities may flow into the first electrode 151 and the second electrode 152 to cauterize the tissue between the first jaw 101 and the second jaw 102. At this time, the generator (not shown) which supplies power to the electrodes may perform monitoring of at least some of a current, a voltage, a resistance, an impedance, and a temperature, and discontinue the power supply when the cautery is completed.

When the cautery is completed, and the blade pulley 161 rotates in the direction of arrow A of FIGS. 16 and 17, the blade link 173 coupled to the blade pulley 161 may move in the direction of arrow B of FIGS. 16 and 17 and sequentially arrive at the positions of FIGS. 16 and 17. Then, the blade 171 coupled to the blade link 173 may move from the first position of the proximal end 101g of the first jaw 101 towards the second position of the distal end 101f of the first jaw 101.

That is, in the state where the second guide portion 171c in the protrusion shape is fit into the first guide portion 101e in the groove shape, when the blade pulley 161 rotates in the arrow A direction, the blade link 173 coupled to the blade pulley 161 may push the blade 171 in the arrow B direction, and the blade 171 may entirely move along the first guide portion 101e.

In this case, as the first guide portion 101e having the groove shape is formed in an inclined manner to a certain degree in a certain section, the blade 171 may perform a linear motion in a direction protruding at a certain degree to the outside of the first jaw 101 from the inside (i.e., move in the Y-axis direction), simultaneously with performing a straight-line motion in a direction towards the distal end 104 of the end tool 100 (i.e., move in the X-axis direction).

As described above, as the blade 171 performs movement both in the X-axis direction and the Y-axis direction, the tissue between the first jaw 101 and the second jaw 102 may be cut.

However, the linear motion of the blade 171 may not refer to a motion in a strictly straight line, and may refer to the motion of cutting tissue in a straight-line in general even when the straight line is not completely straight, e.g., the line is bent in the middle at a certain angle, includes a section with a gradual curvature, etc.

In addition, as described above, the plurality of grooves included in the first guide portion 101e may have different shapes, and this may cause a certain degree of change to the linear motion of the blade 171.

When the blade pulley 161 continues to rotate in the arrow A direction and reaches the position of FIG. 17, the blade pulley 161 and the blade 171 may be positioned at the second position, and may not move any further.

When the blade pulley 161 rotates in a direction opposite to the arrow A direction, the blade link 173 coupled to the blade pulley 161 may also move approximately in a direction opposite to the arrow B direction and return to the first position.

Finally, as shown in FIG. 20, when first jaw 101 and the second jaw 102 are reopened, the tissue between the first jaw 101 and the second jaw 102 may be found cut.

According to the present disclosure, a multi-joint/multi-degree-of-freedom surgical instrument capable of pitch/yaw/actuation motions may also perform cautery and cutting.

(Manipulation Portion)

Figure 23:
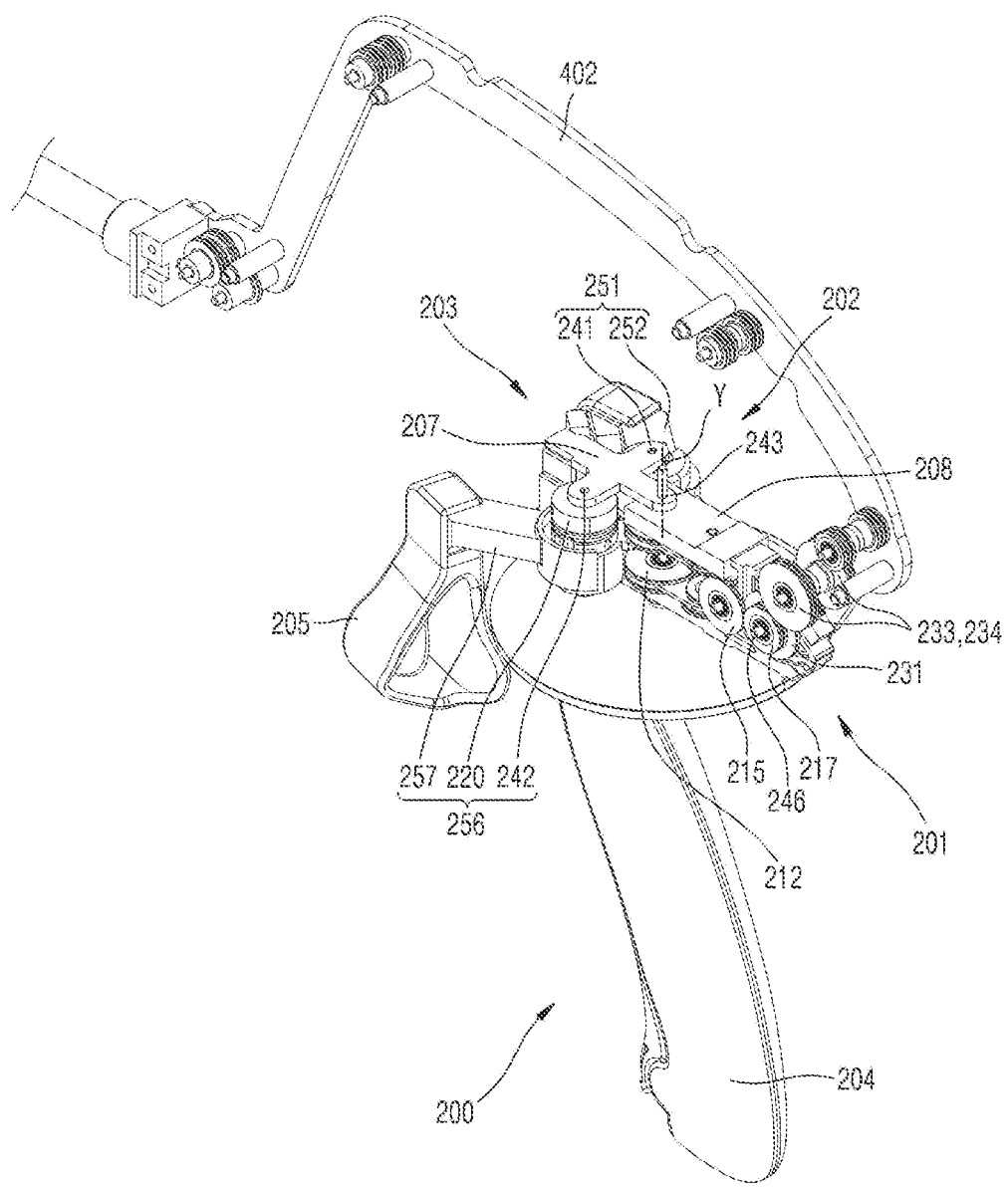
FIGS. 23 and 24 are perspective views illustrating a manipulation portion of the surgical instrument for electrocautery of FIG. 2.
Figure 24:
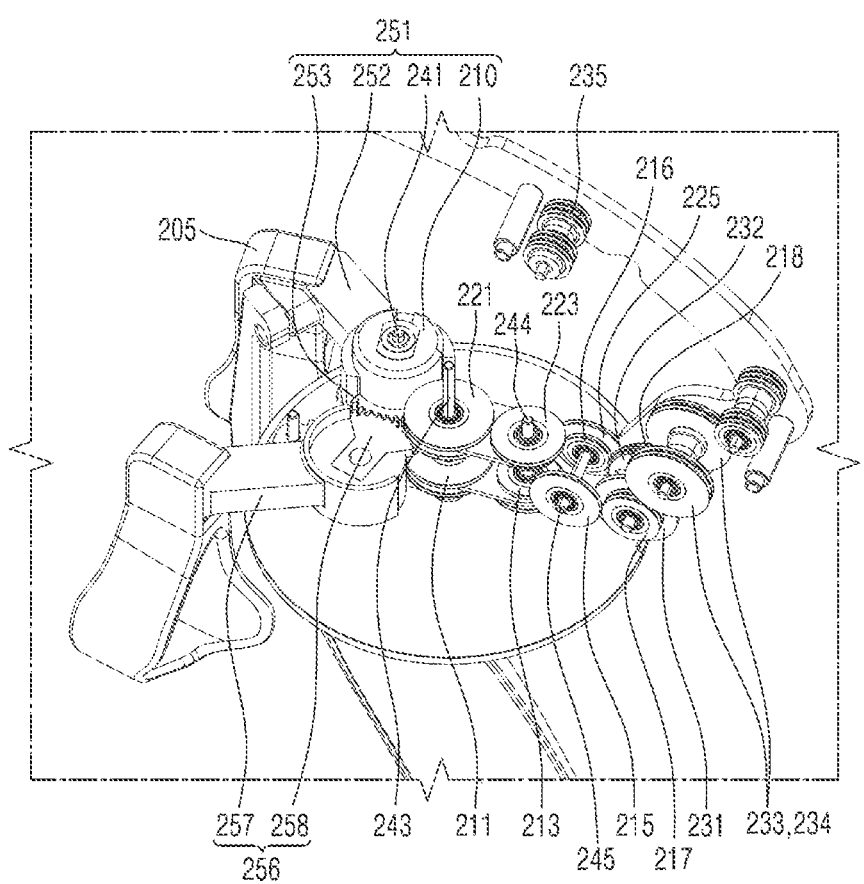
Figure 25:
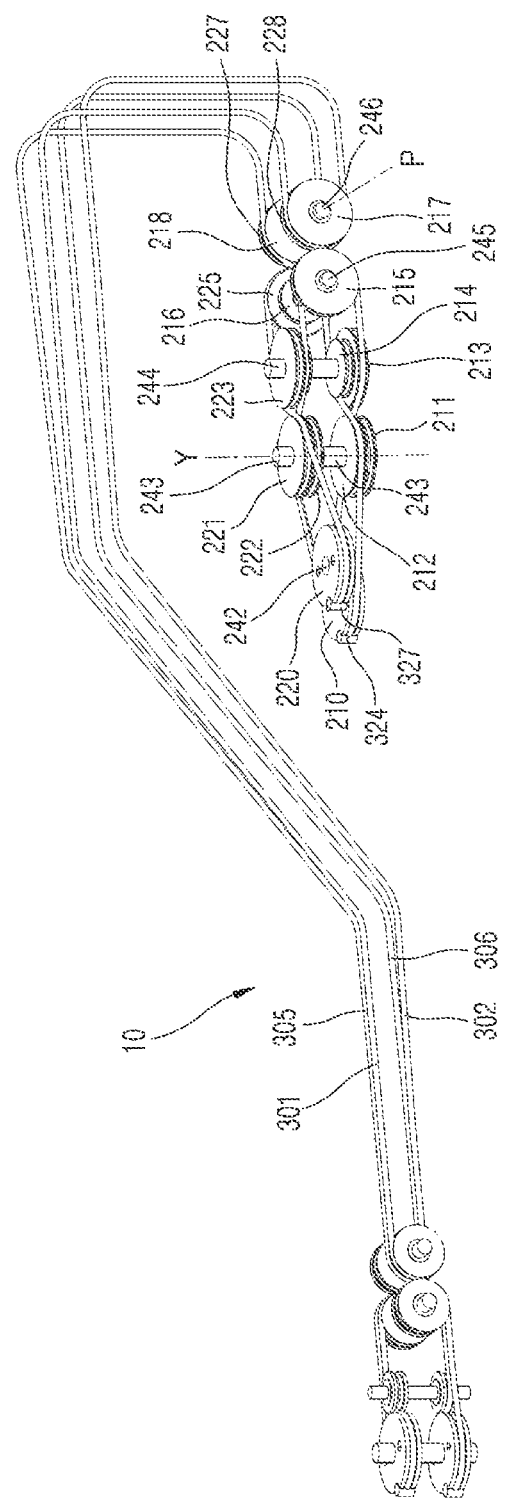
FIG. 25 is a diagram schematically showing a structure of a pulley and a wire configuring a joint of the surgical instrument for electrocautery of FIG. 2.

FIGS. 23 and 24 are perspective views illustrating the manipulation portion 200 of the surgical instrument of FIG. 2. FIG. 25 is a diagram schematically illustrating only the pulleys and the wires constituting the joint of the surgical instrument for electrocautery of FIG. 2.

With reference to FIGS. 2 to 25, the manipulation portion 200 of the electric cauterization surgical instrument 10 according to the first embodiment may include the first handle 204 which a user may hold, the actuation manipulation portion 203 configured to control the actuation motion of the end tool 100, the yaw manipulation portion 202 configured to control the yaw motion of the end tool 100, and the pitch manipulation portion 201 configured to control the pitch motion of the end tool 100. FIGS. 23 and 24 illustrate components only associated with the pitch/yaw/actuation motions of the electric cauterization surgical instrument 10.

In addition, the manipulation portion 200 of the electric cauterization surgical instrument 10 may further include a blade manipulation portion 260 performing cutting by controlling the movement of the blade 171 of the end tool 100, and a cautery manipulation portion 270 performing cautery by supplying electrical energy to the first electrode 151 and the second electrode 152 of the end tool 100.

The manipulation portion 200 may include a pulley 210, a pulley 211, a pulley 212, a pulley 213, a pulley 214, a pulley 215, a pulley 216, a pulley 217, and a pulley 218, which are associated with the rotational motion of the first jaw 101. In addition, the manipulation portion 200 may include a pulley 220, a pulley 221, a pulley 222, a pulley 223, a pulley 224, a pulley 225, a pulley 226, a pulley 227, and a pulley 228, which are associated with the rotational motion of the second jaw 102. In one embodiment, the manipulation portion 200 may include a pulley 231, a pulley 232, a pulley 233, and a pulley 234, which are associated with the pitch motion. The manipulation portion 200 may include a pulley 235 which is an intermediate pulley arranged in some positions of the bent portion 402 of the connection portion 400.

Here, the drawings illustrate that the pulleys facing each other are arranged in parallel with each other; however, the technical concepts of the present disclosure are not limited thereto, and each pulley may be formed in various positions and sizes suitable for the configuration of the manipulation portion 200.

In addition, the manipulation portion 200 of the first embodiment may include a rotation shaft 241, a rotation shaft 242, a rotation shaft 243, a rotation shaft 244, a rotation shaft 245, and a rotation shaft 246. Here, the rotation shaft 241 may function as a manipulation portion first jaw actuation rotation shaft, and the rotation shaft 242 may function as a manipulation portion second jaw actuation rotation shaft. In addition, the rotation shaft 243 may function as a manipulation portion yaw main rotation shaft, and the rotation shaft 244 may function as a manipulation portion yaw subsidiary rotation shaft. The rotation shaft 245 may function as a manipulation portion pitch subsidiary rotation shaft, and the rotation shaft 246 may function as a manipulation portion pitch main rotation shaft.

The rotation shaft 241, the rotation shaft 242, the rotation shaft 243, the rotation shaft 244, the rotation shaft 245, and the rotation shaft 246 may be sequentially arranged in a direction towards a proximal end 206 from a distal end 205.

One or more pulleys may be fit into each of the rotation shafts 241, 242, 243, 244, 245, and 246 which will be described in detail below.

The pulley 210 may function as a manipulation portion first jaw actuation pulley, the pulley 220 may function as a manipulation portion second jaw actuation pulley, and these components may be collectively referred to as a manipulation portion actuation pulley.

The pulley 211 and the pulley 212 may function as a manipulation portion first jaw yaw main pulley, the pulley 221 and the pulley 222 may function as a manipulation portion second jaw yaw main pulley, and these two components may collectively be referred to as a manipulation portion yaw main pulley.

The pulley 213 and the pulley 214 may function as a manipulation portion first jaw yaw subsidiary pulley, the pulley 223 and the pulley 224 may function as a manipulation portion second jaw yaw subsidiary pulley, and these two components may collectively be referred to as a manipulation portion yaw subsidiary pulley.

The pulley 215 and the pulley 216 may function as a manipulation portion first jaw pitch subsidiary pulley, the pulley 225 and the pulley 226 may function as a manipulation portion second jaw pitch subsidiary pulley, and these two components may collectively be referred to as a manipulation portion pitch subsidiary pulley.

The pulley 217 and the pulley 218 may function as a manipulation portion first jaw pitch main pulley, the pulley 227 and the pulley 228 may function as a manipulation portion second jaw pitch main pulley, and these two components may collectively be referred to as a manipulation portion pitch main pulley.

The pulley 231 and the pulley 232 may function as a manipulation portion pitch wire main pulley, and the pulley 233 and the pulley 234 may function as a manipulation portion pitch wire subsidiary pulley.

The components may be classified from the viewpoint of the manipulation portion in connection with each motion (i.e., pitch/yaw/actuation) as follows.

The pitch manipulation portion 201 controlling the pitch motion of the end tool 100 may include a pulley 215, a pulley 216, a pulley 217, a pulley 218, a pulley 225, a pulley 226, and a pulley 227, a pulley 228, a pulley 231, a pulley 232, and a pulley 234. In addition, the pitch manipulation portion 201 may include the rotation shaft 245 and the rotation shaft 246. In one embodiment, the pitch manipulation portion 201 may further include a pitch frame 208.

The yaw manipulation portion 202 controlling the yaw motion of the end tool 100 may include a pulley 211, a pulley 212, a pulley 213, a pulley 214, a pulley 221, a pulley 222, a pulley 223, and a pulley 224. In addition, the yaw manipulation portion 202 may include the rotation shaft 243 and the rotation shaft 244. In one embodiment, the yaw manipulation portion 202 may further include a yaw frame 207.

The actuation manipulation portion 203 controlling the actuation motion of the end tool 100 may include the pulley 210, the pulley 220, the rotation shaft 241, and the rotation shaft 242. In one embodiment, the actuation manipulation portion 203 may further include a first actuation manipulation portion 251 and a second actuation manipulation portion 256.

Hereinafter, each component of the manipulation portion 200 will be described in more detail.

The first handle 204 may be held by a user, and more particularly, a user may hold the first handle 204 by wrapping it with his or her hand. The actuation manipulation portion 203 and the yaw manipulation portion 202 may be formed on the first handle 204, and the pitch manipulation portion 201 may be formed on one side of the yaw manipulation portion 202. In addition, another end of the pitch manipulation portion 201 may be connected to the bent portion 402 of the connection portion 400.

The actuation manipulation portion 203 may include the first actuation manipulation portion 251 and the second actuation manipulation portion 256. The first actuation manipulation portion 251 may include the rotation shaft 241, the pulley 210, a first actuation extension portion 252, and a first actuation gear 253. The second actuation manipulation portion 256 may include the rotation shaft 242, the pulley 220, a second actuation extension portion 257, and a second actuation gear 258. Here, ends of the first actuation extension portion 252 and the second actuation extension portion 257 may be formed in the shape of a hand ring, and may operate as a second handle.

The rotation shaft 241 and the rotation shaft 242, which are the actuation rotation shaft, may be formed to have a certain angle with the XY plane on which the connection portion 400 is formed. For example, the rotation shaft 241 and the rotation shaft 242 may be formed in a direction parallel with the Z-axis, and when the pitch manipulation portion 201 or the yaw manipulation portion 202 rotates, a coordinate system of the actuation manipulation portion 203 may be changed relatively. However, the technical ides of the present disclosure are not limited thereto, and by an ergonomic design, the rotation shaft 241 and the rotation shaft 242 may be formed in various directions suitable for a hand shape of a user holding the actuation manipulation portion 203.

The pulley 210, the first actuation extension portion 252, and the first actuation gear 253 may be fixedly coupled to each other and rotatable together around the rotation shaft 241. Here, the pulley 210 may include one pulley or two pulleys fixedly coupled to each other.

Likewise, the pulley 220, the second actuation extension portion 257, and the second actuation gear 258 may be fixedly coupled to each other and rotatable together around the rotation shaft 242. Here, the pulley 220 may include one pulley or two pulleys fixedly coupled to each other.

The first actuation gear 253 and the second actuation gear 258 may be formed to engage with each other, and when either one of them rotates in one direction, the other one may rotate concurrently in the opposite direction.

The yaw manipulation portion 202 may include the rotation shaft 243, the pulley 211 and the pulley 212, which are the manipulation portion first jaw yaw main pulley, the pulley 221 and the pulley 222, which are the manipulation portion second jaw yaw main pulley, and the yaw frame 207. In addition, the yaw manipulation portion 202 may further include the pulley 213 and the pulley 214, which are the manipulation portion first jaw yaw subsidiary pulley and arranged on one side of the pulley 211 and the pulley 212, and the pulley 223 and the pulley 224, which are the manipulation portion second jaw yaw subsidiary pulley and arranged on one side of the pulley 221 and the pulley 222. Here, the pulley 213, the pulley 214, the pulley 223, and the pulley 224 may be coupled to the pitch frame 208 to be described later.

The drawings illustrate that the yaw manipulation portion 202 includes the pulley 211, the pulley 212, the pulley 221, and the pulley 222, and as the pulley 211 faces the pulley 212 and the pulley 221 faces the pulley 222, two pulleys may be rotatable independently of each other; however the technical concepts of the present disclosure are not limited thereto. That is, one or more pulleys having the same diameter or different diameters may be provided according to the configuration of the yaw manipulation portion 202.

More specifically, on the first handle 204, the rotation shaft 243, which is the manipulation portion yaw main rotation shaft, may be formed on one side of the actuation manipulation portion 203. In this case, the first handle 204 may be formed to be rotatable around the rotation shaft 243.

Here, the rotation shaft 243 may be formed to have a certain angle with the XY plane on which the connection portion 400 is formed. For example, the rotation shaft 243 may be formed in a direction parallel with the Z-axis, and when the pitch manipulation portion 201 rotates, the coordinate system of the rotation shaft 243 may be changed relatively as described above. However, the technical ides of the present disclosure are not limited thereto, and by an ergonomic design, the rotation shaft 243 may be formed in various directions suitable for a hand shape of a user holding the manipulation portion 200.

The pulley 211, the pulley 212, the pulley 221, and the pulley 222 may be coupled to the rotation shaft 243 to be rotatable around the rotation shaft 243. In addition, the wire 301 or the wire 305, which is the first jaw wire, may be wound around the pulley 211 and the pulley 212, and the wire 302 or the wire 306, which is the second jaw wire, may be wound around the pulley 221 and the pulley 222. Moreover, as the pulley 211 faces the pulley 212, and the pulley 221 faces the pulley 222, there may be two pulleys which are rotatable independently. Accordingly, as the wire wound inward and the wire wound outward may be respectively wound around separate pulleys, the pulleys may operate without interfering with each other.

The yaw frame 207 may rigidly connect the first handle 204, the rotation shaft 241, the rotation shaft 242, and the rotation shaft 243, and accordingly, the first handle 204, the yaw manipulation portion 202, and the actuation manipulation portion 203 may yaw-rotate around the rotation shaft 243 in an integrated manner.

The pitch manipulation portion 201 may include the rotation shaft 246, the pulley 217 and the pulley 218, which are the manipulation portion first jaw pitch main pulley, the pulley 227 and the pulley 228, which are the manipulation portion second jaw pitch main pulley, and the pitch frame 208. In addition, the pitch manipulation portion 201 may further include the rotation shaft 245, the pulley 215 and the pulley 216, which are the manipulation portion first jaw pitch subsidiary pulley and arranged on one side of the pulley 217 and the pulley 218, and the pulley 225 and the pulley 226, which are the manipulation portion second jaw pitch subsidiary pulley and arranged on one side of the pulley 227 and pulley 228. The pitch manipulation portion 201 may be connected to the bent portion 402 of the connection portion 400 through the rotation shaft 246.

More specifically, the pitch frame 208 may be a base frame of the pitch manipulation portion 201, and one end of the pitch frame 208 may be rotatably coupled to the rotation shaft 243. That is, the yaw frame 207 may be formed to be rotatable around the rotation shaft 243 with respect to the pitch frame 208.

As described above, the yaw frame 207 may connect the first handle 204, the rotation shaft 243, the rotation shaft 241, and the rotation shaft 242, and as the yaw frame 207 is axially coupled to the pitch frame 208, when the pitch frame 208 pitch-rotates around the rotation shaft 246, the yaw frame 207, the first handle 204, the rotation shaft 241, the rotation shaft 242, and the rotation shaft 243, which are connected to the pitch frame 208, may also pitch rotate. That is, when the pitch manipulation portion 201 rotates around the rotation shaft 246, the actuation manipulation portion 203 and the yaw manipulation portion 202 may be rotated together with the pitch manipulation portion 201. In other words, when the user pitch-rotates the first handle 204 around the rotation shaft 246, the actuation manipulation portion 203, the yaw manipulation portion 202, and the pitch manipulation portion 201 may also move together with the first handle 204.

The pulley 217, the pulley 218, the pulley 227, and the pulley 228 may be coupled to the rotation shaft 246 so that they are rotatable around the rotation shaft 246 of the pitch frame 208.

Here, the pulley 217 and the pulley 218 may face each other and rotate independently. Accordingly, as the wire wound inward and the wire wound outward may be respectively wound around separate pulleys, the pulleys may operate without interfering with each other. Likewise, the pulley 227 and the pulley 228 may face each other and rotate independently. Accordingly, as the wire wound inward and the wire wound outward may be respectively wound around separate pulleys, the pulleys may operate without interfering with each other.

Next, the motions of the wire 303 and the wire 304 which are the pitch wire are described below.

In the end tool 100, the pulley 131, which is the end tool pitch pulley, may be fixedly coupled to the end tool hub 180, and in the manipulation portion 200, the pulley 231 and the pulley 232, which are the manipulation portion pitch pulley, may be fixedly coupled to the pitch frame 208. These pulleys may be connected to each other by the wire 303 and the wire 304, which are the pitch wire, to facilitate the pitch motion of the end tool 100 according to the pitch manipulation of the manipulation portion 200. Here, the wire 303 may be fixedly coupled to the pitch frame 208 via the pulley 231 and the pulley 233, and the wire 304 may be fixedly coupled to the pitch frame 208 via the pulley 232 and the pulley 234. That is, the pitch frame 208, the pulley 231, and the pulley 232 may rotate together around the rotation shaft 246 by the pitch rotation of the manipulation portion 200. As a result, the wire 303 and the wire 304 may also move, and separately from the pitch motion of the end tool 100 by the wire 301, the wire 302, the wire 305, and the wire 306, which are the jaw wire, additional pitch rotation power may be transmitted.

The connection relation among the first handle 204, the pitch manipulation portion 201, the yaw manipulation portion 202, and the actuation manipulation portion 203 is described below. On the first handle 204, the rotation shaft 241, the rotation shaft 242, the rotation shaft 243, the rotation shaft 244, the rotation shaft 245, and the rotation shaft 246 may be formed. Moreover, as the rotation shaft 241 and the rotation shaft 242 are directly formed on the first handle 204, the first handle 204 and the actuation manipulation portion 203 may be directly connected to each other. As the rotation shaft 243 is directly formed on the first handle 204, the first handle 204 and the yaw manipulation portion 202 may be directly connected to each other. As the pitch manipulation portion 201 is arranged on one side of the yaw manipulation portion 202 and connected to the yaw manipulation portion 202, the pitch manipulation portion 201 may not be directly connected to the first handle 204 and the pitch manipulation portion 201 and the first handle 204 may be indirectly connected to each other through the yaw manipulation portion 202.

With reference to the drawings, in the electric cauterization surgical instrument 10 according to the first embodiment, the pitch manipulation portion 201 and the end tool 100 may be formed on the same or parallel axis (i.e., the X-axis). That is, the rotation shaft 246 of the pitch manipulation portion 201 may be formed at one end of the bent portion 402 of the connection portion 400, and the end tool 100 may be formed at the other end of the connection portion 400.

In addition, one or more intermediate pulleys 235 changing or guiding a path of the wires may be arranged in some positions of the connection portion 400, in particular, in positions on the bent portion 402. At least a part of the wires may be wound around the intermediate pulleys 235 to guide the path of the wires so that the wires are arranged along the bent shape of the bent portion 402.

Here, the drawings illustrate that the connection portion 400 includes the bent portion 402 and thus is formed in a curved manner with a certain curvature; however, the technical concepts of the present disclosure are not limited thereto, and the connection portion 400 may be formed straightly, if necessary, or curved in one or more points. Even in such cases, the pitch manipulation portion 201 and the end tool 100 may be formed on the substantially same or parallel axis. In addition, although FIG. 3 illustrates that the pitch manipulation portion 201 and the end tool 100 are respectively formed on an axis parallel with the X-axis, the technical concepts of the present disclosure are not limited thereto, and the pitch manipulation portion 201 and the end tool 100 may be formed on different axes.

(Actuation Motion, Yaw Motion, Pitch Motion)

Actuation motion, yaw motion, and pitch motion in this embodiment will be described as follows.

First, the actuation motion is as follows.

When a user puts the index finger in a hand ring formed at the first actuation extension 252, puts the thumb in a hand ring formed at the second actuation extension 257, and rotates the first actuation extension 252 and the second actuation extension 257 using any one of or both the fingers, the pulley 210 and the first actuation gear 253 fixedly coupled to the first actuation extension 252 rotate around the rotation shaft 241, and the pulley 220 and the second actuation gear 258 fixedly coupled to the second actuation extension 257 rotate around the rotation shaft 242. In this case, the pulley 210 and the pulley 220 rotate in opposite directions, and thus the wire 301 and the wire 305 each having one end fixedly coupled to and wound around the pulley 210 and the wire 302 and the wire 306 each having one end fixedly coupled to and wound around the pulley 220 move in opposite directions as well. This rotational force is transmitted to an end tool 100 through a power transmission portion 300, two jaws 103 of the end tool 100 perform the actuation motion.

Here, the actuation motion refers to an action of opening or closing the jaws 101 and 102 while the two jaws 101 and 102 rotate in opposite directions to each other, as described above. In other words, when the actuation extensions 252 and 257 of the actuation manipulation portion 203 are rotated in directions toward each other, the first jaw 101 rotates counterclockwise and the second jaw 102 rotates clockwise, and thus the end tool 100 is closed. Conversely, when the actuation extensions 252 and 257 of the actuation manipulation portion 203 are rotated in directions away from each other, the first jaw 121 rotates clockwise and the second jaw 122 rotates counterclockwise, and thus the end tool 100 is opened.

In this embodiment, for the above-described actuation manipulation, the first actuation extension 252 and the second actuation extension 257 were provided to constitute a second handle, and two fingers were gripped to enable manipulation. However, unlike the above, the actuation manipulation portion 203 for actuation manipulation to open and close the two jaws of the end tool 100 with each other may be configured differently so that, for example, two actuation pulleys (the pulley 210 and the pulley 220) operate opposite to each other by one actuation rotating portion.

Next, the yaw motion is as follows.

When the user rotates a first handle 204 around a rotation shaft 243 while holding the first handle 204, the actuation manipulation portion 203 and the yaw manipulation portion 202 yaw-rotates around the rotation shaft 243. In other words, when the pulley 210 of the first actuation manipulation portion 251 to which the wire 301 and the wire 305 are fixedly coupled rotates about the rotation shaft 243, the wire 301 and the wire 305 respectively wound around the pulley 211 and the pulley 212 move. Likewise, when the pulley 220 of the second actuation manipulation portion 256 to which the wire 302 and the wire 306 are fixedly coupled rotates about the rotation shaft 243, the wire 302 and the wire 306 respectively wound around the pulley 221 and the pulley 222 move. In this case, the wire 301 and the wire 305 connected to the first jaw 101 and the wire 302 and the wire 306 connected to the second jaw 102 are respectively wound around the pulley 211 and the pulley 212 and the pulley 221 and the pulley 222, such that the first jaw 101 and the second jaw 102 rotate in the same direction during a yaw rotation. And, this rotational force is transmitted to the end tool 100 through the power transmission portion 300, the two jaws 103 of the end tool 100 performs the yaw motion that rotates in the same direction.

In this case, since the yaw frame 207 connects the first handle 204, the rotation shaft 241, the rotation shaft 242, and the rotation shaft 243, the first handle 204, the yaw manipulation portion 202, and the actuation manipulation portion 203 rotate together around the rotation shaft 243.

Next, the pitch motion is as follows.

When the user rotates a first handle 204 around a rotation shaft 246 while holding the first handle 204, the actuation manipulation portion 203, the yaw manipulation portion 202, and the pitch manipulation portion 201 make pitch rotation around the rotation shaft 246. In other words, when the pulley 210 of the first actuation manipulation portion 251 to which the wire 301 and the wire 305 are fixedly coupled rotates about the rotation shaft 246, the wire 301 and the wire 305 respectively wound around the pulley 217 and the pulley 218 move. Likewise, when the pulley 220 of the second actuation manipulation portion 256 to which the wire 302 and the wire 306 are fixedly coupled rotates about the rotation shaft 246, the wire 302 and the wire 306 respectively wound around the pulley 227 and the pulley 228 move. Here, as described above with reference to FIG. 5, the wire 301, the wire 305, the wire 302, and the wire 306, which are jaw wires, are wound around the pulley 217, the pulley 218, the pulley 227, and the pulley 228, which are manipulation portion pitch main pulleys, such that the wire 301 and wire 305, which are first jaw wires, move in the same direction and the wire 302 and the wire 306, which are second jaw wires, move in the same direction to enable pitch rotation of the first jaw 101 and the second jaw 102. And, this rotational force is transmitted to an end tool 100 through a power transmission portion 300, two jaws 103 of the end tool 100 perform the pitch motion.

In this case, the pitch frame 208 is connected to the yaw frame 207 and the yaw frame 207 connects the first handle 204, the rotation shaft 241, the rotation shaft 242, and the rotation shaft 243. Therefore, when the pitch frame 208 rotates around the rotation shaft 246, the yaw frame 207 connected to the pitch frame 208, the first handle 204, the rotation shaft 241, the rotation shaft 242, and the rotation shaft 243 rotate together. That is, when a pitch manipulation portion 201 rotates around the rotation shaft 246, the actuation manipulation portion 203 and the yaw manipulation portion 202 are rotated together with the pitch manipulation portion 201.

In summary, in an electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 100 is induced. Furthermore, auxiliary pulleys may be formed on one side of each pulley, and the wire may not be wound several times on one pulley by these auxiliary pulleys.

FIG. 25 is a schematic view of only the configuration of pulleys and wires constituting joints of the electric cauterization surgical instrument 10 according to an embodiment of the present disclosure shown in FIG. 2. In FIG. 25, intermediate pulleys that are for changing paths of wires and are not associated with joint motions are omitted.

Referring to FIG. 25, the manipulation portion 200 may include the pulley 210, the pulley 211, the pulley 212, the pulley 213, the pulley 214, the pulley 215, the pulley 216, the pulley 217, and the pulley 218 that are associated with the rotational motion of the first jaw 101.

Also, the manipulation portion 200 may include the pulley 220, the pulley 221, the pulley 222, the pulley 223, the pulley 224, the pulley 225, the pulley 226, the pulley 227, and the pulley 228 associated with the rotational motion of the second jaw 122. (The arrangement and the configuration of pulleys in the manipulation portion 200 are the same as the arrangement and the configuration of the pulleys in the end tool 100 in principle, and thus some of the reference numerals thereof will be omitted in the drawings.)

The pulley 211 and the pulley 212 and the pulley 221 and the pulley 222 may be formed to be rotatable independently of each other around the same axis, that is, the rotation shaft 243. Moreover, the pulley 211 and the pulley 212 may be formed to face the pulley 221 and the pulley 222, respectively, thereby forming two independently rotatable pulleys.

The pulley 213 and the pulley 214 and the pulley 223 and the pulley 224 may be formed to be rotatable independently of each other around the same axis, that is, the rotation shaft 244. Moreover, the pulley 213 and the pulley 214 may be formed to face each other as two independently rotatable pulleys, and, in this case, the two pulleys may be formed to have different diameters. Likewise, the pulley 223 and the pulley 224 may be formed to face each other as two independently rotatable pulleys, and, in this case, the two pulleys may be formed to have different diameters.

The pulley 215 and the pulley 216 and the pulley 225 and the pulley 226 may be formed to be rotatable independently of each other around the same axis, that is, the rotation shaft 245. In this case, the pulley 215 and the pulley 216 may be formed to have different diameters. Also, the pulley 225 and the pulley 226 may be formed to have different diameters.

The pulley 217 and the pulley 218 and the pulley 227 and the pulley 228 may be formed to be rotatable independently of each other around the same axis, that is, the rotation shaft 246.

The wire 301 sequentially passes through the pulley 217, the pulley 215, the pulley 213, and the pulley 211 of the manipulation portion 200, is wound around the pulley 210, and then is coupled to the pulley 210 by a fastening member 324. Meanwhile, the wire 305 sequentially passes through the pulley 218, the pulley 216, the pulley 214, and the pulley 212 of the manipulation portion 200 and is coupled to the pulley 210 by the fastening member 324. Therefore, as the pulley 210 rotates, the wire 301 and the wire 305 are wound around or unwound from the pulley 210, and thus the first jaw 101 rotates.

The wire 306 sequentially passes through the pulley 227, the pulley 225, the pulley 223, and the pulley 221 of the manipulation portion 200, is wound around the pulley 220, and then is coupled to the pulley 220 by a fastening member 327. Meanwhile, the wire 302 sequentially passes through the pulley 228, the pulley 226, the pulley 224, and the pulley 222 of the manipulation portion 200 and is coupled to the pulley 220 by the fastening member 327. Therefore, as the pulley 220 rotates, the wire 302 and the wire 306 are wound around or unwound from the pulley 220, and thus the second jaw 102 rotates.

(Pulley and Wire Conceptual Diagram)

Figure 27:
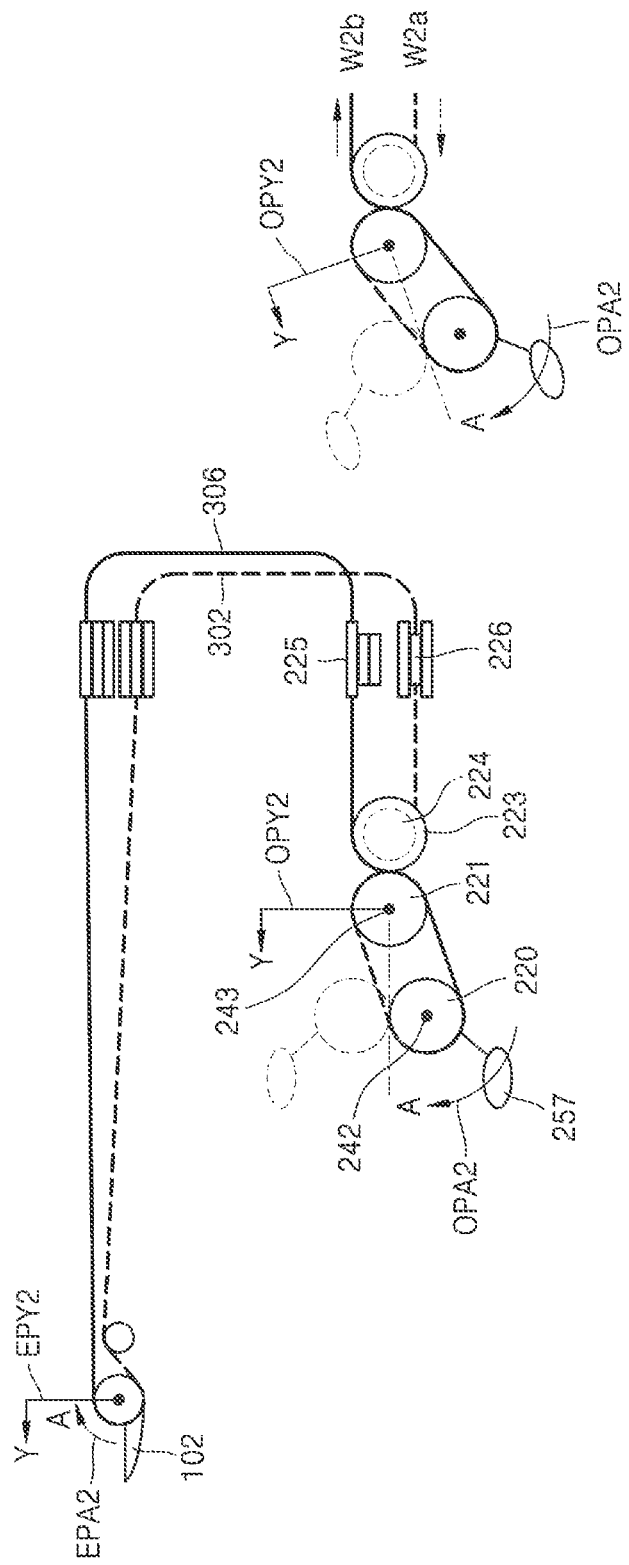
FIGS. 27 and 28 are diagrams showing a configuration of a pulley and a wire associated with an actuation movement and a yaw movement of the surgical instrument for electrocautery of FIG. 2, in detail with respect to each of a first jaw and a second jaw.
Figure 28:
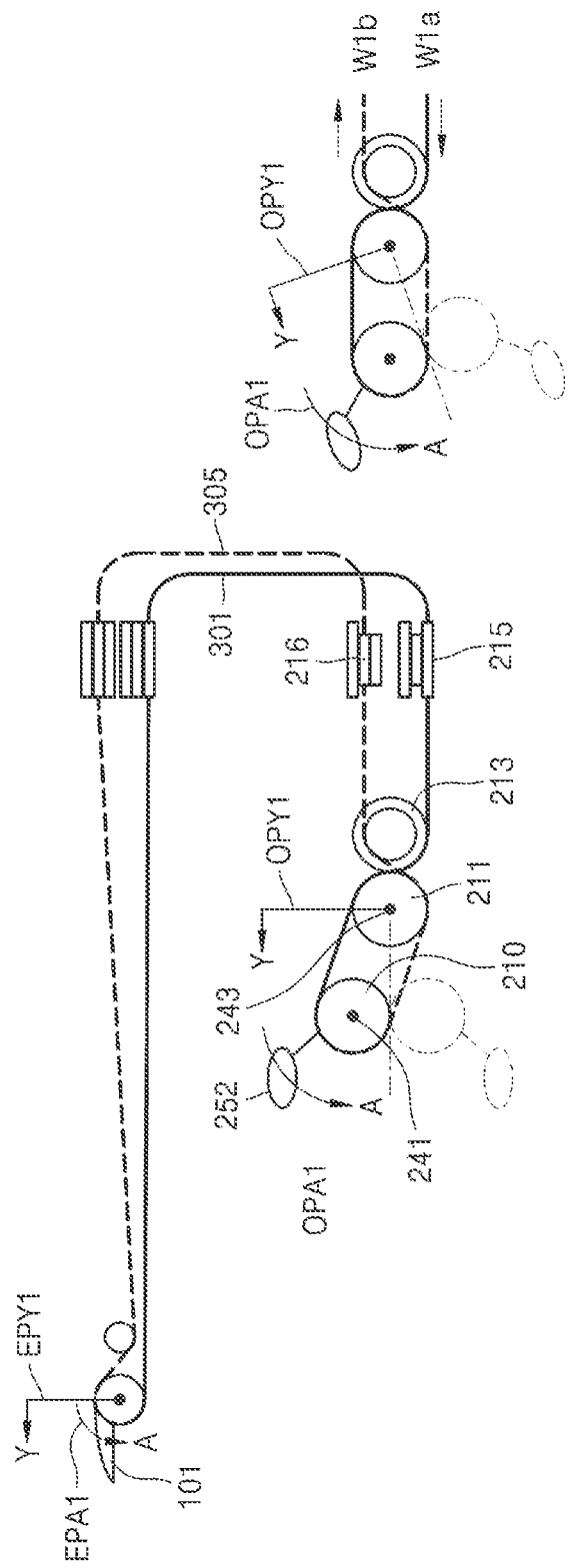

FIGS. 27 and 28 are diagrams illustrating configurations of pulleys and wires associated with an actuation motion and a yaw motion of the electric cauterization surgical instrument 10 according to an embodiment of the present disclosure shown in FIG. 2 for a first jaw and a second jaw, respectively. FIG. 27 is a diagram showing only pulleys and wires associated with the second jaw, and FIG. 28 is a diagram showing only pulleys and wires associated with the first jaw. FIG. 26 is a perspective view showing the yaw motion of the surgical instrument of FIG. 2. Here, components associated with a cutting motion are omitted in FIG. 26.

First, the operation of wires in an actuation motion will be described.

Referring to FIG. 27, when the first actuation extension 252 rotates in the direction indicated by an arrow OPA1 around the rotation shaft 241, the pulley 210 connected to the first actuation extension 252 rotates, and the wire 301 and the wire 305 wound around the pulley 210 move in directions W1a and W1b, respectively. As a result, the first jaw 101 of the end tool 100 rotates in the direction indicated by an arrow EPA1.

Referring to FIG. 28, when the second actuation extension 257 rotates in the direction indicated by an arrow OPA2 around the rotation shaft 242, the pulley 220 connected to the second actuation extension 257 rotates, and the wire 302 and the wire 306 wound around the pulley 220 move in directions W2a and W2b, respectively. As a result, the second jaw 102 of the end tool 100 rotates in the direction indicated by an arrow EPA2. Therefore, when a user manipulates the first actuation extension 252 and the second actuation extension 257 in directions toward each other, a motion of moving the first jaw 101 and the second jaw 102 of an end tool toward each other is performed.

Next, the operation of wires in a yaw motion will be described.

First, since the rotation shaft 243, the rotation shaft 241, and the rotation shaft 242 are connected to one another by a yaw frame (refer to 207 of FIG. 26), the rotation shaft 243, the rotation shaft 241, and the rotation shaft 242 rotate together.

Referring to FIG. 28, when the first handle 204 rotates in a direction indicated by an arrow OPY1 around the rotation shaft 243, the pulley 210, the pulley 211 and the pulley 212, and the wire 301 and the wire 305 wound around the pulley 211 and the pulley 212 rotate together around the rotation shaft 243. As a result, the wire 301 and the wire 305 wound around the pulley 211 and the pulley 212 move in the directions W1a and W1b, respectively, and thus the first jaw 101 of the end tool 100 rotates in the direction indicated by an arrow EPY1.

Referring to FIG. 27, when the first handle 204 rotates in a direction indicated by an arrow OPY2 around the rotation shaft 243, the pulley 220, the pulley 221 and the pulley 222, and the wire 302 and the wire 306 wound therearound rotate together around the rotation shaft 243. As a result, the wire 302 and the wire 306 wound around the pulley 221 and the pulley 222 move in a direction opposite to the direction W1a and a direction opposite to the direction W1b, respectively, and thus the second jaw 102 of the end tool 100 rotates in the direction indicated by an arrow EPY2.

Figure 29:
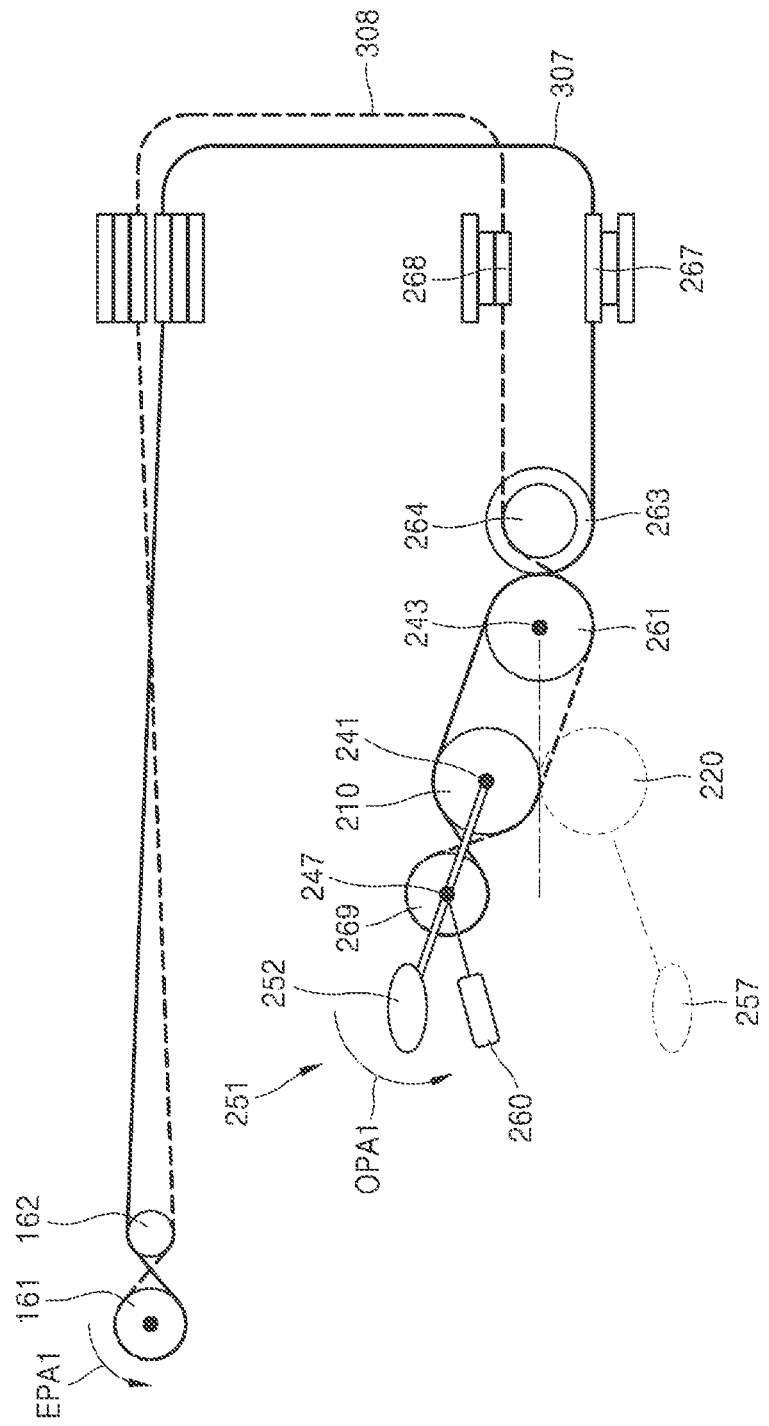
FIGS. 29, 30 and 31 are diagrams showing a configuration of a pulley and a wire associated with a cutting movement of the surgical instrument for electrocautery of FIG. 2, in detail with respect to each of a first jaw and a second jaw.
Figure 30:
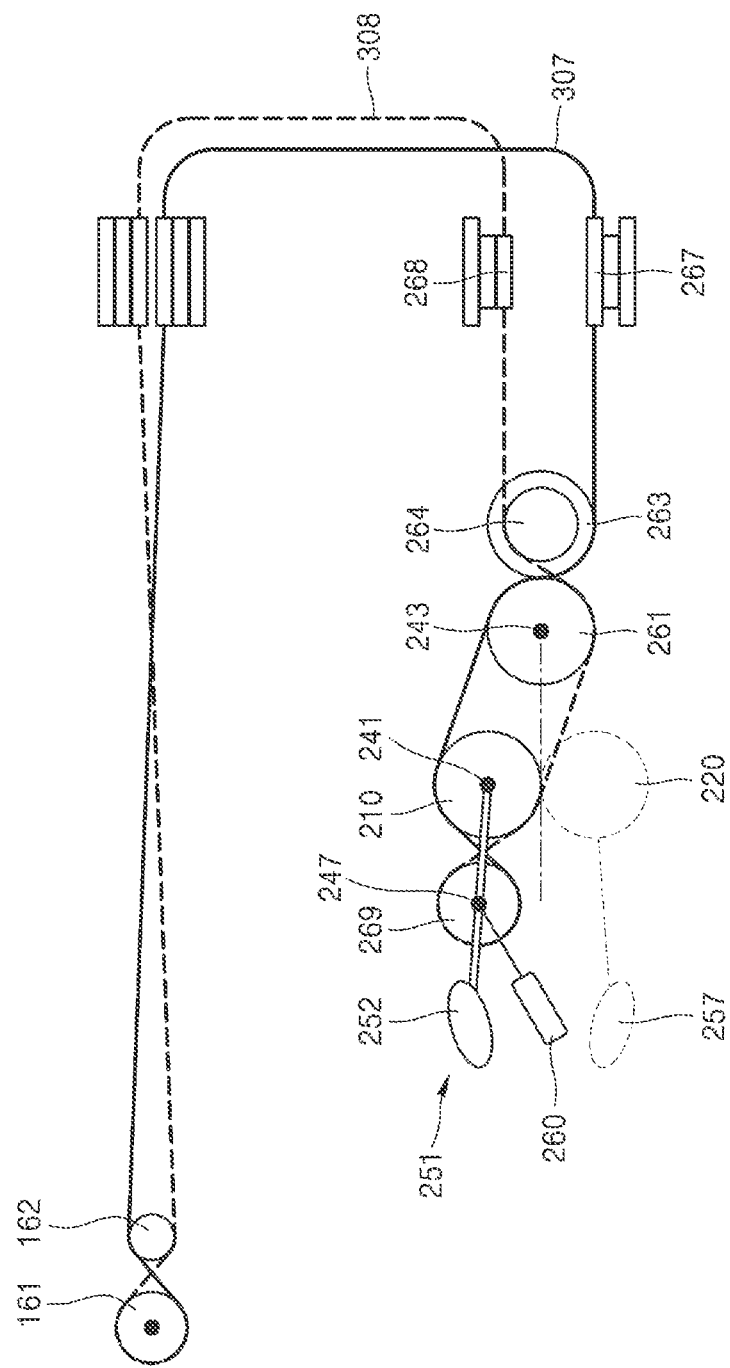
Figure 31:
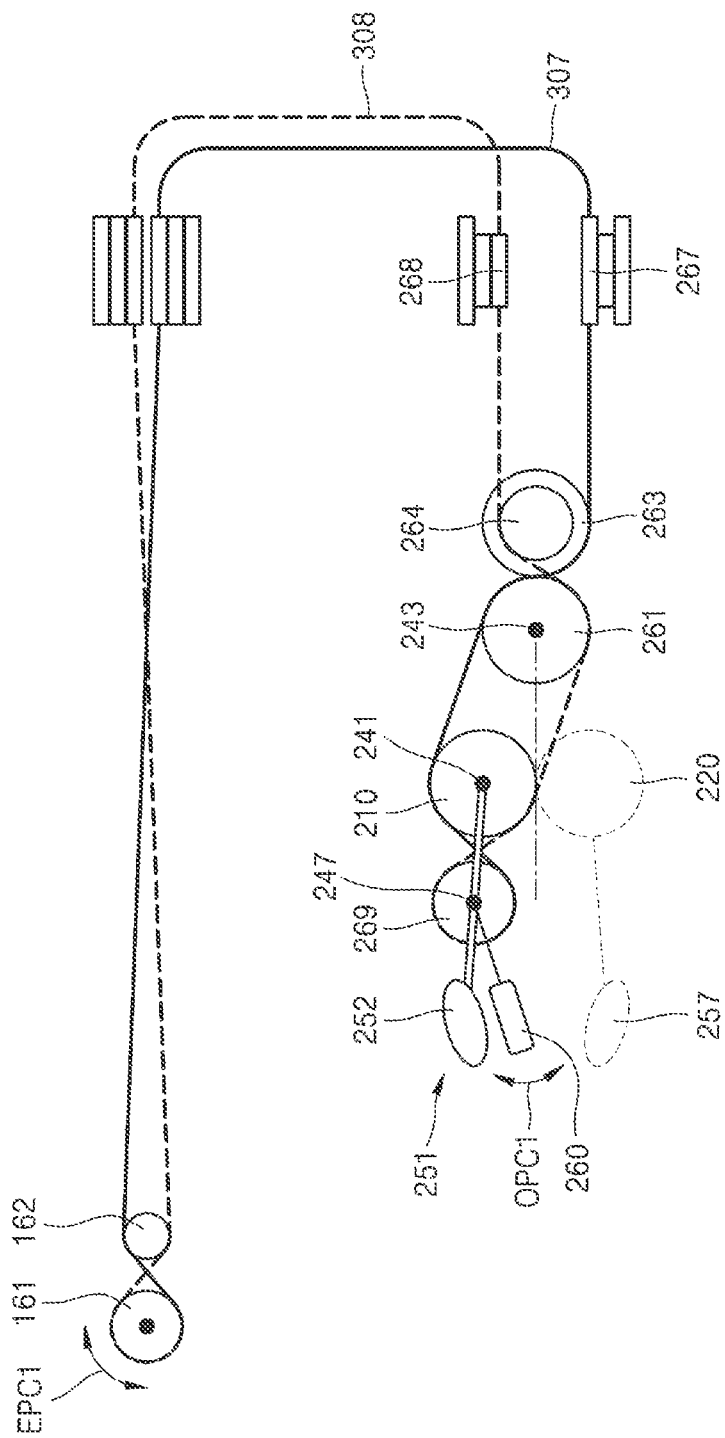

FIGS. 29, 30, and 31 are diagrams illustrating configurations of pulleys and wires associated with the cutting motion of the electric cauterization surgical instrument 10 according to an embodiment of the present disclosure shown in FIG. 2 for a first jaw and a second jaw, respectively. Here, FIGS. 29 to 31 are views mainly showing pulley and wires associated with the second jaw.

Here, FIGS. 29 to 30 show an actuation motion for closing two jaws, and FIGS. 30 to 31 show a cutting motion for cutting a tissue interposed between the two jaws.

First, the operation of wires in an actuation motion will be described.

Referring to FIGS. 29 and 30, when the first actuation extension 252 of the first actuation manipulation portion 251 rotates in the direction indicated by the arrow OPA1 around the rotation shaft 241, the pulley 210 connected to the first actuation extension 252 rotates, and a wire (refer to 301 of FIG. 25) and a wire (refer to 305 of FIG. 25) wound around the pulley 210 move. As a result, the first jaw 101 of the end tool 100 rotates in the direction indicated by the arrow EPA1.

In this case, an operation unit blade pulley 269 of the blade operation unit 260 is formed to be rotatable about the rotation shaft 241 together with the first actuation manipulation portion 251. Therefore, when the first actuation extension 252 rotates about the rotation shaft 241, the blade operation unit 260 also rotates about the rotation shaft 241 together with the first actuation manipulation portion 251.

As a result, during the actuation motion, when the pulley 111 rotates in the end tool 100, the blade pulley 161 also rotates together with the pulley 111, and thus, when the first jaw 101 rotates, the blade 171 rotates together with the first jaw 101.

Next, the operation of wires in a cutting motion will be described.

Referring to FIGS. 30 and 31, when the blade operation unit 260 rotates in the direction indicated by an arrow OPC1 around the rotation shaft 247, which is an operation unit cutting rotation axis, the operation unit blade pulley 269 and the wire 307 and the wire 308, which are blade wires wound around the operation unit blade pulley 269, rotate around a rotation shaft 247. As a result, the wire 307 and the wire 308 wound around the operation unit blade pulley 269 move, and thus the blade pulley 161 of the end tool 100 rotates in the direction indicated by an arrow EPC1.

On the other hand, when the blade operation unit 260 rotates, the operation unit blade pulley 269 rotates around the rotation shaft 247. In this case, the rotation of the blade operation unit 260 does not affect the first actuation manipulation portion 251.

As a result, when the operation unit blade pulley 269 rotates, the blade pulley 161 of the end tool 110 rotates alone regardless of the first jaw 101. When the blade pulley 161 rotates alone in the regard, the blade 171 is drawn out from the first jaw 101 (or while being drawn into the first jaw 101), and thus cutting of a tissue is performed.

Figure 33:
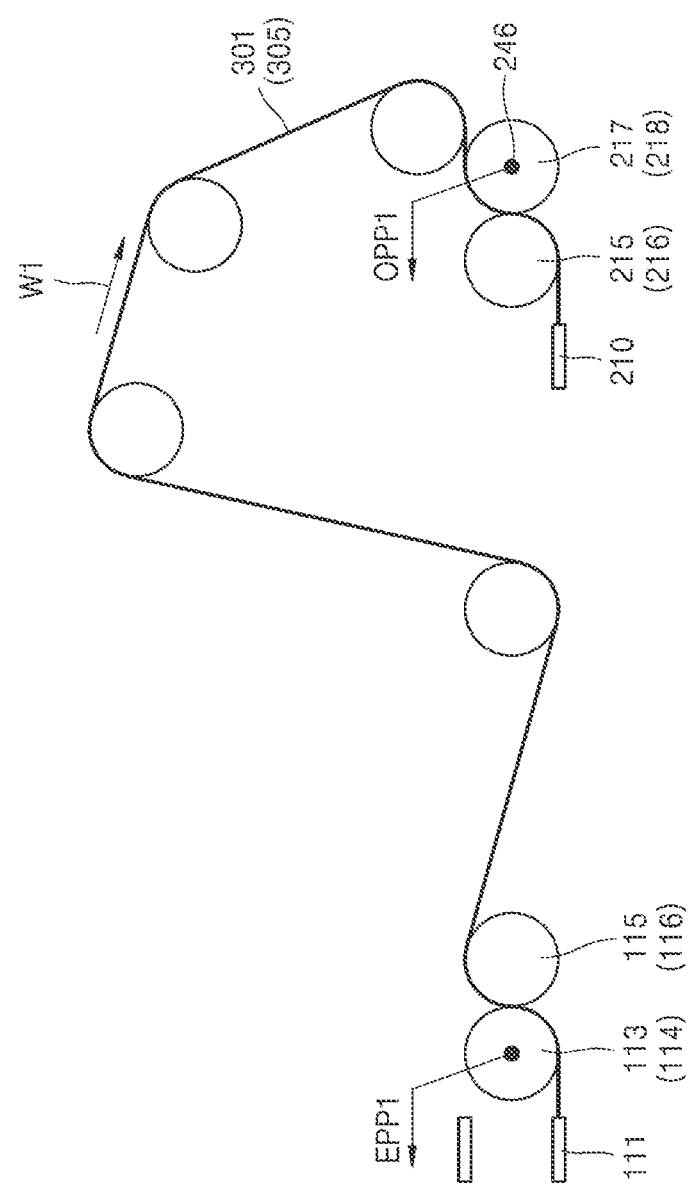
FIGS. 33, 34, and 35 are diagrams showing a configuration of a pulley and a wire associated with a pitch movement of the surgical instrument for electrocautery of FIG. 2, in detail with respect to each of a first jaw and a second jaw.
Figure 34:
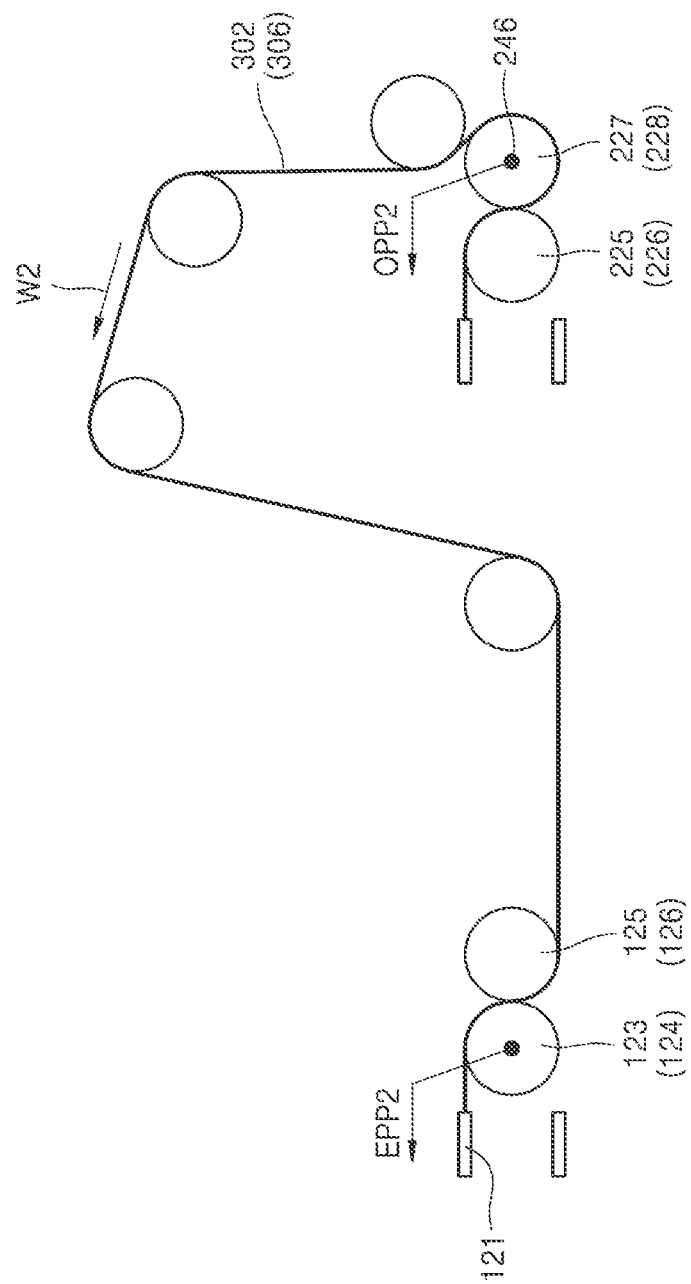
Figure 35:
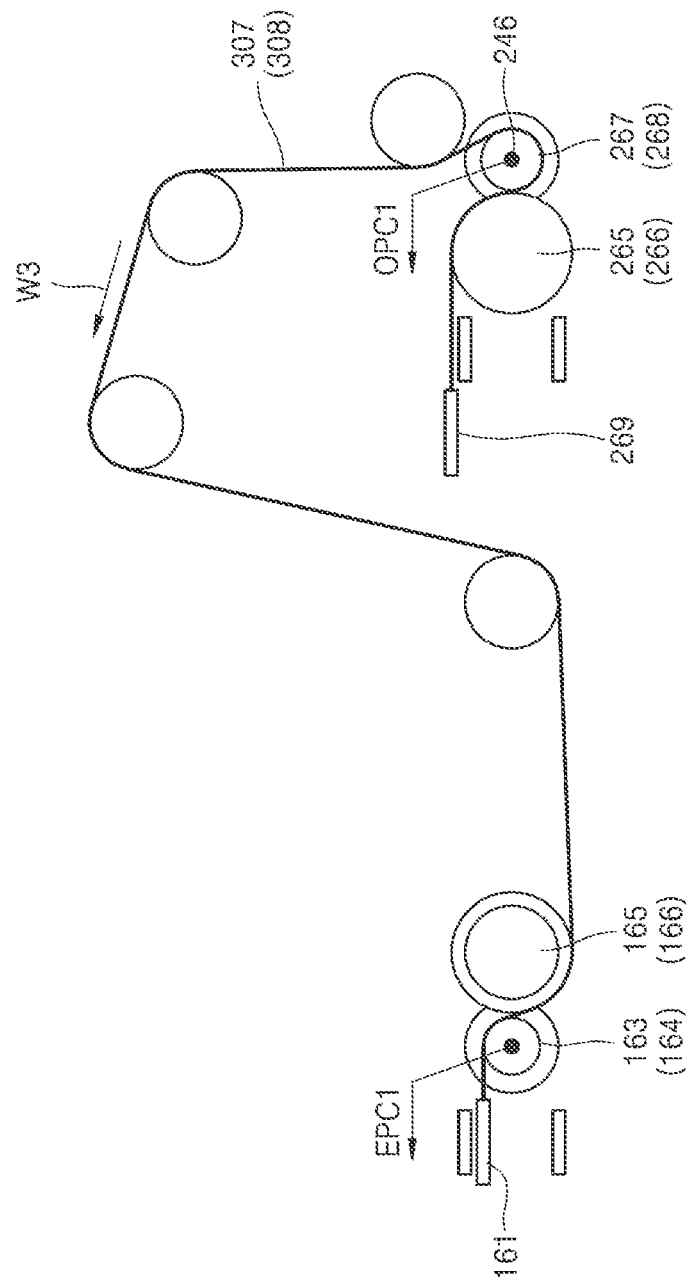

FIGS. 33, 34, and 35 are diagrams illustrating configurations of pulleys and wires associated with the pitch motion of the electric cauterization surgical instrument 10 according to an embodiment of the present disclosure shown in FIG. 2 for a first jaw and a second jaw, respectively. FIG. 33 is a diagram showing only pulleys and wires associated with the second jaw, and FIG. 34 is a diagram showing only pulleys and wires associated with the first jaw. FIG. 35 is a diagram showing only pulleys and wires associated with a blade pulley. As shown in FIG. 9 and the like, there are two pulleys associated with the pitch motion, and wires are wound in the same path, which are indicated as single lines in FIGS. 33 and 35. FIG. 32 is a perspective view showing the pitch motion of the surgical instrument of FIG. 2. Here, components associated with a cutting motion are omitted in FIG. 32.

Referring to FIG. 33, when the first handle 204 is rotated in the direction indicated by an arrow OPP1 around the rotation shaft 246, pulleys including the pulley 210, the pulley 215, and the pulley 217, and wires including the wire 301 wound therearound rotate around the rotation shaft 246 together. In this case, as shown in FIG. 24, the wire 301 and wire 305, which are first jaw wires, are wound on upper portions of the pulley 217 and the pulley 218, and thus the wire 301 and the wire 305 move in the direction indicated by an arrow W1. As a result, as described with reference to FIG. 5, the first jaw 101 of the end tool 100 rotates in the direction indicated by an arrow EPP1.

Referring to FIG. 34, when the first handle 204 is rotated in the direction indicated by an arrow OPP2 around the rotation shaft 246, pulleys including the pulley 220, the pulley 225, and the pulley 227, and wires including the wire 302 wound therearound rotate around the rotation shaft 246 together. In this case, as shown in FIG. 24, the wire 302 and wire 306, which are second jaw wires, are wound on lower portions of the pulley 227 and the pulley 228, and thus the wire 302 and the wire 306 move in the direction indicated by an arrow W2. As a result, as described with reference to FIG. 5, the second jaw 102 of the end tool 100 rotates in the direction indicated by an arrow EPP2.

Referring to FIG. 35, when the first handle 204 is rotated in the direction indicated by the arrow OPC1 around the rotation shaft 246, pulleys including the operation unit blade pulley 269, a pulley 265, and a pulley 267, and wires including the wire 307 and the wire 308 wound therearound rotate around the rotation shaft 246 together. In this case, the wire 307 and wire 308, which are blade wires, are wound on lower portions of the pulley 267 and a pulley 268, and thus the wire 307 and the wire 308 move in the direction indicated by an arrow W3. As a result, as described with reference to FIG. 5, the blade pulley 161 of the end tool 100 rotates in the direction indicated by the arrow EPC1.

As a result, during a pitch motion, when the pulley 111 rotates around the rotation shaft 143 in the end tool 100, the blade pulley 161 also rotates around the rotation shaft 143 together with the pulley 111. Therefore, when the first jaw 101 rotates, the blade 171 also pitch-rotates together with the first jaw 101.

Therefore, an actuation motion, a yaw motion, and a pitch motion may be manipulated independently of one another.

As described through FIG. 1, the actuation manipulation portion 203, yaw manipulation portion 202, and pitch manipulation portion 201 have their own rotation shafts located at the back of each manipulation portion, so it is configured the same as the joint configuration of the end tool, allowing the user to perform intuitively matching operations.

Especially, in the electric cauterization surgical instrument 10 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys, so that the wires wound on the pulley do not come into contact with each other, and the path of the wire that goes into the pulley and the wire that comes out is also formed safely, so the safety and efficiency of power transmission of the wire may be improved.

On the other hand, as described above, the yaw manipulation portion 202 and the actuation manipulation portion 203 are formed directly on the first handle 204. Therefore, when the first handle 204 rotates around the rotation shaft 246, the yaw manipulation portion 202 and the actuation manipulation portion 203 also rotate together with the first handle 204. Due to this, a coordinate system of the yaw manipulation portion 202 and the actuation manipulation portion 203 is not fixed, but continues to change relatively according to the rotation of the first handle 204. That is, in FIG. 2 and the like, the yaw manipulation portion 202 and the actuation manipulation portion 203 are illustrated as being parallel to a Z-axis. However, when the first handle 204 is rotated, the yaw manipulation portion 202 and the actuation manipulation portion 203 are not parallel to the Z-axis. That is, the coordinate system of the yaw manipulation portion 202 and the actuation manipulation portion 203 is changed according to the rotation of the first handle 204. However, in the present specification, for convenience of explanation, if there is no separate explanation, the coordinate system of the yaw manipulation portion 202 and the actuation manipulation portion 203 was described based on a state in which the first handle 204 is positioned vertically with respect to the connection portion 400 as illustrated in FIG. 2.

(Correlation Between Cutting Motion and Other Motions)

Hereinafter, the correlation between a cutting motion and other motions (pitch motion, yaw motion, and actuation motion) will be described.

First, during a pitch motion of the end tool 100, the blade pulley 161 also performs a pitch motion. In other words, when the pulley 111 and the pulley 121 perform a pitch motion in which the pulley 111 and the pulley 121 rotate in the same direction around the rotation shaft 143, the blade pulley 161 also needs to rotate in the same direction together with the pulley 111 and the pulley 121. Otherwise, the blade 171 relatively moves with respect to the first jaw 101.

Next, during a yaw motion of the end tool 100, the blade pulley 161 also performs a yaw motion. In other words, when the pulley 111 and the pulley 121 perform a yaw motion in which the pulley 111 and the pulley 121 rotate in the same direction around the rotation shaft 141, the blade pulley 161 also needs to rotate in the same direction together with the pulley 111 and the pulley 121. Otherwise, the blade 171 moves in relation to the first jaw 101.

Next, during an actuation motion of the end tool 100, the blade pulley 161 rotates together with the pulley 111. In other words, when the pulley 111 and the pulley 121 perform an actuation motion in which the pulley 111 and the pulley 121 rotate in opposite directions around the rotation shaft 141, the blade pulley 161 needs to rotate in the same direction together with the pulley 111. Otherwise, the blade 171 moves in relation to the first jaw 101.

Meanwhile, during a cutting motion of the end tool 100, the pulley 111 and the pulley 121 do not rotate. In other words, while the blade pulley 161 is rotating around the rotation shaft 141 and the blade 171 is being drawn outward from the first jaw 101 or drawn into the first jaw 101, the pulley 111 and the pulley 121 may not rotate. Otherwise, the first jaw 101 and the blade 171 move together, and the blade 171 is not drawn out from the first jaw 101, and thus cutting may not be performed.

As a result, when the pulley 111, which is a first jaw pulley, rotates, the blade pulley 161 connected to the blade 171 accommodated in the first jaw 101 may also rotate together with the pulley 111. On the other hand, the pulley 111 and the pulley 121 may be formed to maintain their positions without rotation when the blade pulley 161 rotates for cutting. The correlation between a cutting motion and the other motions (a yaw motion and an actuation motion) is as described above.

In other words, the pulley 111 and the pulley 121 may be independent of the rotation of the blade pulley 161. In other words, even when the blade pulley 161 is rotated by blade wires, the pulley 111 and the pulley 121 may not rotate. Conversely, the blade pulley 161 may be dependent on the rotation of the pulley 111 and the pulley 121. In other words, the blade pulley 161 may be formed to rotate together with the pulley 111 or the pulley 121 when the pulley 111 or the pulley 121 is rotated by jaw wires.

Figure 36:
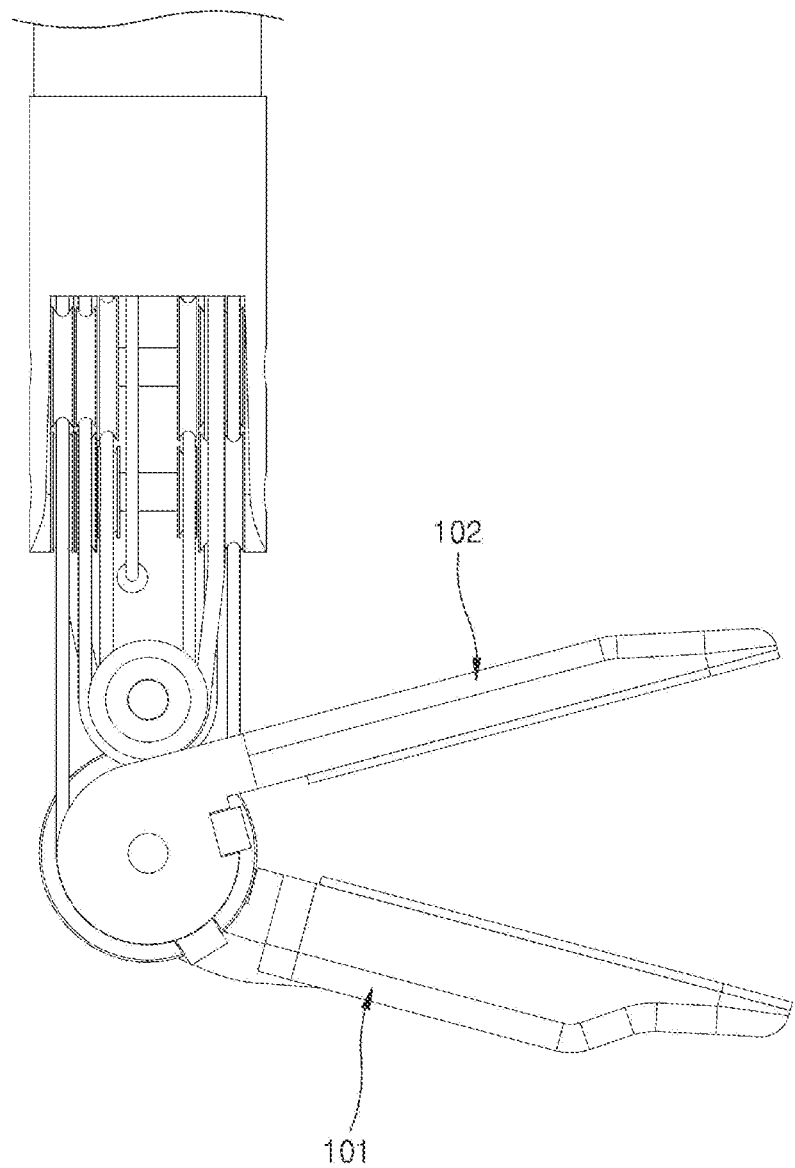
FIGS. 36 and 37 are plan views illustrating a yaw-rotated state of the end tool of the surgical instrument for electrocautery of FIG. 2.
Figure 37:
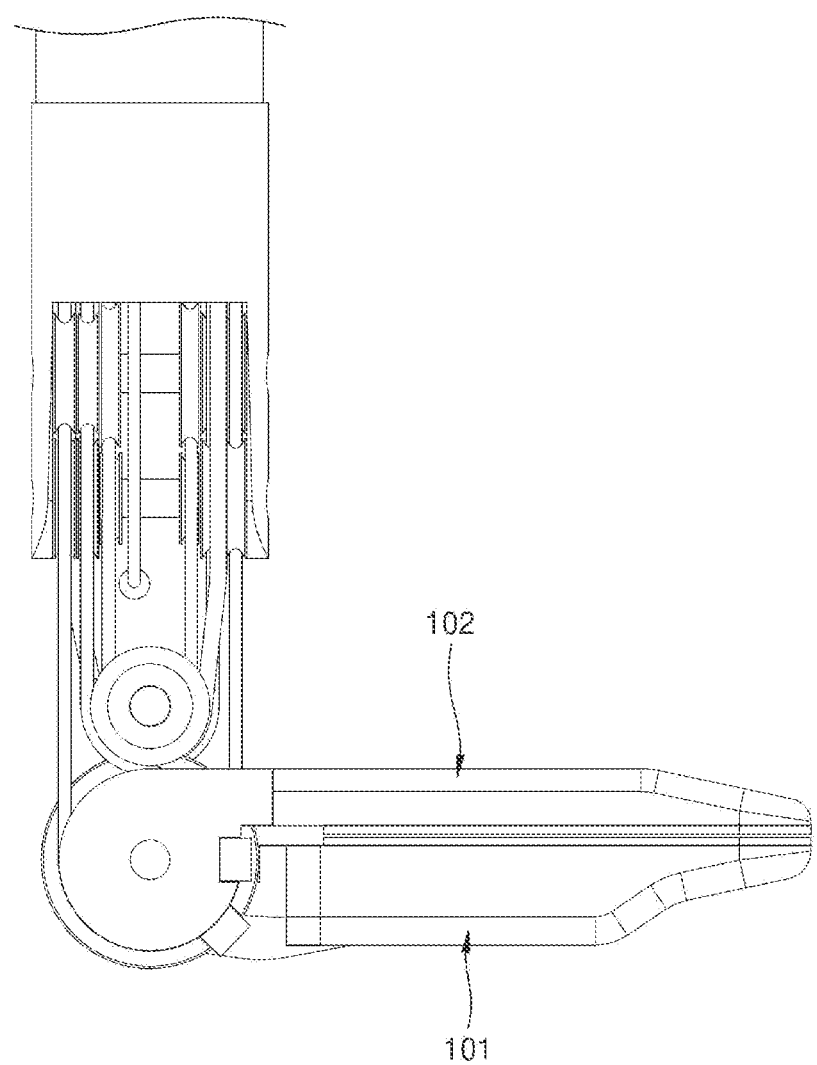

FIG. 36 is a diagram showing a state in which jaws are yaw-rotated by +90°, and FIG. 37 is a diagram showing a process of performing an actuation motion in the state in which jaws are yaw-rotated by +90°.

Figure 38:
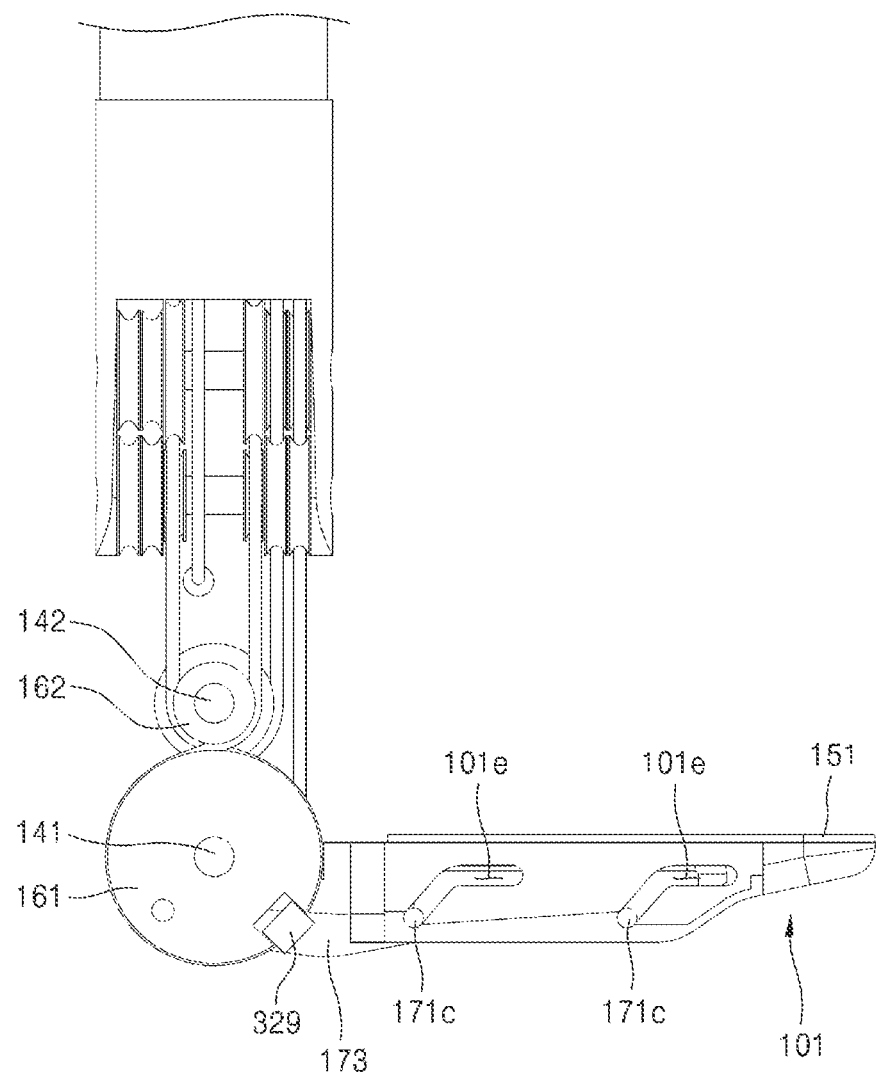
FIGS. 38, 39, and 40 are plan views illustrating a cutting movement of the end tool of the surgical instrument for electrocautery of FIG. 2, that is, a process of performing a cutting movement while jaws are yaw-rotated by +90°.
Figure 39:
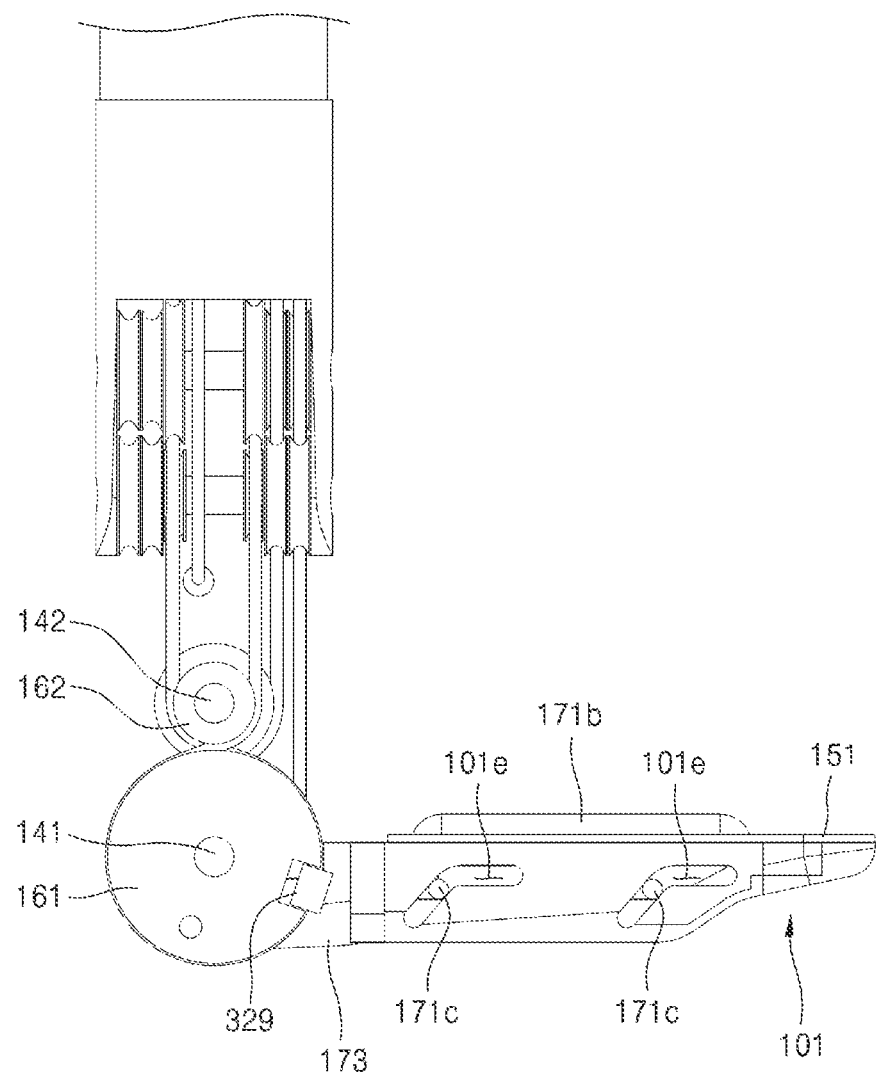
Figure 40:
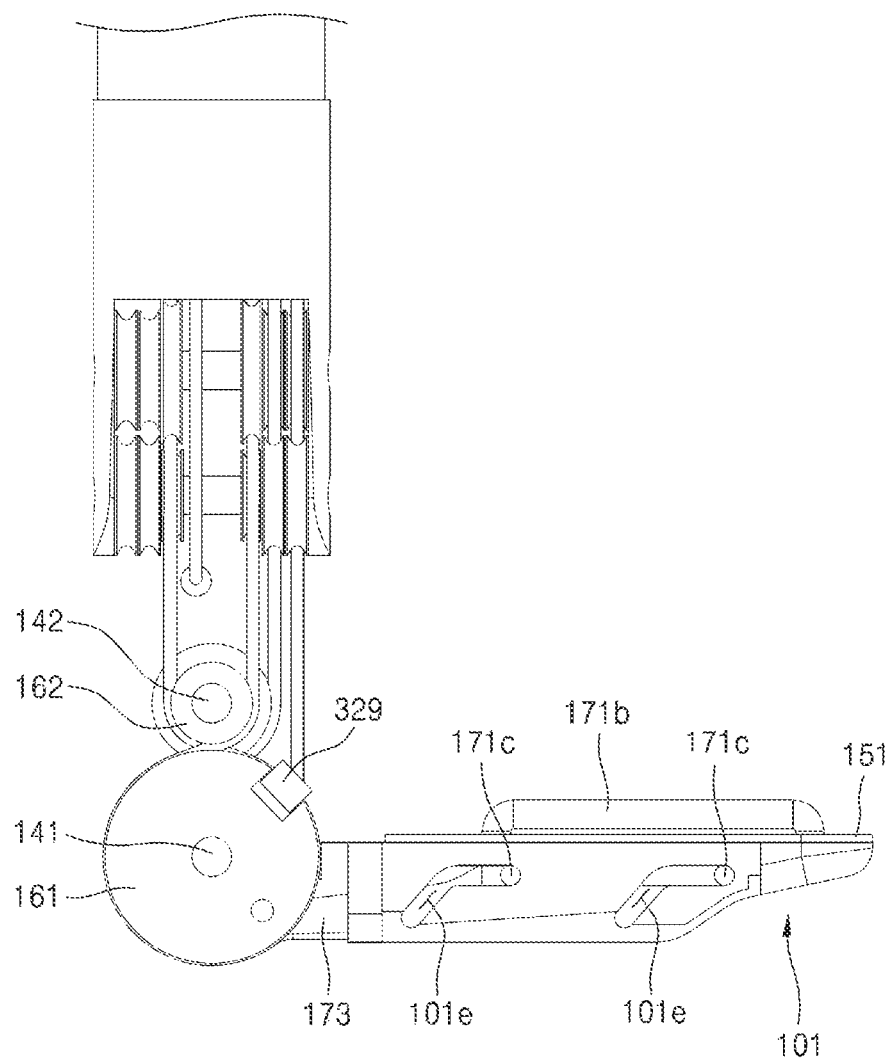

FIGS. 38, 39, and 40 are plan views showing a cutting motion of an end tool of the electric cauterization surgical instrument of FIG. 2 and show a process of performing a cutting motion in a state in which the jaws are yaw-rotated by +90°. As shown in FIGS. 38 to 40, the end tool of the electric cauterization surgical instrument according to a first embodiment of the present disclosure is formed to be capable of normally performing a cutting motion even in a state in which the jaws are yaw-rotated by +90°.

Figure 41:
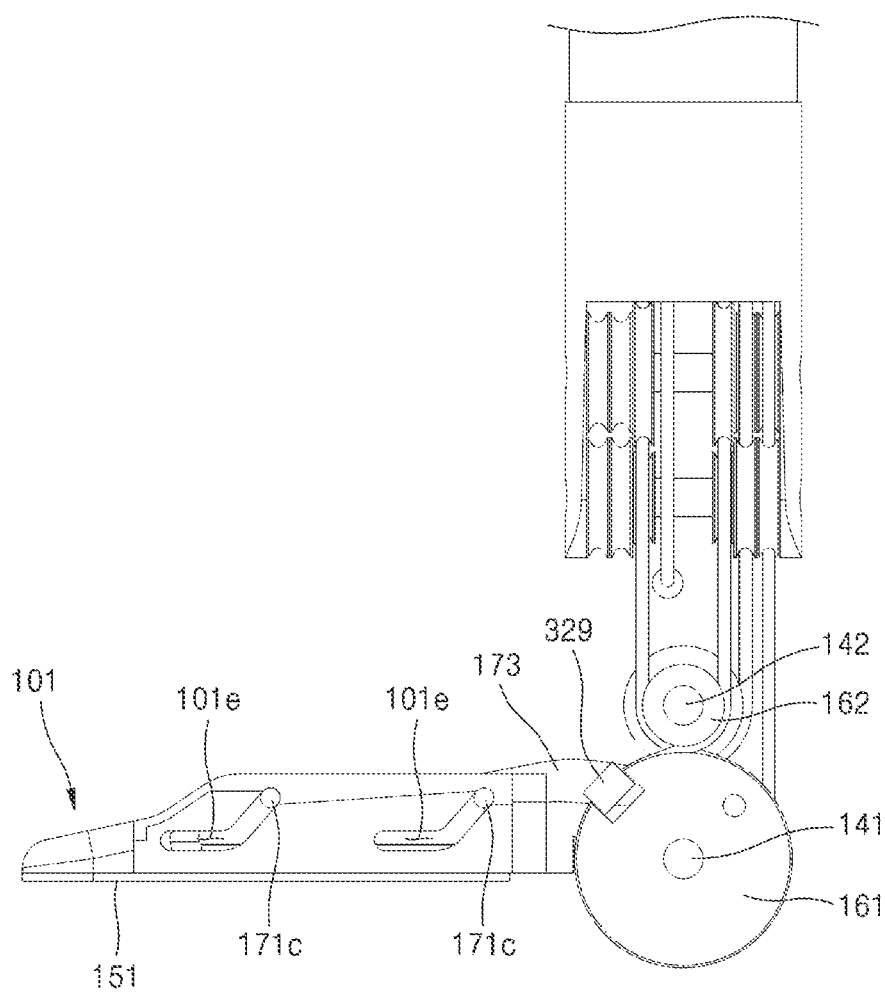
FIGS. 41, 42, and 43 are plan views illustrating a cutting movement of the end tool of the surgical instrument for electrocautery of FIG. 2, that is, a process of performing a cutting movement while jaws are yaw-rotated by −90°.
Figure 42:
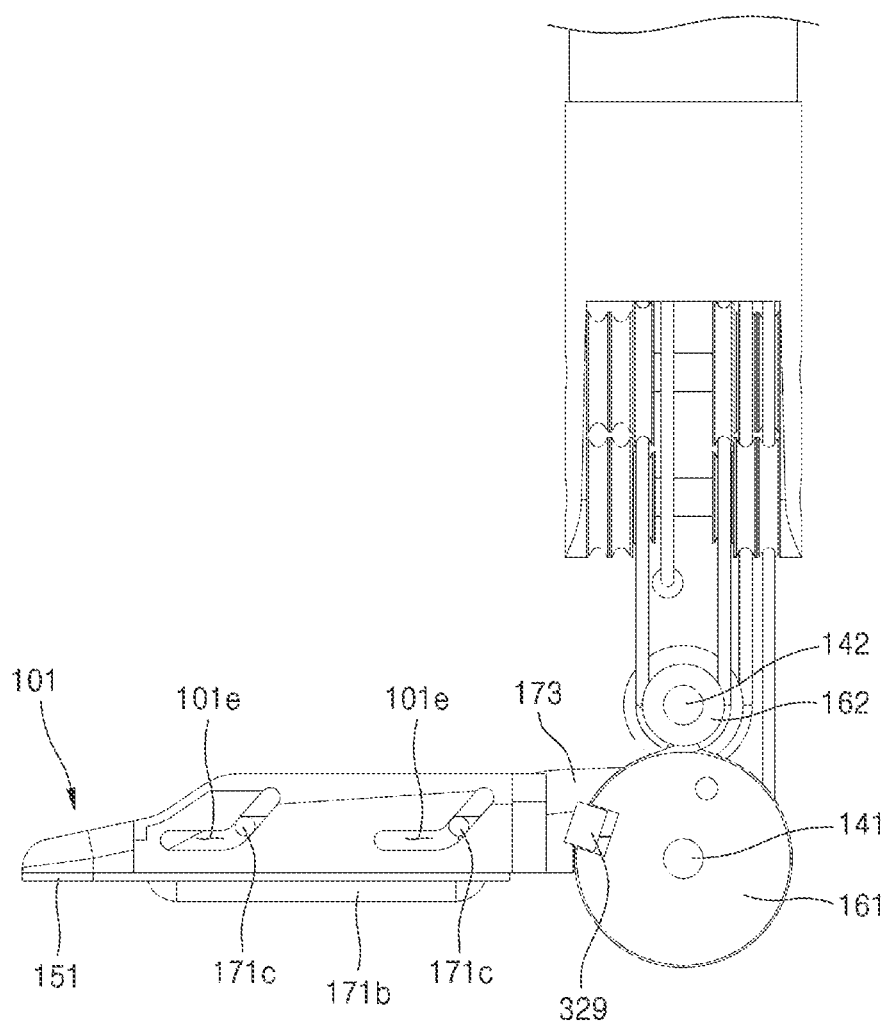
Figure 43:
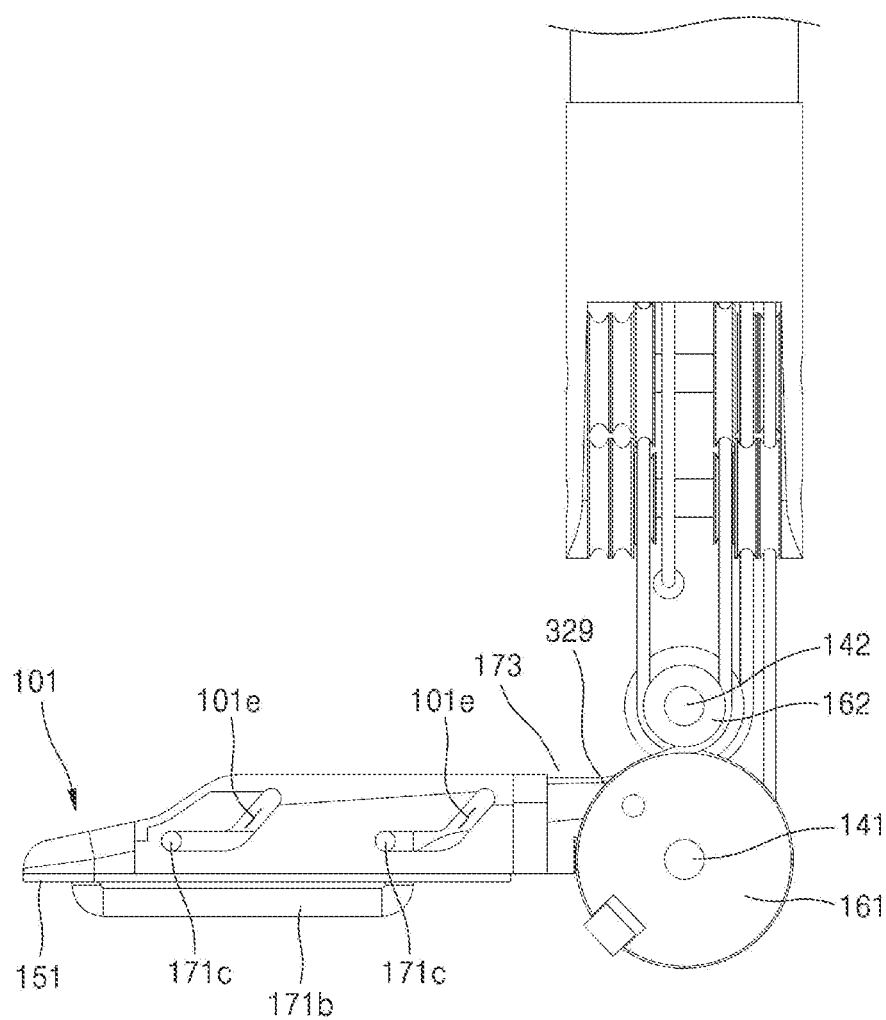

FIGS. 41, 42, and 43 are plan views showing a cutting motion of the end tool of the electric cauterization surgical instrument of FIG. 2 and show a process of performing a cutting motion in a state in which the jaws are yaw-rotated by −90°. As shown in FIGS. 41 to 43, the end tool of the electric cauterization surgical instrument according to a first embodiment of the present disclosure is formed to be capable of normally performing a cutting motion even in a state in which the jaws are yaw-rotated by −90°.

Figure 44:
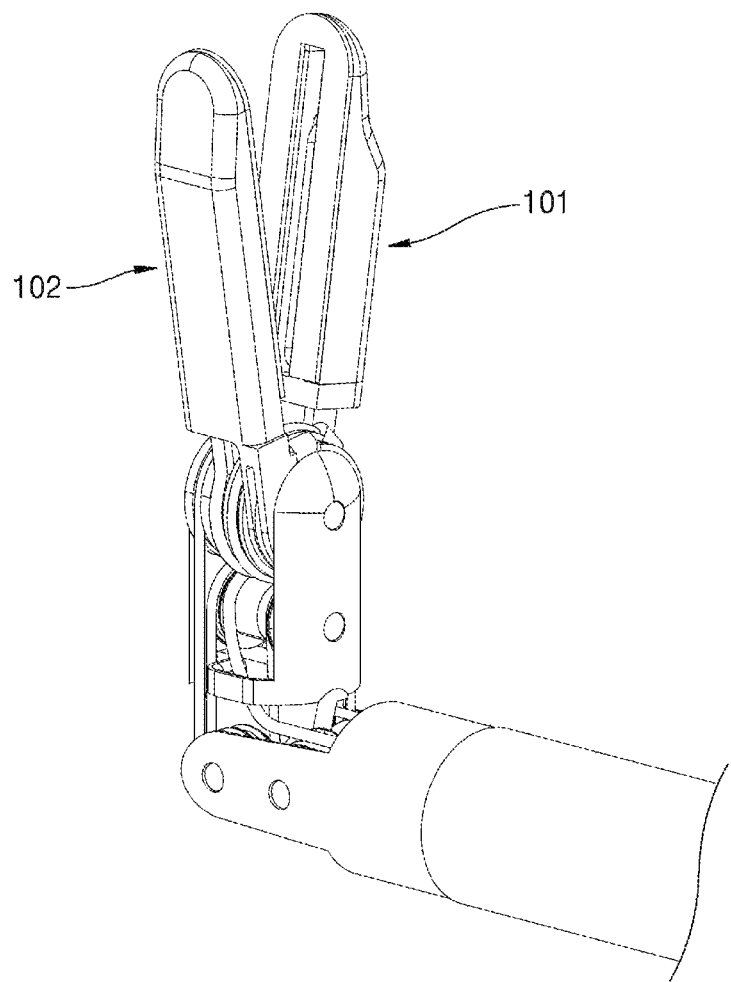
FIG. 44 is a plan view illustrating a pitch-rotated state of the end tool of the surgical instrument for electrocautery of FIG. 2.
Figure 45:
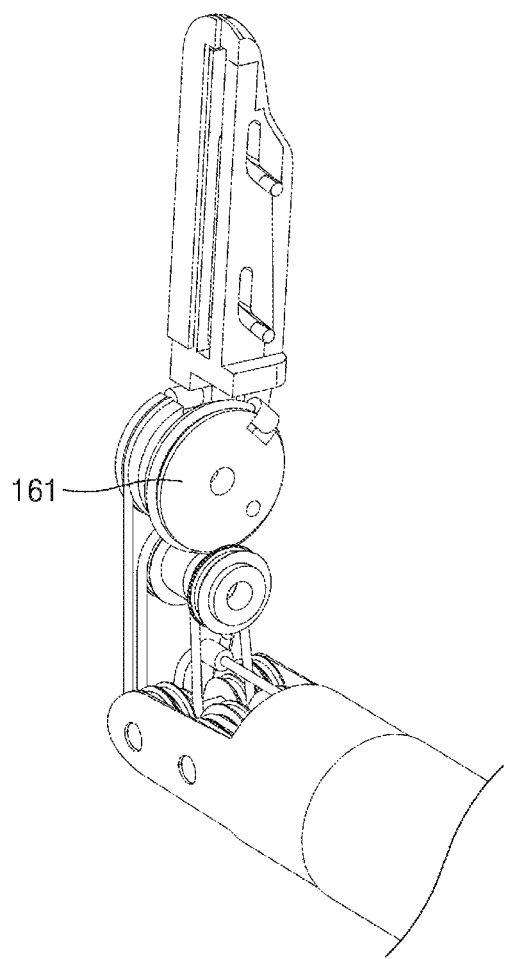
FIGS. 45, 46, and 47 are plan views illustrating a cutting movement of an end tool of the surgical instrument for electrocautery of FIG. 2, that is, a process of performing a cutting movement while jaws are pitch-rotated by −90°.
Figure 46:
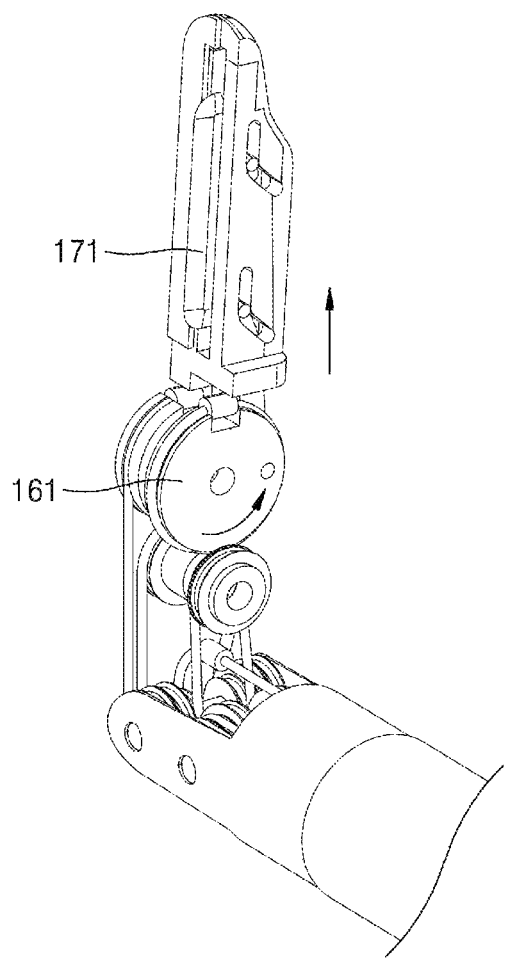
Figure 47:
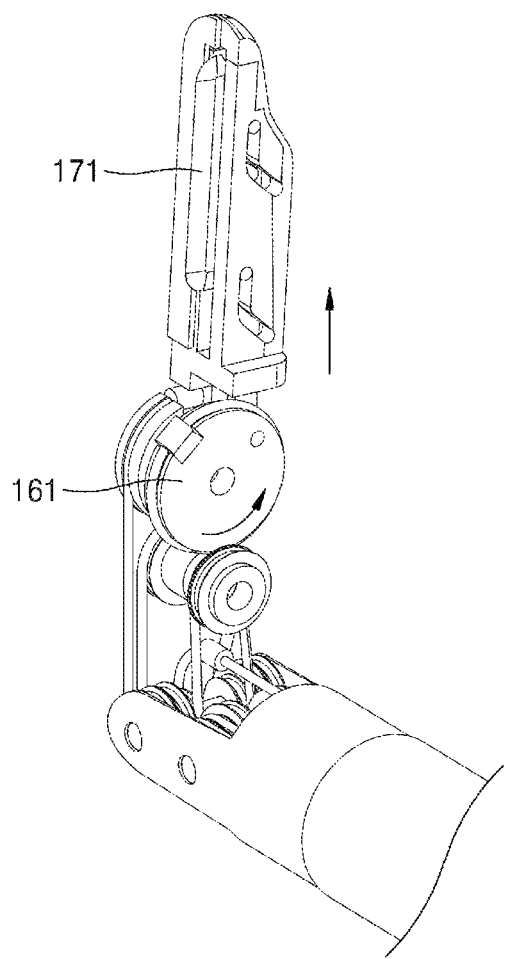

Meanwhile, FIG. 44 is a diagram showing a state in which jaws are pitch-rotated by −90°. FIGS. 45, 46, and 47 are perspective views showing a cutting motion of the end tool of the electric cauterization surgical instrument of FIG. 2 and show a process of performing a cutting motion in a state in which the jaws are pitch-rotated by −90°. As shown in FIGS. 45 to 47, the end tool of the electric cauterization surgical instrument according to the first embodiment of the present disclosure is formed to be capable of normally performing a cutting motion even in a state in which the jaws are pitch-rotated by −90°.

Figure 48:
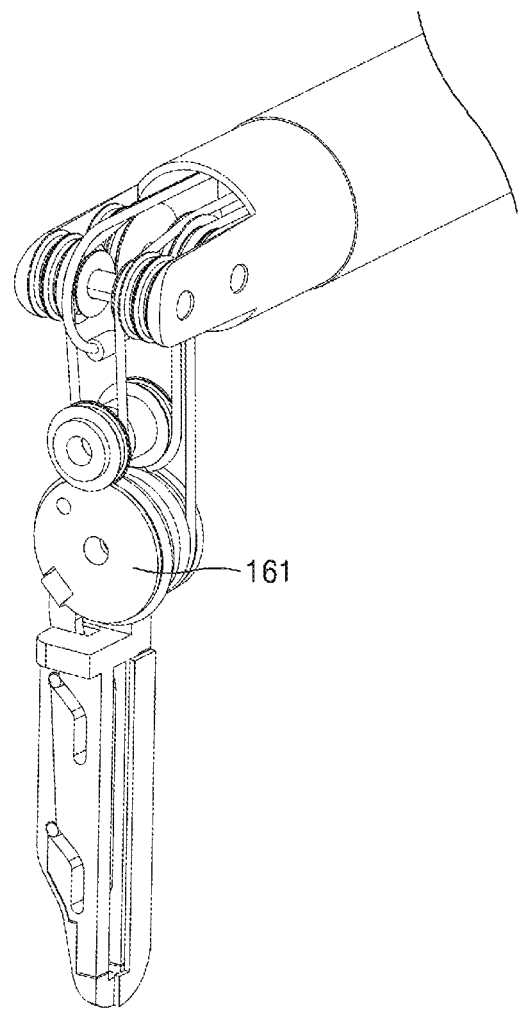
FIGS. 48, 49, and 50 are plan views illustrating a cutting movement of the end tool of the surgical instrument for electrocautery of FIG. 2, that is, a process of performing a cutting movement while jaws are pitch-rotated by +90°.
Figure 49:
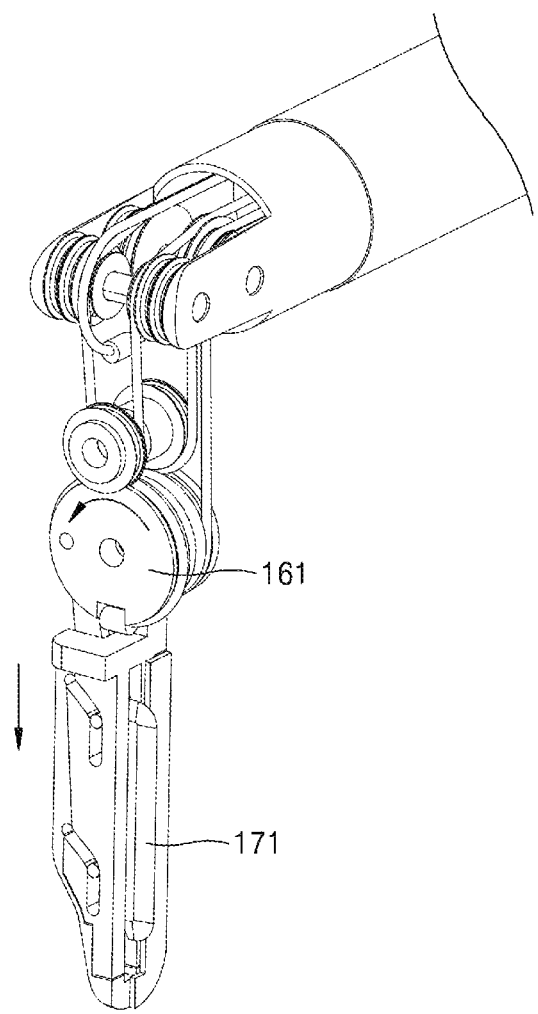
Figure 50:
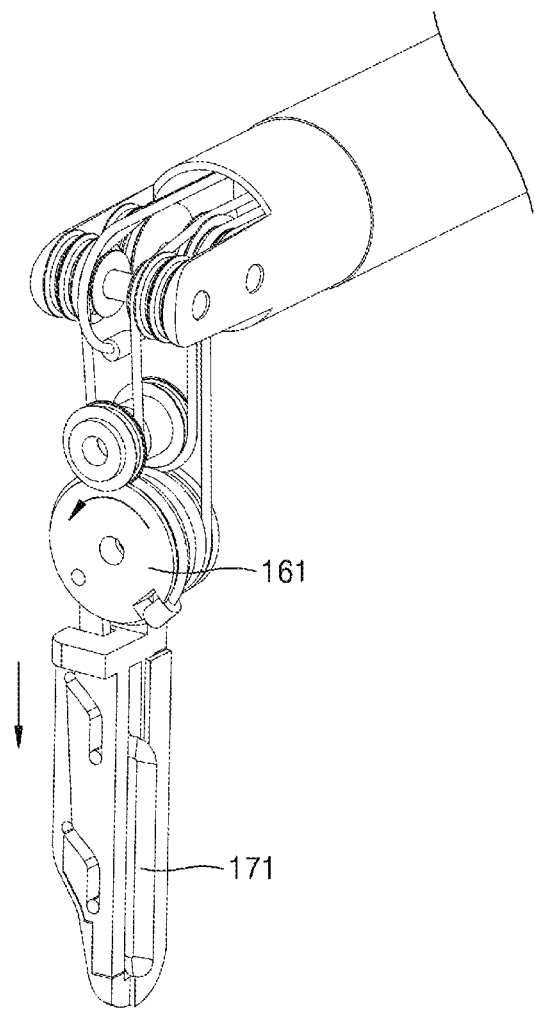

FIGS. 48, 49, and 50 are perspective views showing a cutting motion of the end tool of the electric cauterization surgical instrument of FIG. 2 and show a process of performing a cutting motion in a state in which the jaws are pitch-rotated by +90°. As shown in FIGS. 48 to 50, the end tool of the electric cauterization surgical instrument according to the first embodiment of the present disclosure is formed to be capable of normally performing a cutting motion even in a state in which the jaws are pitch-rotated by +90°.

Figure 51:
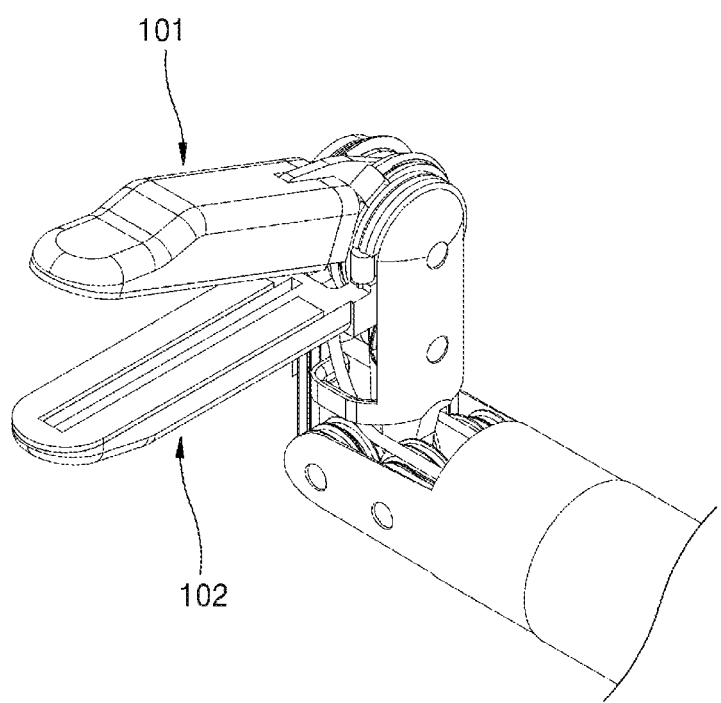
FIG. 51 is a plan view illustrating a pitch-rotated and yaw-rotated state of the end tool of the surgical instrument for electrocautery of FIG. 2.
Figure 52:
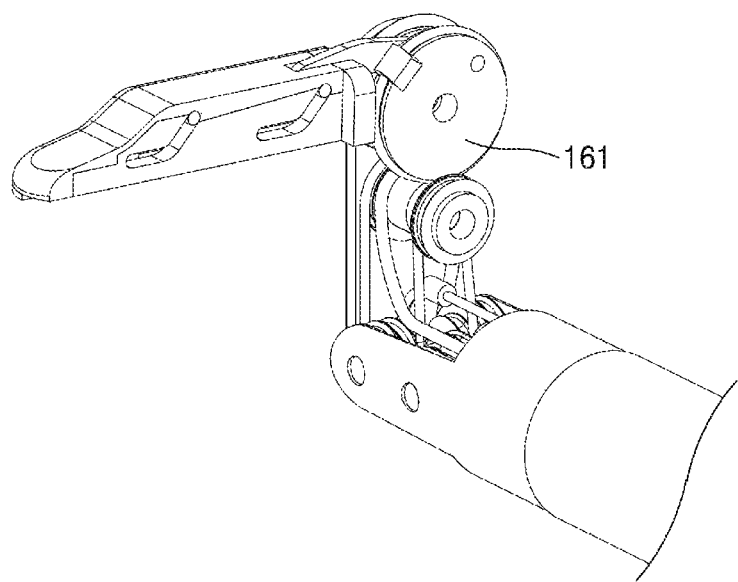
FIGS. 52, 53, and 54 are perspective views illustrating a cutting movement of the end tool of the surgical instrument for electrocautery of FIG. 2, that is, an aspect of performing the cutting movement while jaws are pitch-rotated by −90° and at the same time, yaw-rotated by +90°.
Figure 53:
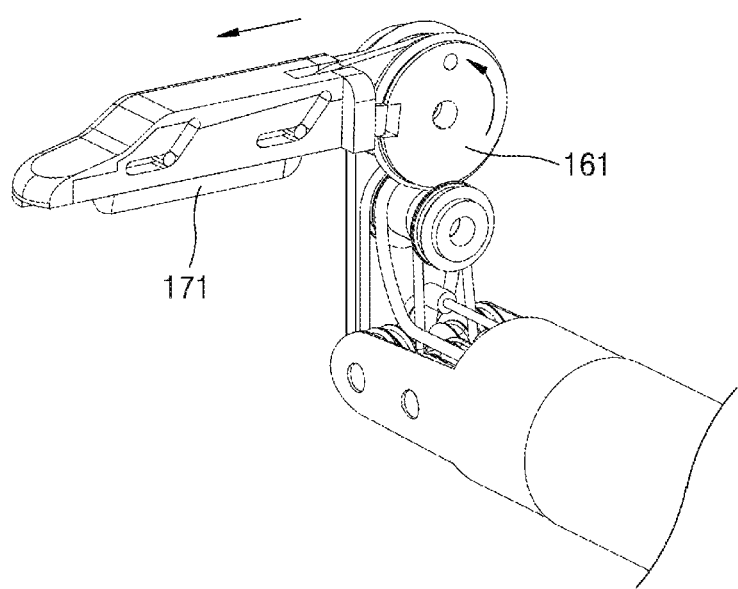
Figure 54:
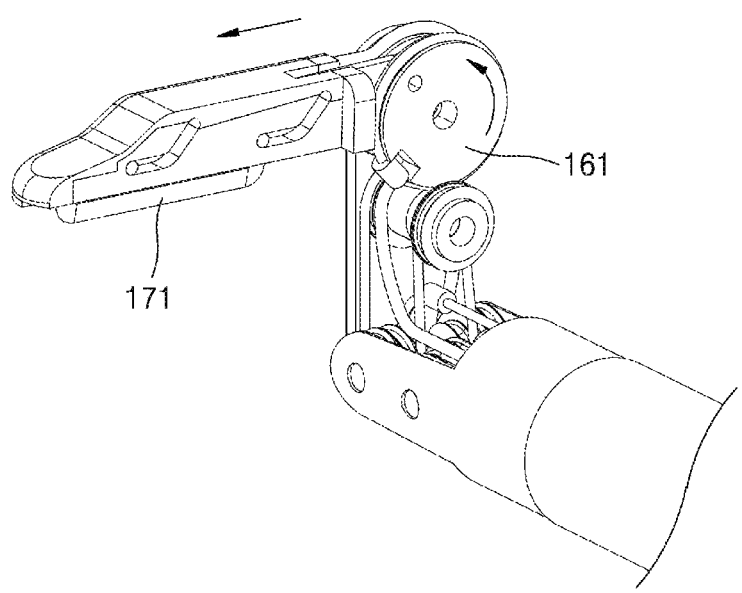

On the other hand, FIG. 51 is a diagram showing a state in which jaws are pitch-rotated by −90° and yaw-rotated by +90° at the same time, and FIGS. 52, 53 and 54 are perspective views showing a cutting motion of the electric cauterization surgical instrument of FIG. 2 and show a process of performing a cutting motion in a state in which the jaws are pitch-rotated by −90° and yaw-rotated by +90° at the same time. As shown in FIGS. 52 to 54, the end tool of the electric cauterization surgical instrument according to the first embodiment of the present disclosure is formed to be capable of normally performing a cutting motion even in a state in which the jaws are pitch-rotated by −90° and yaw-rotated by +90° at the same time.

Figure 55:
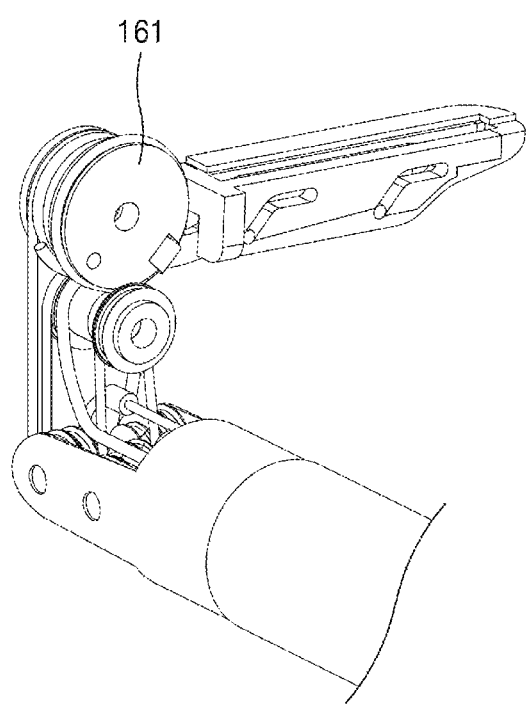
FIGS. 55, 56, and 57 are perspective views illustrating a cutting movement of the end tool of the surgical instrument for electrocautery of FIG. 2, that is, an aspect of performing the cutting movement while jaws are pitch-rotated by −90° and at the same time, yaw-rotated by −90°.
Figure 56:
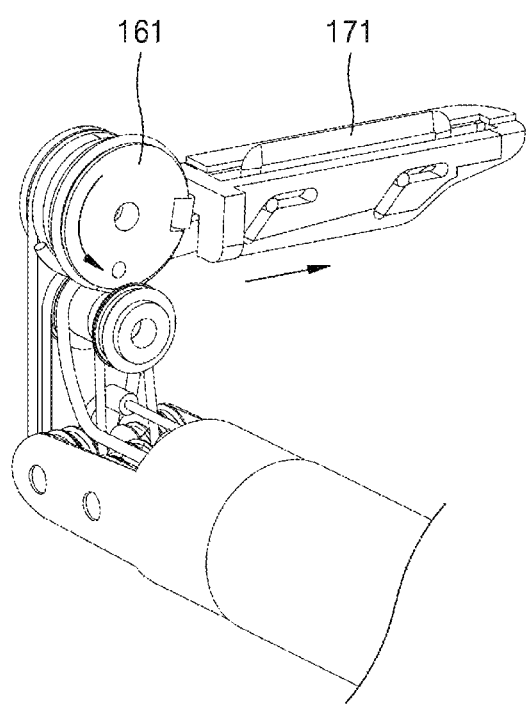
Figure 57:
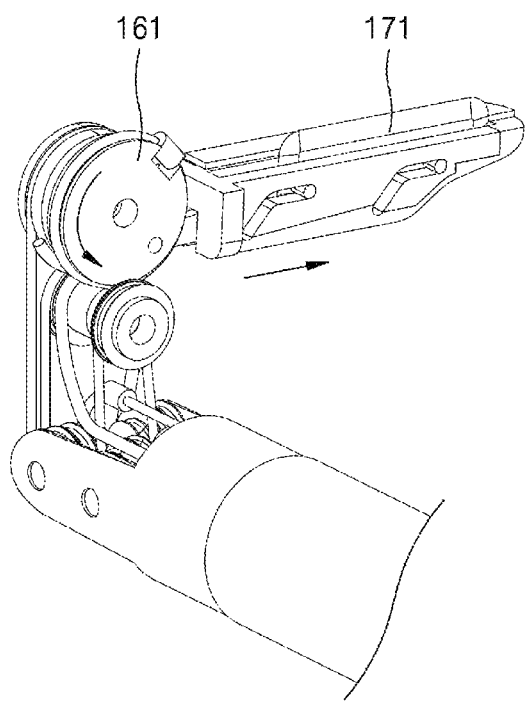

FIGS. 55, 56, and 57 are perspective views showing a cutting motion of the end tool of the electric cauterization surgical instrument of FIG. 2 and show a process of performing a cutting motion in a state in which the jaws are pitch-rotated by −90° and yaw-rotated by −90° at the same time. As shown in FIGS. 55 to 57, the end tool of the electric cauterization surgical instrument according to the first embodiment of the present disclosure is formed to be capable of normally performing a cutting motion even in a state in which the jaws are pitch-rotated by −90° and yaw-rotated by −90° at the same time.

EMBODIMENTS OF DISCLOSURE

First Modified Example of the First Embodiment—Engrave

Hereinafter, an end tool 500 of a surgical instrument according to a first modified example of the first embodiment of the present disclosure will be described below. Here, the end tool 500 of the surgical instrument according to the first modified example of the first embodiment of the present disclosure is different from the end tool (see 100 of FIG. 2, etc.) of the surgical instrument according to the first embodiment of the present disclosure, in view of a configuration of an end tool hub 580 functioning as an auxiliary pulley. The different structure from that of the first embodiment will be described later in more detail.

Figure 58:
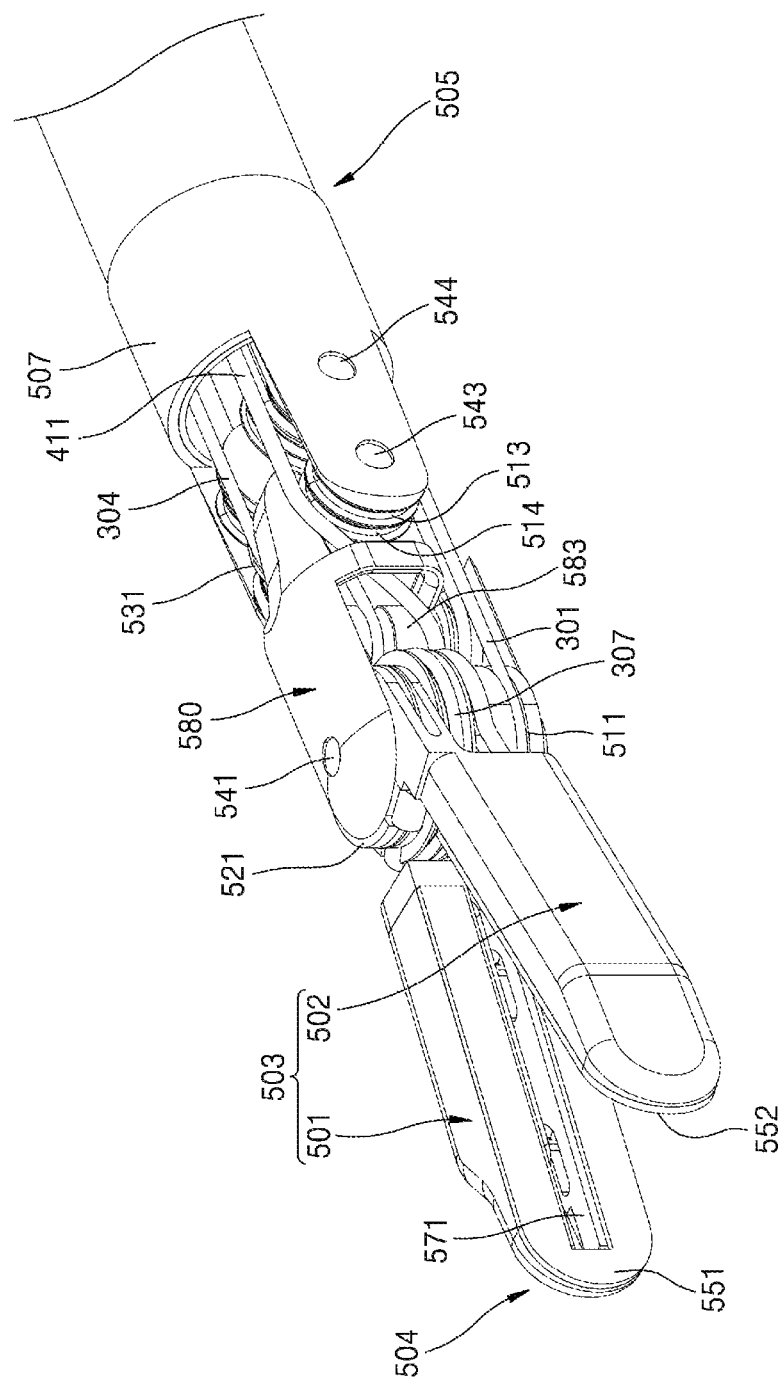
FIGS. 58 to 63 are diagrams illustrating an end tool of a surgical instrument for electrocautery according to a first modified example of a first embodiment of the present disclosure.
Figure 59:
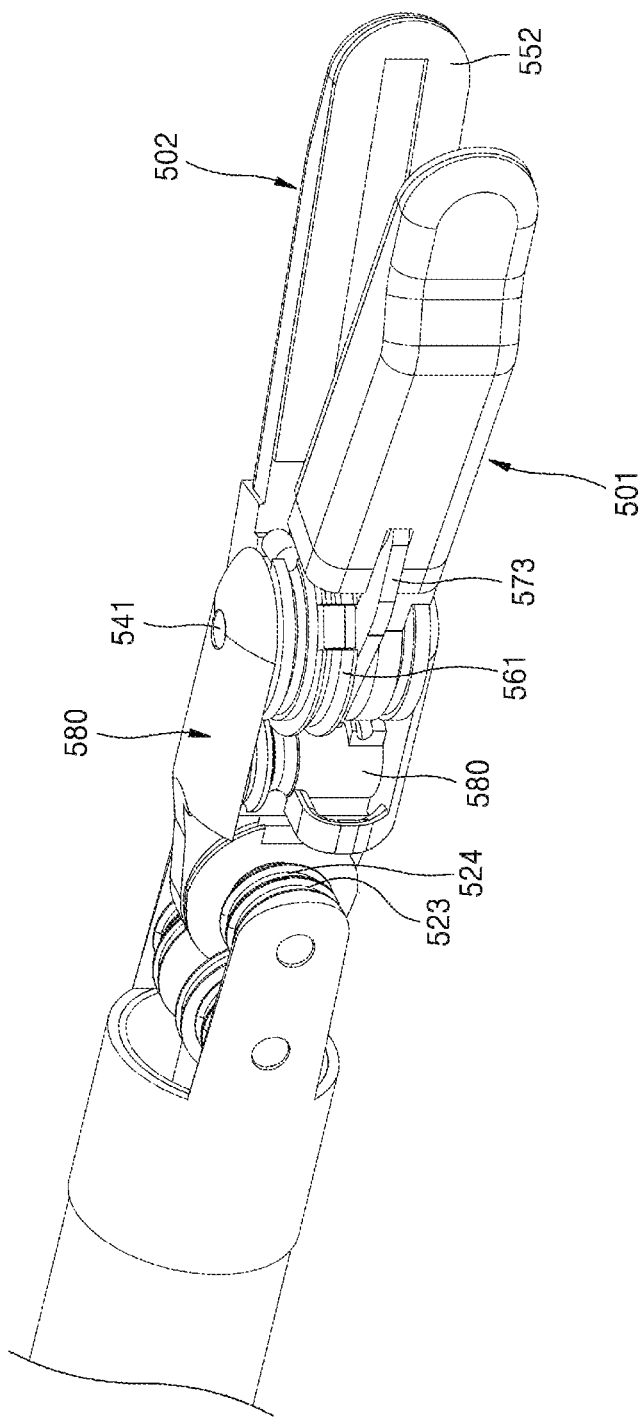
Figure 60:
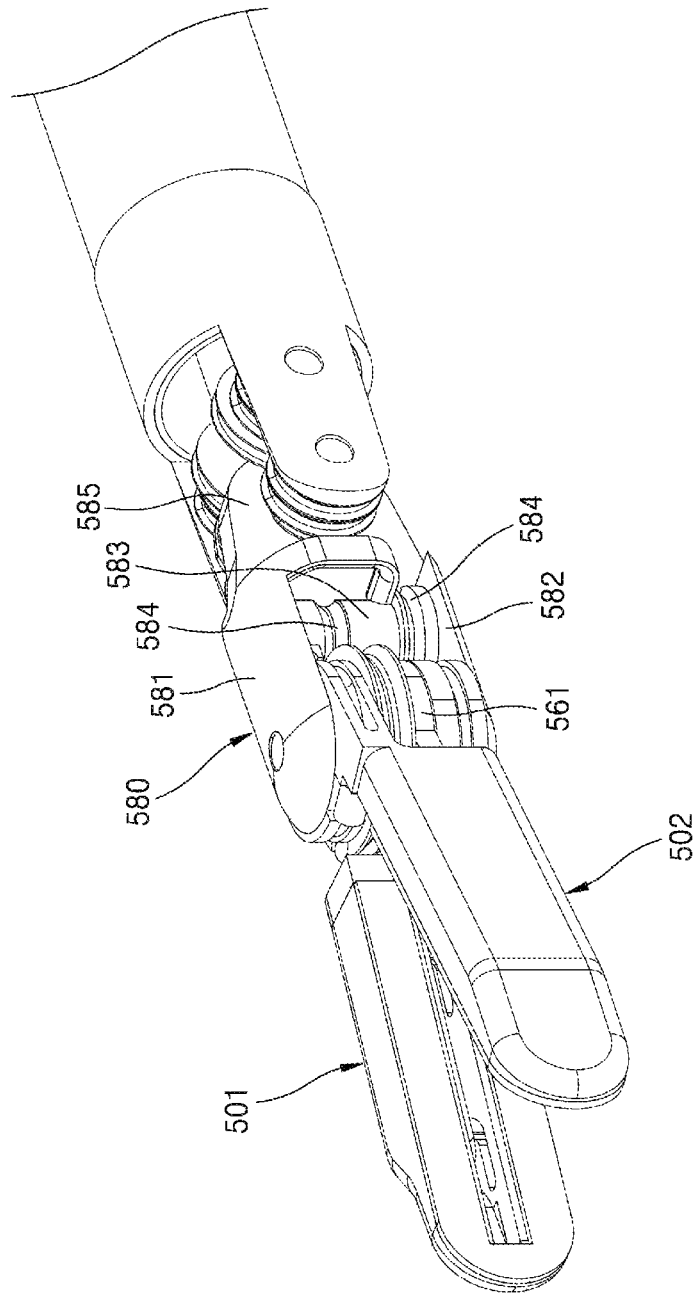
Figure 61:
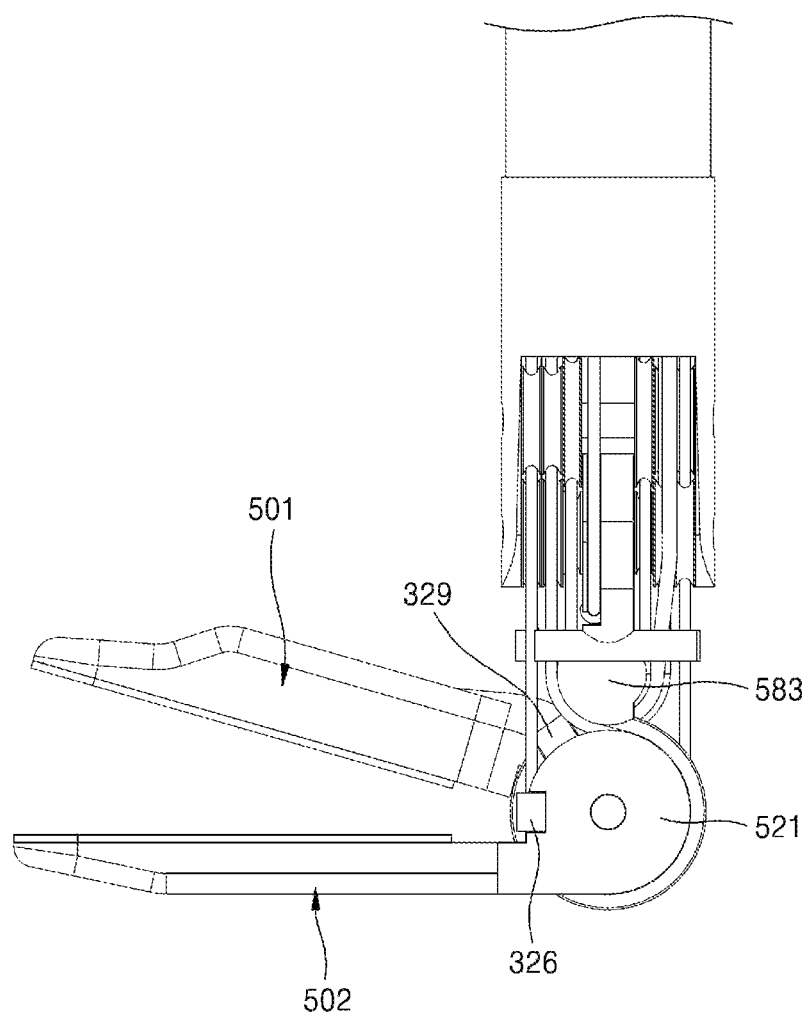
Figure 62:
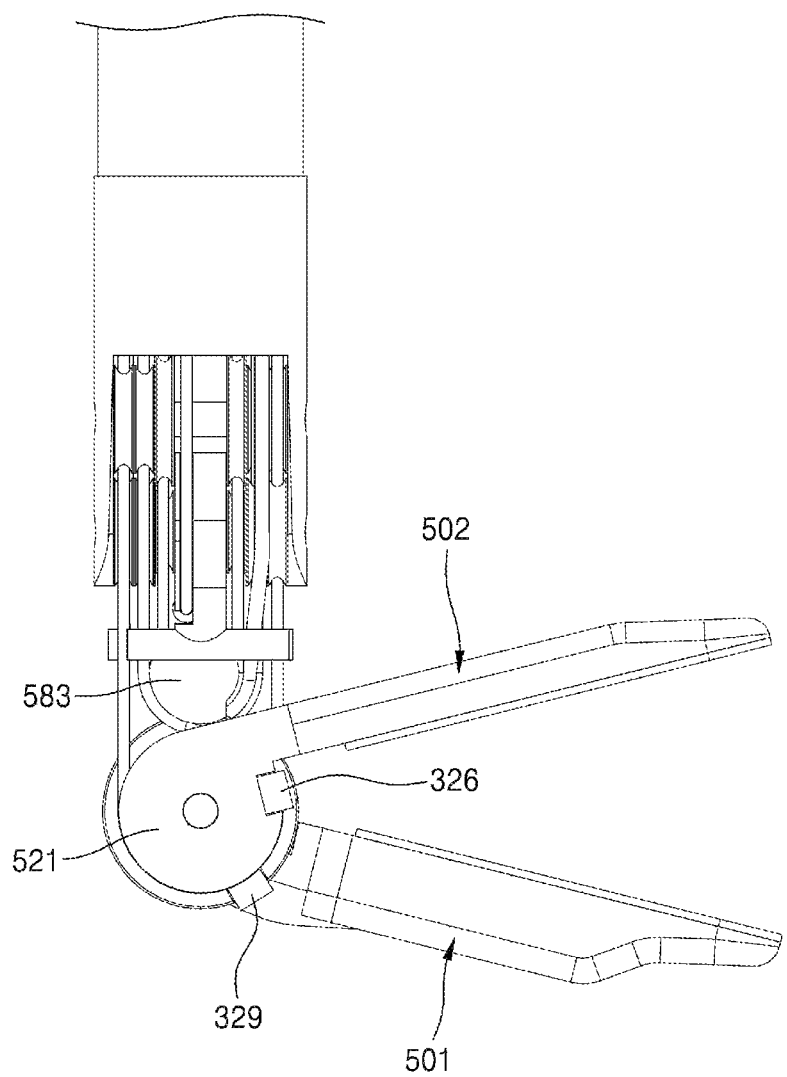
Figure 63:
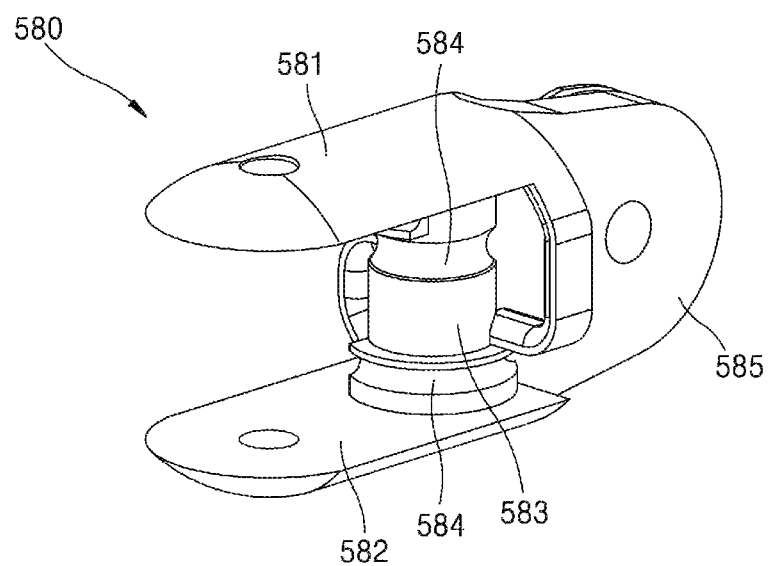

FIGS. 58 to 60 are perspective views of an end tool of a surgical instrument for electrocautery according to the first modified example of the first embodiment of the present disclosure, FIG. 61 is a diagram showing a state in which jaws are yaw-rotated by 90° in a clockwise direction, and FIG. 62 is a diagram showing a state in which jaws are yaw-rotated by 90° in a counter-clockwise direction. FIG. 63 is a magnified perspective view illustrating an end tool hub of a surgical instrument for electrocautery of FIG. 58.

Here, FIGS. 59 and 60 show a state in which wires are removed, and FIGS. 61 and 62 show a state in which jaw-pulley coupling portions of the end tool hub are removed.

Referring to FIGS. 58 to 63, the end tool 500 according to the first modified example of the first embodiment of the present disclosure includes a pair of jaws for performing a gripping motion, which include a first jaw 501 and a second jaw 502, and an element indicating each of the first jaw 501 and the second jaw 502, or both the first jaw 501 and the second jaw 502 may be collectively referred to as a jaw 503.

In addition, the end tool 500 may include a plurality of pulleys including a pulley 511, a pulley 513, and a pulley 514 associated with the rotational motion of the first jaw 501. In the present embodiment, the pulleys associated with the rotational motion of the first jaw 501 are substantially the same as the pulley 113, the pulley 114, the pulley 115, and the pulley 116 described above with reference to FIG. 11, etc. of the first embodiment, and detailed descriptions thereof are omitted.

In addition, the end tool 500 may include a plurality of pulleys including a pulley 521 associated with the rotational motion of the second jaw 502. In the present embodiment, the pulleys associated with the rotational motion of the second jaw 502 are substantially the same as the pulley 123, the pulley 124, the pulley 125, and the pulley 126 described above with reference to FIG. 11, etc. of the first embodiment, and detailed descriptions thereof are omitted.

The end tool 500 according to the first modified example of the first embodiment may include a rotary shaft 541, a rotary shaft 543, and a rotary shaft 544. Here, the rotary shaft 541 may be inserted through the end tool hub 580, and the rotary shaft 543 and the rotary shaft 544 may be inserted through a pitch hub 507. The rotary shaft 541, the rotary shaft 543, and the rotary shaft 544 may be arranged sequentially from a distal end 504 towards a proximal end 505 of the end tool 500.

In addition, the end tool 500 according to the first modified example of the first embodiment may include the end tool hub 580 and the pitch hub 507.

A rotary shaft 541 that will be described later is inserted through the end tool hub 580, and the pulley 511 and the pulley 521 axially coupled to the rotary shaft 541 and the first jaw 501 and the second jaw 502 coupled to the pulleys 511 and 521 may be at least partially accommodated in the end tool hub 580. Here, the end tool hub 580 has a guide portion 583 functioning as an auxiliary pulley formed thereon according to the embodiment. That is, the end tool hub 580 may have the guide portion 583 guiding a passage of a wire 305 and a wire 302. The guide portion 583 of the end tool hub 580 as above may function as the auxiliary pulley (see 112, 122, 162 of FIG. 9) in the first embodiment to change the passage of the wire, and the guide portion 583 of the end tool hub 580 functioning as the auxiliary pulley will be described later in more detail.

Meanwhile, the pulley 531 serving as an end tool pitch pulley may be formed at one end of the end tool hub 580. As shown in FIG. 58, the pulley 531 may be formed as a separate member from the end tool hub 580 and may be coupled to the end tool hub 580. Alternatively, the pulley 531 may be formed as one-body with the end tool hub 580. In addition, the wire 303 (see FIG. 13) and the wire 304 are coupled to the pulley 531 functioning as the end tool pitch pulley, and the pulley 531 rotates about the rotary shaft 543 and carries out the pitch motion.

The rotary shaft 543 and the rotary shaft 544 are inserted through the pitch hub 507, and the pitch hub 507 may be axially coupled to the end tool hub 580 and the pulley 531 via the rotary shaft 543. Accordingly, the end tool hub 580 and the pulley 531 may be formed to be pitch-rotatable around the rotary shaft 543 with respect to the pitch hub 507.

In addition, the end tool 500 according to the first modified example of the first embodiment of the present disclosure may further include such elements as a first electrode 551, a second electrode 552, a blade pulley 561, a blade link 573, a blade 571, etc. in order to perform cautery and cutting motions. Here, components associated with the driving of the blade, such as the blade pulley 561, the blade 571, and the blade link 573, etc. may be collectively referred to as the blade assembly 170 (see FIG. 7). In the modified example, by arranging the blade assembly 170 (see FIG. 7) including the blade 571 between the pulley 511 which is the first jaw pulley and the pulley 521 which is the second jaw pulley, not only the pitch motion and the yaw motion of the end tool 500 but also the cutting motion using the blade 571 may be performed. In the embodiment, the components for performing the cautery and cutting motions are substantially the same as the components described above in the first embodiment, and thus, detailed descriptions thereof are omitted here.

The surgical instrument for electrocautery according to the first modified example of the first embodiment may include the wire 301, the wire 302, the wire 303, the wire 304, the wire 305, the wire 306, the wire 307, and the wire 308, like in the first embodiment shown in FIG. 13, etc.

Also, the surgical instrument for electrocautery according to the first modified example of the first embodiment may include the fastening member 321, the fastening member 323, the fastening member 324, the fastening member 326, the fastening member 327, and the fastening member 329 which are coupled to each of respective ends of the wires in order to couple the wires and the pulleys, like in the first embodiment shown in FIG. 13, etc.

Hereinafter, the end tool hub 580 according to the first modified example of the first embodiment will be described in detail later, and in particular, the guide portion 583 of the end tool hub 580 functioning as the auxiliary pulley will be described.

The end tool hub 580 may include a first jaw pulley coupling portion 581, a second jaw pulley coupling portion 582, the guide portion 583, a guide groove 584, and a pitch pulley coupling portion 585.

The first jaw pulley coupling portion 581 and the second jaw pulley coupling portion 582 are formed to face each other and accommodate the pulley 511, the pulley 521, and the blade pulley 561. Also, each of the jaw pulley coupling portions 581 and 582 includes a through-hole, and the rotary shaft 541 passes through the first and second jaw pulley coupling portions 581 and 582, the pulley 511, the pulley 521, and the blade pulley 561 to axially couple the same.

The first jaw pulley coupling portion 581 and the second jaw pulley coupling portion 582 may be connected to each other by the guide portion 583. That is, the first jaw pulley coupling portion 581 and the second jaw pulley coupling portion 582 which are parallel to each other may be coupled to each other by the guide portion 583 formed approximately perpendicular thereto, and accordingly, the first jaw pulley coupling portion 581, the second jaw pulley coupling portion 582, the guide portion 583 may form the shape of C-shape in which the pulley 511, the pulley 521, and the blade pulley 561 are accommodated.

In other words, it may be considered that the first jaw pulley coupling portion 581 and the second jaw pulley coupling portion 582 are formed by extending in the X-axis direction from both end portions of the guide portion 583 that is elongated in the Z-axis direction.

Here, the guide portion 583 may be formed as a semi-cylindrical shape having a semi-circular cross-section. In addition, arc of the semi-circular portion may be formed to protrude toward the pulley 511, the pulley 521, and the blade pulley 561. In other words, the guide portion 583 may be formed to protrude toward the space formed by the first jaw pulley coupling portion 581, the second jaw pulley coupling portion 582, and the guide portion 583. In other words, area of the guide portion 583, which is adjacent to the first and second jaw pulley coupling portions 581 and 582, is formed to be curved so that the cross-sections thereof have certain curvatures.

Alternatively, because the wire 305, the wire 302, the wire 307, and the wire 308 are wound on the outer circumference of the guide portion 583, the guide portion 583 may function as a pulley member guiding the passages of the wire 305, the wire 302, the wire 307, and the wire 308. Here, the guide portion 583 may not be a member rotating about a certain shaft, like the pulley in its original meaning, but is formed to be fixed as a part of the end tool hub 580, and may similarly perform functions of the pulley because the wires are wound on the circumference thereof.

Here, the guide portion 583 is formed as a semi-cylindrical shape having a semi-circular cross-section in the drawings. That is, at least a part of the cross-section of the guide portion 583 on an XY plane forms a certain arc shape. However, the technical concepts of the present disclosure are not limited thereto, that is, the cross-section of the guide portion 583 may be formed to have a certain curvature such as an elliptical shape, a parabolic shape, etc. or formed as a polygonal pillar having round corners, provided that the guide portion 583 has various shapes and sizes suitable for guiding the passages of the wire 305, the wire 302, the wire 307, and the wire 308.

Here, in the guide portion 583, the portion contacting the wire 305, the wire 302, the wire 307, and the wire 308 may further have guide groove 584 for guiding the passages of the wire 305, the wire 302, the wire 307, and the wire 308. The guide groove 584 may be formed in the form of a groove that is depressed a certain degree from the protruding surface of the guide portion 583.

Here, in the drawings, the guide groove 584 is formed entirely in the arc surface of the guide portion 583, but the technical concepts of the present disclosure are not limited thereto, and in other case, the guide groove 584 may be formed only in a part of the arc surface of the guide portion 583.

As described above, as the guide groove 584 is further formed in the guide portion 583, unnecessary friction with the wires may be reduced and the durability of the wires may be improved.

The pitch pulley coupling portion 585 may be further formed at the side of the guide portion 583, opposite to the portion where the jaw pulley coupling portions 581 and 582 are formed. The pitch pulley coupling portion 585 may be formed parallel to the pulley 531 that is the pitch pulley, that is, on an XZ plane. The pitch pulley coupling portion 585 may have a through-hole through which the rotary shaft 543 is inserted, and when the rotary shaft 543 passes through the pitch pulley coupling portion 585 and the pulley 531 so that two members may be coupled to each other. Here, the pitch pulley coupling portion 585 may be formed to be biased a certain degree toward one side over the center portion when seen on the XY plane, and thus, may be entirely balanced when being coupled to the pulley 531.

Hereinafter, role and functions of the guide portion 583 will be described in more detail below.

The guide portion 583 may change the arrangement path of the wire 305 and the wire 302 by a certain degree by coming into contact with the wire 305 and the wire 302 so as to expand a rotation radius of each of the first jaw 501 and the second jaw 502.

Moreover, the guide portion 583 may be in contact with the wire 307 and the wire 308, which are the blade wires, and change the arrangement path of the wire 307 and the wire 308 to a certain extent, which leads to expansion of a rotation radius of the blade pulley 561.

That is, when the auxiliary pulley is not arranged, each of the pulley 511 that is the first jaw pulley, the pulley 521 that is the second jaw pulley, and the blade pulley 561 may be rotated up to the right angle, but according to the first modified example of the first embodiment, the end tool hub 580 additionally includes the guide portion 583 to increase the maximum rotation angle of each pulley.

This enables the opening motion of the two jaws of the end tool 500 for the actuation motion when the two jaws of the end tool 500 are yaw-rotated by 90°. In other words, through the guide portion 583 of the end tool hub 580, a range of yaw rotation allowing the actuation motion may be expanded.

Also, while the two jaws are yaw-rotated by 90° by the guide portion 583 of the end tool hub 580 performing as the auxiliary pulley, it may be possible that the blade pulley 561 is further rotated for the cutting motion. In other words, through the configuration of the guide portion 583 of the end tool hub 580, a range of yaw rotation allowing the cutting motion to be performed may be expanded.

Moreover, without adding an additional structure such as the auxiliary pulley, the guide portion 583 is formed on the end tool hub 580 that already exists, and thus, the expanding of the rotation range may be implemented without adding components and manufacturing processes.

As described above, an additional structure for expanding the rotation angle may not be additionally arranged, and thus, the number of components is reduced and the manufacturing processes may be simplified. In addition, a length of the end tool may be reduced by the size of the auxiliary pulley and results in reducing of the length of the end tool when the pitch motion is performed. Therefore, the operating motion may be facilitated within a narrow space.

This will be described below in more detail.

In the end tool 500 of the surgical instrument according to the first modified example of the first embodiment, the guide portion 583 which may change the passage of the wire is formed in the inner wall of the end tool hub 580, and thus, the arrangement path of the wire may be changed without using an additional structure. As described above, the arrangement path of the wire 305, the wire 302, the wire 307, and the wire 308 is changed by a certain degree by forming the guide portion 583 in the end tool hub 580, and thereby changing the tangential direction of the wire 305, the wire 302, the wire 307, and the wire 308, and accordingly, the rotation angle of the fastening member 323, the fastening member 326, and the fastening member 329 for coupling respective wires to the pulley may be expanded.

That is, the fastening member 326, which is a coupling portion between the wire 302 and the pulley 521, may be rotatable until it is positioned on a common internal tangent of the pulley 521 and the guide portion 583. Likewise, the fastening member 323 (see FIG. 6) for coupling the wire 305 to the pulley 511 may be rotated until it is positioned on a common internal tangent of the pulley 511 and the guide portion 583, and thus, the rotation angle of the fastening member 323 (see FIG. 6) may be expanded. Likewise, the fastening member 329 for coupling the wire 307 and the wire 308 to the pulley 561 may be rotated until it is positioned on a common internal tangent of the pulley 561 and the guide portion 583, and thus, the rotation angle of the fastening member 329 may be expanded.

In other words, the wire 301 and the wire 305 wound on the pulley 511 via the guide portion 583 may be arranged at one side based on a plane that is perpendicular to the Y-axis and passes the X-axis. At the same time, the wire 302 and the wire 306 wound on the pulley 521 via the guide portion 583 may be arranged at the other side based on the plane that is perpendicular to the Y-axis and passes the X-axis.

In other words, the pulley 513 and the pulley 514 may be arranged on one side with respect to the plane perpendicular to the Y-axis and passing through the X-axis, and the pulley 523 and the pulley 524 may be arranged on the other side with respect to the plane perpendicular to the Y-axis and passing through the X-axis.

In other words, the wire 305 may be arranged on an internal tangent of the pulley 511 and the guide portion 583, and the rotation angle of the pulley 511 may be expanded by the guide portion 583. Also, the wire 302 may be arranged on an internal tangent of the pulley 521 and the guide portion 583, and the rotation angle of the pulley 521 may be expanded by the guide portion 583.

As compared with the surgical instrument in which a separate auxiliary pulley is formed according to the first embodiment, in the surgical instrument according to the first modified example, in which the guide portion 583 capable of changing the passage of the wire is formed on the inner wall of the end tool hub 580 without forming the auxiliary pulley, the length of the end tool may be reduced. As described above, when the length of the end tool is reduced, an operator may easily manipulate when an operation is carried out in a narrow operation site in a human body, and thus, side-effects of the operation may be reduced.

According to the disclosure, the rotation radius of the pulley 511 that is the first jaw pulley, the pulley 521 that is the second jaw pulley, and the blade pulley 561 may be increased, and thus, the yaw motion range allowing a normal opening/closing actuation motion and the cutting motion to be performed may be increased.

Second Modified Example of the First Embodiment—Saw-Toothed Blade

Hereinafter, an end tool 600 of a surgical instrument according to a second modified example of the first embodiment of the present disclosure will be described below. Here, the end tool 600 of the surgical instrument according to the second modified example of the first embodiment of the present disclosure is different from the end tool (see 100 of FIG. 2, etc.) of the surgical instrument according to the first embodiment of the present disclosure, in view of a configuration of a blade 671. The different structure from that of the first embodiment will be described below in detail.

Figure 64:
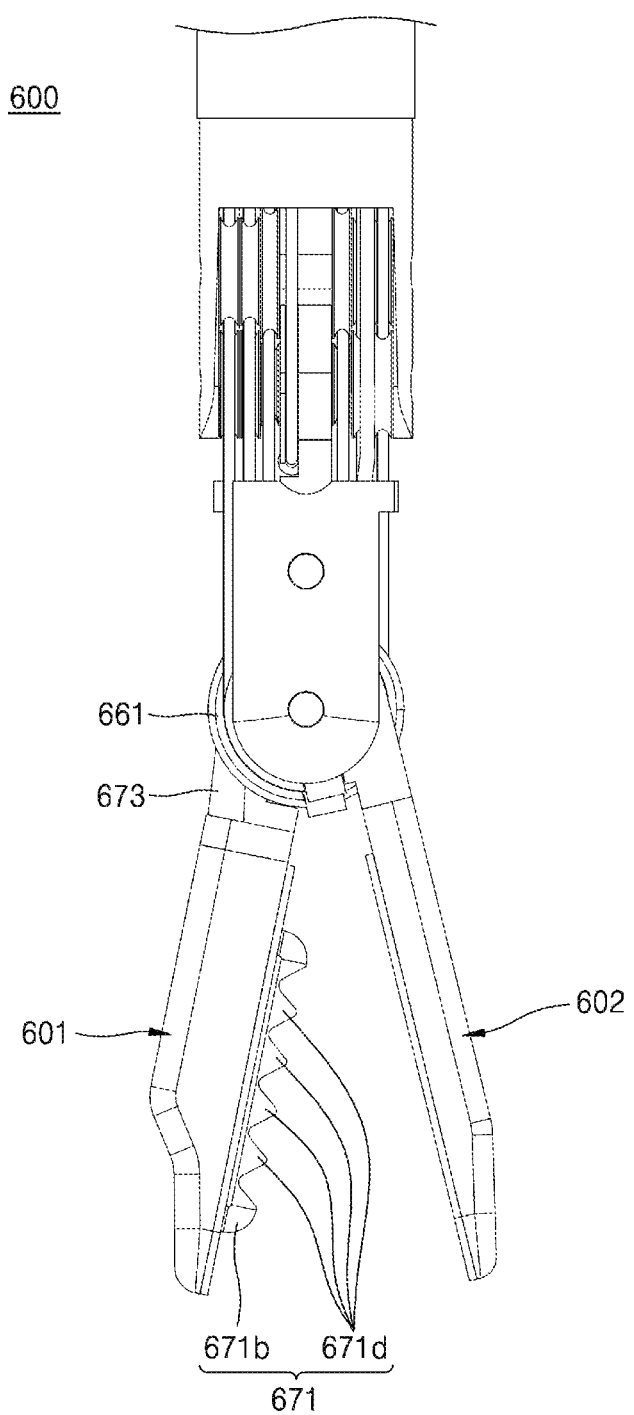
FIG. 64 is a perspective view illustrating an end tool of a surgical instrument for electrocautery according to a third embodiment of the present disclosure.
Figure 65:
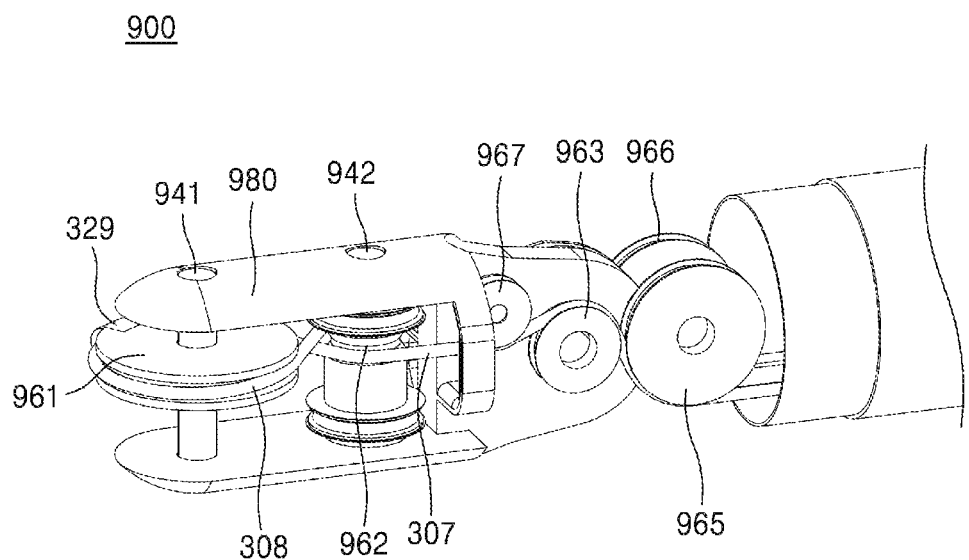
FIGS. 65 to 68 are diagrams illustrating an end tool of a surgical instrument for electrocautery according to a third modified example of a first embodiment of the present disclosure.
Figure 66:
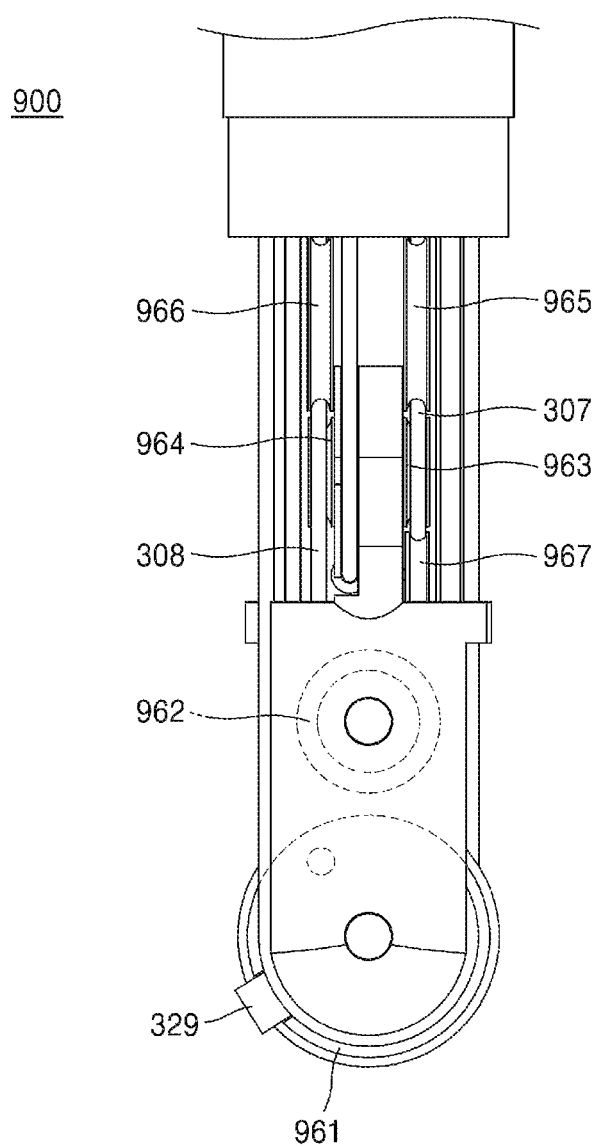
Figure 67:
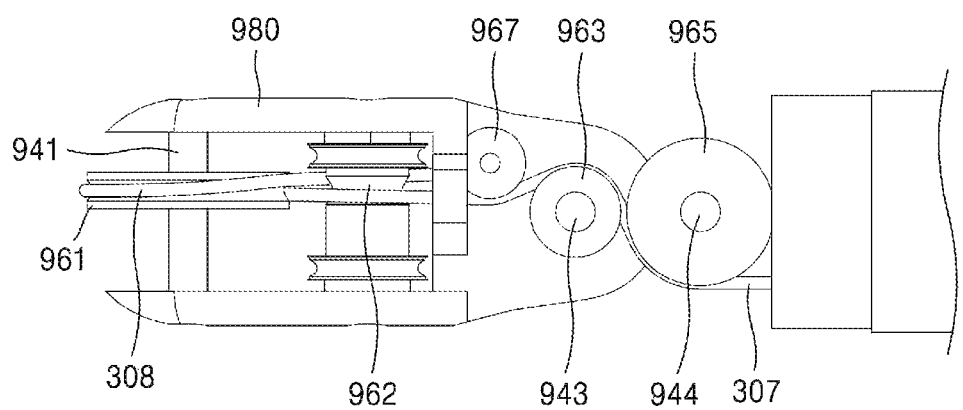
Figure 68:
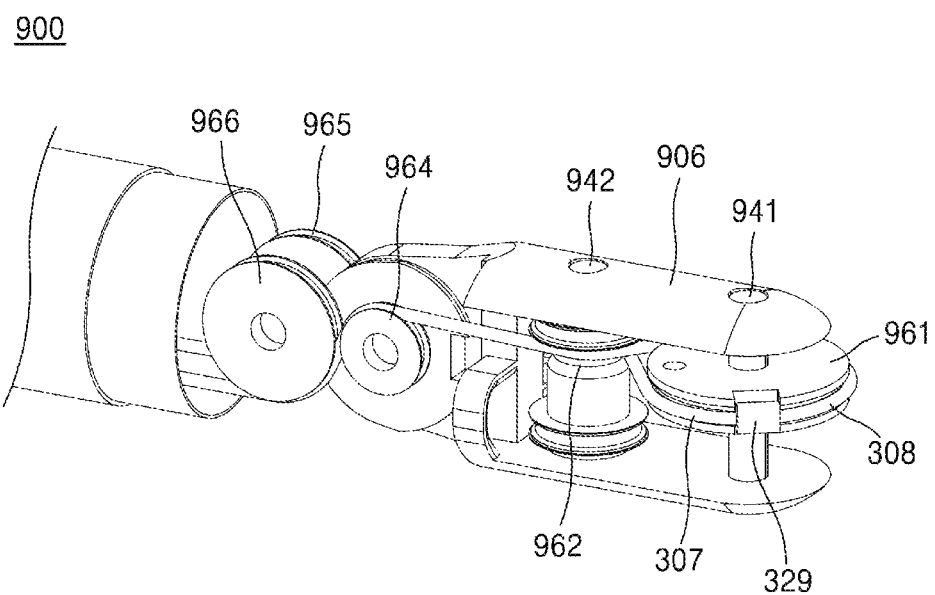

FIG. 64 is a perspective view illustrating an end tool of a surgical instrument for electrocautery according to a second modified example of the first embodiment.

Referring to FIG. 64, the end tool 600 according to the second modified example of the first embodiment may include a pair of jaws for performing a grip motion, i.e., a first jaw 601 and a second jaw 602. Also, the end tool 600 may include a blade 671 for the cutting motion, a blade pulley 661 related to linear/rotating motion of the blade link 673 and the blade 671, and a plurality of associated pulleys.

The blade 671 may include a body portion (see 171a of FIG. 7), an edge portion 671b, and one or more second guide portions (see 171c of FIG. 7).

In an area of the body portion 171a (see FIG. 7), the edge portion 671b which is sharp and cuts tissue may be formed. At least a part of the edge portion 671b may be drawn to the outside of the first jaw 601 to cut the tissue positioned between the first jaw 601 and the second jaw 602.

In addition, in the other area of the body portion 171a (see FIG. 7), one or more second guide portions 171c (see FIG. 7) may be formed. For example, the second guide portions 171c (see FIG. 7) are formed as protrusions. In a state in which the second guide portion 171c (see FIG. 7) is inserted in the first guide portion 101e (see FIG. 11), when the second guide portion 171c (see FIG. 7) is moved along the first guide portion 101e (see FIG. 11), the blade 671 may be moved relative to the first jaw 601. Also, the blade link 673 may be axially coupled to the second guide portion 171c (see FIG. 7).

The blade link 673 may connect the blade pulley 661 to the blade 671 and transmit the rotation of the blade pulley 661 to the blade 671 so that the blade 671 linearly moves in a direction towards the distal end from the proximal end of the first jaw 601. The blade link 673 may be formed in the shape of an elongated bar, and one end of the blade link 673 may be connected to the blade pulley 661, and the other end may be connected to the blade 671.

Here, the end tool 600 according to the second modified example of the first embodiment has a plurality of sawtooth portions 671d on the edge portion 671b of the blade 671. As described above, when the plurality of sawtooth portions 671*d* are formed on the edge portion 671*b* of the blade 671, a cutting force of the blade 671 may be improved and the effect of rapidly and accurately cutting tissue may be obtained.

Third Modified Example of the First Embodiment—Adding a Second Auxiliary Pulley for a Blade Wire Hereinafter, an end tool 900 of a surgical instrument according to a third modified example of the first embodiment of the present disclosure will be described below. Here, the end tool 900 of the surgical instrument according to the third modified example of the first embodiment of the present disclosure is different from the end tool (see 100 of FIG. 2, etc.) of the surgical instrument according to the first embodiment of the present disclosure, in that a blade second auxiliary pulley 967 that is an auxiliary pulley for the blade wire is additionally provided. The different structure from that of the first embodiment will be described below in detail.

FIGS. 65 to 68 are diagrams illustrating an end tool of a surgical instrument for electrocautery according to the third modified example of the first embodiment of the present disclosure. FIGS. 65 to 68 mainly show pulleys related to the blade pulley 961.

Referring to FIGS. 65 to 68, the end tool 900 according to the third modified example of the first embodiment may include the blade pulley 961, the blade auxiliary pulley 962, a pulley 963, a pulley 964, a pulley 965, and a pulley 966 that are associated with linear/rotation motions of the blade. Also, the end tool 900 according to the third modified example of the first embodiment may further include the blade second auxiliary pulley 967.

The blade pulley 961 may face the pulley 111 (see FIG. 6) and the pulley 121 (see FIG. 6), which are the end tool jaw pulleys, and may be rotatable independently around the rotation shaft 941 which is the end tool jaw pulley rotation shaft.

Here, the blade pulley 961, the pulley 111 (see FIG. 6), and the pulley 121 (see FIG. 6) may be formed to rotate about a substantially the same shaft. As described above, as the blade pulley 961, the pulley 111 (see FIG. 6), and the pulley 121 (see FIG. 6) are formed to rotate about a substantially the same shaft, simultaneously with the pitch motion/yaw motion/actuation motion, a cutting motion using the blade may also be performed.

The blade auxiliary pulley 962 may be additionally provided on one side of the blade pulley 961. In other words, the blade auxiliary pulley 962 may be arranged between the pulley 961 and the pulley 963/the pulley 964. The blade auxiliary pulley 962 may be formed to be rotatable about a rotary shaft 942 independently from the pulley 112 (see FIG. 6) and the pulley 122 (see FIG. 6).

The pulley 963 and the pulley 964 may function as a blade pitch main pulley, and the pulley 965 and the pulley 966 may function as a blade pitch sub-pulley.

The blade second auxiliary pulley 967 may be arranged between the blade auxiliary pulley 962 and the pulley 963/the pulley 964. The blade auxiliary pulley 962 may be formed to be rotatable about a certain shaft that is parallel to the rotary shaft 943 that is the central axis of the pulley 963 and the pulley 964.

Hereinafter, components associated with the rotation of the blade pulley 961 will be described.

The pulley 963 and the pulley 964 may function as the blade pitch main pulley. Here, the wire 307, which is the blade wire, may be wound around the pulley 963, and the wire 308, which is the blade wire, may be wound around the pulley 964.

The pulley 965 and the pulley 966 may function as the blade pitch sub-pulley. Here, the wire 307, which is the blade wire, may be wound around the pulley 965, and the wire 308, which is the blade wire, may be wound around the pulley 966.

Here, on one side of the blade pulley 961 and the blade auxiliary pulley 962, the pulley 963 and the pulley 964 may be arranged to face each other. The pulley 963 and the pulley 964 may be formed to be rotatable independently of each other around the rotary shaft 943 which is the end tool pitch rotation shaft. In addition, on one side of each of the pulley 963 and the pulley 964, the pulley 965 and the pulley 966 may be arranged to face each other. The pulley 965 and the pulley 966 may be formed to be rotatable independently of each other around a rotary shaft 944 which is the end tool pitch auxiliary rotation shaft. Although the drawings illustrate that the pulley 963, the pulley 965, the pulley 964, and the pulley 966 are formed to be rotatable around the Y-axis direction, the technical concepts of the present disclosure are not limited thereto, and the rotation shafts of each pulley may be formed in various directions suitable for their respective configurations.

The wire 307, which is the blade wire, may be sequentially wound so that at least a part thereof is in contact with the pulley 965, the pulley 963, the blade auxiliary pulley 962, and the blade pulley 961. In addition, the wire 308 connected to the wire 307 by the fastening member 329 may be sequentially wound so that at least a part thereof is in contact with the blade pulley 961, the blade auxiliary pulley 962, the pulley 964, and the pulley 966.

In other words, the wire 307 and the wire 308, which are the blade wire, may be sequentially wound so that at least a part thereof is in contact with the pulley 965, the pulley 963, the blade auxiliary pulley 962, the blade pulley 961, the blade auxiliary pulley 962, the pulley 964, and the pulley 966, and the wire 307 and the wire 308 may be formed to move along the pulleys while rotating the pulleys.

Accordingly, when the wire 307 is pulled, the fastening member 329 coupled to the wire 307 and the blade pulley 961 coupled to the fastening member 329 may rotate in one direction. On the contrary, when the wire 308 is pulled, the fastening member 329 coupled to the wire 308 and the blade pulley 961 coupled to the fastening member 329 may rotate in the opposite direction.

Here, the end tool 900 according to the third modified example of the first embodiment further includes the blade second auxiliary pulley 967, and thus, friction between the wire 307 and the wire 308, that is, blade wires, may be prevented.

That is, the blade second auxiliary pulley 967 is arranged between the blade auxiliary pulley 962 and the pulley 963 to change the passage of the wire 307 entering the end tool hub 980 to a certain degree. That is, in the end tool hub 980, a height of the wire 307 in the Z-axis direction and a height of the wire 308 in the Z-axis direction are different from each other. As described above, the wire 307 and the wire 308 that are two strands of wires wound on the blade auxiliary pulley 962 may have a definite height difference in the Z-axis direction, and thus, the wire 307 and the wire 308 crossing each other in the end tool hub 980 may be prevented from coming into contact with each other.

According to the present disclosure, the friction between the wire 307 and the wire 308 that are the blade wires is prevented, so that the cutting motion may be sufficiently performed.

Second Embodiment—Guide Member and Blade Link Modification

Hereinafter, an end tool 700 of a surgical instrument according to a second embodiment of the present disclosure will be described. Here, the end tool 700 of the surgical instrument according to the second embodiment is different from the end tool (100 of FIG. 2, etc.) of the surgical instrument described above according to the first embodiment in view of the configuration of a blade 771 and a blade link 773. The different structure from that of the first embodiment will be described below in detail.

Figure 69:
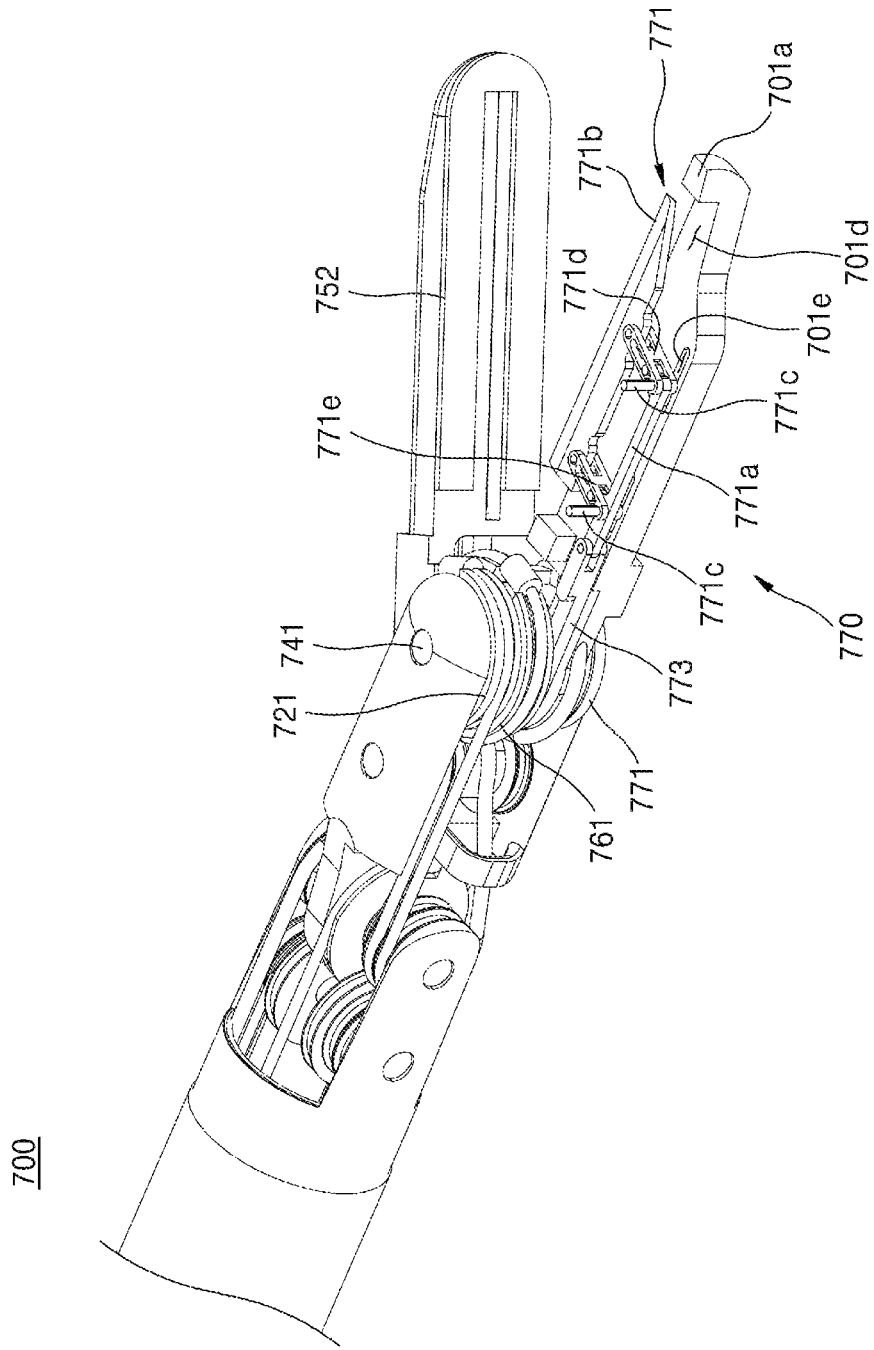
FIG. 69 is a perspective view illustrating an end tool of a surgical instrument for electrocautery according to a second embodiment of the present disclosure.
Figure 70:
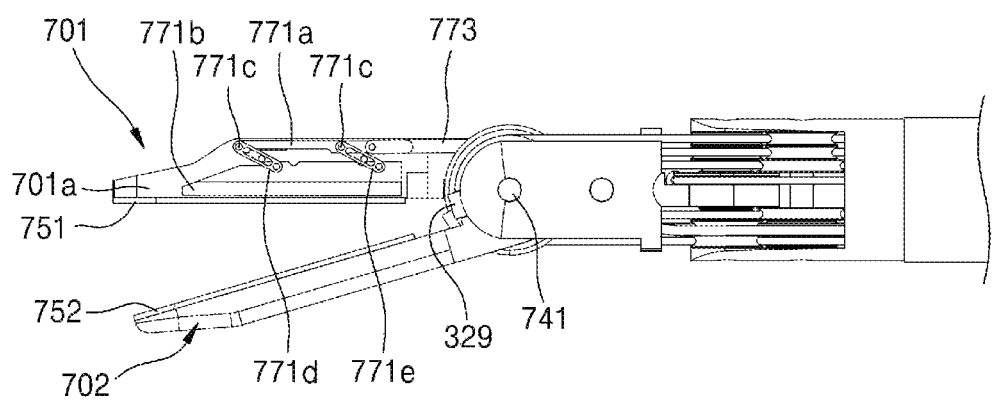
FIGS. 70, 71, and 72 are plan views illustrating a cutting movement of the end tool of the surgical instrument for electrocautery of FIG. 69.
Figure 71:
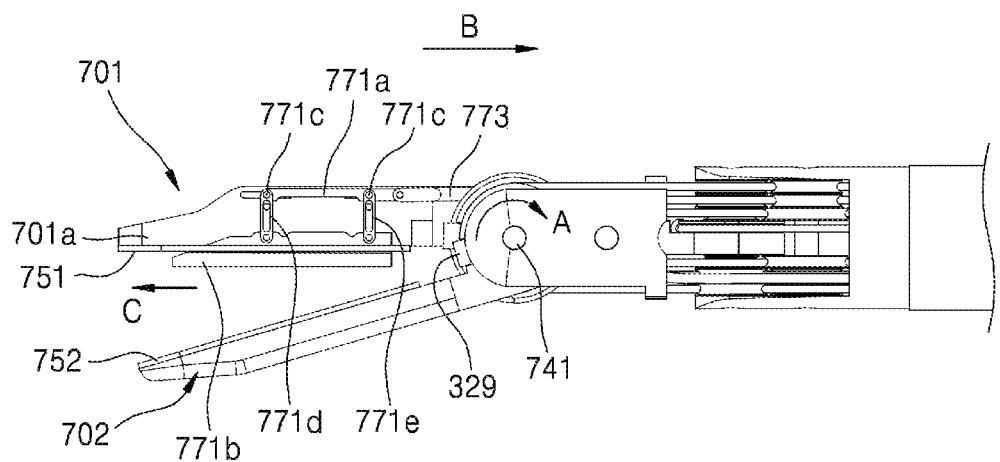
Figure 72:
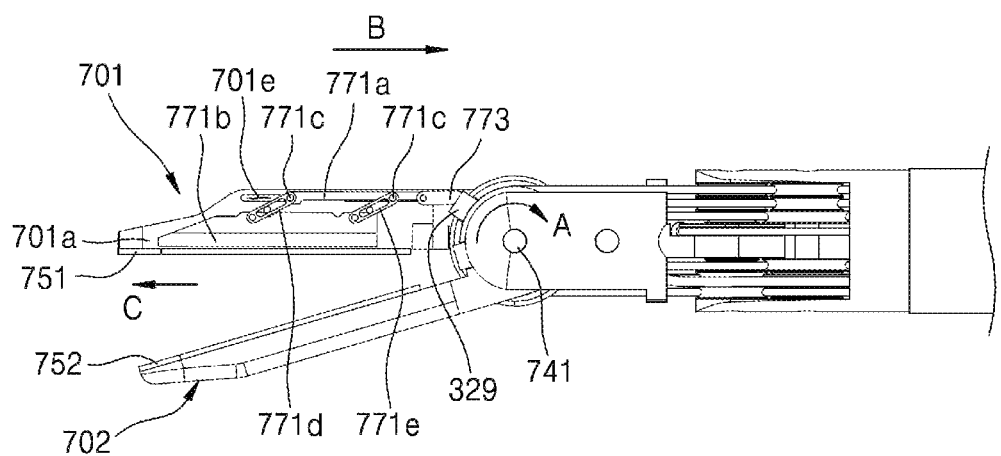

FIG. 69 is a perspective view of an end tool of the surgical instrument for electrocautery according to the second embodiment of the present disclosure, and FIGS. 70, 71, and 72 are plan views showing a cutting motion of the end tool of the surgical instrument for electrocautery shown in FIG. 69.

Referring to FIGS. 69 to 72, the end tool 700 may include a first jaw 701, a second jaw 702, a first electrode 751, a second electrode 752, a blade pulley 761, a blade link 773, a blade 771, and a plurality of related pulleys for performing cautery/cutting motions. Here, components associated with the driving of the blade, such as the blade pulley 761, the blade 771, and the blade link 773, etc. may be collectively referred to as the blade assembly 770. In the second embodiment, by arranging the blade assembly 770 including the blade 771 between the pulley 711 which is the first jaw pulley and the pulley 721 which the second jaw pulley, not only the pitch motion and the yaw motion of the end tool 700 but also the cutting motion using the blade 771 may be performed. In the embodiment, the components for performing the cautery and cutting motions are substantially the same as the components described above in the first embodiment, and thus, detailed descriptions thereof are omitted here.

The pulley 711 coupled to the first jaw 701, the pulley 721 coupled to the second jaw 702, and the blade pulley 761 connected to the blade 771 are axially coupled to the rotary shaft 741 to be rotatable about the rotary shaft 741.

The first jaw 701 may include a guide member 701a and a case (not shown).

A blade accommodation portion 701d and a first guide portion 701e may be formed in the guide member 701a. The guide member 701a is coupled to the pulley 711 and may be formed to guide the moving path of the blade 771 accommodated therein. For example, the guide member 701a may be formed in the form of two long bars facing each other, and the blade accommodation portion 701d in which at least a part of the blade 771 and the blade link 773 are accommodated may be formed inside the guide member 701a. The blade accommodation portion 701d may be formed in an elongated manner in a direction towards a distal end from a proximal end of the first jaw 701, and in the blade accommodation portion 701d, the blade 771 may be entirely accommodated or at least a part of the blade 771 may protrude from the blade accommodation portion 701d to the outside. In other words, as the blade 771 moves along the blade accommodation portion 701d, the cutting motion may be performed on the tissue. This will be described in more detail later.

In addition, the first guide portion 701e for guiding the movement of the blade 771 that will be described later may be formed in the guide member 701a of the first jaw 701. For example, the first guide portion 701e may be formed in the shape of a groove formed along the movement path of the blade 771. In addition, in a state in which a second guide portion 771c of the blade 771 formed in the protrusion shape is fit into the first guide portion 701e in the groove shape, because the second guide portion 771c moves along the first guide portion 701e, the blade 771 may move with respect to the first jaw 701.

The blade 771 may include a first link 771a, an edge portion 771b, a second guide portion 771c, a second link 771d, and a third link 771e.

The edge portion 771b is formed in a long bar shape extending along the direction in which the connecting portion 400 (see FIG. 3) extends, and a region facing the second jaw 702 is formed to be sharp so that the tissue may be cut. At least a part of the edge portion 771b may be drawn to the outside of the first jaw 701 to cut the tissue positioned between the first jaw 701 and the second jaw 702.

One end portion of the edge portion 771b may be axially coupled to the second link 771d, and the other end portion of the edge portion 771b may be axially coupled to the third link 771e. Also, the first link 771a may be arranged parallel to the edge portion 771b, and the second link 771d and the third link 771e may be also coupled to the first link 771a.

Consequently, the first link 771a, the edge portion 771b, the second link 771d, and the third link 771e may form a four-bar linkage or parallelogram. In other words, the four links are connected to one another to form a closed loop, and a connecting portion of each link is axially coupled to entirely form the four-bar linkage or the parallelogram. Therefore, when any one of the links moves, the other three links move along with the link, while maintaining a parallelogram shape as a whole In addition, second guide portions 771c may be formed as protrusions near the point where the first link 771a and the second link 771d meet each other and near the point where the first link 771a and the third link 771e meet each other. In addition, while the second guide portion 771c is inserted in the first guide portion 701e of the first jaw 701, the second guide portion 771c is moved along the first guide portion 701e, and thus, the blade 771 may be moved relative to the first jaw 701. In addition, the blade link 773 that will be described later may be axially coupled to the second guide portions 771c.

The blade link 773 may connect the blade pulley 761 to the blade 771 and transmit the rotation of the blade pulley 761 to the blade 771 so that the blade 771 linearly moves along a direction in which the connecting portion 400 (see FIG. 3) extends (that is, X-axis direction). The blade link 773 may be formed in the shape of an elongated bar, and one end of the blade link 773 may be connected to the blade pulley 761, and the other end may be connected to the blade 771 (in particular, the first link 771a).

For example, through-holes may be formed at both ends of the blade link 773, and a protrusion portion 161a (see FIG. 14) formed on one surface of the blade pulley 761 and the first link 771a of the blade 771 may be fit into the through-holes, respectively. In other words, the blade pulley 761 may be axially coupled to one end of the blade link 773 and simultaneously, the blade 771 may be axially coupled to the other end of the blade link 773.

In this state, when the blade pulley 761 rotates around the rotation shaft 741, the rotational motion of the blade pulley 761 may be transmitted to the blade 771 by the blade link 773 coupled to the blade pulley 761. In addition, the transferred rotational motion of the blade pulley 761 is converted into the linear motion of the blade 771, so that the blade 771 may be drawn from the first jaw 701 while linearly moving along the direction from the proximal end toward the distal end of the first jaw 701, or may be pulled in the first jaw 701.

That is, the blade link 773 and the blade 771 are coupled to form a kind of driving mechanism, and then, the rotational motion of the blade pulley 761 is converted into the linear motion of the blade 771.

As described above, the end tool 700 according to the second embodiment includes the blade pulley 761 arranged between the pulley 711 and the pulley 721 and the blade 771 connected to the blade pulley 761 and moving between the first position and the second position according to the rotation of the blade pulley 761. In addition, in order for the blade 771 to move between the first position and the second position due to the rotational motion of the blade pulley 761, four links have the parallelogram structure. By providing the blade pulley 761 and the blade 771, in a bipolar type surgical instrument for tissue cautery and cutting, the pitch/yaw/actuation motion may be performed using a pulley/wire method.

FIG. 70 is a diagram showing a state in which the blade pulley 761 and the blade 771 are located at the first position (that is, the proximal end of the first jaw), FIG. 72 is a diagram showing a state in which the blade pulley 761 and the blade 771 are located at the second position (that is, the distal end of the first jaw), and FIG. 71 is a diagram showing a state in which the blade pulley 761 and the blade 771 are located at an arbitrary position between the first position and the second position.

FIG. 70 shows that the blade 771 is located at the first position, that is, the proximal end of the first jaw 701. In the state as shown in FIG. 70, when the blade pulley 761 is rotated in the direction indicated by the arrow A of FIG. 71, the blade link 773 coupled to the blade pulley 761 is moved in the direction indicated by the arrow B to reach the position shown in FIG. 71. Then, the blade 771 coupled to the blade link 773 is moved to a degree from the proximal end toward the distal end of the first jaw 701.

That is, while the second guide portion 771c formed as a protrusion is inserted in the first guide portion 701e of a groove shape, when the blade pulley 761 is rotated in the direction indicated by the arrow A shown in FIG. 71, the blade link 773 coupled to the blade pulley 761 moves the first link 771a of the blade 771 in the direction indicated by the arrow B.

Here, because the blade 771 forms the parallelogram structure including four links, the second link 771d and the third link 771e connected to the first link 771a are rotated in the clockwise direction in the drawing. In addition, the edge portion 771b connected to the second link 771d and the third link 771e is drawn from the inside to the outside of the first jaw 701, and at the same time, is moved in the direction indicated by the arrow C shown in FIG. 71.

In other words, the edge portion 771b of the blade 771 performs the linear motion in the direction towards the distal end of the end tool 700 (that is, the movement in the X-axis direction), and at the same time, may perform the linear motion in the direction of protruding to a certain degree from the inside to the outside of the first jaw 701 (that is, movement in the Y-axis direction). As described above, as the blade 771 performs movement both in the X-axis direction and the Y-axis direction, the tissue (not shown) between the first jaw 701 and the second jaw 702 may be cut.

However, the linear motion of the blade 771 may not refer to a motion in a strictly straight line, and may refer to the motion of cutting tissue in a straight-line in general even when the straight line is not completely straight, e.g., the line is bent in the middle at a certain angle, includes a section with a gradual curvature, etc.

When the blade pulley 761 is continuously rotated in the direction indicated by the arrow A of FIG. 72, the blade link 773 coupled to the blade pulley 761 moves the first link 771a of the blade 771 in the direction indicated by the arrow B of FIG. 72.

Here, the second link 771d and the third link 771e connected to the first link 771a are rotated in the clockwise direction when seen on the drawing. In addition, the edge portion 771b connected to the second link 771d and the third link 771e are pulled into the first jaw 701 again, and at the same time, is moved in the direction indicated by the arrow C of FIG. 71 to reach the second position at the distal end of the first jaw 701.

In other words, the edge portion 771b of the blade 771 performs the linear motion in the direction towards the distal end of the end tool 700 (that is, the movement in the X-axis direction), and at the same time, may perform the linear motion in the direction of being accommodated to a certain degree from the outside to the inside of the first jaw 701 (that is, movement in the Y-axis direction).

As described above, by providing the blade pulley 761 and the blade 771, a multi-joint/multi-degree-of-freedom surgical instrument capable of pitch/yaw/actuation motions may also perform cautery and cutting.

In particular, in the present embodiment, because the blade 771 forms the parallelogram structure including four links, the cutting is carried out while drawing the blade 771 from the first jaw 701 while drawing a certain arc, and thus, an effect of smoothly performing the cutting operation may be obtained.

Third Embodiment—Simple Rotation Blade

Hereinafter, an end tool 800 of a surgical instrument according to a third embodiment of the present disclosure will be described. Here, the end tool 800 of the surgical instrument according to the third embodiment is different from the end tool (100 of FIG. 2, etc.) of the surgical instrument described above according to the first embodiment in view of a connecting relationship between a blade pulley 861 and a blade 871. The different structure from that of the first embodiment will be described below in detail.

Figure 73:
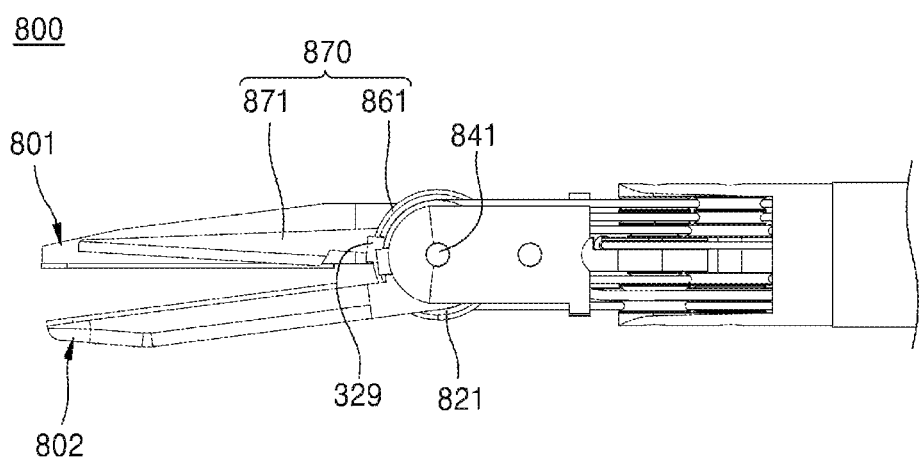
FIGS. 73 and 74 are perspective views illustrating an end tool of a surgical instrument for electrocautery according to a third embodiment of the present disclosure.
Figure 74:
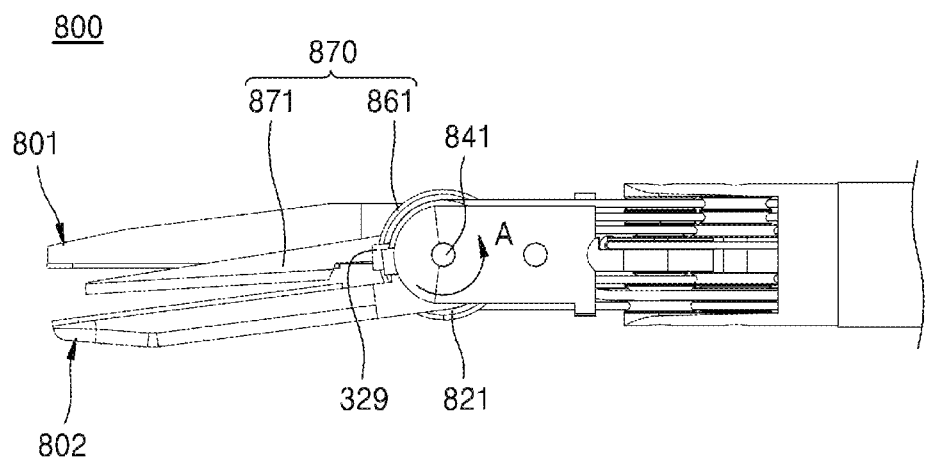

FIGS. 73 and 74 are perspective views illustrating an end tool of a surgical instrument for electrocautery according to a third embodiment of the present disclosure.

With reference to FIGS. 73 and 74, the end tool 800 of the third embodiment may include a pair of jaws for performing a grip motion, i.e., the first jaw 801 and the second jaw 802.

In addition, the end tool 800 may include a plurality of pulleys related to the rotational motion of the first jaw 801 and the second jaw 802, e.g., a first jaw pulley (not shown), a second jaw pulley 821, etc. Also, the end tool 800 according to the third embodiment includes a plurality of rotary shafts related to the rotational motion of the first jaw 801 and the second jaw 802, e.g., the rotary shaft 541, etc.

Also, the end tool 800 may include a blade 871 for the cutting motion, a blade pulley 861 related to linear/rotating motion of the blade 871, and a plurality of associated pulleys. Here, components associated with the driving of the blade, such as the blade pulley 861, the blade 871, etc. may be collectively referred to as the blade assembly 870. In the third embodiment of the present disclosure, by arranging the blade assembly 870 including the blade 871 between the pulley 811 which is the first jaw pulley and the pulley 821 which the second jaw pulley, not only the pitch motion and the yaw motion of the end tool 800 but also the cutting motion using the blade 871 may be performed. In the embodiment, the components for performing the cautery and cutting motions are substantially the same as the components described above in the first embodiment, and thus, detailed descriptions thereof are omitted here.

Here, the end tool 800 of the surgical instrument according to the third embodiment does not include an additional blade link for connecting the blade pulley 861 to the blade 871, and the blade 871 is directly connected to the blade pulley 861. Therefore, when the blade pulley 861 is rotated about the rotary shaft 841, and then, the blade 871 is also rotated to perform the cutting motion.

Here, the blade pulley 861 and the blade 871 may be formed as one-body, or may be formed as separate members and coupled to each other.

FIG. 73 shows that the blade pulley 861 and the blade 871 are located at a first position, and FIG. 74 shows that the blade pulley 861 and the blade 871 are located at a second position.

Here, while the blade 871 is located at the first position as shown in FIG. 73, when the blade pulley 861 is rotated in a direction indicated by the arrow A of FIG. 74, the blade 871 coupled to the blade pulley 861 is also rotated. Thus, as shown in FIG. 74, the blade 871 is drawn to the outside of the first jaw 801 and moved to the second position to cut the tissue (not shown) between the first jaw 801 and the second jaw 802.

As described above, by providing the blade pulley 861 and the blade 871, a multi-joint/multi-degree-of-freedom surgical instrument capable of pitch/yaw/actuation motions may also perform cautery and cutting.

In particular, in the embodiment, the blade pulley 861 and the blade 871 are directly connected to each other without using an additional connecting structure, and thus, the number of components may be reduced and the manufacturing may be easily performed.

Fourth Embodiment—Triple Blade

Hereinafter, an end tool 1100 of a surgical instrument according to a fourth embodiment of the present disclosure will be described. Here, the end tool 1100 of the surgical instrument according to the fourth embodiment is different from the end tool (100 of FIG. 2, etc.) of the surgical instrument described above according to the first embodiment in view of the configuration of a blade assembly 1170. The different structure from that of the first embodiment will be described later in more detail.

Figure 75:
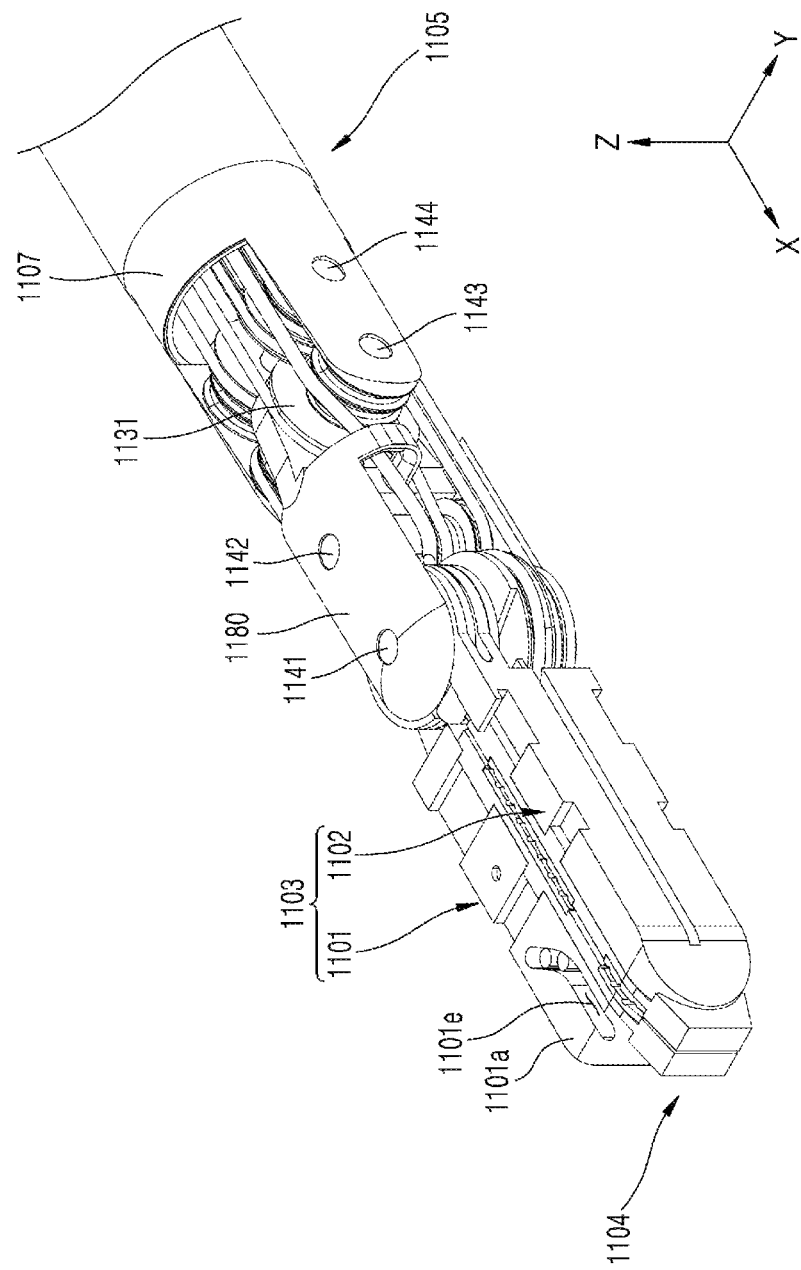
FIG. 75 is a perspective view illustrating an end tool of a surgical instrument for electrocautery according to a fourth embodiment of the present disclosure, in particular, when jaws are closed.
Figure 76:
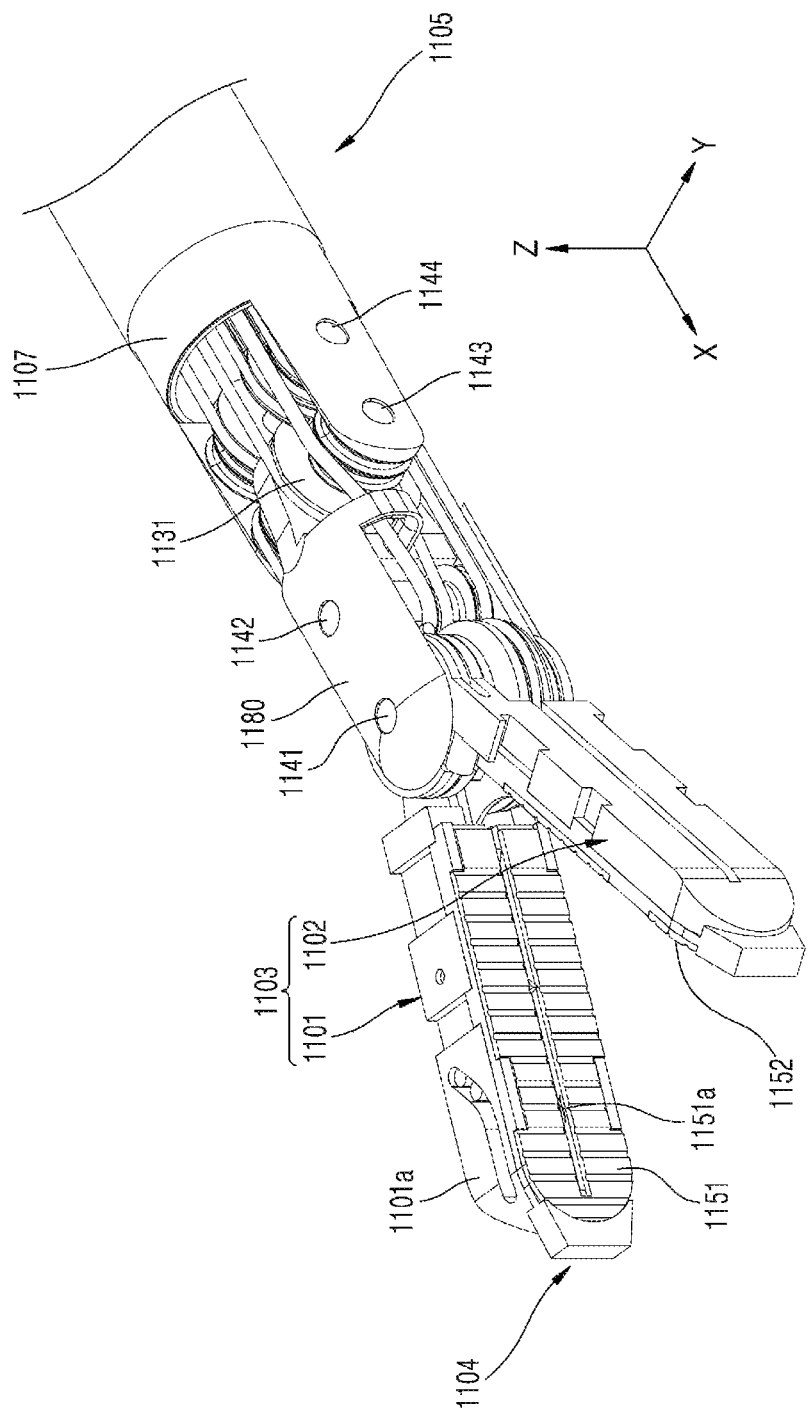
FIG. 76 is a perspective view illustrating the end tool of the surgical instrument for electrocautery of FIG. 75, in particular, when jaws are opened.
Figure 77:
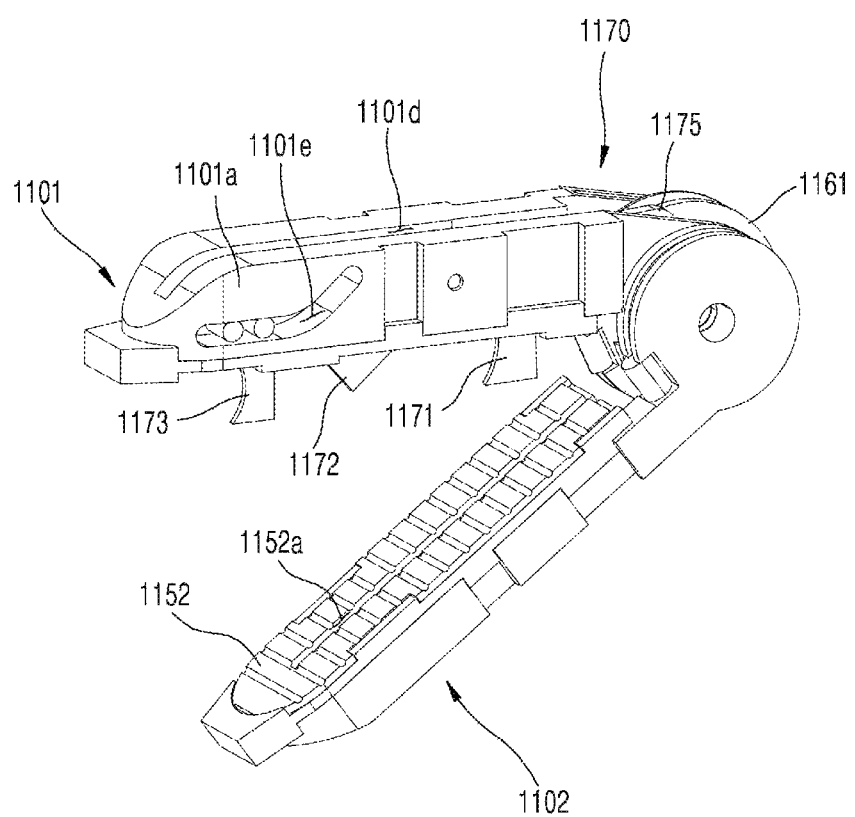
FIG. 77 is a perspective view illustrating the end tool of the surgical instrument for electrocautery of FIG. 75, in particular, when blades are drawn out.
Figure 78:
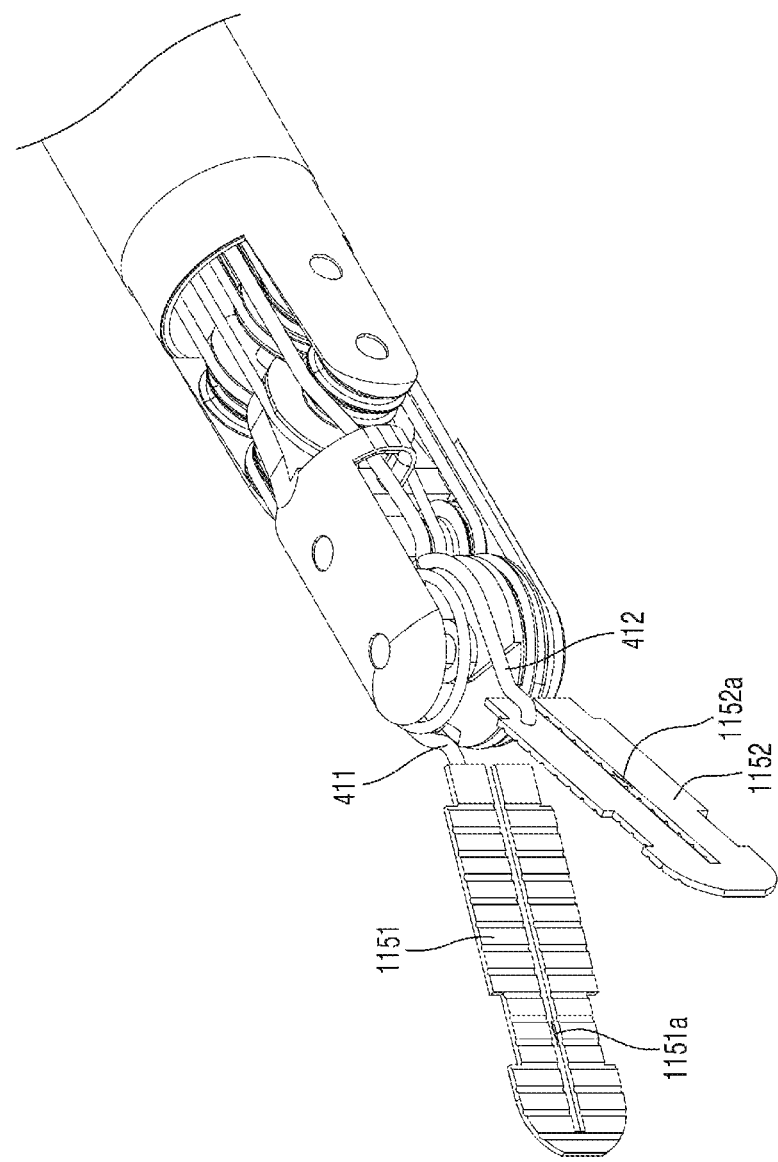
FIG. 78 is a perspective view illustrating the end tool of the surgical instrument for electrocautery of FIG. 75, in particular, mainly showing electrodes and electric wires.
Figure 79:
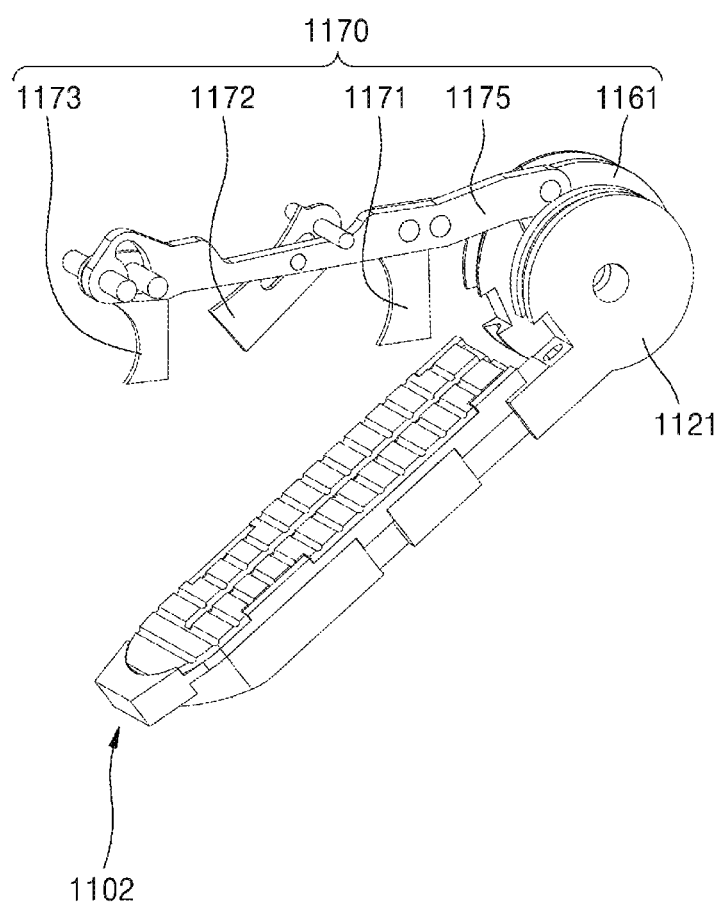
FIG. 79 is a perspective view illustrating the end tool of the surgical instrument for electrocautery of FIG. 75, in particular, mainly showing a blade assembly.
Figure 80:
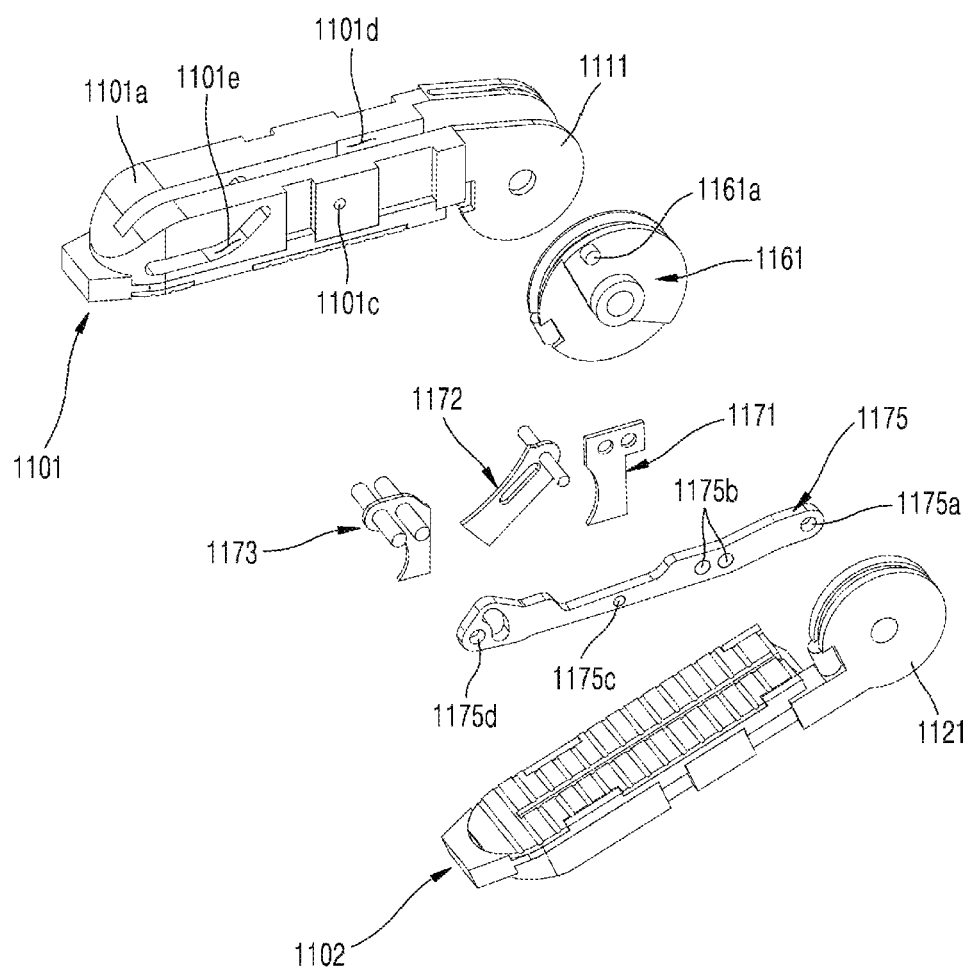
FIGS. 80 and 81 are exploded perspective views illustrating the end tool of the surgical instrument for electrocautery of FIG. 75.
Figure 81:
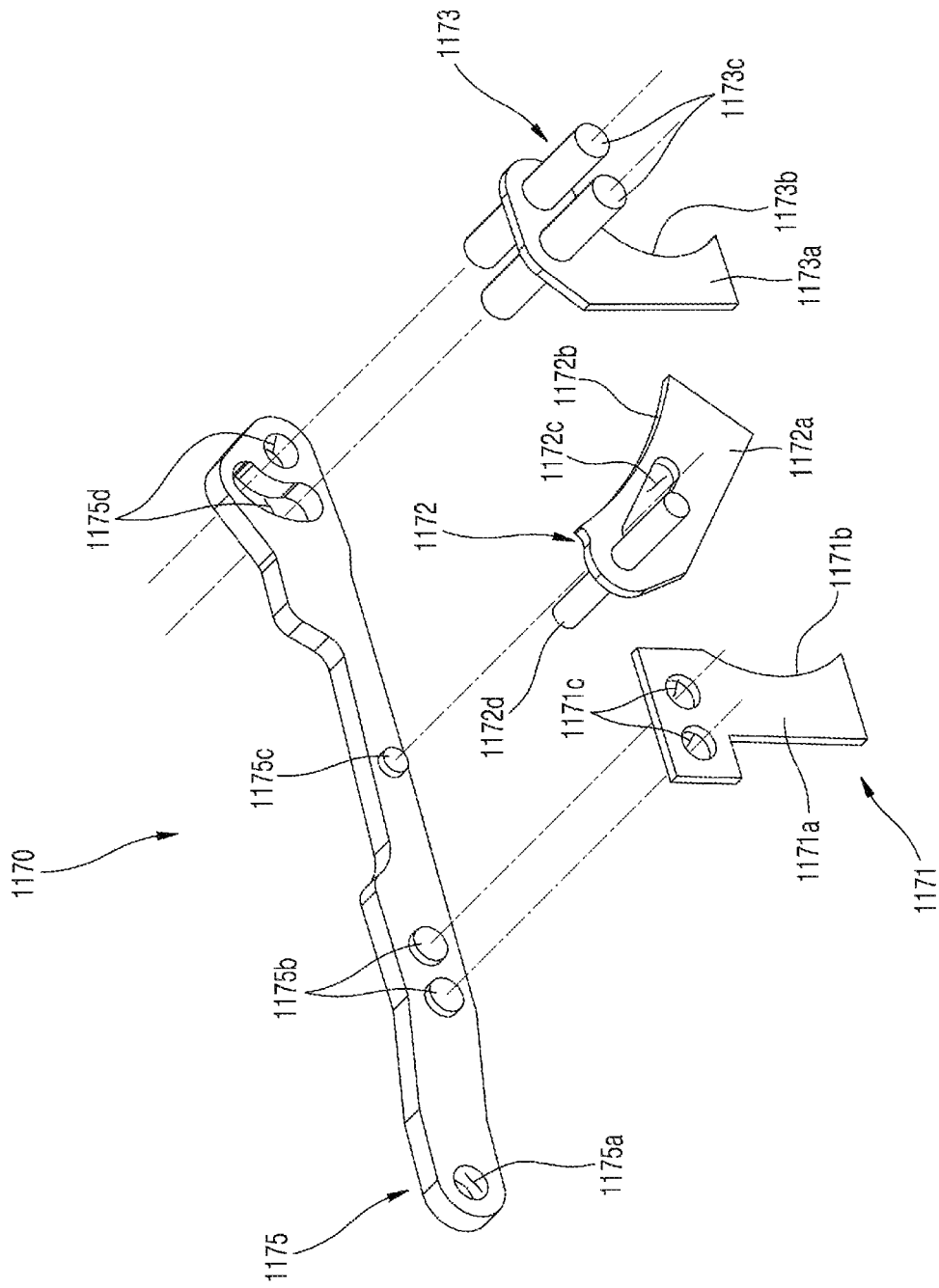
Figure 82:
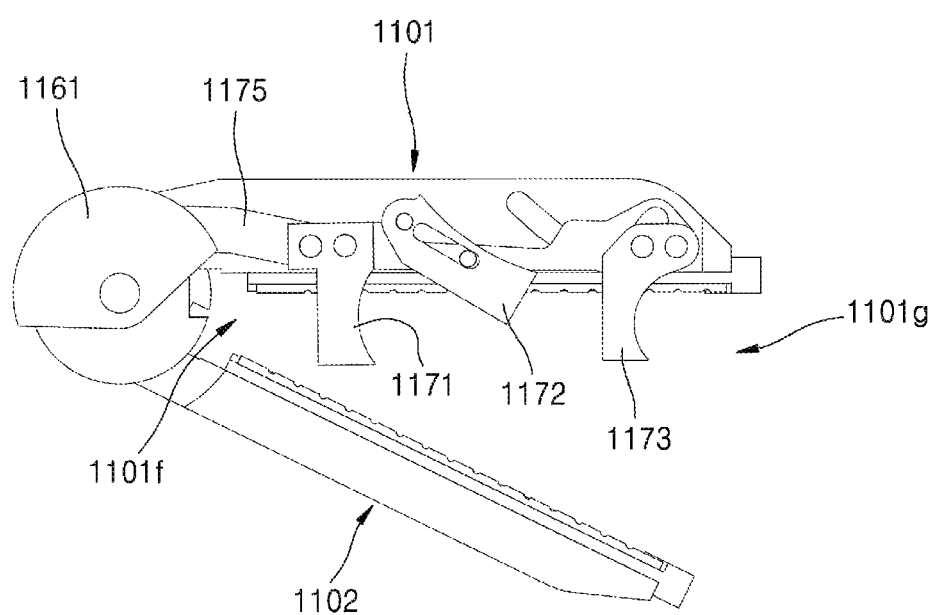
FIG. 82 is a side view illustrating the end tool of the surgical instrument for electrocautery of FIG. 75.
Figure 83:
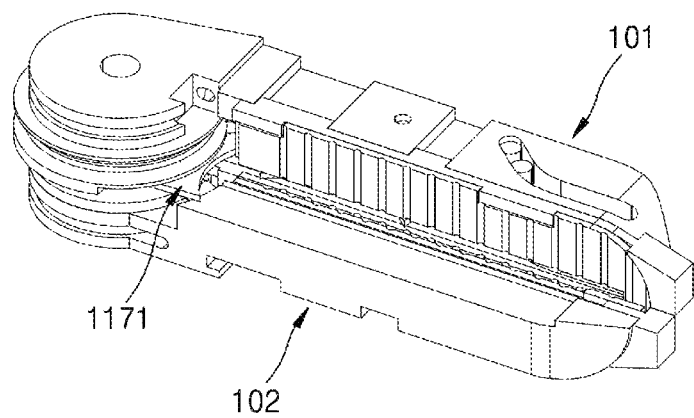
FIG. 83 is a perspective view illustrating the end tool of the surgical instrument for electrocautery of FIG. 75, in particular, a second jaw that is partially cut.

FIGS. 75 and 76 are perspective views illustrating an end tool of a surgical instrument for electrocautery according to a fourth embodiment of the present disclosure, in particular, FIG. 75 shows a state in which jaws are closed and FIG. 76 shows a state in which jaws are open. FIG. 77 is a perspective view illustrating the end tool of the surgical instrument for electrocautery of FIG. 75, in particular, when blades are drawn out. FIGS. 78 and 79 are perspective views showing an end tool of a surgical instrument for electrocautery shown in FIG. 75, in particular, FIG. 78 mainly shows electrodes and wires and FIG. 79 mainly shows the blade assembly. FIGS. 80 and 81 are exploded perspective views illustrating the end tool of the surgical instrument for electrocautery of FIG. 75. FIG. 82 is a side view of the end tool of the surgical instrument for electrocautery shown in FIG. 75, and FIG. 83 is a perspective view of the end tool of the surgical instrument for electrocautery shown in FIG. 75, in which the second jaw is partially cut.

Referring to FIGS. 75 to 83, the end tool 1100 according to the fourth embodiment of the present disclosure includes a pair of jaws for performing a grip motion, that is, a first jaw 1101 and a second jaw 1102, and components indicating each of the first jaw 1101 and the second jaw 1102, or both the first jaw 1101 and the second jaw 1102 may be collectively referred to as a jaw 1103.

In addition, the end tool 1100 includes a plurality of pulleys including a pulley 1111 that is the first jaw pulley coupled to the first jaw 1101. In the present embodiment, the pulleys associated with the rotational motion of the first jaw 1101 are substantially the same as the pulley 112, the pulley 113, the pulley 114, the pulley 115, and the pulley 116 described above with reference to FIG. 11, etc. of the first embodiment, and detailed descriptions thereof are omitted.

In addition, the end tool 1100 includes a plurality of pulleys including a pulley 1121 that is the second jaw pulley coupled to the second jaw 1102. In the present embodiment, the pulleys associated with the rotational motion of the second jaw 1102 are substantially the same as the pulley 122, the pulley 123, the pulley 124, the pulley 125, and the pulley 126 described above with reference to FIG. 11, etc. of the first embodiment, and detailed descriptions thereof are omitted.

The end tool 1100 of the fourth embodiment may include the rotary shaft 1141, the rotary shaft 1142, the rotary shaft 1143, and the rotary shaft 1144. Here, the rotary shaft 1141 and the rotary shaft 1142 may penetrate and be inserted into the end tool hub 1180, and the rotary shaft 1143 and the rotary shaft 1144 may be inserted through the pitch hub 1107. The rotary shaft 1141, the rotary shaft 1142, the rotary shaft 1143, and the rotary shaft 1144 may be arranged sequentially from a distal end 1104 towards a proximal end 1105.

Also, the end tool 1100 according to the fourth embodiment may include an end tool hub 1180 and the pitch hub 1107.

The rotary shaft 1141 and the rotary shaft 1142 that will be described later are inserted through the end tool hub 1180, and the pulley 1111 and the pulley 1121 axially coupled to the rotary shaft 1141 and at least a part of the first jaw 1101 and the second jaw 1102 coupled to the pulleys may be accommodated in the end tool hub 1180.

Meanwhile, the pulley 1131 serving as an end tool pitch pulley may be formed at one end of the end tool hub 1180. As shown in FIG. 75, the pulley 1131 may be formed as a separate member from the end tool hub 1180 and may be coupled to the end tool hub 1180. Alternatively, the pulley 1131 may be formed as one-body with the end tool hub 1180. In addition, the wire 303 (see FIG. 13) and the wire 304 (see FIG. 13) are coupled to the pulley 1131 functioning as the end tool pitch pulley, and the pulley 1131 rotates about the rotary shaft 1143 and carries out the pitch motion.

The rotary shaft 1143 and the rotary shaft 1144 are inserted through the pitch hub 1107, and the pitch hub 1107 may be axially coupled to the end tool hub 1180 and the pulley 1131 via the rotary shaft 1143. Accordingly, the end tool hub 1180 and the pulley 1131 may be formed to be rotatable around the rotation shaft 1143 with respect to the pitch hub 1107.

In addition, the end tool 1100 according to the fourth embodiment may further include, in order to perform cautery and cutting motions, components such as a first electrode 1151, a second electrode 1152, the blade pulley 1161, a blade link 1175, a first blade 1171, a second blade 1172, a third blade 1173, etc. Here, components such as the blade pulley 1161, the first blade 1171, the second blade 1172, the third blade 1173, the blade link 1175, etc. associated with the driving of the blade may be collectively referred to as a blade assembly 1170. In the fourth embodiment, by arranging the blade assembly 1170 including a plurality of blades between the pulley 1111 which is the first jaw pulley and the pulley 1121 which the second jaw pulley, not only the pitch motion and the yaw motion of the end tool 1100 but also the cutting motion using the blades may be performed. In the embodiment, the components for performing the cautery and cutting motions are substantially the same as the components described above in the first embodiment, and thus, detailed descriptions thereof are omitted here.

The surgical instrument for electrocautery according to the fourth embodiment may include the wire 301, the wire 302, the wire 303, the wire 304, the wire 305, the wire 306, the wire 307, and the wire 308, like in the first embodiment shown in FIG. 13, etc.

Also, the surgical instrument for electrocautery according to the fourth embodiment may include the fastening member 321, the fastening member 323, the fastening member 324, the fastening member 326, the fastening member 327, and the fastening member 329 which are coupled to respective ends of the wires in order to couple the wires and the pulleys, like in the first embodiment shown in FIG. 13, etc.

Hereinafter, the blade assembly 1170 of the surgical instrument for electrocautery according to the fourth embodiment of the present disclosure will be described below in more detail.

The first jaw 1101 may include a guide member 1101a and a case (not shown).

A blade accommodation portion 1101d and a first guide portion 1101e may be formed in the guide member 1101a. The guide member 1101a is coupled to the pulley 1111 and may be formed to guide the moving paths of the first blade 1171, the second blade 1172, and the third blade 1173. For example, the guide member 1101a may be formed in the form of two long bars facing each other, and the blade accommodation portion 1101d in which at least a part of the first blade 1171, the second blade 1172, the third blade 1173, and the blade link 1175 are accommodated may be formed inside the guide member 1101a. The blade accommodation portion 1101d may be formed lengthily in the direction from a proximal end 1101f toward a distal end 1101g of the first jaw 1101, and the first blade 1171, the second blade 1172, and the third blade 1173 may be totally accommodated in the blade accommodation portion 1101d. Alternatively, at least some parts of the first blade 1171, the second blade 1172, and the third blade 1173 may protrude outside from the blade accommodation portion 1101d. In other words, the tissue may be cut while the first blade 1171, the second blade 1172, and the third blade 1173 move along the blade accommodation portion 1101d. This will be described in more detail later.

In addition, the first guide portion 1101e for guiding the movement of the third blade 1173 may be formed in the guide member 1101a of the first jaw 1101. Here, the first guide portion 1101e may be formed in both inner sidewalls in the guide member 1101a forming the blade accommodation portion 1101d. The first guide portion 1101e may be formed in the shape of a groove formed along the movement path of the third blade 1173. In addition, in a state where a link coupling portion 1173c of the third blade 1173 formed in the protrusion shape is fit into the first guide portion 101e formed in the groove shape, as the link coupling portion 1173c moves along the first guide portion 1101e, the third blade 1173 may move with respect to the first jaw 1101.

Although the drawings illustrate that the first guide portion 1101e is integrated with the guide member 1101a as one component of the first jaw 1101, the technical concepts of the present disclosure are not limited thereto, and the first guide portion 1101e may be formed as a separate member from the guide member 1101a and be coupled to the guide member 1101a.

The first electrode 1151 may be formed on a surface of the first jaw 1101 facing the second jaw 1102. The second electrode 1152 may be formed on a surface of the second jaw 1102 facing the first jaw 1101.

Here, a slit 1151a may be formed in the first electrode 1151, and at least some parts of the first blade 1171, the second blade 1172, and the third blade 1173 may protrude out of the first jaw 1101 and the first electrode 1151 via the slit 1151a.

Furthermore, a slit 1152a may be formed at the second electrode 1152. In addition, at least some parts of the first blade 1171, the second blade 1172, and the third blade 1173 protruding out of the first jaw 1101 may be accommodated in the second jaw 1102 via the slit 1152a.

The first blade 1171 may include a body portion 1171a, an edge portion 1171b, and one or more link coupling portions 1171c.

In an area of the body portion 1171a, the edge portion 1171b which is sharp and cuts tissue may be formed. At least a part of the edge portion 1171b may be drawn to the outside of the first jaw 1101 to cut the tissue positioned between the first jaw 1101 and the second jaw 1102.

In another area of the body portion 1171a, the one or more link coupling portions 1171c may be formed. For example, the link coupling portion 1171c may be formed in a through-hole shape so that the first blade coupling portion 1175b formed in a protrusion shape may be inserted therein.

The second blade 1172 may include a body portion 1172a, an edge portion 1172b, one or more link coupling portions 1172c, and a jaw coupling portion 1172d.

In an area of the body portion 1172a, the edge portion 1172b which is sharp and cuts tissue may be formed. At least a part of the edge portion 1172b may be drawn to the outside of the first jaw 1101 to cut the tissue positioned between the first jaw 1101 and the second jaw 1102.

In another area of the body portion 1172a, the one or more link coupling portions 1172c may be formed. For example, the link coupling portion 1172c may be formed in the shape of an elongated slit so that the second blade coupling portion 1175c formed in a protrusion shape may be inserted therein.

In another area of the body portion 1172a, the jaw coupling portion 1172d may be formed. For example, the jaw coupling portion 1172d may be formed in an axis shape and may be inserted through the second blade coupling portion 1101c that is formed in a through-hole shape in the guide member 1101a of the first jaw 1101.

The third blade 1173 may include a body portion 1173a, an edge portion 1173b, and one or more link coupling portions 1173c.

In an area of the body portion 1173a, the edge portion 1173b which is sharp and cuts tissue may be formed. At least a part of the edge portion 1173b may be drawn to the outside of the first jaw 1101 to cut the tissue positioned between the first jaw 1101 and the second jaw 1102.

In another area of the body portion 1173a, the one or more link coupling portions 1173c may be formed. For example, the link coupling portion 1173c may be formed in an axis shape and may be inserted in the first guide portion 1101e of the first jaw 1101. Here, the link coupling portion 1173c of the third blade 1173 according to the embodiment may correspond to the second guide portion 171c (see FIG. 7) according to the first embodiment, and may perform substantially the same functions as those of the second guide portion 171c (see FIG. 7).

The blade link 1175 connects the blade pulley 1161 to the first blade 1171, the second blade 1172, and the third blade 1173 so as to transfer the rotation of the blade pulley 1161 to the first blade 1171, the second blade 1172, and the third blade 1173 so that the first blade 1171, the second blade 1172, and the third blade 1173 may be moved along the direction from the proximal end 1101f to the distal end 1101g of the first jaw 1101. The blade link 1175 may be formed in an elongated bar shape, and one end portion of the blade link 1175 may be connected to the blade pulley 1161 and the other regions may be respectively connected to the first blade 1171, the second blade 1172, and the third blade 1173. This will be described below in more detail.

A pulley coupling portion 1175a, a first blade coupling portion 1175b, a second blade coupling portion 1175c, and a third blade coupling portion 1175d may be sequentially formed in the blade link 1175 from the proximal end 1101f toward the distal end 1101g.

In detail, the blade pulley coupling portion 1175a formed in a through-hole shape may be formed in the end portion of the blade link 1175 at the side of the proximal end 1101f. In addition, the protrusion 1161a formed on one surface of the blade pulley 1161 may be inserted in the blade pulley coupling portion 1175a. In other words, one end portion of the blade link 1175 may be axially coupled to the blade pulley 1161.

The first blade coupling portion 1175b of the blade link 1175 may include a plurality of protrusions. In addition, the link coupling portion 1171c of the first blade 1171 may include a plurality of through-holes. Here, the respective protrusions and respective through-holes coupled to each other are formed to have substantially the same diameters. In addition, the plurality of protrusions of the first blade coupling portion 1175b and the plurality of through-holes of the link coupling portion 1171c are coupled to each other.

Through the above configuration, the relative position of the first blade 1171 with respect to the blade link 1175 is fixed, and thus, the blade link 1175 and the first blade 1171 are integrally moved with each other. In other words, when the blade link 1175 linearly moves, the first blade 1171 also linearly moves.

In the drawings, the first blade coupling portion 1175b includes a plurality of protrusions, and the link coupling portion 1171c includes a plurality of through-holes. However, the technical concepts of the present disclosure are not limited thereto, and positions of forming the protrusions and the through-holes may be changed with each other.

The second blade coupling portion 1175c of the blade link 1175 includes a protrusion. In addition, the link coupling portion 1172c of the second blade 1172 is formed in the shape of an elongated slit. In addition, the protrusion of the second blade coupling portion 1175c is inserted in the slit of the link coupling portion 1172c.

In addition, the jaw coupling portion 1172d of the second blade 1172 includes a protrusion. In addition, the second blade coupling portion 1101c formed in the shape of hole is formed in the guide member 1101a of the first jaw 1101. In addition, the jaw coupling portion 1172d of the second blade 1172 may be inserted through the second blade coupling portion 1101c of the guide member 1101a, so that the second blade 1172 may be rotated with respect to the guide member 1101a by using the jaw coupling portion 1172d as a shaft.

Therefore, when the blade link 1175 linearly moves, the second blade coupling portion 1175c of the blade link 1175 pushes or pulls the link coupling portion 1172c of the second blade 1172. Here, because the jaw coupling portion 1172d of the second blade 1172 is axially coupled to the guide member 1101a, the second blade 1172 is rotated with respect to the guide member 1101a.

In the drawings, the second blade coupling portion 1175c includes the protrusion, and the link coupling portion 1171c includes the slit. However, the technical concepts of the present disclosure are not limited thereto, and locations of the protrusion and the slit may be switched with each other.

Also, in the drawings, the jaw coupling portion 1172d of the second blade 1172 is formed in the shape of an axis and the guide member 1101a includes the second blade coupling portion 1101c formed in the shape of the through-hole. However, the technical concepts of the present disclosure are not limited thereto, and the locations of forming the axis and the through-hole may be switched with each other.

The third blade coupling portion 1175d of the blade link 1175 may include one or more through-holes and one or more slits. In addition, the link coupling portion 1173c of the third blade 1173 may include a plurality of protrusions. In addition, the plurality of protrusions of the link coupling portion 1173c may be respectively inserted in the through-hole and the slits of the third blade coupling portion 1175d.

Here, the link coupling portion 1173c of the third blade 1173 may be inserted in the first guide portion 1101e of the first jaw 1101 after passing through the third blade coupling portion 1175d of the blade link 1175.

Therefore, when the blade link 1175 linearly moves, the third blade coupling portion 1175d of the blade link 1175 pushes or pulls the link coupling portion 1173c of the third blade 1173, and accordingly, the third blade 1173 may move along the first guide portion 1101e of the first jaw 1101. Here, the movement trajectory of the third blade 1173 may be determined according to the shape of the first guide portion 1101e.

In the drawings, the link coupling portion 1173c of the third blade 1173 is formed in the shape of an axis, and the first guide portion 1101e of the guide member 1101a is formed in the shape of an elongated groove. However, the technical concepts of the present disclosure are not limited thereto, and the locations of forming the axis and the groove may be switched with each other.

In this state, when the blade pulley 1161 rotates about the rotary shaft 1141, the rotational motion of the blade pulley 1161 is transferred to the first blade 1171, the second blade 1172, and the third blade 1173 via the blade link 1175 coupled to the blade pulley 1161. In addition, locations of the first blade 1171, the second blade 1172, and the third blade 1173 are changed due to the transferred rotational motion of the blade pulley 1161, the first blade 1171, the second blade 1172, and the third blade 1173 may be drawn out from the first jaw 1101 while moving along the direction from the proximal end 1101f toward the distal end 1101g of the first jaw 1101 or the first blade 1171, the second blade 1172, and the third blade 1173 may be pulled in the first jaw 1101 in the opposite case.

That is, the blade link 1175, the first guide portion 1101e of the first jaw 1101, and respective blades are coupled to form a kind of a power transmission mechanism, and thus, when the blade pulley 1161 is rotated, the first blade 1171, the second blade 1172, and the third blade 1173 connected to the blade pulley 1161 are moved between the distal end 1101g and the proximal end 1101f of the first jaw 1101.

Hereinafter, motions of each blade will be described below in detail.

Figure 87:
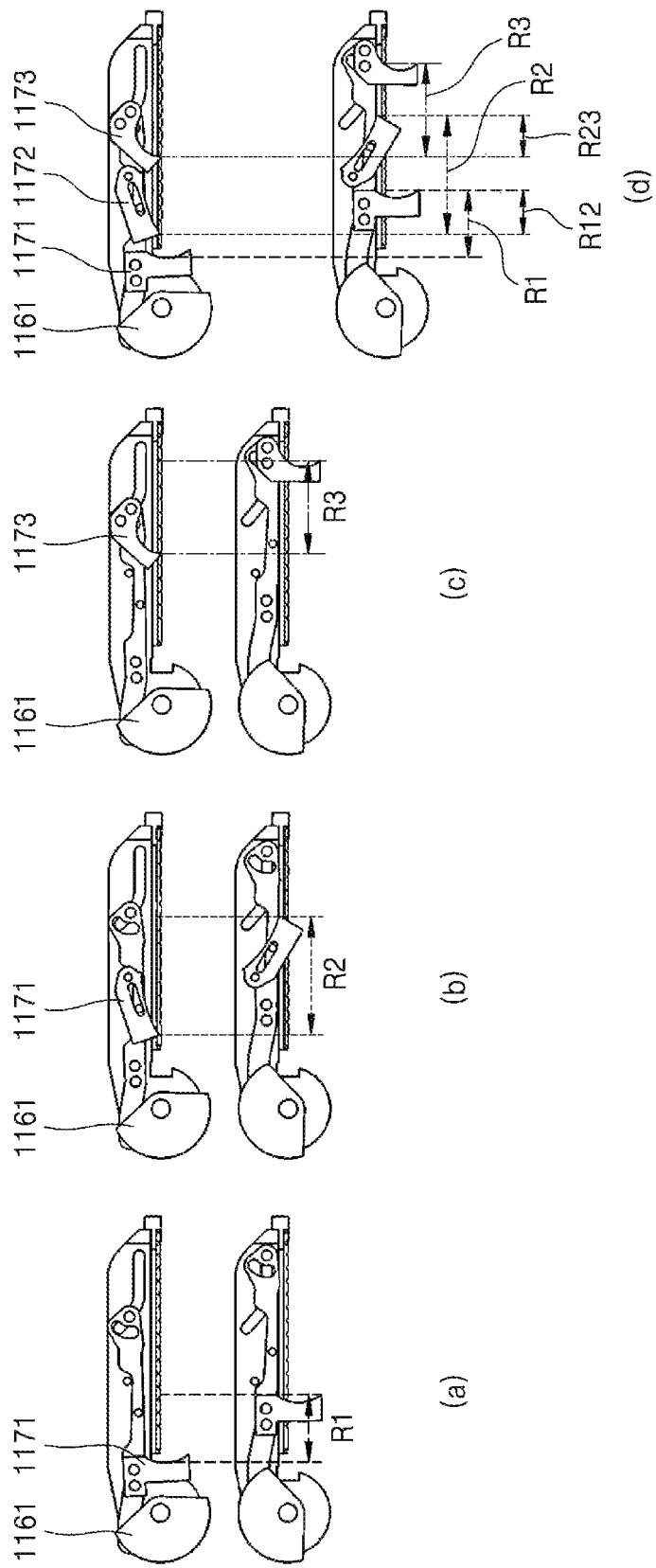
FIG. 87 is a perspective view illustrating a cutting movement of an end tool of a surgical instrument for electrocautery of FIG. 75, in particular, movement trajectories of respective blades.

FIGS. 84, 85, and 86 are side views illustrating a cutting movement of the end tool of the surgical instrument for electrocautery of FIG. 75, when jaws are closed, and FIG. 87 is a side view illustrating a cutting motion of the end tool of the surgical instrument for electrocautery of FIG. 75, for showing movement trajectories of respective blades.

First, in the state shown in FIG. 84, when the blade pulley 1161 is sequentially rotated in the direction indicated by the arrow R1 of FIG. 85 and the direction indicated by the arrow R2 of FIG. 86, the blade link 1175 coupled to the blade pulley 1161 is moved in the direction indicated by the arrow D1 of FIG. 85 and the direction indicated by the arrow D2 of FIG. 86 to sequentially reach the positions in FIG. 85 and FIG. 86.

Then, the first blade 1171 coupled to the blade link 1175 is moved in the direction indicated by the arrow A1 of FIG. 85 and the direction indicated by the arrow A2 of FIG. 86, to sequentially reach the positions of FIG. 85 and FIG. 86. Here, because the blade link 1175 and the first blade 1171 are 2-point coupled to each other, the blade link 1175 and the first blade 1171 are integrally moved with each other. In other words, when the blade link 1175 linearly moves (or moves nearly straight), the first blade 1171 also linearly moves (or moves nearly straight).

Then, the second blade 1172 coupled to the blade link 1175 is moved in the direction indicated by the arrow B1 of FIG. 85 and the direction indicated by the arrow B2 of FIG. 86, to sequentially reach the positions of FIG. 85 and FIG. 86. Here, because the jaw coupling portion 1172d of the second blade 1172 is axially coupled to the guide member 1101a of the first jaw 1101, the second blade 1172 is rotationally moved with respect to the guide member 1101a.

In addition, the third blade 1173 coupled to the blade link 1175 is moved in the direction indicated by the arrow C1 of FIG. 85 and the direction indicated by the arrow C2 of FIG. 86, to sequentially reach the positions of FIG. 85 and FIG. 86.

Here, while the link coupling portion 1173c formed in the shape of a protrusion is inserted in the first guide portion 1101e formed in the shape of a groove, the blade link 1175 pushes the third blade 1173, and accordingly, the third blade 1173 is entirely moved along the first guide portion 1101e.

At this time, since the groove-shaped first guide portion 1101e is formed to be inclined to a certain degree in a certain section, the blade 1171 performs a linear motion (i.e., movement in the X-axis direction) in the direction toward the distal end 1104 of the end tool 1100. At the same time, linear motion (i.e., Y-axis movement) is performed in a direction protruding to a certain extent from the inside of the first jaw 1101 to the outside. As described above, as the blade 1171 performs movement both in the X-axis direction and the Y-axis direction, the tissue (not shown) between the first jaw 1101 and the second jaw 1102 may be cut.

However, the linear movement of the third blade 1173 may not refer to a motion in a strictly straight line, and may refer to the motion of cutting tissue in a straight-line in general even when the straight line is not completely straight, e.g., the line is bent in the middle at a certain angle, includes a section with a gradual curvature, etc.

In other words, the first blade 1171 is two-point coupled to the blade link 1175, and thus, when the blade link 1175 linearly moves, the first blade 1171 linearly moves with the blade link 1175. One end portion of the second blade 1172 is axially coupled to the first jaw 1101, and thus, when the blade link 1175 linearly moves, the second blade 1172 is rotationally moved. The third blade 1173 is inserted in the blade link 1175 and the guide member 1101a of the first jaw 1101, and thus, when the blade link 1175 linearly moves, the third blade 1173 is moved along the first guide portion 1101e of the guide member 1101a of the first jaw 1101.

In other words, the first blade 1171 performs a motion close to the linear movement (although it is not a strictly linear movement). A trajectory of the second blade 1172 forms an arc while performing the rotational motion about the rotary shaft. The third blade 1173 is moved along the first guide portion 1101e formed in the shape of a slit in the first jaw 1101, and the path thereof is determined according to the shape of the first guide portion 1101e. That is, the path of the third blade 1173 may be controlled by adjusting the shape of the first guide portion 1101e.

In other words, three blades 1171, 1172, and 1173 are connected to the blade link 1175, and thus, when the blade pulley 1161 is rotated, the three blades 1171, 1172, and 1173 connected thereto are moved together. In detail, when the blade pulley 1161 is rotated, the three blades 1171, 1172, and 1173 cut the tissue while moving between the proximal end 1101f and the distal end 1101g of the end tool.

Here, the first blade 1171 formed at the innermost side, that is, the proximal end 1101f side of the end tool 1100, may be moved while performing a motion close to the linear movement. Here, at least a part of the first blade 1171 is exposed to outside of the first jaw 1101 during every motion.

The second blade 1172 formed at the center is moved while drawing a trajectory close to a semi-circle. Here, at a start point (first position) and an end point (second position) of the motion, at least a part of the second blade 1172 is accommodated in the first jaw 1101, and the second blade 1172 is exposed to outside of the first jaw 1101 only in the middle of moving from the first position to the second position.

The third blade 1173 formed at the outermost side, that is, the distal end 1101g side of the end tool 1100, is moved drawing a trajectory close to an arc from the start point (first position) to a certain point in the middle (third position), and then, is moved performing a nearly linear motion after the certain position (third position). Here, at the start point (first position) of the motion, the third blade 1173 is accommodated in the first jaw 1101, and after that, at least a part of the third blade 1173 is exposed to outside of the first jaw 1101 when moving to the end point.

According to the embodiment, a plurality of blades having different trajectories are provided, and movement ranges of the blades partially overlap each other so as to perform the cutting motion twice or more, and thereby cutting the tissue more securely.

Referring to FIG. 87, there is an overlapping region R12 between a movement range R1 of the first blade 1171 and a movement range R2 of the second blade 1172, so that the blade passes the corresponding regions at least twice to perform the cutting motion and to obtain secure cutting effect.

Likewise, there is an overlapping region R23 between the movement range R2 of the second blade 1172 and a movement range R3 of the third blade 1173, so that the blade passes the corresponding region at least twice to perform the cutting motion and to obtain secure cutting effect.

As described above, the blade pulley 1161 and the plurality of blades 1171, 1172, and 1173 are provided, and thus, the multi-joint/multi-degree of freedom surgical instrument capable of performing pitch/yaw/actuation motions may possibly perform the electrocautery and cutting motions.

In particular, in the embodiment, a plurality of blades having different trajectories are provided, and movement ranges of the blades partially overlap each other so as to perform the cutting motion twice or more, and thereby obtaining the effect of securely cutting the tissue.

Figure 88:
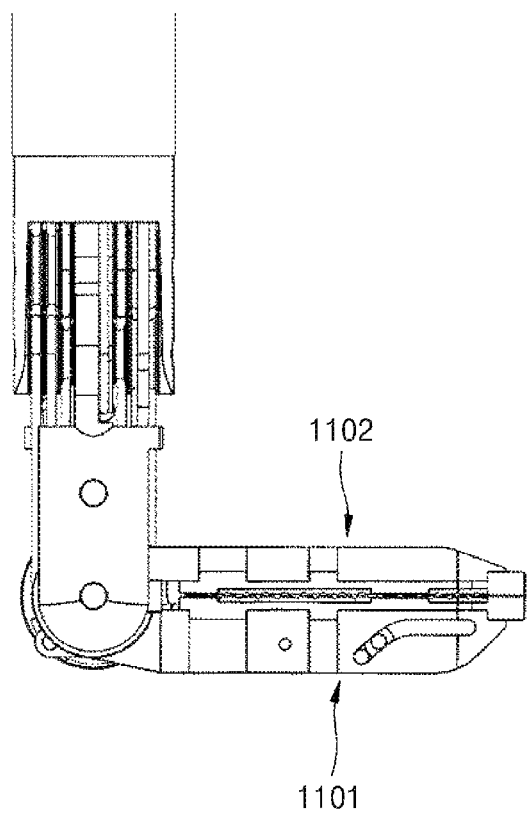
FIG. 88 is a perspective view illustrating a yaw movement of the surgical instrument for electrocautery of FIG. 75.
Figure 89:
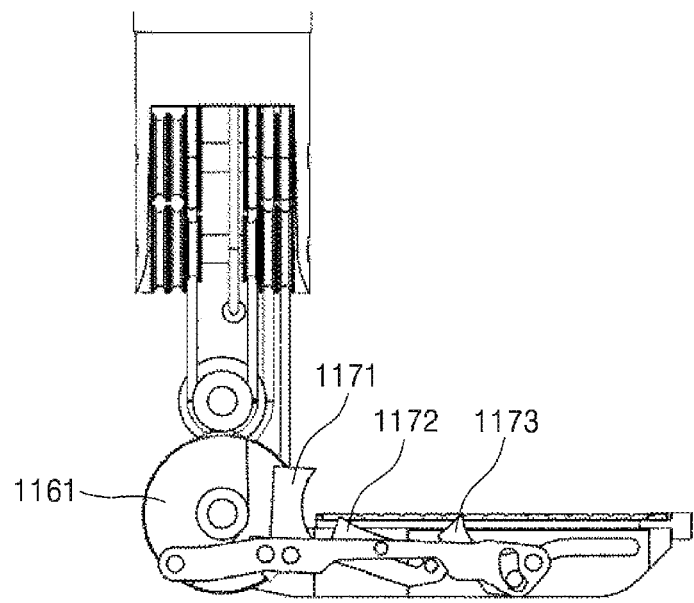
FIGS. 89, 90, and 91 are plan views illustrating a cutting movement of the end tool of the surgical instrument for electrocautery of FIG. 75, and show a process of performing a cutting movement while jaws are yaw-rotated by +90°.
Figure 90:
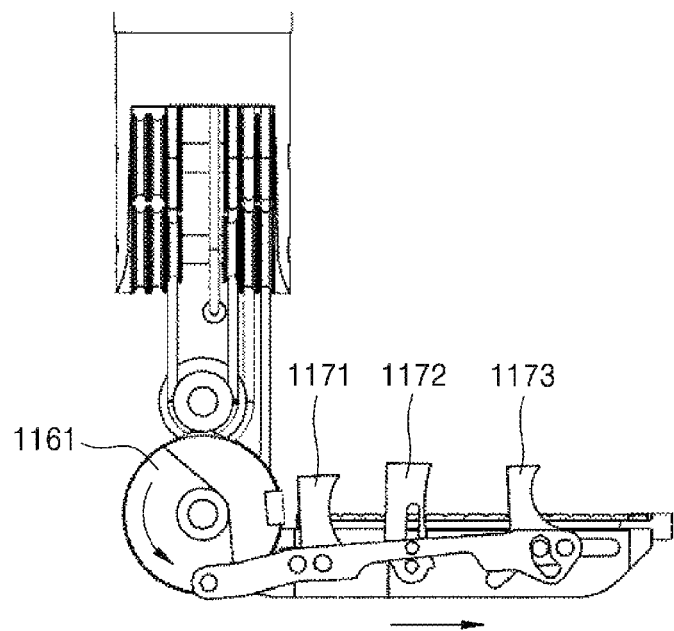
Figure 91:
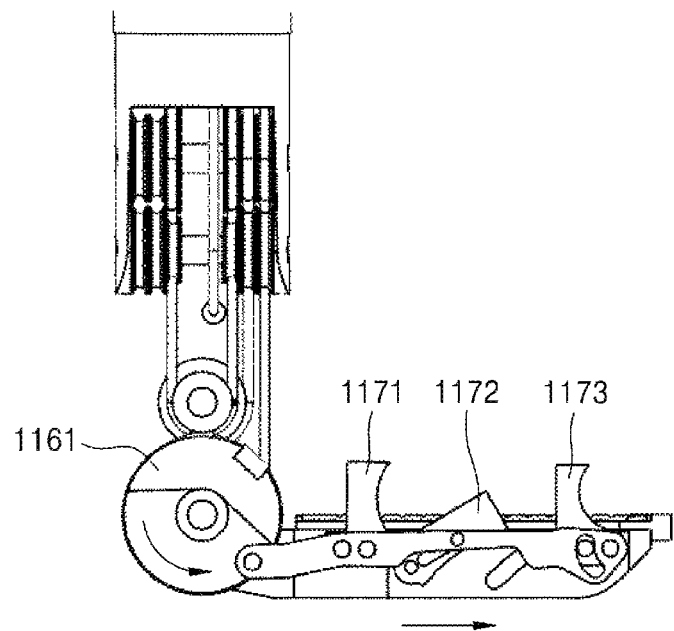

FIG. 88 is a diagram showing a state in which jaws are rotated by +90°, and FIGS. 89, 90, and 91 are plan views illustrating a cutting motion of the end tool of the surgical instrument for electrocautery in FIG. 75, in which the cutting motion is performed while the jaws are yaw-rotated by +90°. As shown in FIGS. 89 to 91, the end tool of the surgical instrument for electrocautery according to the fourth embodiment of the present disclosure is formed to be capable of normally performing a cutting motion even in a state in which the jaws are yaw-rotated by +90°.

Figure 92:
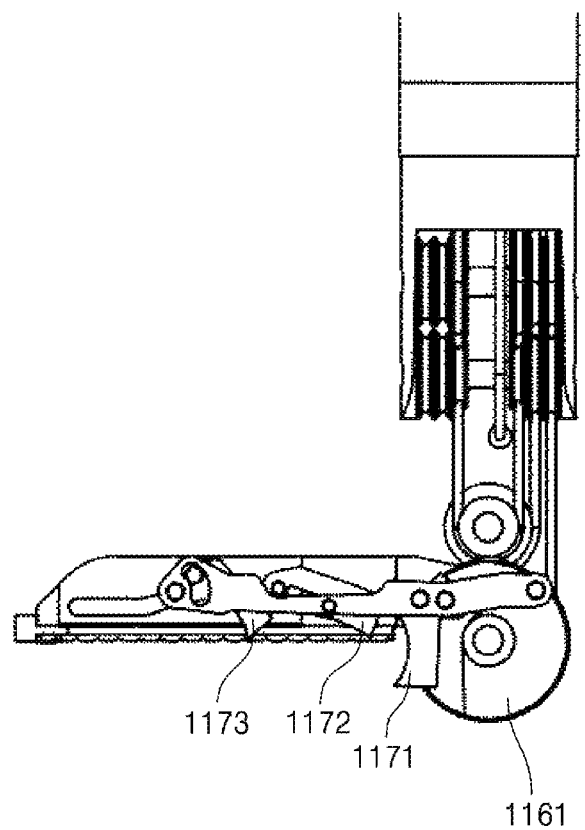
FIGS. 92, 93, and 94 are plan views illustrating a cutting movement of the end tool of the surgical instrument for electrocautery of FIG. 75, and show a process of performing a cutting movement while jaws are yaw-rotated by −90°.
Figure 93:
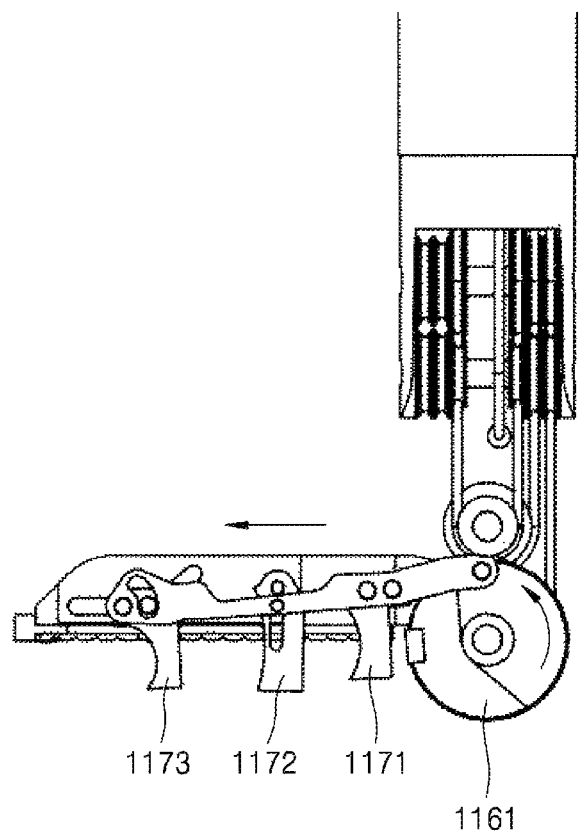
Figure 94:
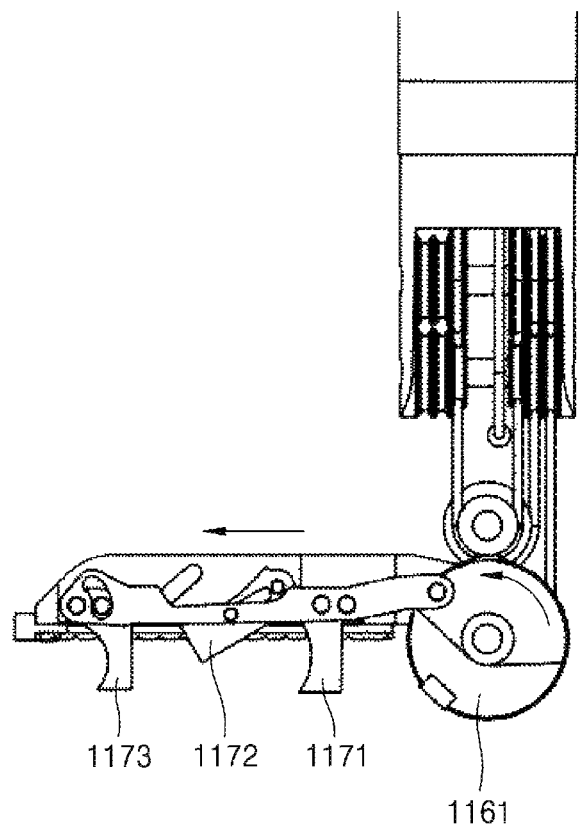

FIGS. 92, 93, and 94 are plan views illustrating a cutting movement of the end tool of the surgical instrument for electrocautery of FIG. 75, and show a process of performing a cutting movement while jaws are yaw-rotated by −90°. As shown in FIGS. 92 to 94, the end tool of the surgical instrument for electrocautery according to the fourth embodiment of the present disclosure is formed to be capable of normally performing a cutting motion even in a state in which the jaws are yaw-rotated by −90°.

Figure 95:
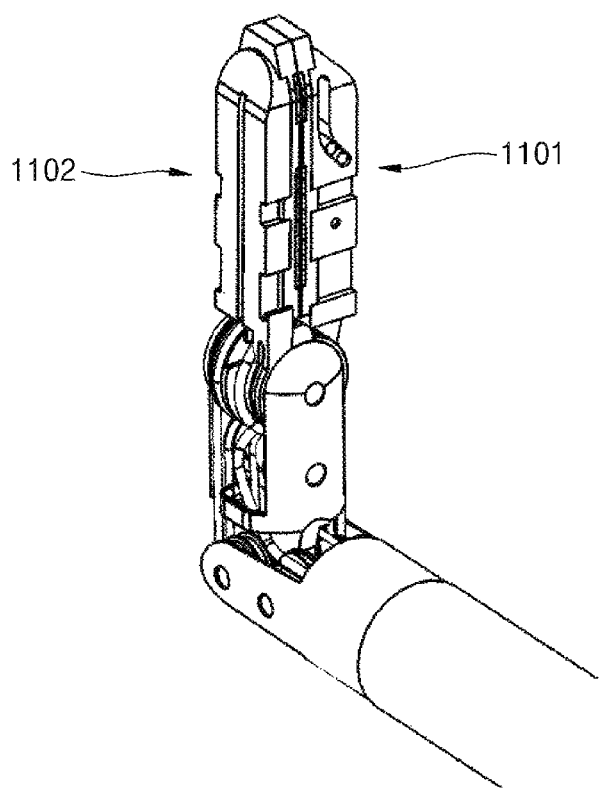
FIG. 95 is a perspective view illustrating a pitch-rotated state of the end tool of the surgical instrument for electrocautery of FIG. 75.
Figure 96:
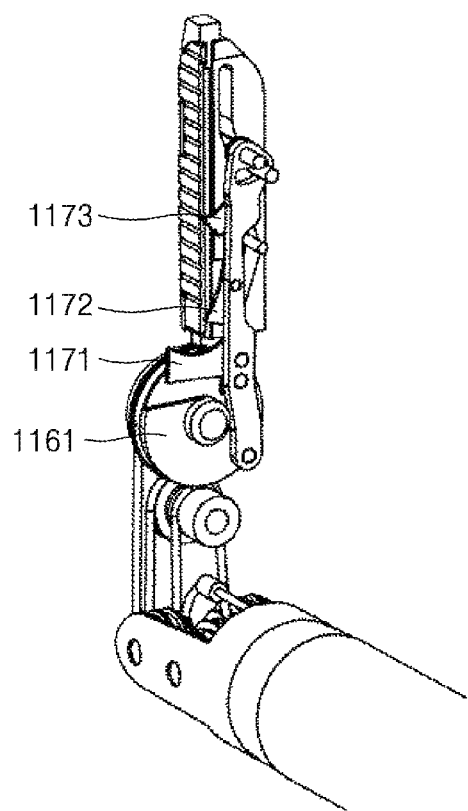
FIGS. 96, 97, and 98 are plan views illustrating a cutting movement of the end tool of the surgical instrument for electrocautery of FIG. 75, and show a process of performing a cutting movement while jaws are pitch-rotated by −90°.
Figure 97:
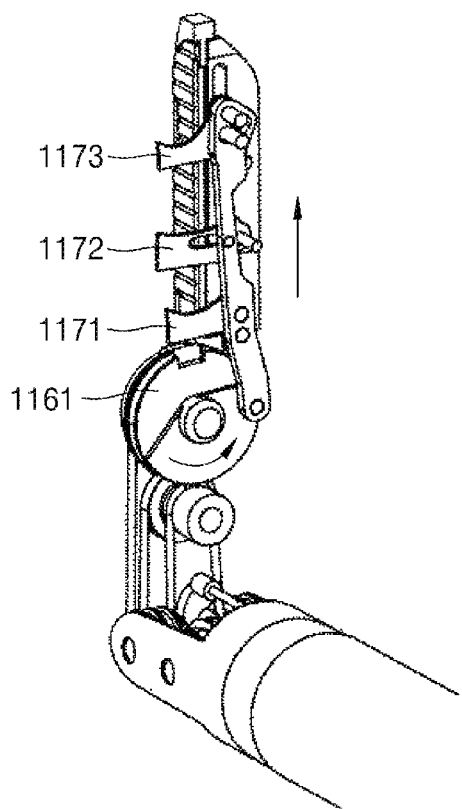
Figure 98:
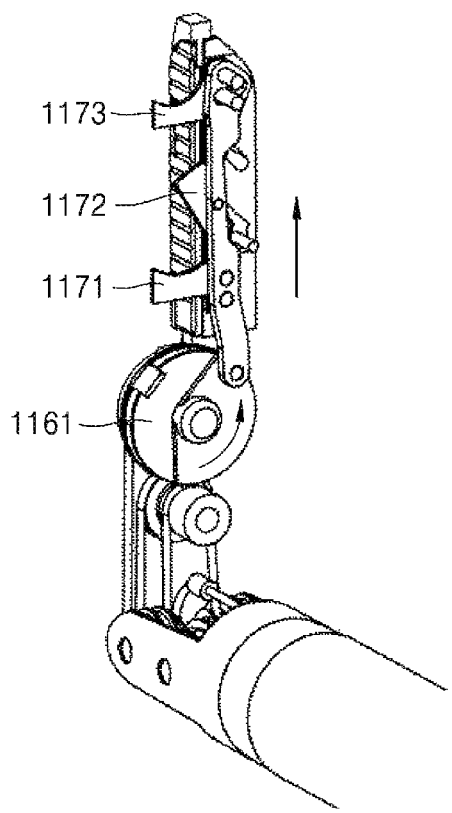

Meanwhile, FIG. 95 is a diagram showing a state in which jaws are pitch-rotated by −90°. In addition, FIGS. 96, 97, and 98 are perspective views showing a cutting motion of the end tool of the surgical instrument for electrocautery of FIG. 75 and show a process of performing a cutting motion in a state in which the jaws are pitch-rotated by −90°. As shown in FIGS. 96 to 98, the end tool of the surgical instrument for electrocautery according to the fourth embodiment of the present disclosure is formed to be capable of normally performing a cutting motion even in a state in which the jaws are pitch-rotated by −90°.

Figure 99:
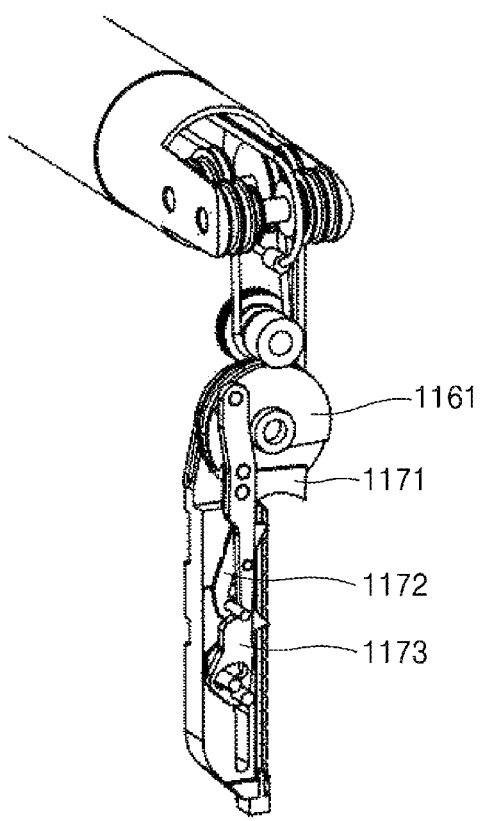
FIGS. 99, 100, and 101 are plan views illustrating a cutting movement of the end tool of the surgical instrument for electrocautery of FIG. 75, and show a process of performing a cutting movement while jaws are pitch-rotated by +90°.
Figure 100:
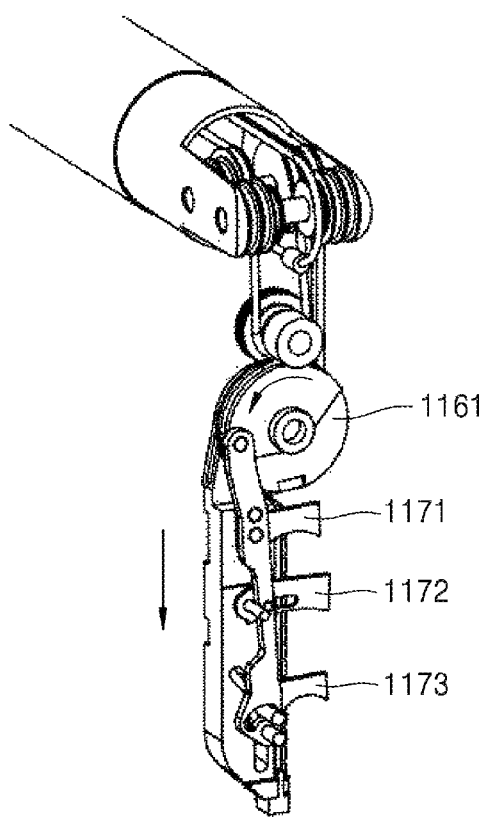
Figure 101:
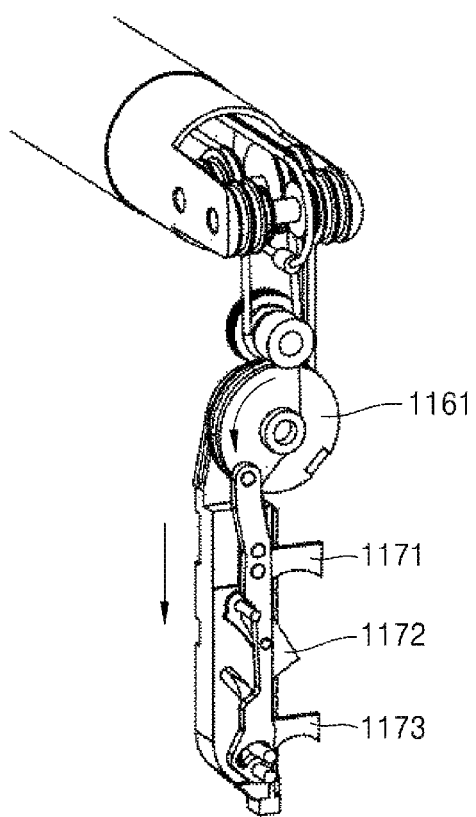

In addition, FIGS. 99, 100, and 101 are perspective views showing a cutting motion of the end tool of the surgical instrument for electrocautery of FIG. 75 and show a process of performing a cutting motion in a state in which the jaws are pitch-rotated by +90°. As shown in FIGS. 99 to 101, the end tool of the surgical instrument for electrocautery according to the fourth embodiment of the present disclosure is formed to be capable of normally performing a cutting motion even in a state in which the jaws are pitch-rotated by +90°.

Figure 102:
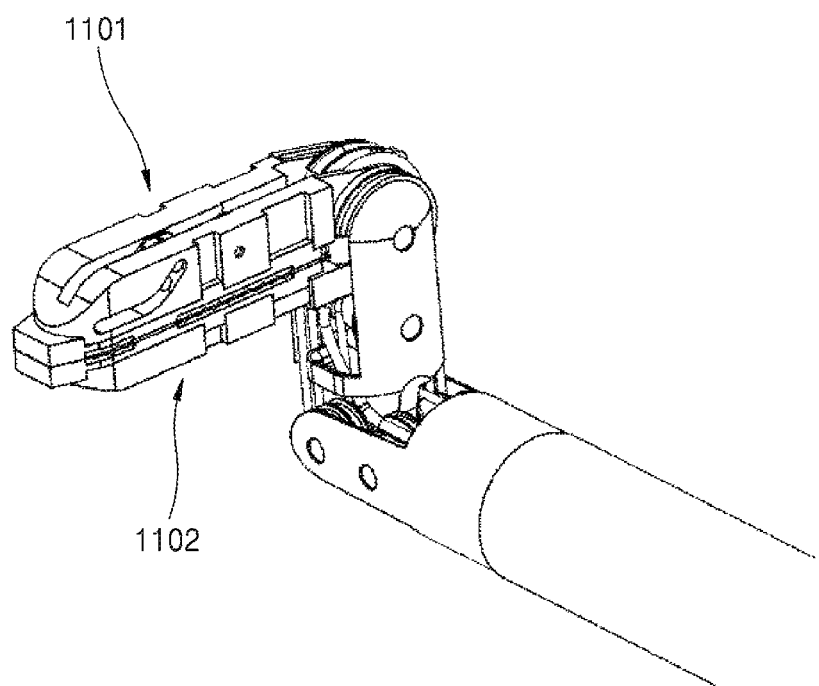
FIG. 102 is a plan view illustrating a pitch-rotated and yaw-rotated state of the end tool of the surgical instrument for electrocautery of FIG. 75.
Figure 103:
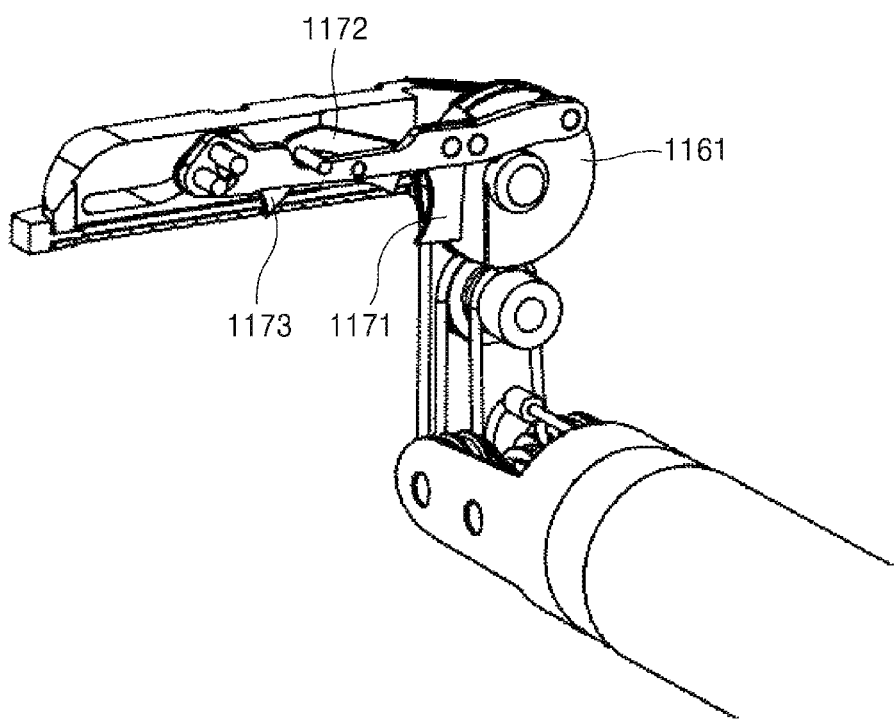
FIGS. 103, 104, and 105 are perspective views illustrating a cutting movement of the end tool of the surgical instrument for electrocautery of FIG. 75, and show an aspect of performing the cutting movement while jaws are pitch-rotated by −90° and at the same time, yaw-rotated by +90°.
Figure 104:
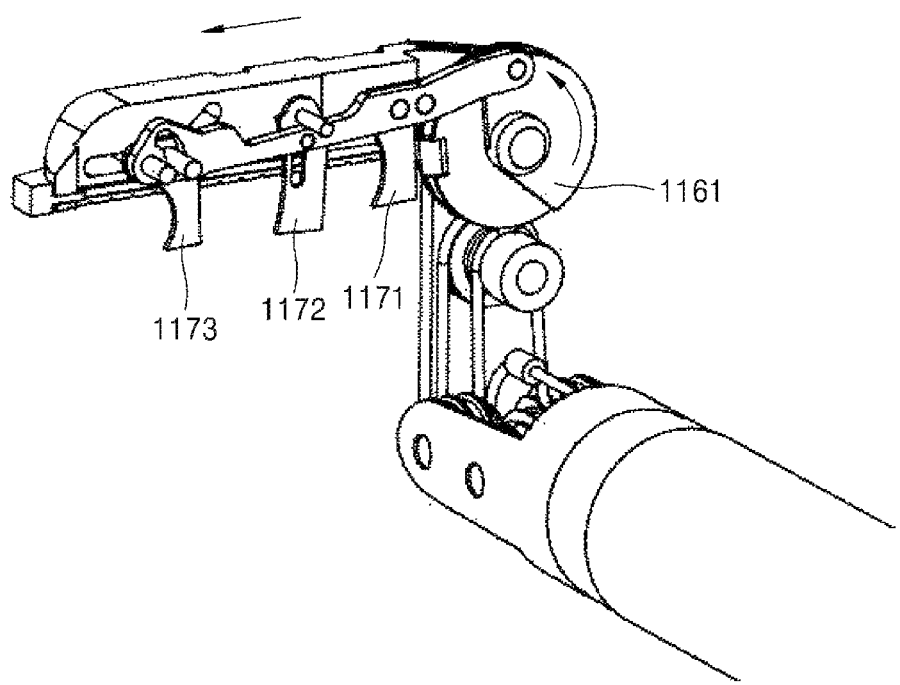
Figure 105:
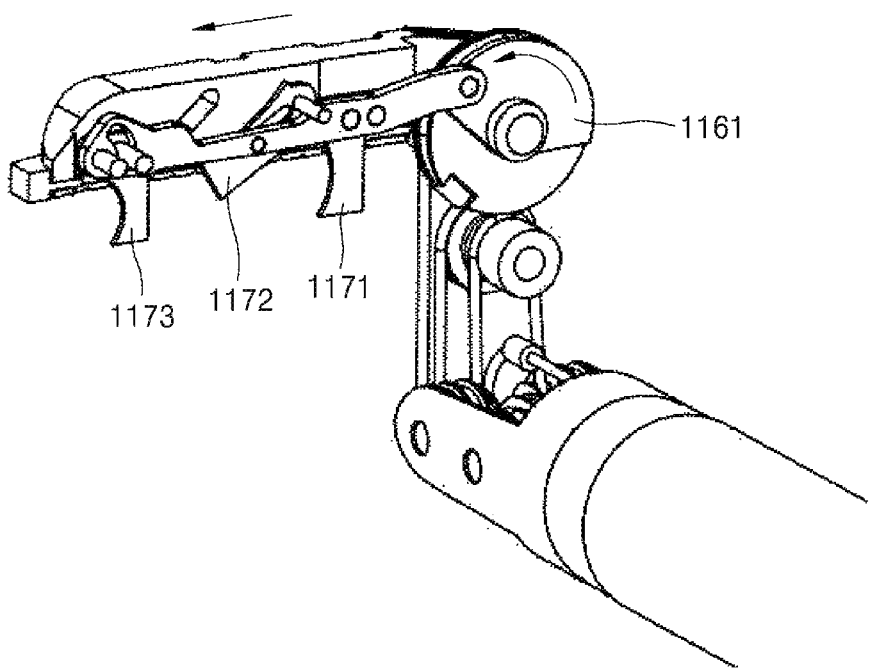

In addition, FIG. 102 is a diagram showing a state in which the jaws are pitch-rotated by −90° and yaw-rotated by +90° at the same time. FIGS. 103, 104, and 105 are perspective views illustrating a cutting movement of the end tool of the surgical instrument for electrocautery of FIG. 75, and show an aspect of performing the cutting movement while jaws are pitch-rotated by −90° and at the same time, yaw-rotated by +90°. As shown in FIGS. 103 to 105, the end tool of the surgical instrument for electrocautery according to the fourth embodiment of the present disclosure is formed to be capable of normally performing a cutting motion even in a state in which the jaws are pitch-rotated by −90° and yaw-rotated by +90° at the same time.

Figure 106:
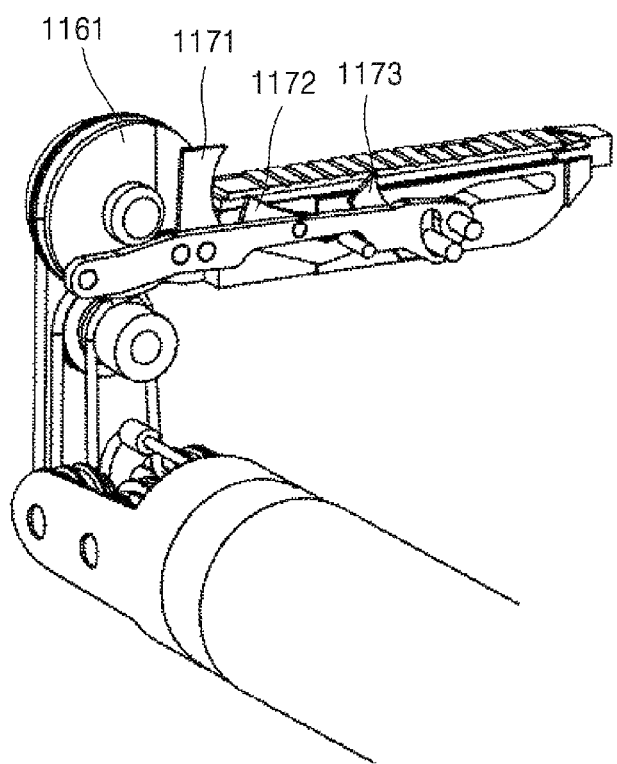
FIGS. 106, 107, and 108 are perspective views illustrating a cutting movement of the end tool of the surgical instrument for electrocautery of FIG. 75, and show an aspect of performing the cutting movement while jaws are pitch-rotated by −90° and at the same time, yaw-rotated by −90°.
Figure 107:
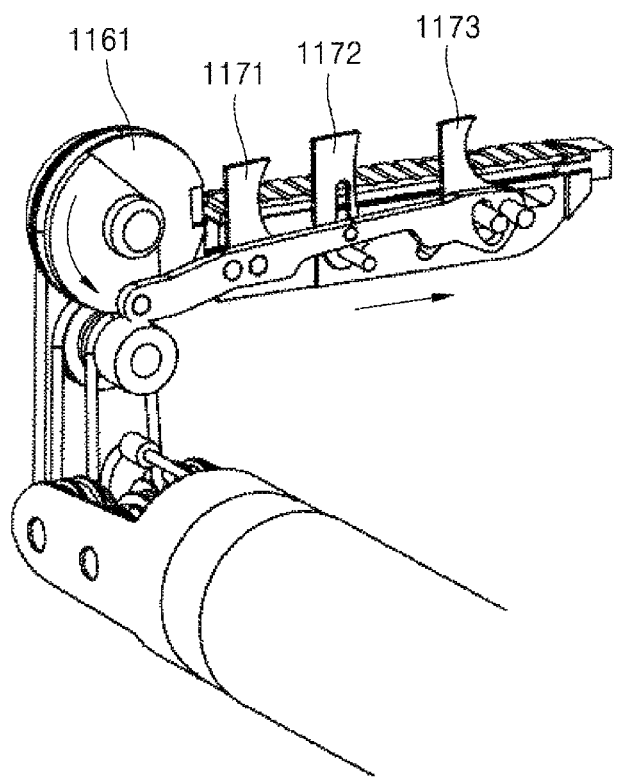
Figure 108:
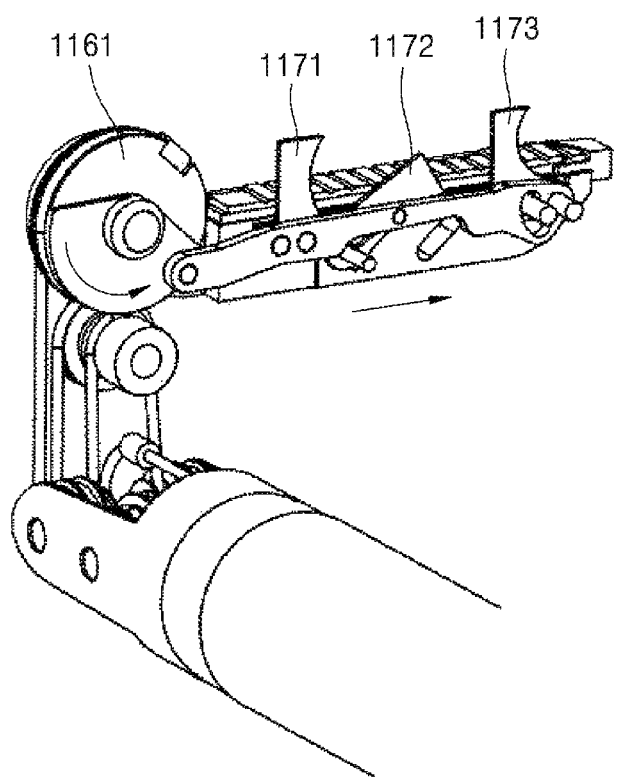

FIGS. 106, 107, and 108 are perspective views illustrating a cutting movement of the end tool of the surgical instrument for electrocautery of FIG. 75, and show an aspect of performing the cutting movement while jaws are pitch-rotated by −90° and at the same time, yaw-rotated by −90°. As shown in FIGS. 106 to 108, the end tool of the surgical instrument for electrocautery according to the fourth embodiment of the present disclosure is formed to be capable of normally performing a cutting motion even in a state in which the jaws are pitch-rotated by −90° and yaw-rotated by −90° at the same time.

Fifth Embodiment—Blade Link Assembly

Hereinafter, an end tool 1200 of a surgical instrument according to a fifth embodiment of the present disclosure will be described. Here, the end tool 1200 of the surgical instrument according to the fifth embodiment is different from the end tool (100 of FIG. 2, etc.) of the surgical instrument described above according to the first embodiment in view of the configuration of a blade assembly 1270. The different structure from that of the first embodiment will be described later in more detail.

Figure 109:
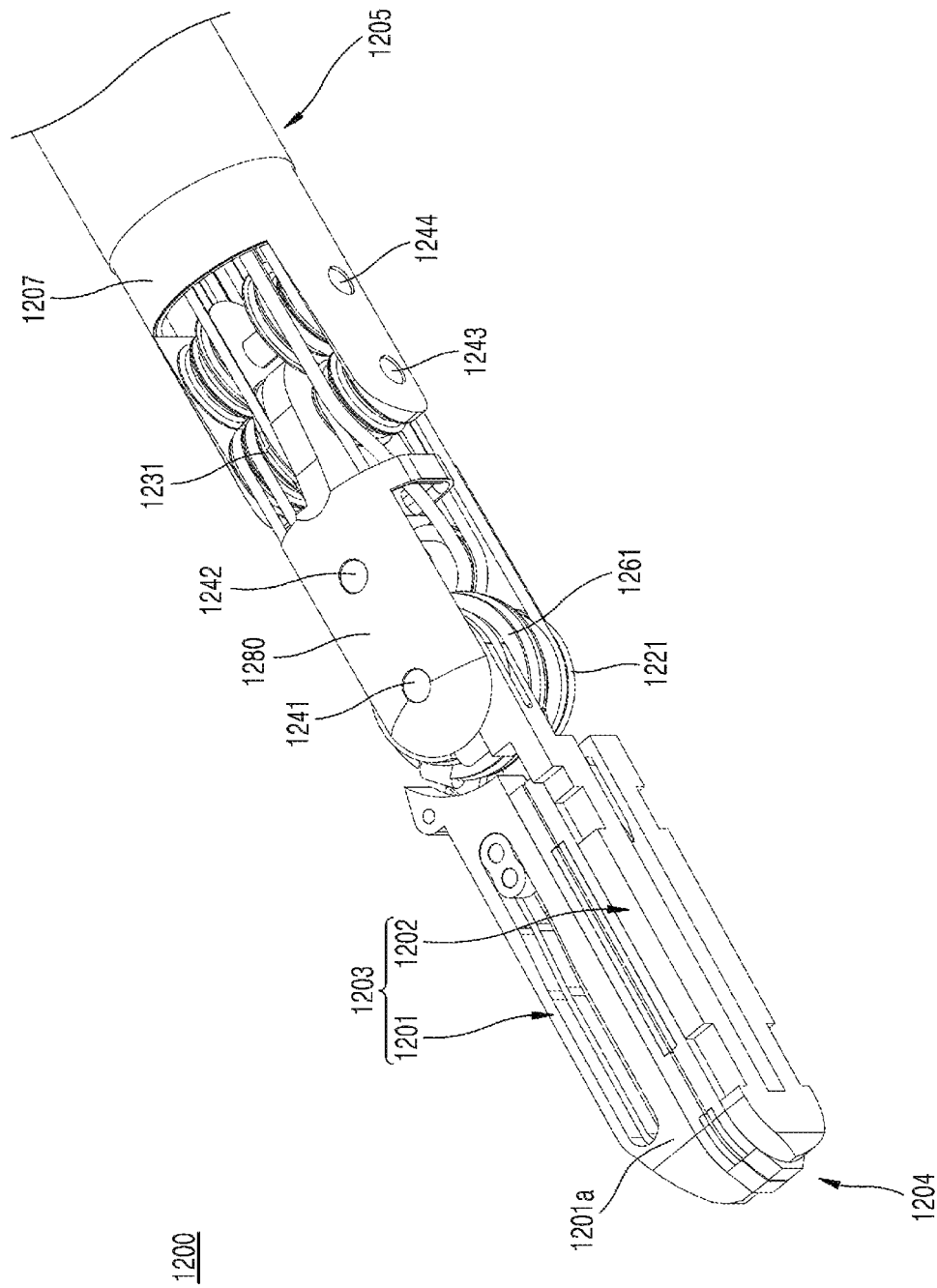
FIGS. 109 to 112 are perspective views illustrating an end tool of a surgical instrument for electrocautery according to a fifth embodiment of the present disclosure.
Figure 110:
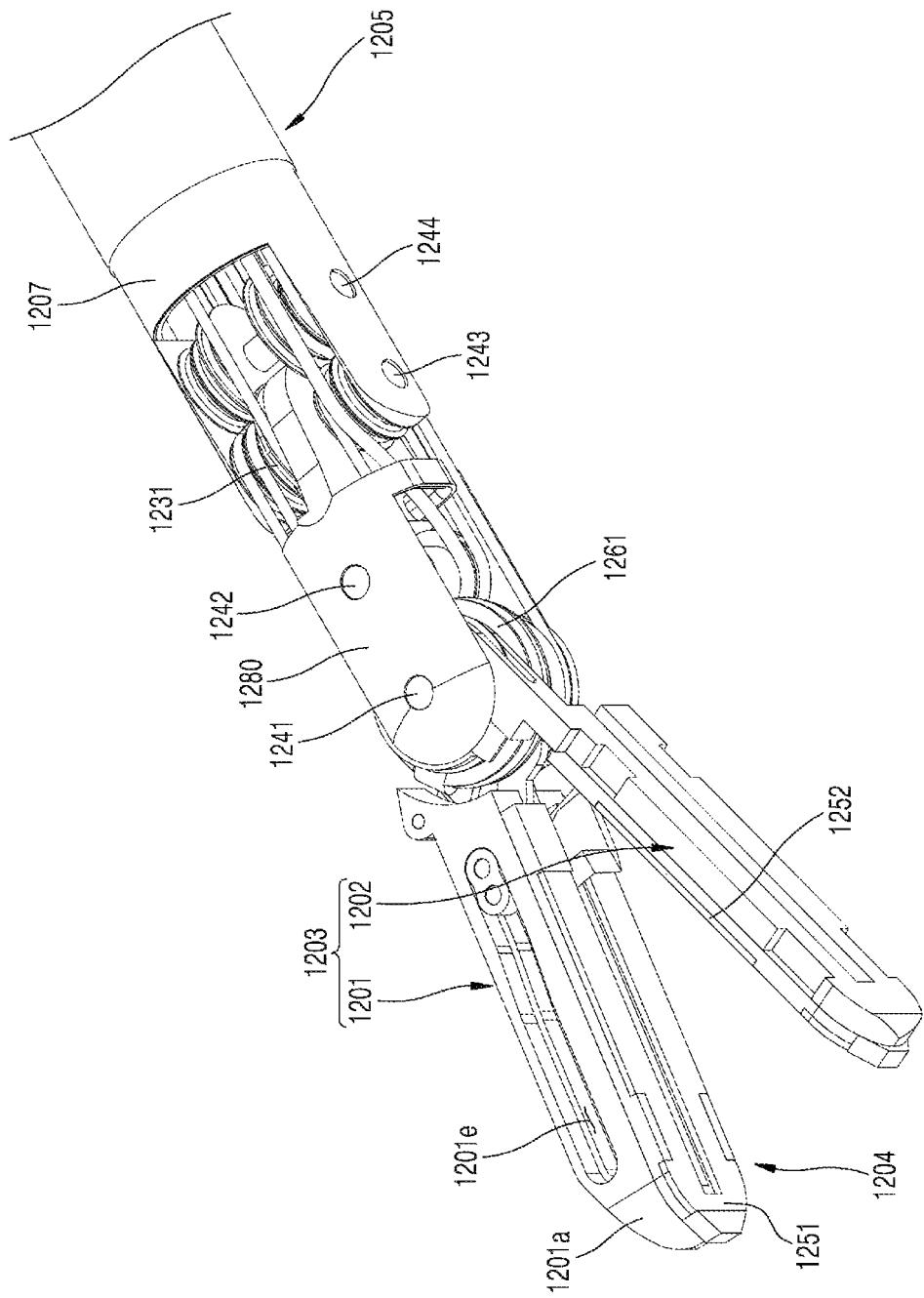
Figure 111:
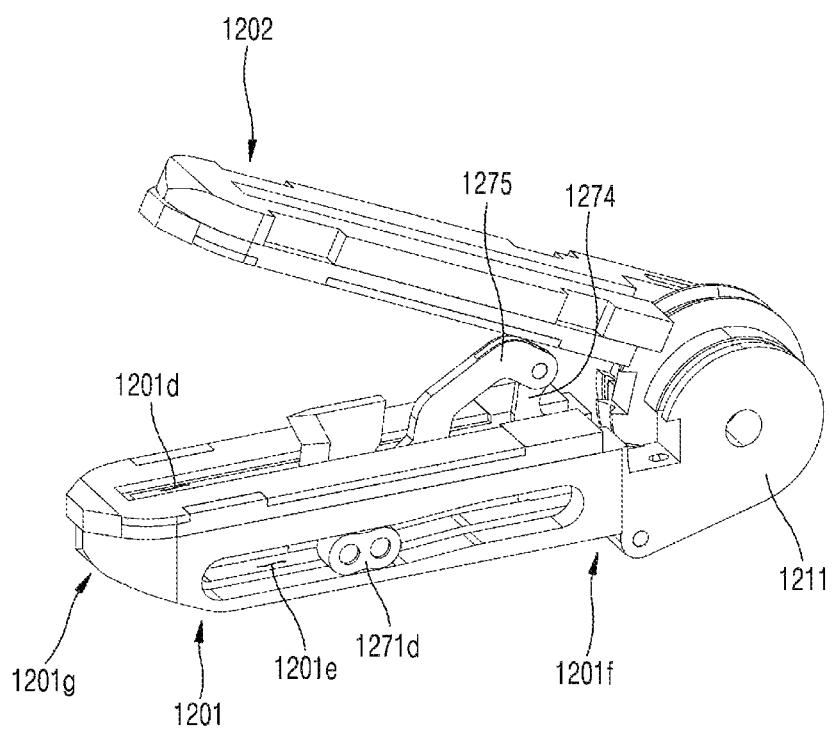
Figure 112:
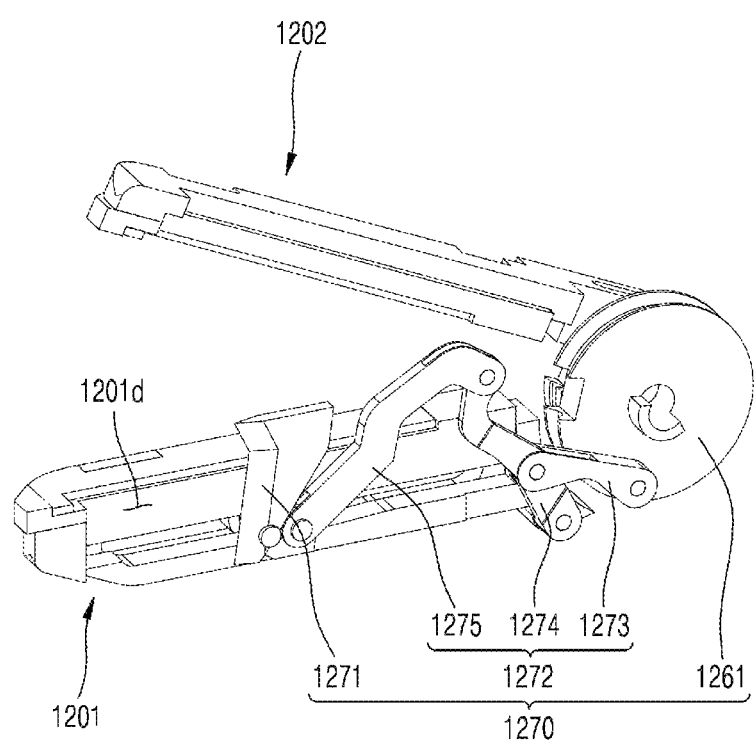
Figure 113:
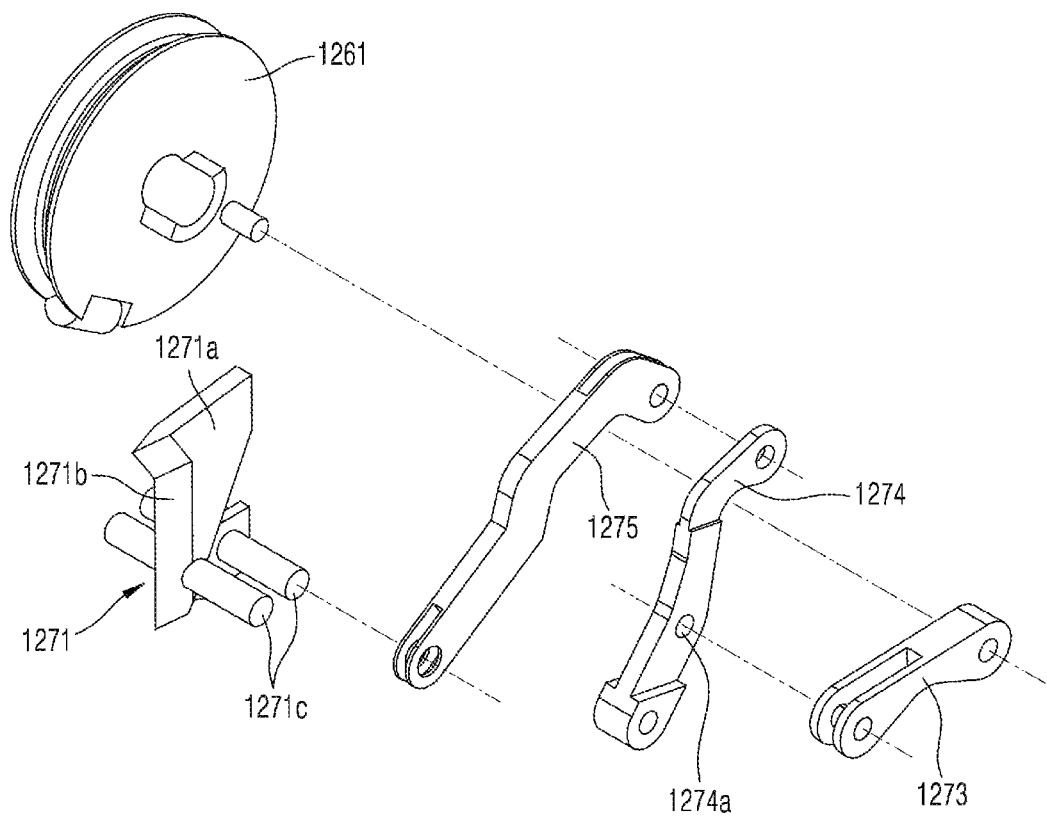
FIG. 113 is an exploded perspective view of the end tool of the surgical instrument for electrocautery of FIG. 109.
Figure 114:
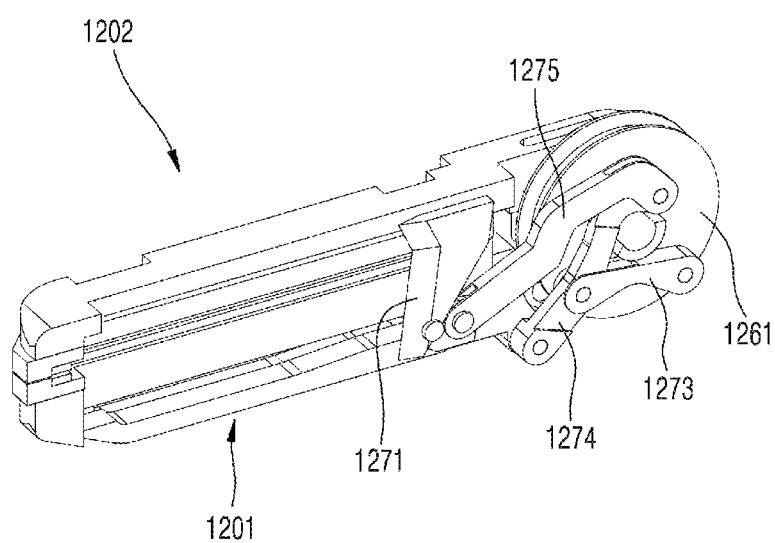
FIGS. 114, 115, and 116 are perspective views illustrating a cutting movement of the end tool of the surgical instrument for electrocautery of FIG. 109.
Figure 115:
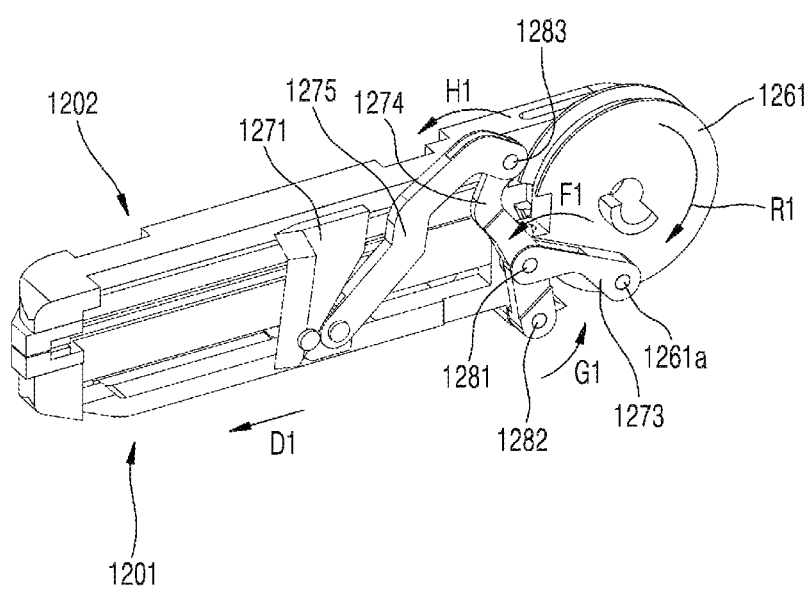
Figure 116:
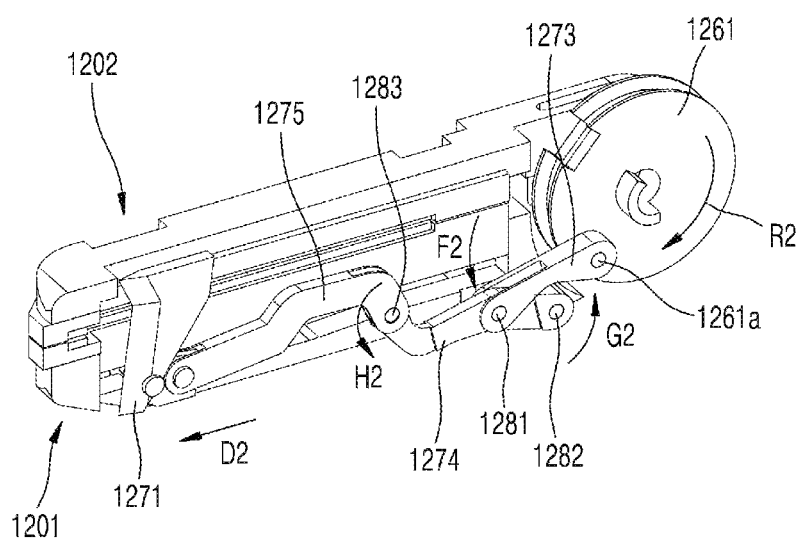
Figure 117:
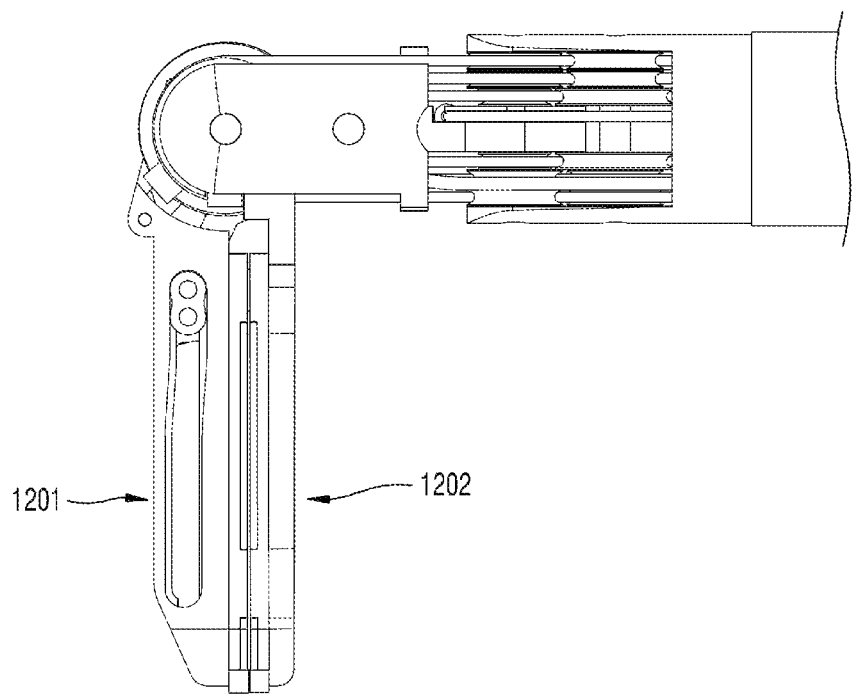
FIG. 117 is a perspective view illustrating a yaw movement of the surgical instrument for electrocautery of FIG. 109.
Figure 118:
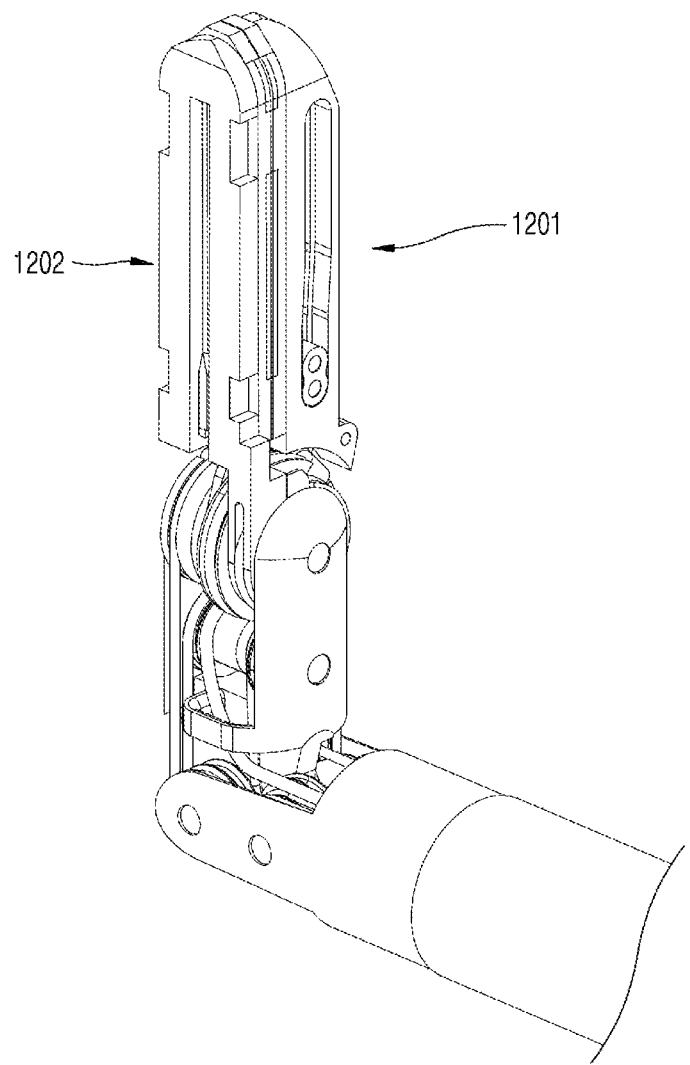
FIG. 118 is a perspective view illustrating a pitch movement of the surgical instrument for electrocautery of FIG. 109.
Figure 119:
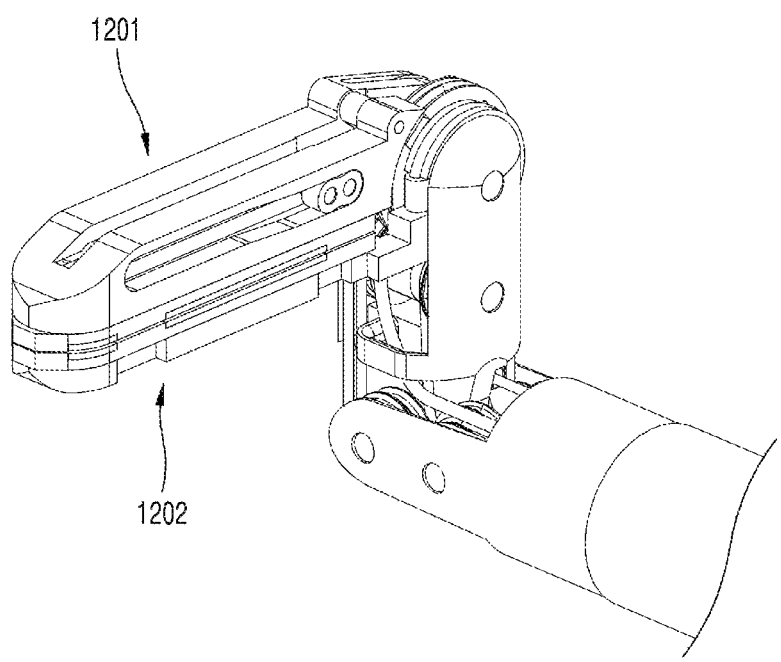
FIG. 119 is a plan view illustrating a pitch-rotated and yaw-rotated state of the end tool of the surgical instrument for electrocautery of FIG. 109.

FIGS. 109 to 112 are perspective views illustrating an end tool of a surgical instrument for electrocautery according to a fifth embodiment of the present disclosure, in particular, FIG. 109 shows a state in which jaws are closed and FIG. 110 shows a state in which jaws are open. FIG. 111 is an expanded perspective view showing the end tool of the surgical instrument for electrocautery shown in FIG. 110, and FIG. 112 is a cut perspective view of FIG. 111. FIG. 113 is an exploded perspective view illustrating the end tool of the surgical instrument for electrocautery of FIG. 110. FIGS. 114, 115, and 116 are perspective views illustrating a cutting movement of the end tool of the surgical instrument for electrocautery of FIG. 109. FIG. 117 is a perspective view showing a yaw motion of the surgical instrument for electrocautery of FIG. 109, FIG. 118 is a perspective view showing a pitch motion of the surgical instrument for electrocautery of FIG. 109, and FIG. 119 is a plan view showing a state in which the end tool of the surgical instrument for electrocautery of FIG. 109 is pitch-rotated and yaw-rotated.

Referring to FIGS. 109 to 113, the end tool 1200 according to the fifth embodiment of the present disclosure includes a pair of jaws for performing gripping operation, that is, a first jaw 1201 and a second jaw 1202, and an element indicating each of the first jaw 1201 and the second jaw 1202, or both the first jaw 1201 and the second jaw 1202 may be referred to as a jaw 1203.

In addition, the end tool 1200 includes a plurality of pulleys including a pulley 1211 that is the first jaw pulley coupled to the first jaw 1201. In the present embodiment, the pulleys associated with the rotational motion of the first jaw 1201 are substantially the same as the pulley 112, the pulley 113, the pulley 114, the pulley 115, and the pulley 116 described above with reference to FIG. 11, etc. of the first embodiment, and detailed descriptions thereof are omitted.

In addition, the end tool 1200 includes a plurality of pulleys including a pulley 1221 that is the second jaw pulley coupled to the second jaw 1202. In the present embodiment, the pulleys associated with the rotational motion of the second jaw 1202 are substantially the same as the pulley 122, the pulley 123, the pulley 124, the pulley 125, and the pulley 126 described above with reference to FIG. 11, etc. of the first embodiment, and detailed descriptions thereof are omitted.

The end tool 1200 of the fifth embodiment may include the rotary shaft 1241, the rotary shaft 1242, the rotary shaft 1243, and the rotary shaft 1244. Here, the rotary shaft 1241 and the rotary shaft 1242 may penetrate and be inserted into the end tool hub 1280, and the rotary shaft 1243 and the rotary shaft 1244 may penetrate and be inserted into the pitch hub 1207. The rotary shaft 1241, the rotary shaft 1242, the rotary shaft 1243, and the rotary shaft 1244 may be arranged sequentially from a distal end 1204 towards a proximal end 1205.

Also, the end tool 1200 according to the fifth embodiment may include an end tool hub 1280 and the pitch hub 1207.

A rotary shaft 1241 and a rotary shaft 1242 that will be described later are inserted through the end tool hub 1280, and the pulley 1211 and the pulley 1221 axially coupled to the rotary shaft 1241 and at least a part of the first jaw 1201 and the second jaw 1202 coupled to the pulleys 1211 and 1221 may be accommodated in the end tool hub 1280.

Meanwhile, the pulley 1231 serving as an end tool pitch pulley may be formed at one end of the end tool hub 1280. As shown in FIG. 109, the pulley 1231 may be formed as a separate member from the end tool hub 1280 and may be coupled to the end tool hub 1280. Alternatively, the pulley 1231 may be formed as one-body with the end tool hub 1280. In addition, the wire 303 (see FIG. 13) and the wire 304 (see FIG. 13) are coupled to the pulley 1231 functioning as the end tool pitch pulley, and the pulley 1231 rotates about the rotary shaft 1243 and carries out the pitch motion.

The rotary shaft 1243 and the rotary shaft 1244 are inserted through the pitch hub 1207, and the pitch hub 1207 may be axially coupled to the end tool hub 1280 and the pulley 1231 via the rotary shaft 1243. Accordingly, the end tool hub 1280 and the pulley 1231 may be formed to be rotatable around the rotary shaft 1243 with respect to the pitch hub 1207.

In addition, the end tool 1200 according to the fifth embodiment may further include, in order to perform cautery and cutting motions, components such as a first electrode 1251, a second electrode 1252, the blade pulley 1261, a blade 1271, a first blade link 1273, a second blade link 1274, a third blade link 1275, etc.

Here, components such as the blade pulley 1261, the blade 1271, the first blade link 1273, the second blade link 1274, the third blade link 1275, etc. associated with the driving of the blade may be collectively referred to as a blade assembly 1270. Also, components such as the first blade link 1273, the second blade link 1274, the third blade link 1275, etc. may be collectively referred to as a blade link assembly 1272.

In the fifth embodiment, by arranging the blade assembly 1270 including a plurality of blade links between the pulley 1211 which is the first jaw pulley and the pulley 1221 which the second jaw pulley, not only the pitch motion and the yaw motion of the end tool 1200 but also the cutting motion using the blades may be performed. In the embodiment, the components for performing the cautery and cutting motions are substantially the same as the components described above in the first embodiment, and thus, detailed descriptions thereof are omitted here.

The surgical instrument for electrocautery according to the fifth embodiment may include the wire 301, the wire 302, the wire 303, the wire 304, the wire 305, the wire 306, the wire 307, and the wire 308, like in the first embodiment shown in FIG. 13, etc.

Also, the surgical instrument for electrocautery according to the fifth embodiment may include the fastening member 321, the fastening member 323, the fastening member 324, the fastening member 326, the fastening member 327, and the fastening member 329 which are coupled to respective ends of the wires in order to couple the wires and the pulleys, like in the first embodiment shown in FIG. 13, etc.

Hereinafter, the blade assembly 1270 of the surgical instrument for electrocautery according to the fifth embodiment of the present disclosure will be described below in more detail.

The first jaw 1201 may include a guide member 1201*a* and a case (not shown).

A blade accommodation portion 1201*d* and a first guide portion 1201*e* may be formed in the guide member 1201*a*. The guide member 1201*a* may be coupled to the pulley 1211 and may guide a movement path of the blade 1271. For example, the guide member 1201*a* may be formed in the form of two elongated bars facing each other, and the blade accommodation portion 1201*d* in which at least a part of the blade 1271 and the blade link 1275 to be described later are accommodated may be formed inside the guide member 1201*a*. The blade accommodation portion 1201*d* may be formed in an elongated manner in a direction towards a distal end 1201*g* from a proximal end 1201*f*, and in the blade accommodation portion 1201*d*, the blade 1271 may be entirely accommodated or at least a part of the blade 1271 may protrude from the blade accommodation portion 1201*d* to the outside. In other words, as the blade 1271 moves along the blade accommodation portion 1201*d*, the cutting motion may be performed on the tissue. This will be described in more detail later.

In addition, the first guide portion 1201*e* for guiding the movement of the blade 1271 may be formed at the guide member 1201*a* of the first jaw 1201. Here, the first guide portion 1201*e* may be formed in both inner sidewalls inside the guide member 1201*a* forming the blade accommodation portion 1201*d*. The first guide portion 1201*e* may be formed in the shape of a groove formed along the movement path of the blade 1271. In addition, in a state where a second guide portion 1271*c* of the blade 1271 formed in the protrusion shape is fit into the first guide portion 1201*e* in the groove shape, as the second guide portion 1271*c* moves along the first guide portion 1201*e*, the blade 1271 may move with respect to the first jaw 1201.

Here, the first guide portion 1201*e* may be formed in a direction that is substantially the same as the direction from a proximal end 1201*f* toward the distal end 1201*g* of the first jaw 1201, that is, in the X-axis direction. Therefore, the blade 1271 moving along the first guide portion 1201*e* may perform the linear movement in the X-axis direction. That is, the rotational motion of the blade pulley 1261 is converted into the linear motion of the blade 1271 in the X-axis direction due to the blade link assembly 1272. This will be described in more detail later.

Although the drawings illustrate that the first guide portion 1201*e* is integrated with the guide member 1201*a* as a component of the first jaw 1201, the technical concepts of the present disclosure are not limited thereto, and the first guide portion 1201*e* may be formed as a separate member from the guide member 1201*a* and be coupled to the guide member 1201*a*.

The first electrode 1251 may be formed on a surface of the first jaw 1201 facing the second jaw 1202. The second electrode 1252 may be formed on a surface of the second jaw 1202 facing the first jaw 1201.

Here, a part of the blade 1271 is accommodated in the first jaw 1201, and the other part of the blade 1271 may be accommodated in the second jaw 1202. In detail, unlike the previous embodiments, in the surgical instrument for electrocautery according to the fifth embodiment, a part of the blade 1271 is accommodated in the first jaw 1201 and the other part of the blade 1271 is accommodated in the second jaw 1202 during the entire processes of the cutting motion.

That is, in the embodiment, it may be expressed that the blade 1271 linearly moves between the proximal end 1201*f* and the distal end 1201*g* of the first jaw 1201, rather than the blade 1271 moving from the first jaw 1201 toward the second jaw. This will be described in more detail later.

The blade 1271 may include a body portion 1271*a*, an edge portion 1271*b*, and one or more second guide portions 1271*c*.

In an area of the body portion 1271*a*, the edge portion 1271*b* which is sharp and cuts tissue may be formed. The tissue arranged between the first jaw 1201 and the second jaw 1201 may be cut while at least a part of the edge portion 1271*b* moves between the proximal end 1201*f* and the distal end 1201*g* of the first jaw 1201.

In another area of the body portion 1271*a*, the one or more second guide portions 1271*c* may be formed. For example, the second guide portion 1271*c* may include a plurality of protrusions. One of the protrusions may be put onto the through-hole formed in the third blade link 1275. Also, the plurality of protrusions of the second guide portion 1271*c* may be inserted in the first guide portion 1201*e* of the first jaw 1201.

In addition, a guide cap 1271*d* may be further coupled to the plurality of protrusions of the second guide portion 1271*c* so that the second guide portion 1271*c* may stably perform the linear motion in the first guide portion 1201*e*.

The blade link assembly 1272 incudes a plurality of blade links and connects the blade pulley 1261 and the blade 1271 to each other, so as to transfer the rotation of the blade pulley 1261 to the blade 1271, and thus, the blade 1271 is moved in the direction from the proximal end 1201*f* toward the distal end 1201*g* of the first jaw 1201.

Here, the blade link assembly 1272 may include the first blade link 1273, the second blade link 1274, and the third blade link 1275.

One end portion of the first blade link 1273 is axially coupled to a protrusion 1261*a* of the blade pulley 1261 and the other end portion is axially coupled to a link coupling portion 1274*a* of the second blade link 1274 via a rotary shaft 1281.

One end portion of the second blade link 1274 is axially coupled to the first jaw 1201 by a rotary shaft 1282 and the other end is axially coupled to the third blade link 1275 by a rotary shaft 1283. In addition, the link coupling portion 1274*a* is formed on one region between both end portions of the second blade link 1274 and is axially coupled to the first blade link 1273 by the rotary shaft 1281.

Here, when the relative position of the first jaw 1201 is fixed, the second blade link 1274 seems to rotate about the rotary shaft 1282 that is coupling portion to the first jaw 1201.

One end portion of the third blade link 1275 is axially coupled to the second blade link 1274 and the other end portion is axially coupled to the blade 1271, in particular, to one of a plurality of protrusions of the second guide portion 1271*c* of the blade 1271.

Here, in the drawings, through-holes are respectively formed in both end portions of the first blade link 1273, the second blade link 1274, and the third blade link 1275 and the link coupling portion 1274*a* of the second blade link 1274, and separate shafts are inserted through the through-holes. However, the technical concepts of the present disclosure are not limited thereto. That is, various coupling structures may be implemented, for example, a protrusion is formed on one component and a through-hole is formed in corresponding component so that the two components may be coupled to each other.

FIGS. 114, 115, and 116 are perspective views illustrating a cutting movement of the end tool of the surgical instrument for electrocautery of FIG. 109.

In the state of FIG. 114, when the blade pulley 1261 is rotated in a direction indicated by the arrow R1 of FIG. 115, the first blade link 1273 axially coupled to the blade pulley 1261 is also rotated along with the blade pulley 1261 and is rotated in a direction indicated by the arrow F1 about the protrusion 1261*a*. Then the first blade link 1273 pushes the second blade link 1274, and due to the above force, the second blade link 1274 is rotated in a direction indicated by the arrow G1 about the rotary shaft 1282. As described above, the second blade link 1274 pushes the third blade link 1275 in the direction indicated by the arrow H1 while rotating, and the third blade link 1275 is entirely moved due to the second blade link 1274 and at the same time is rotated about the rotary shaft 1283 to move the blade 1271 in a direction indicated by the arrow D1.

Likewise, in the state of FIG. 115, when the blade pulley 1261 is further rotated in a direction indicated by the arrow R2 of FIG. 116, the first blade link 1273 axially coupled to the blade pulley 1261 is also rotated along with the blade pulley 1261 and is rotated in a direction indicated by the arrow F2 about the protrusion 1261*a*. Then the first blade link 1273 pushes the second blade link 1274, and due to the above force, the second blade link 1274 is rotated in a direction indicated by the arrow G2 about the rotary shaft 1282. As described above, the second blade link 1274 pushes the third blade link 1275 in the direction indicated by the arrow H2 while rotating, and the third blade link 1275 is entirely moved due to the second blade link 1274 and at the same time is rotated about the rotary shaft 1283 to move the blade 1271 in a direction indicated by the arrow D2.

The end tool of the surgical instrument for electrocautery according to the fifth embodiment of the present disclosure includes the blade link assembly 1272 including the plurality of blade links, and thus, the blade 1271 performs the linear motion in a direction that is substantially the same as the direction from the proximal end 1201*f* toward the distal end 1201*g* of the first jaw 1201, that is, the X-axis direction. That is, the rotational movement of the blade pulley 1261 is converted into the linear motion of the blade 1271 in the X-axis direction due to the blade link assembly 1272.

In addition, corresponding to this, a part of the blade 1271 is accommodated in the first jaw 1201 during all motions, and the other part of the blade 1271 is accommodated in the second jaw 1202 during all motions. That is, the blade 1271 does not move from the first jaw 1201 toward the second jaw 1202, but the blade 1271 is linearly moved between the proximal end 1201*f* and the distal end 1201*g* of the first jaw 1201 and the cutting is performed.

According to the above configuration, the cutting is performed while the blade 1271 performs the linear motion, and thus, the moving path of the blade 1271 is reduced and the cutting is simply performed.

FIG. 117 is a diagram showing a state in which jaws are yaw-rotated by 90°, FIG. 118 is a diagram showing a state in which jaws are pitch-rotated by 90°, and FIG. 119 is a diagram showing a state in which jaws are pitch-rotated by 90° and yaw-rotated by 90° at the same time.

As shown in FIGS. 117 to 119, the end tool of the surgical instrument for electrocautery according to the fifth embodiment of the present disclosure is formed to be capable of normally performing a cutting motion even in a state in which the jaws are pitch-rotated by 90° or yaw-rotated by 90°.

Sixth Embodiment—Double Blade

Hereinafter, an end tool 1300 of a surgical instrument according to a sixth embodiment of the present disclosure will be described. Here, the end tool 1300 of the surgical instrument according to the sixth embodiment is different from the end tool (100 of FIG. 2, etc.) of the surgical instrument described above according to the first embodiment in view of the configuration of a blade assembly 1370. The different structure from that of the first embodiment will be described later in more detail.

Figure 120:
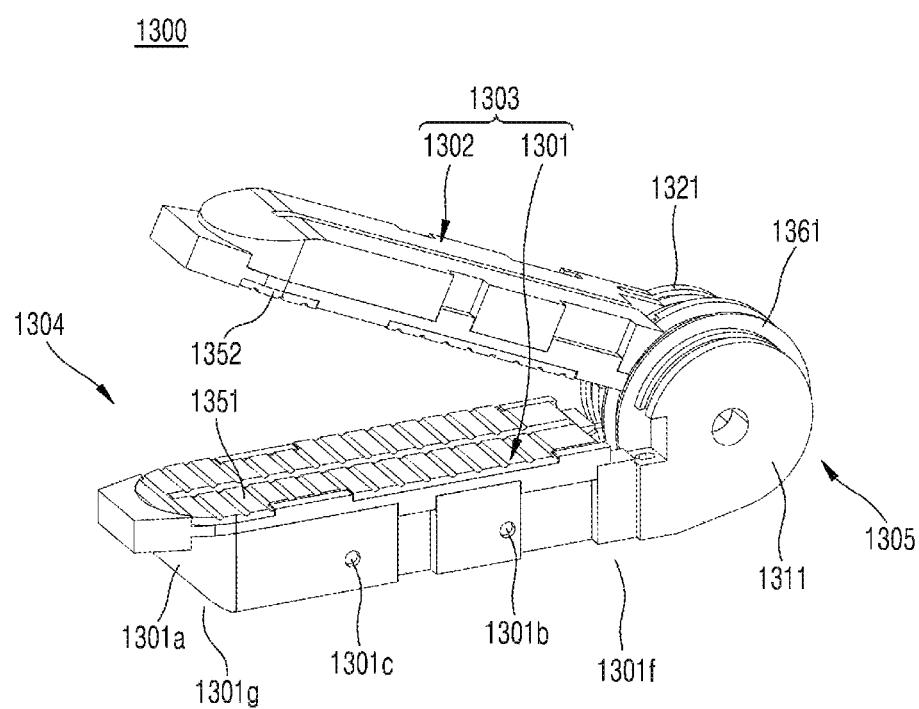
FIG. 120 is a perspective view illustrating an end tool of a surgical instrument for electrocautery according to a sixth embodiment of the present disclosure.
Figure 121:
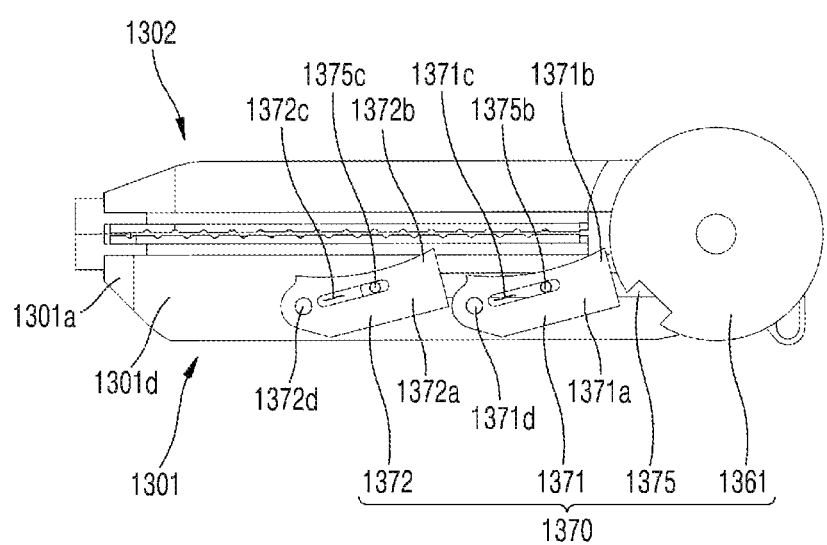
FIG. 121 is a side sectional view illustrating the end tool of the surgical instrument for electrocautery of FIG. 119.
Figure 122:
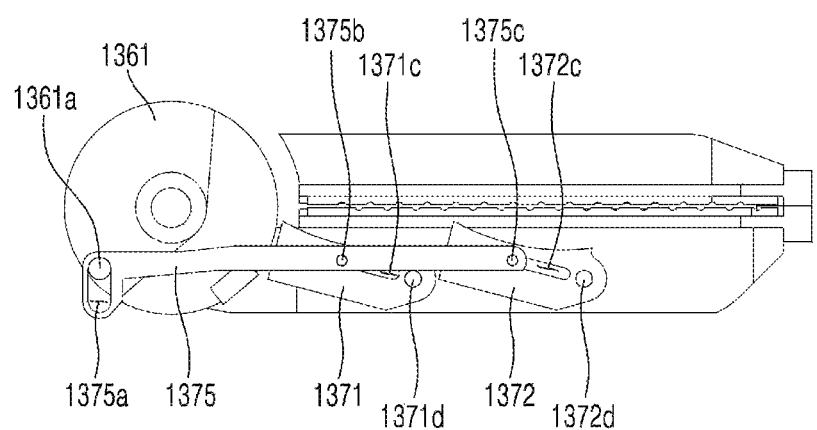
FIGS. 122, 123, and 124 are perspective views illustrating a cutting movement of the end tool of the surgical instrument for electrocautery of FIG. 119.

FIGS. 120, 121, and 122 are perspective views illustrating an end tool of a surgical instrument for electrocautery according to a sixth embodiment of the present disclosure, in particular, FIG. 120 shows a state in which jaws are open and FIG. 121 shows a state in which jaws are closed.

Referring to FIGS. 120 to 122, the end tool 1300 according to the sixth embodiment of the present disclosure includes a pair of jaws for performing a grip motion, that is, a first jaw 1301 and a second jaw 1302, and components indicating each of the first jaw 1301 and the second jaw 1302, or both the first jaw 1301 and the second jaw 1302 may be collectively referred to as a jaw 1303.

In addition, the end tool 1300 includes a plurality of pulleys including a pulley 1311 that is the first jaw pulley coupled to the first jaw 1301. In the present embodiment, the pulleys associated with the rotational motion of the first jaw 1301 are substantially the same as the pulley 112, the pulley 113, the pulley 114, the pulley 115, and the pulley 116 described above with reference to FIG. 11, etc. of the first embodiment, and detailed descriptions thereof are omitted.

In addition, the end tool 1300 includes a plurality of pulleys including a pulley 1321 that is the second jaw pulley coupled to the second jaw 1302. In the present embodiment, the pulleys associated with the rotational motion of the second jaw 1302 are substantially the same as the pulley 122, the pulley 123, the pulley 124, the pulley 125, and the pulley 126 described above with reference to FIG. 11, etc. of the first embodiment, and detailed descriptions thereof are omitted.

Hereinafter, the blade assembly 1370 of the surgical instrument for electrocautery according to the sixth embodiment of the present disclosure will be described below in more detail.

The first jaw 1301 may include a guide member 1301*a* and a case (not shown).

A blade accommodation portion 1301*d* may be formed in the guide member 1301*a*. The guide member 1301*a* is coupled to the pulley 1311 and may be formed to guide the moving paths of the first blade 1371 and the second blade 1372. In addition, in the guide member 1301*a*, a blade accommodation portion 1301*d* in which at least a part of the first blade 1371, the second blade 1372, and a blade link 1375 that will be described later may be accommodated may be formed. The blade accommodation portion 1301*d* may be formed lengthily in the direction from a proximal end 1301*f* toward a distal end 1301*g* of the first jaw 1301, and the first blade 1371 and the second blade 1372 may be totally accommodated in the blade accommodation portion 1301*d*. Alternatively, at least some parts of the first blade 1371 and the second blade 1372 may protrude outside from the blade accommodation portion 1301*d*. In other words, the tissue may be cut while the first blade 1371 and the second blade 1372 move along the blade accommodation portion 1301*d*. This will be described in more detail later.

Also, a first blade coupling portion 1301*b* and a second blade coupling portion 1301*c* formed in the shape of through-holes may be formed in the guide member 1301*a*. A jaw coupling portion 1371*d* of the first blade 1371 may be inserted through the first blade coupling portion 1301*b*, and a jaw coupling portion 1372*d* of the second blade 1372 may be inserted through the second blade coupling portion 1301*c*.

In addition, a first electrode 1351 may be formed on a surface of the first jaw 1301 facing the second jaw 1302. The second electrode 1352 may be formed on a surface of the second jaw 1302 facing the first jaw 1301.

The first blade 1371 may include a body portion 1371*a*, an edge portion 1371*b*, one or more link coupling portions 1371*c*, and a jaw coupling portion 1371*d*.

In an area of the body portion 1371*a*, the edge portion 1371*b* which is sharp and cuts tissue may be formed. At least a part of the edge portion 1371*b* may be drawn to the outside of the first jaw 1301 to cut the tissue positioned between the first jaw 1301 and the second jaw 1302.

In another area of the body portion 1371*a*, the one or more link coupling portions 1371*c* may be formed. For example, the link coupling portion 1371*c* may be formed in an elongated slit shape so that the first blade coupling portion 1375*b* formed in a protrusion shape may be inserted therein.

In another area of the body portion 1371*a*, the jaw coupling portion 1371*d* may be formed. For example, the jaw coupling portion 1371*d* may be formed in an axis shape and may be inserted through the first blade coupling portion 1301*b* that is formed in a through-hole shape in the guide member 1301*a* of the first jaw 1301.

The second blade 1372 may include a body portion 1372*a*, an edge portion 1372*b*, one or more link coupling portions 1372*c*, and a jaw coupling portion 1372*d*.

In a region of the body portion 1372*a*, the edge portion 1372*b* which is sharp and cuts tissue may be formed. At least a part of the edge portion 1372*b* may be drawn to the outside of the first jaw 1301 to cut the tissue positioned between the first jaw 1301 and the second jaw 1302.

In another area of the body portion 1372*a*, the one or more link coupling portions 1372*c* may be formed. For example, the link coupling portion 1372*c* may be formed in an elongated slit shape so that the second blade coupling portion 1375*c* formed in a protrusion shape may be inserted therein.

In another area of the body portion 1372*a*, the jaw coupling portion 1372*d* may be formed. For example, the jaw coupling portion 1372*d* may be formed in an axis shape and may be inserted through the second blade coupling portion 1301*c* that is formed in a through-hole shape in the guide member 1301*a* of the first jaw 1301.

The blade link 1375 connects the blade pulley 1361 to the first blade 1371 and the second blade 1372, so as to transfer the rotation of the blade pulley 1361 to the first blade 1371 and the second blade 1372 and to allow the first blade 1371 and the second blade 1372 to move between a proximal end 1301*f* and a distal end 1301*g* of the first jaw 1301. The blade link 1375 may be formed in an elongated bar shape, and one end portion of the blade link 1375 may be connected to the blade pulley 1361 and the other region may be respectively connected to the first blade 1371 and the second blade 1372. This will be described below in more detail.

A pulley coupling portion 1375*a*, a first blade coupling portion 1375*b* and a second blade coupling portion 1375*c* may be sequentially formed in the blade link 1375 from the proximal end 1301*f* toward the distal end 1301*g*.

In detail, the blade pulley coupling portion 1375*a* formed in the shape of a slit may be formed in the end portion of the blade link 1375 at the side of the proximal end 1301*f*. In addition, the protrusion 1361a formed on one surface of the blade pulley 1361 may be inserted in the blade pulley coupling portion 1375a.

The first blade coupling portion 1375b of the blade link 1375 includes the protrusion. In addition, the link coupling portion 1371c of the first blade 1371 is formed in the shape of an elongated slit. In addition, the protrusion of the first blade coupling portion 1375b is inserted in the slit of the link coupling portion 1371c.

In addition, the jaw coupling portion 1371d of the first blade 1371 includes a protrusion. In addition, the first blade coupling portion 1301b formed in the shape of hole is formed in the guide member 1301a of the first jaw 1301. In addition, the jaw coupling portion 1371d of the first blade 1371 may be inserted through the first blade coupling portion 1301b of the guide member 1301a, so that the first blade 1371 may be rotated with respect to the guide member 1301a by using the jaw coupling portion 1371d as a shaft.

Therefore, when the blade link 1375 linearly moves, the first blade coupling portion 1375b of the blade link 1375 pushes or pulls the link coupling portion 1371c of the first blade 1371. Here, because the jaw coupling portion 1371d of the first blade 1371 is axially coupled to the guide member 1301a, the first blade 1371 is rotated with respect to the guide member 1301a.

In the drawings, the first blade coupling portion 1375b includes the protrusion, and the link coupling portion 1371c includes the slit. However, the technical concepts of the present disclosure are not limited thereto, and locations of the protrusion and the slit may be switched with each other.

Also, in the drawings, the jaw coupling portion 1371d of the first blade 1371 is formed in the shape of an axis and the guide member 1301a includes the first blade coupling portion 1301b formed in the shape of the through-hole. However, the technical concepts of the present disclosure are not limited thereto, and the locations of forming the axis and the through-hole may be switched with each other.

The second blade coupling portion 1375c of the blade link 1375 includes the protrusion. In addition, the link coupling portion 1372c of the second blade 1372 is formed in the shape of an elongated slit. In addition, the protrusion of the second blade coupling portion 1375c is inserted in the slit of the link coupling portion 1372c.

In addition, the jaw coupling portion 1372d of the second blade 1372 includes a protrusion. In addition, the second blade coupling portion 1301c formed in the shape of hole is formed in the guide member 1301a of the first jaw 1301. In addition, the jaw coupling portion 1372d of the second blade 1372 may be inserted through the second blade coupling portion 1301c of the guide member 1301a, so that the second blade 1372 may be rotated with respect to the guide member 1301a by using the jaw coupling portion 1372d as a shaft.

Therefore, when the blade link 1375 linearly moves, the second blade coupling portion 1375c of the blade link 1375 pushes or pulls the link coupling portion 1372c of the second blade 1372. Here, because the jaw coupling portion 1372d of the second blade 1372 is axially coupled to the guide member 1301a, the second blade 1372 is rotated with respect to the guide member 1301a.

In the drawings, the second blade coupling portion 1375c includes the protrusion, and the link coupling portion 1371c includes the slit. However, the technical concepts of the present disclosure are not limited thereto, and locations of the protrusion and the slit may be switched with each other.

Also, in the drawings, the jaw coupling portion 1372d of the second blade 1372 is formed in the shape of an axis and the guide member 1301a includes the second blade coupling portion 1301c formed in the shape of the through-hole. However, the technical concepts of the present disclosure are not limited thereto, and the locations of forming the axis and the through-hole may be switched with each other.

In this state, when the blade pulley 1361 rotates about the rotary shaft 1341, the rotational motion of the blade pulley 1361 is transferred to the first blade 1371 and the second blade 1372 via the blade link 1375 coupled to the blade pulley 1361. In addition, positions of the first blade 1371 and the second blade 1372 are changed due to the transferred rotational motion of the blade pulley 1361, the first blade 1371 and the second blade 1372 may be drawn out from the first jaw 1301 while moving in the direction from the proximal end 1301f toward the distal end 1301 of the first jaw 1301 or the first blade 1371 and the second blade 1372 may be pulled into the first jaw 1301.

That is, the blade link 1375, the first guide portion 1301e of the first jaw 1301, and respective blades are coupled to form a kind of a power transmission mechanism, and thus, when the blade pulley 1361 is rotated, the first blade 1371 and the second blade 1372 connected to the blade pulley 1361 are moved between the distal end 1301g and the proximal end 1301f of the first jaw 1301.

Hereinafter, motions of each blade will be described below in detail.

Figure 123:
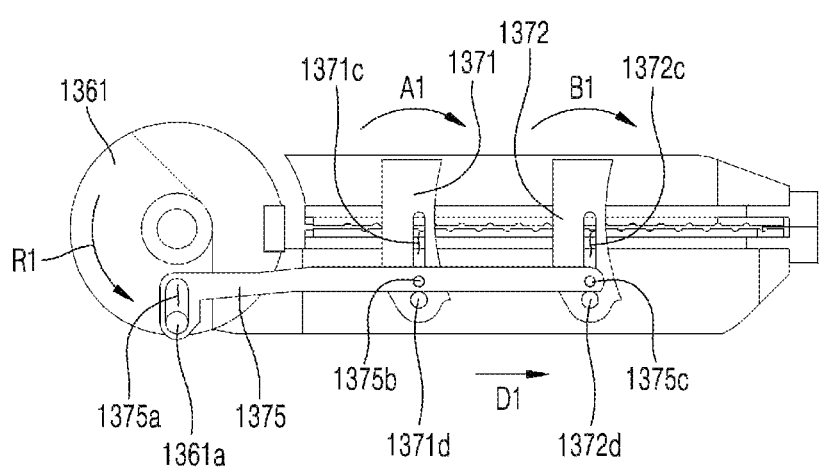
Figure 124:
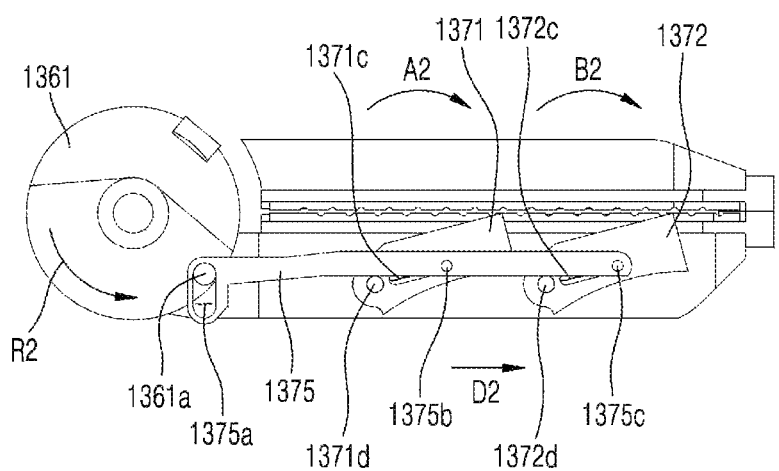

FIGS. 122, 123, and 124 are side views illustrating a cutting movement of the end tool of the surgical instrument for electrocautery of FIG. 120, when jaws are closed.

First, in the state shown in FIG. 122, when the blade pulley 1361 is sequentially rotated in the direction indicated by the arrow R1 of FIG. 123 and the direction indicated by the arrow R2 of FIG. 124, the blade link 1375 coupled to the blade pulley 1361 is moved in the direction indicated by the arrow D1 of FIG. 123 and the direction indicated by the arrow D2 of FIG. 124 to sequentially reach the positions in FIG. 123 and FIG. 124.

Then, the second blade 1372 coupled to the blade link 1375 is moved in the direction indicated by the arrow B1 of FIG. 123 and the direction indicated by the arrow B2 of FIG. 124, to sequentially reach the positions of FIG. 123 and FIG. 124. Here, because the jaw coupling portion 1372d of the second blade 1372 is axially coupled to the guide member 1301a of the first jaw 1301, the second blade 1372 is rotationally moved with respect to the guide member 1301a.

In other words, one end portion of the second blade 1372 is axially coupled to the first jaw 1301, and thus, when the blade link 1375 linearly moves, the second blade 1372 is accordingly rotated.

In other words, the second blade 1372 rotationally rotates about a rotary shaft while the trajectory thereof forms an arc.

In other words, two blades 1371 and 1372 are connected to the blade link 1375, and thus, when the blade pulley 1361 is rotated, the two blades 1371 and 1372 connected thereto are moved together. In detail, when the blade pulley 1361 is rotated, the two blades 1371 and 1372 cut the tissue while moving between the proximal end 1301f and the distal end 1301g of the end tool.

The second blade 1372 formed at the center is moved while drawing a trajectory close to a semi-circle. Here, at a start point (first position) and an end point (second position) of the motion, at least a part of the second blade 1372 is accommodated in the first jaw 1301, and the second blade 1372 is exposed to outside of the first jaw 1301 only in the middle of moving from the first position to the second position.

Seventh Embodiment—Blade Link Assembly

Hereinafter, an end tool 1400 of a surgical instrument according to a seventh embodiment of the present disclosure will be described. Here, the end tool 1400 of the surgical instrument according to the seventh embodiment is different from the end tool (100 of FIG. 2, etc.) of the surgical instrument described above according to the first embodiment in view of the configuration of a blade assembly 1470. The different structure from that of the first embodiment will be described later in more detail.

Figure 125:
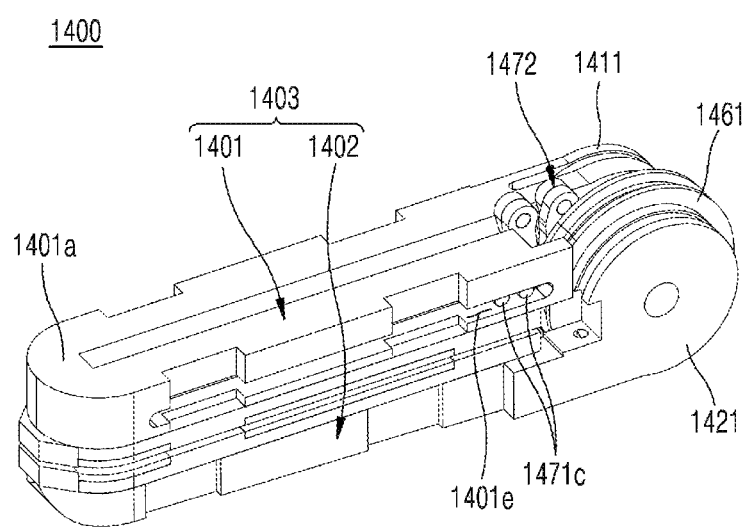
FIGS. 125 and 126 are perspective views illustrating an end tool of a surgical instrument for electrocautery according to a seventh embodiment of the present disclosure.
Figure 126:
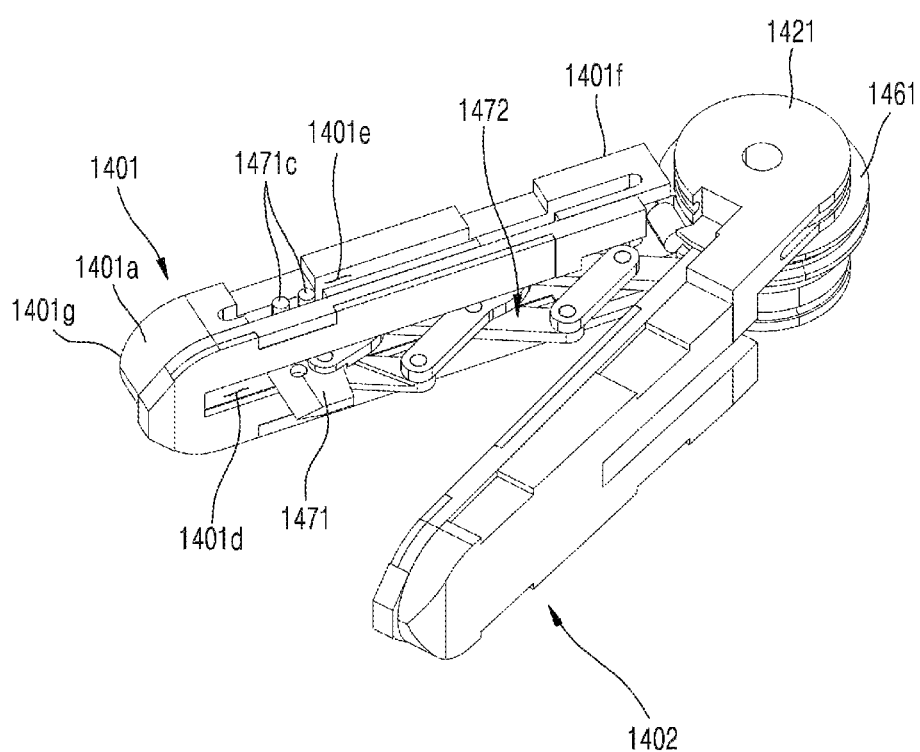
Figure 127:
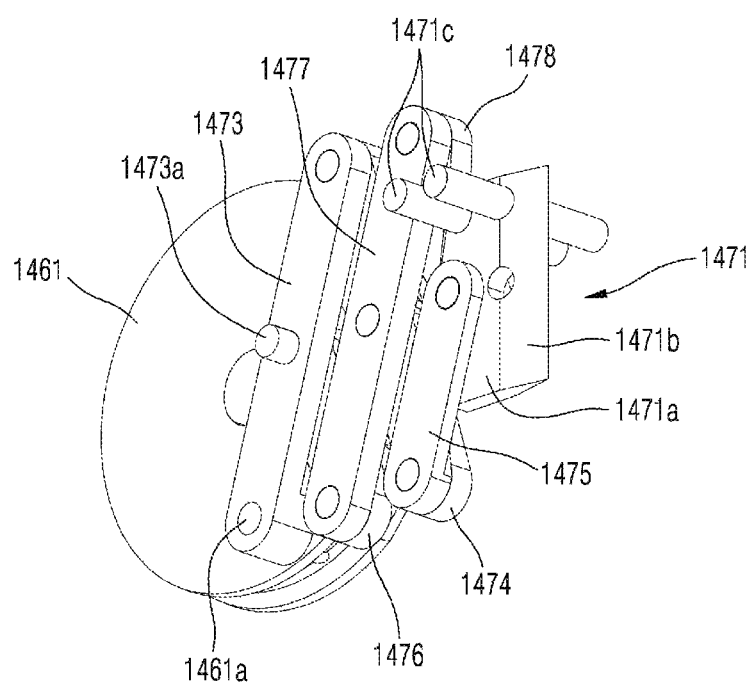
FIG. 127 is a perspective view illustrating a blade link assembly of the end tool of the surgical instrument for electrocautery of FIG. 125.

FIGS. 125 and 126 are perspective views illustrating an end tool of a surgical instrument for electrocautery according to a seventh embodiment of the present disclosure, in particular, FIG. 125 shows a state in which jaws are closed and FIG. 126 shows a state in which jaws are open. FIG. 127 is a perspective view illustrating a blade link assembly of the end tool of the surgical instrument for electrocautery of FIG. 125. FIGS. 128 to 132 are perspective views illustrating a cutting motion of an end tool of the surgical instrument for electrocautery of FIG. 125.

Referring to FIGS. 125 to 127, the end tool 1400 according to the seventh embodiment of the present disclosure includes a pair of jaws for performing a grip motion, that is, a first jaw 1401 and a second jaw 1402, and components indicating each of the first jaw 1401 and the second jaw 1402, or both the first jaw 1401 and the second jaw 1402 may be collectively referred to as a jaw 1403.

In addition, the end tool 1400 includes a plurality of pulleys including a pulley 1411 that is the first jaw pulley coupled to the first jaw 1401. In the present embodiment, the pulleys associated with the rotational motion of the first jaw 1401 are substantially the same as the pulley 112, the pulley 113, the pulley 114, the pulley 115, and the pulley 116 described above with reference to FIG. 11, etc. of the first embodiment, and detailed descriptions thereof are omitted.

In addition, the end tool 1400 includes a plurality of pulleys including a pulley 1421 that is the second jaw pulley coupled to the second jaw 1402. In the present embodiment, the pulleys associated with the rotational motion of the second jaw 1402 are substantially the same as the pulley 122, the pulley 123, the pulley 124, the pulley 125, and the pulley 126 described above with reference to FIG. 11, etc. of the first embodiment, and detailed descriptions thereof are omitted.

In addition, the end tool 1400 according to the seventh embodiment of the present disclosure may further include such elements as a first electrode 1451, a second electrode 1452, a blade pulley 1461, a blade 1471, a blade link assembly 1472, etc. in order to perform operations such as cautery and cutting motions.

Here, components associated with the driving of the blade, such as the blade pulley 1461, the blade 1471, and the blade link assembly 1472, etc. may be collectively referred to as the blade assembly 1470. Also, components such as a first blade link 1473, a second blade link 1474, a third blade link 1475, a fourth blade link 1476, a fifth blade link 1477, etc. may be collectively referred to as the blade link assembly 1472.

In the seventh embodiment, by arranging the blade assembly 1470 including a plurality of blade links between the pulley 1411 which is the first jaw pulley and the pulley 1421 which the second jaw pulley, not only the pitch motion and the yaw motion of the end tool 1400 but also the cutting motion using the blades may be performed. In the embodiment, the components for performing the cautery and cutting motions are substantially the same as the components described above in the first embodiment, and thus, detailed descriptions thereof are omitted here.

Hereinafter, the blade assembly 1470 of the surgical instrument for electrocautery according to the seventh embodiment of the present disclosure will be described below in more detail.

The first jaw 1401 may include a guide member 1401a and a case (not shown).

A blade accommodation portion 1401d and a first guide portion 1401e may be formed in the guide member 1401a. The guide member 1401a may be coupled to the pulley 1411 and may guide a movement path of the blade 1471. For example, the guide member 1401a may be formed in the form of two long bars facing each other, and the blade accommodation portion 1401d in which at least a part of the blade 1471 and the blade link assembly 1472 to be described later are accommodated may be formed inside the guide member 1401a. The blade accommodation portion 1401d may be formed in an elongated manner in a direction towards a distal end 1401g from a proximal end 1401f, and in the blade accommodation portion 1401d, the blade 1471 may be entirely accommodated or at least a part of the blade 1471 may protrude from the blade accommodation portion 1401d to the outside. In other words, as the blade 1471 moves along the blade accommodation portion 1401d, the cutting motion may be performed on the tissue. This will be described in more detail later.

In addition, the first guide portion 1401e for guiding the movement of the blade 1471 may be formed in the guide member 1401a of the first jaw 1401. Here, the first guide portion 1401e may be formed on both inner sidewalls inside the guide member 1401a forming the blade accommodation portion 1401d. The first guide portion 1401e may be formed in the shape of a groove formed along the movement path of the blade 1471. In one embodiment, in a state where a second guide portion 1471c of the blade 1471 formed in the protrusion shape is fit into the first guide portion 1401e in the groove shape, as the second guide portion 1471c moves along the first guide portion 1401e, the blade 1471 may move with respect to the first jaw 1401.

Here, the first guide portion 1401e may be formed in a direction that is substantially the same as the direction from a proximal end 1401f toward the distal end 1401g of the first jaw 1401, that is, in the X-axis direction. Therefore, the blade 1471 moving along the first guide portion 1401e may perform the linear motion in the X-axis direction. That is, the rotational motion of the blade pulley 1461 is converted into the linear motion of the blade 1471 in the X-axis direction due to the blade link assembly 1472. This will be described in more detail later.

Although the drawings illustrate that the first guide portion 1401e is integrated with the guide member 1401a as one component of the first jaw 1401, the technical concepts of the present disclosure are not limited thereto, and the first guide portion 1401e may be formed as a separate member from the guide member 1401a and be coupled to the guide member 1401a.

In addition, a first link guide portion 1401b for guiding the movement of the blade link assembly 1472 may be further formed on the first jaw 1401. The first link guide portion 1401b may be formed in the shape of a groove formed along the movement path of the blade link assembly 1472. In addition, in a state in which a second link guide portion 1473a of the first blade link 1473 is inserted in the first link guide portion 1401b formed in the shape of a groove, the second link guide portion 1473a moves along the first link guide portion 1401b, and thus, the blade link assembly 1472 is moved relative to the first jaw 1401.

Here, the first link guide portion 1401b may be formed in a direction that is substantially the same as the direction from a proximal end 1401f toward the distal end 1401g of the first jaw 1401, that is, in the X-axis direction. Therefore, the blade link assembly 1472 moving along the first link guide portion 1401b may perform the linear motion in the X-axis direction. That is, the rotational motion of the blade pulley 1461 is converted into the linear motion of the blade link assembly 1472 in the X-axis direction. This will be described in more detail later.

In addition, a first electrode 1451 may be formed on a surface of the first jaw 1401 facing the second jaw 1402. The second electrode 1452 may be formed on a surface of the second jaw 1402 facing the first jaw 1401.

Here, a part of the blade 1471 is accommodated in the first jaw 1401, and the other part of the blade 1471 may be accommodated in the second jaw 1402. In detail, unlike the previous embodiments, in the surgical instrument for electrocautery according to the seventh embodiment, a part of the blade 1471 is accommodated in the first jaw 1401 and the other part of the blade 1471 is accommodated in the second jaw 1402 during the entire processes of the cutting motion. That is, in the embodiment, it may be expressed that the blade 1471 linearly moves between the proximal end 1401f and the distal end 1401g of the first jaw 1401, rather than the blade 1471 moving from the first jaw 1401 toward the second jaw 1402. This will be described in more detail later.

The blade 1471 may include a body portion 1471a, an edge portion 1471b, and one or more second guide portions 1471c.

In a region of the body portion 1471a, the edge portion 1471b which is sharp and cuts tissue may be formed. The tissue arranged between the first jaw 1401 and the second jaw 1402 may be cut while at least a part of the edge portion 1471b moves between the proximal end 1401f and the distal end 1401g of the first jaw 1401.

In another area of the body portion 1471a, the one or more second guide portions 1471c may be formed. For example, the second guide portion 1471c may include a plurality of protrusions. The plurality of protrusions of the second guide portion 1471c may be inserted in the first guide portion 1401e of the first jaw 1401.

The blade link assembly 1472 incudes a plurality of blade links and connects the blade pulley 1461 and the blade 1471 to each other, so as to transfer the rotation of the blade pulley 1461 to the blade 1471, and thus, the blade 1471 is moved in the direction from the proximal end 1401f toward the distal end 1401g of the first jaw 1401.

Here, the blade link assembly 1472 may include the first blade link 1473, the second blade link 1474, the third blade link 1475, a fourth blade link 1476, a fifth blade link 1477, a sixth blade link 1478, etc.

The first blade link 1473 is formed in the shape of an elongated bar, and the second link guide portion 1473a may be formed at the center. In a state in which a second link guide portion 1473a of the first blade link 1473 is inserted in the first link guide portion 1401b formed in the shape of a groove, the second link guide portion 1473a moves along the first link guide portion 1401b, and thus, the blade link assembly 1472 is moved relative to the first jaw 1401.

Here, the second link guide portion 1473a may be formed integrally with the first blade link 1473, or the second link guide portion 1473a formed in the shape of a shaft formed as a separate member may be inserted through the first blade link 1473 and the fourth blade link 1476.

One end portion of the first blade link 1473 is axially coupled to a protrusion 1461a of the blade pulley 1461, and the other end portion is axially coupled to one end portion of the second blade link 1474. The other end portion of the second blade link 1474 is axially coupled to one end portion of the third blade link 1475. The other end portion of the third blade link 1475 is axially coupled to the blade 1471.

In addition, one end portion of the fourth blade link 1476 is axially coupled to the second link guide portion 1473a of the first blade link 1473, and the other end portion is axially coupled to one end portion of the fifth blade link 1477. The other end portion of the fifth blade link 1477 is axially coupled to one end portion of the sixth blade link 1478. The other end portion of the sixth blade link 1478 is axially coupled to the blade 1471.

Here, the first blade link 1473 and the fourth blade link 1476 are formed to cross each other in X-shape, the second blade 1474 and the fifth blade 1477 are formed to cross each other in X-shape, and the third blade 1475 and the sixth blade 1478 are formed to cross each other in X-shape.

Here, the center portion of the second blade 1474 and the center portion of the fifth blade 1477 may be axially coupled to each other. Here, a protrusion may be formed on one side of the center portion of the second blade 1474 and the center portion of the fifth blade 1477, and a through-hole may be formed in the other side so that the second blade 1474 and the fifth blade 1477 may be coupled to each other. Alternatively, a through-hole is formed in each of the center portion of the second blade 1474 and the center portion of the fifth blade 1477, and an additional shaft may be coupled to the through-holes of the second blade 1474 and the fifth blade 1477.

In addition, the third blade 1475 and the sixth blade 1478 may be axially coupled to the blade 171, respectively.

That is, the blade link assembly 1472 may be formed so that a plurality of links repeatedly cross one another in the X-shape. As described above, a structure in which the plurality of links repeatedly cross each other in the X-shape may be referred to as a scissor mechanism or a pantograph mechanism.

In the drawings, the blade link assembly 1472 includes six links, but the technical concepts of the present disclosure are not limited thereto. The blade link assembly 1472 may be configured so that the plurality of links repeatedly cross one another in the X-shape according to the configuration and specification of the end tool 1400.

In addition, in the drawings, the through-holes are respectively formed in both opposite end portions of the first blade link 1473, the second blade link 1474, the third blade link 1475, the fourth blade link 1476, the fifth blade link 1477, and the sixth blade link 1478 and separate shafts are inserted through the through-holes. However, the technical concepts of the present disclosure are not limited thereto. That is, various coupling structures may be implemented, for example, a protrusion is formed on one component and a through-hole is formed in corresponding component so that the two components may be coupled to each other.

Figure 130:
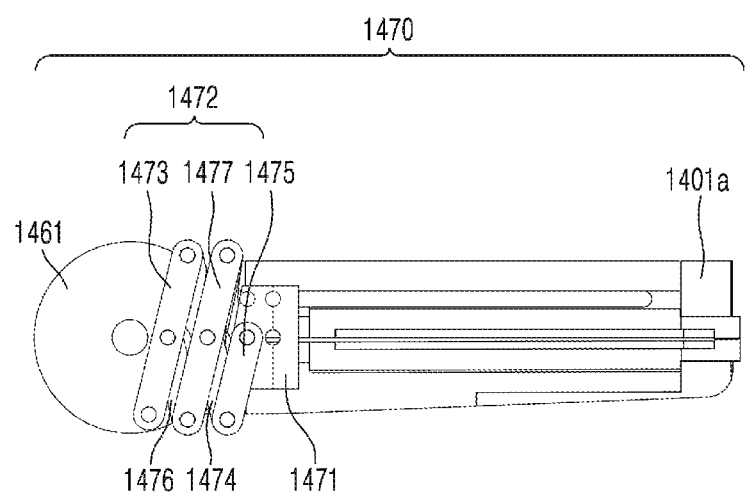
Figure 131:
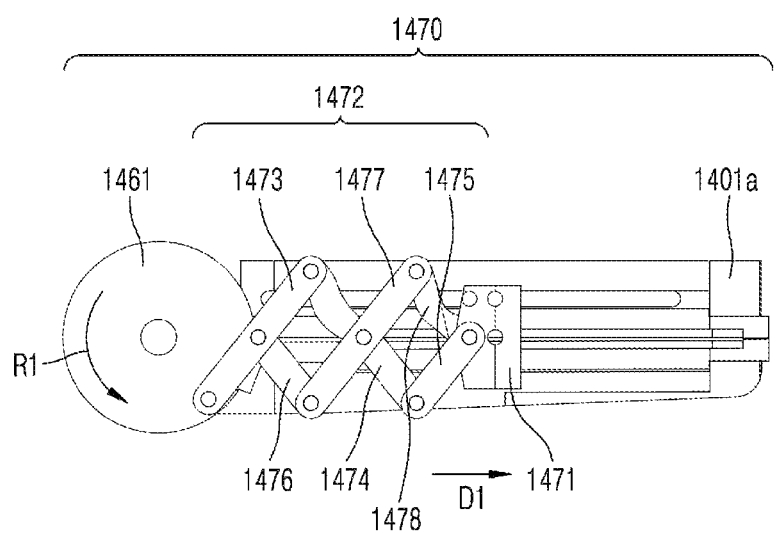
Figure 132:
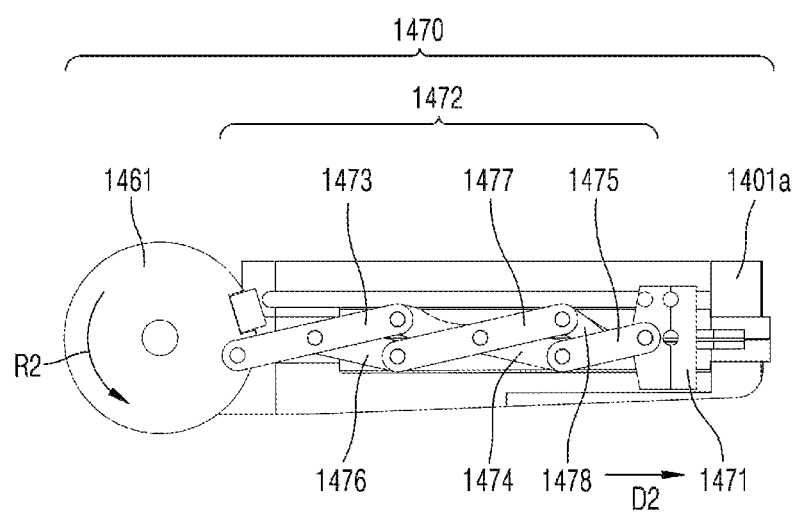

FIGS. 130, 131, and 132 are perspective views illustrating a cutting movement of the end tool of the surgical instrument for electrocautery of FIG. 125.

In the state of FIG. 130, when the blade pulley 1461 is rotated in a direction indicated by the arrow R1 of FIG. 131, the first blade link 1473 axially coupled to the blade pulley 1461 is also rotated along with the blade pulley 1461. Here, the second link guide portion 1473a of the first blade link 1473 is inserted in the first link guide portion 1401b formed in the shape of a groove, and thus, the second link guide portion 1473a linearly moves along the first link guide portion 1401b in a direction indicated by the arrow D1 of FIG. 131. That is, the first blade link 1473 rotates, and at the same time, linearly moves along the first link guide portion 1401b.

In addition, because the first blade link 1473 is connected to the second blade link 1474 and the second blade link 1474 is connected to the third blade link 1475, when the first blade link 1473 linearly moves in the direction indicated by the arrow D1 while rotating, the second blade link 1474 and the third blade link 1475 also linearly move in the direction indicated by the arrow D1 while rotating.

Likewise, because the fourth blade link 1476 is connected to the first blade link 1473, the fourth blade link 1476 is connected to the fifth blade link 1477, and the fifth blade link 1477 is connected to the sixth blade link 1478, when the first blade link 1473 linearly moves in the direction indicated by the arrow D1 while rotating, the fourth blade link 1476, the fifth blade link 1477, and the sixth blade link 1478 also linearly move in the direction indicated by the arrow D1 while rotating.

Consequently, when the blade pulley 1461 rotates in the direction indicated by the arrow R1 of FIG. 131, the total length of the blade link assembly 1472 increases, and the blade 1471 moves in the direction indicated by the arrow D1.

In this state, when the blade pulley 1461 is further rotated in the direction indicated by the arrow R2 of FIG. 132, the total length of the blade link assembly 1472 is further increased, and the blade 1471 further moves in the direction indicated by the arrow D2 so that the blade 1471 reaches the distal end 1401g of the first jaw 1401.

In the other words, the blade link assembly 1472 is entirely compressed in FIG. 130, and when the blade pulley 1461 rotates, it may be expressed that the blade link assembly 1472 is entirely stretched as shown in FIGS. 131 and 132.

The end tool of the surgical instrument for electrocautery according to the seventh embodiment of the present disclosure includes the blade link assembly 1472 including the plurality of blade links, and thus, the blade 1471 performs the linear motion in a direction that is substantially the same as the direction from the proximal end 1401f toward the distal end 1401g of the first jaw 1401, that is, the X-axis direction. That is, the rotational motion of the blade pulley 1461 is converted into the linear motion of the blade 1471 in the X-axis direction due to the blade link assembly 1472.

In addition, corresponding to this, a part of the blade 1471 is accommodated in the first jaw 1401 during all motions, and the other part of the blade 1471 is accommodated in the second jaw 1402 during all motions. That is, the blade 1471 does not move from the first jaw 1401 toward the second jaw 1402, but the blade 1471 is linearly moved between the proximal end 1401f and the distal end 1401g of the first jaw 1401 and the cutting is performed.

According to the above configuration, the cutting is performed while the blade 1471 performs the linear motion, and thus, the moving path of the blade 1471 is reduced and the cutting is simply performed.

INDUSTRIAL APPLICABILITY

The present disclosure relates to an end tool of a surgical instrument and a surgical instrument for electrocautery including the same, and in particular, an end tool of a surgical instrument and a surgical instrument for electrocautery including the end tool that is capable of rotating in two or more directions and intuitively matching a movement of a manipulation portion, wherein the surgical instrument may be installed on a robot arm or manually operable in order to be used in laparoscopic surgery or other various surgeries.

The invention claimed is:

1. An end tool of a surgical instrument, the end tool comprising:
    a first jaw and a second jaw that are rotatable independently from each other;
    a first jaw pulley coupled to the first jaw and formed to be rotatable about a first axis;
    a second jaw pulley coupled to the second jaw, formed to be rotatable about an axis that is substantially same as or parallel to the first axis, and formed to be spaced a certain distance from the first jaw pulley;
    a blade assembly which includes a blade moving between a proximal end and a distal end of the first jaw and a blade pulley coupled to the blade, and of which at least a part is formed between the first jaw pulley and the second jaw pulley;
    a blade wire that is at least partially in contact with the blade assembly and transfers a driving force required to move the blade to the blade;
    an end tool hub including a first jaw pulley coupling portion, a second jaw pulley coupling portion, and a guide portion, wherein the first jaw pulley coupling portion and the second jaw pulley coupling portion are formed to face each other and the guide portion connects the first jaw pulley coupling portion and the second jaw pulley coupling portion;
    a blade auxiliary pulley arranged between the blade pulley and the guide portion and formed to be rotatable about a second axis parallel to the first axis;
    a first jaw auxiliary pulley arranged between the first jaw pulley and the guide portion and formed to be rotatable about the second axis;
    a second jaw auxiliary pulley arranged between the second jaw pulley and the guide portion and formed to be rotatable about the second axis,
    wherein the blade auxiliary pulley is arranged between the first jaw auxiliary pulley and the second jaw auxiliary pulley.

2. The end tool of claim 1,
    wherein the first jaw pulley is arranged adjacent to the first jaw pulley coupling portion of the end tool hub,
    the second jaw pulley is arranged adjacent to the second jaw pulley coupling portion of the end tool hub, and
    at least a part of the blade assembly is formed between the first jaw pulley and the second jaw pulley.

3. The end tool of claim 2, wherein
    the blade pulley is arranged between the first jaw pulley and the second jaw pulley.

4. The end tool of claim 3, wherein the first axis is sequentially inserted through the first jaw pulley coupling portion, the first jaw pulley, the blade pulley, the second jaw pulley, and the second jaw pulley coupling portion.

5. The end tool of claim 3, wherein the first jaw pulley, the blade pulley, and the second jaw pulley are sequentially stacked in the end tool hub.

6. The end tool of claim 3, wherein the first jaw pulley, the blade pulley, and the second jaw pulley are formed to be rotatable independently from one another.

7. The end tool of claim 3, wherein regions of the guide portion, which are adjacent to the first jaw pulley, the blade pulley, and the second jaw pulley, are curved so as to have cross-sections having a certain curvature.

8. The end tool of claim 7, wherein the blade wire is located on a common internal tangent of the blade pulley and the guide portion, and a rotation angle of the blade pulley is increased due to the guide portion.

9. The end tool of claim 1, wherein the blade wire is located on a common internal tangent of the blade pulley and the blade auxiliary pulley, and a rotation angle of the blade pulley is increased due to the blade auxiliary pulley.

10. The end tool of claim 1, wherein
the blade assembly includes a blade pulley, and
the blade pulley is arranged between the first jaw pulley and the second jaw pulley.

11. The end tool of claim 10, wherein
the blade wire is connected to the blade pulley,
the blade pulley is connected to the blade, and
when the blade pulley is rotated by the blade wire, the blade connected to the blade pulley is moved between the proximal end and the distal end of the first jaw.

12. The end tool of claim 10, wherein
the blade assembly further comprises
a blade link that is connected to the blade pulley and the blade and transfers a rotation of the blade pulley to the blade.

13. The end tool of claim 1, wherein
a first electrode is formed on a surface of the first jaw, the surface facing the second jaw, and
a second electrode is formed on a surface of the second jaw, the surface facing the first jaw.

14. The end tool of claim 13, wherein electrocautery for a tissue is performed while an electric current flows in the first electrode and the second electrode.

15. The end tool of claim 14, wherein, when the electrocautery is finished, the blade wire is moved and accordingly, the blade moves from a side of the proximal end toward a side of the distal end of the first jaw, thereby cutting the tissue.

16. The end tool of claim 1, wherein, when the blade is located at the proximal end of the first jaw, at least a part of the blade is accommodated in the first jaw, and the blade is moved toward the second jaw by the blade wire.

17. The end tool of claim 16, wherein the blade is drawn to an outside of the first jaw while moving toward the distal end of the first jaw.

18. The end tool of claim 1, further comprising:
a pair of end tool first jaw pitch main pulleys which are formed on one side of the first jaw pulley and formed to be rotatable about a third axis forming a certain angle with the first axis; and
a pair of end tool second jaw pitch main pulleys which are formed on one side of the second jaw pulley and formed to be rotatable about an axis that is substantially same as or parallel to the third axis.

19. The end tool of claim 18, wherein the end tool is formed to be yaw-rotatable about the first axis, and simultaneously pitch-rotatable about the third axis.

20. The end tool of claim 18, further comprising:
a first jaw wire, of which at least a part is wound on the first jaw pulley and the pair of end tool first jaw pitch main pulleys; and
a second jaw wire, of which at least a part is wound on the second jaw pulley and the pair of end tool second jaw pitch main pulleys.

\* \* \* \* \*